US011344565B2

(12) United States Patent
Axt et al.

(10) Patent No.: US 11,344,565 B2
(45) Date of Patent: May 31, 2022

(54) METHODS FOR THE PREPARATION OF RIBOSIDES

(71) Applicant: Gilead Sciences, Inc., Foster City, CA (US)

(72) Inventors: Steven Donald Axt, Redwood City, CA (US); Pavel Robertovich Badalov, Edmonton (CA); Katrien Brak, Belmont, CA (US); Silvio Campagna, Edmonton (CA); Andrei Chtchemelinine, San Mateo, CA (US); Edward Doerffler, Foster City, CA (US); Morin Mae Frick, San Mateo, CA (US); Detian Gao, Edmonton (CA); Lars V. Heumann, Redwood City, CA (US); Brittanie Hoang, San Francisco, CA (US); Willard Lew, San Mateo, CA (US); Robert Ronald Milburn, Belmont, CA (US); Sean Timothy Neville, San Mateo, CA (US); Bruce Ross, El Granada, CA (US); Erik Rueden, San Mateo, CA (US); Robert William Scott, San Mateo, CA (US); Dustin Siegel, San Carlos, CA (US); Andrew C. Stevens, Edmonton (CA); Clarissa Tadeus, San Carlos, CA (US); Tiago Vieira, Edmonton (CA); Andrew W. Waltman, San Francisco, CA (US); Xianghong Wang, Dublin, CA (US); Mark Charles Whitcomb, Woodside, CA (US); Lydia Wolfe, San Mateo, CA (US); Chia-Yun Yu, Edmonton (CA)

(73) Assignee: Gilead Sciences, Inc., Foster City, CA (US)

( * ) Notice: Subject to any disclaimer, the term of this patent is extended or adjusted under 35 U.S.C. 154(b) by 241 days.

(21) Appl. No.: 14/926,063

(22) Filed: Oct. 29, 2015

(65) Prior Publication Data

US 2016/0122356 A1 May 5, 2016

Related U.S. Application Data

(60) Provisional application No. 62/105,619, filed on Jan. 20, 2015, provisional application No. 62/072,331, filed on Oct. 29, 2014.

(51) Int. Cl.
*C07H 5/06* (2006.01)
*C07H 7/06* (2006.01)
(Continued)

(52) U.S. Cl.
CPC ............ *A61K 31/685* (2013.01); *A61K 31/00* (2013.01); *A61K 31/53* (2013.01); *A61K 31/665* (2013.01); *A61K 31/6615* (2013.01); *A61K 31/675* (2013.01); *A61K 31/683* (2013.01); *A61K 31/706* (2013.01); *A61K 31/7056* (2013.01);
(Continued)

(58) Field of Classification Search
CPC .. C07D 487/04; C07D 519/10; C07D 519/00; C07H 15/18; C07H 11/00; C07H 1/02; C07H 1/00; C07F 9/65616; C07F 9/2429; A61K 31/53; A61K 31/675; A61K 31/685; A61K 31/00; A61K 45/06; A61K 2300/00
See application file for complete search history.

(56) References Cited

U.S. PATENT DOCUMENTS 4,816,570 A 3/1989 Farquhar
4,968,788 A 11/1990 Farquhar
(Continued)

FOREIGN PATENT DOCUMENTS

AU 2010/295392 B2 4/2012
CA 2367921 C 7/2009
(Continued)

OTHER PUBLICATIONS

Alessandrini, et al., "Synthesis of Differently Protected 1-C-methyl-ribofuranoses Intermediates for the Preparation of Biologically Active 1'-C-methyl-ribonucleosides," Journal of Carbohydrate Chemistry, 27(5):; 332-344, 2008.
(Continued)

*Primary Examiner* — Lawrence E Crane
(74) *Attorney, Agent, or Firm* — Fish & Richardson P.C.

(57) ABSTRACT

Provided are methods of preparing compounds and pharmaceutical compositions comprising a compound Formula VIII for treating Filoviridae virus infections. In one aspect, the compound of Formula VIII is formed from a reaction mixture comprising the compound of Formula IX, the compound of Formula X, a coupling agent such as magnesium chloride and a non-nucleophilic base such as diisopropylethylamine. The compound of Formula IX can be formed from a compound of Formula V and a cyanating agent. The compound of Formula V can be synthesized from a reaction mixture comprising a deprotonating agent such as phenylmagnesium chloride; a silylating agent such as chlorotrimethylsilane; a coupling agent such as isopropylmagnesium chloride, an additive such as $LaCl_3 \cdot 2LiCl$, $LaCl_3$, $CeCl_3$, $NdCl_3$, or $YCl_3$; a compound of Formula VI; and 7-iodopyrrolo[2,1-f][1,2,4]triazin-4-amine. The compounds, compositions, and methods provided are particularly useful for the treatment of Marburg virus, Ebola virus and Cueva virus infections.

19 Claims, No Drawings

(51) Int. Cl.

| | | |
|---|---|---|
| *A61K 31/685* | (2006.01) | |
| *A61K 31/706* | (2006.01) | |
| *A61K 31/7056* | (2006.01) | |
| *A61K 31/53* | (2006.01) | |
| *C07H 1/00* | (2006.01) | |
| *C07H 1/02* | (2006.01) | |
| *C07H 11/00* | (2006.01) | |
| *C07H 15/18* | (2006.01) | |
| *A61K 31/6615* | (2006.01) | |
| *A61K 31/665* | (2006.01) | |
| *A61K 31/683* | (2006.01) | |
| *C07D 487/04* | (2006.01) | |
| *C07D 519/00* | (2006.01) | |
| *C07F 9/24* | (2006.01) | |
| *C07F 9/6561* | (2006.01) | |
| *A61K 31/675* | (2006.01) | |
| *A61K 45/06* | (2006.01) | |
| *A61K 31/00* | (2006.01) | |

(52) U.S. Cl.
CPC ............ *A61K 45/06* (2013.01); *C07D 487/04* (2013.01); *C07D 519/00* (2013.01); *C07F 9/2429* (2013.01); *C07F 9/65616* (2013.01); *C07H 1/00* (2013.01); *C07H 1/02* (2013.01); *C07H 11/00* (2013.01); *C07H 15/18* (2013.01)

(56) References Cited

U.S. PATENT DOCUMENTS

| | | | |
|---|---|---|---|
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 * | 9/2010 | Becker .................. | C07H 19/10 514/81 |
| 7,807,653 B2 | 10/2010 | Cook et al. | |
| 7,842,672 B2 | 11/2010 | Boojamra et al. | |
| 7,951,787 B2 * | 5/2011 | McGuigan ............ | C07H 19/10 514/49 |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 * | 3/2015 | Wang ................ | A61K 31/7056 514/47 |
| 9,090,642 B2 | 7/2015 | Cho et al. | |
| 9,243,022 B2 * | 1/2016 | Beigelman ............. | C07H 19/16 |
| 9,249,174 B2 * | 2/2016 | Beigelman ............. | C07H 19/16 |
| 9,278,990 B2 | 3/2016 | Smith et al. | |
| 9,388,208 B2 * | 7/2016 | Clarke ..................... | C07H 7/06 |
| 9,393,256 B2 | 7/2016 | Ray et al. | |
| 9,452,154 B2 | 9/2016 | Delaney et al. | |
| 9,481,703 B2 * | 11/2016 | Kalayanov ............ | C07H 19/06 |
| 9,487,544 B2 * | 11/2016 | Cho ........................ | C07H 1/00 |
| 9,504,701 B2 * | 11/2016 | Casola ................. | A61K 31/675 |
| 9,540,411 B2 * | 1/2017 | Kalayanov ............ | C07H 19/06 |
| 9,549,941 B2 | 1/2017 | Cleary et al. | |
| 9,605,018 B2 * | 3/2017 | Wang ................ | A61K 31/7056 |
| 9,616,076 B2 * | 4/2017 | Casola ................. | A61K 31/675 |
| 9,701,682 B2 * | 7/2017 | Clarke ................ | C07D 405/04 |
| 9,724,360 B2 * | 8/2017 | Chun .................... | C07D 487/04 |
| 9,828,408 B2 * | 11/2017 | Kalayanov ............ | C07H 19/06 |
| RE46,762 E | 3/2018 | Butler et al. | |
| 9,949,994 B2 * | 4/2018 | Chun .................... | C07D 487/04 |
| 10,023,600 B2 * | 7/2018 | Butler ..................... | C07H 1/00 |
| 10,034,893 B2 * | 7/2018 | Luly ..................... | A61K 31/13 |
| 10,059,716 B2 | 8/2018 | Clarke et al. | |
| 10,065,958 B2 | 9/2018 | Mackman et al. | |
| 10,251,898 B2 | 4/2019 | Clarke et al. | |
| 10,251,904 B2 | 4/2019 | Clarke et al. | |
| 10,377,761 B2 * | 8/2019 | Clarke .................... | A61P 31/16 |
| RE47,589 E | 9/2019 | Mcguigan | |
| 10,675,296 B2 | 6/2020 | Larson | |
| 10,682,368 B2 | 6/2020 | Perron et al. | |
| 10,695,357 B2 | 6/2020 | Chun et al. | |
| 10,695,361 B2 | 6/2020 | Clarke et al. | |
| 10,696,679 B2 | 6/2020 | Mackman et al. | |
| 10,836,787 B2 | 11/2020 | Brak et al. | |
| 10,988,498 B2 | 4/2021 | Butler et al. | |
| 11,007,208 B2 | 5/2021 | Clarke et al. | |
| 2003/0050229 A1 | 3/2003 | Sommadossi et al. | |
| 2003/0092775 A1 | 5/2003 | Ernst et al. | |
| 2004/0006002 A1 | 1/2004 | Sommadossi et al. | |
| 2004/0023901 A1 | 2/2004 | Cook et al. | |
| 2004/0063658 A1 | 4/2004 | Roberts et al. | |
| 2004/0067901 A1 | 4/2004 | Bhat et al. | |
| 2004/0138170 A1 | 7/2004 | Montgomery et al. | |
| 2005/0187180 A1 | 8/2005 | Loeb et al. | |
| 2005/0209166 A1 | 9/2005 | Eckhardt et al. | |
| 2005/0215513 A1 | 9/2005 | Boojamra et al. | |
| 2005/0250728 A1 | 11/2005 | Bantia et al. | |
| 2006/0058303 A1 | 3/2006 | Chambers et al. | |
| 2006/0142238 A1 | 6/2006 | McGuigan | |
| 2006/0241064 A1 | 10/2006 | Roberts et al. | |
| 2008/0107628 A1 | 5/2008 | Boojamra et al. | |
| 2008/0161324 A1 | 7/2008 | Johansen et al. | |
| 2008/0280842 A1 | 11/2008 | MacCoss et al. | |
| 2009/0004138 A1 | 1/2009 | Francom et al. | |
| 2009/0221524 A1 | 9/2009 | Kotra et al. | |
| 2009/0233879 A1 | 9/2009 | Reddy et al. | |
| 2009/0317361 A1 | 12/2009 | Cho et al. | |
| 2010/0015094 A1 | 1/2010 | Babu et al. | |
| 2010/0016251 A1 | 1/2010 | Sofia et al. | |
| 2010/0021425 A1 | 1/2010 | Butler et al. | |
| 2010/0035835 A1 | 2/2010 | Narjes et al. | |
| 2010/0035836 A1 | 2/2010 | Francom et al. | |
| 2010/0203015 A1 | 8/2010 | Butler et al. | |
| 2010/0234584 A1 | 9/2010 | Chang | |
| 2010/0249068 A1 | 9/2010 | Beigelman et al. | |
| 2010/0291031 A2 | 11/2010 | Francom et al. | |
| 2010/0298257 A1 | 11/2010 | Ross et al. | |
| 2010/0305202 A1 | 12/2010 | Hwang et al. | |
| 2011/0070194 A1 | 3/2011 | Cho et al. | |
| 2011/0084230 A1 | 4/2011 | Knochel et al. | |
| 2011/0230654 A1 | 9/2011 | Butler et al. | |
| 2011/0257122 A1 | 10/2011 | Sofia et al. | |
| 2011/0293563 A1 | 12/2011 | Butler et al. | |
| 2012/0009147 A1 | 1/2012 | Cho et al. | |
| 2012/0020921 A1 | 1/2012 | Cho et al. | |
| 2012/0027752 A1 | 2/2012 | Mackman et al. | |
| 2012/0071434 A1 | 3/2012 | Smith et al. | |
| 2012/0107274 A1 | 5/2012 | Clarke et al. | |
| 2013/0034521 A1 | 2/2013 | Butler et al. | |
| 2013/0143835 A1 | 6/2013 | Eneroth et al. | |

(56) References Cited

U.S. PATENT DOCUMENTS

| | | | |
|---|---|---|---|
| 2013/0281686 A1 | 10/2013 | Cho et al. | |
| 2013/0315868 A1 | 11/2013 | Mayes | |
| 2013/0344028 A2 | 12/2013 | Butler et al. | |
| 2014/0219958 A1 | 8/2014 | Luly et al. | |
| 2015/0031687 A1 | 1/2015 | Guo et al. | |
| 2015/0111839 A1 | 4/2015 | Mackman et al. | |
| 2015/0133395 A1* | 5/2015 | Clarke | C07H 7/06 514/23 |
| 2015/0152116 A1 | 6/2015 | Mackman et al. | |
| 2015/0210682 A1 | 7/2015 | Han et al. | |
| 2015/0252057 A1 | 9/2015 | Guo et al. | |
| 2016/0058779 A1 | 3/2016 | Casola et al. | |
| 2016/0122344 A1 | 5/2016 | Han et al. | |
| 2016/0122356 A1 | 5/2016 | Axt et al. | |
| 2016/0176899 A1 | 6/2016 | Schwitter et al. | |
| 2016/0220586 A1 | 8/2016 | Andre et al. | |
| 2016/0237090 A1 | 8/2016 | Hu et al. | |
| 2018/0346504 A1 | 12/2018 | Brak et al. | |
| 2019/0083525 A1 | 3/2019 | Larson | |
| 2020/0360420 A1 | 11/2020 | Larson | |
| 2020/0376014 A1 | 12/2020 | Perron et al. | |
| 2021/0052613 A1 | 2/2021 | Chun et al. | |
| 2021/0283150 A1 | 9/2021 | Cihlar et al. | |

FOREIGN PATENT DOCUMENTS

| | | |
|---|---|---|
| CN | 1291994 A | 4/2001 |
| CN | 1443189 A | 9/2003 |
| CN | 1498221 A | 5/2004 |
| CN | 1852915 A | 10/2006 |
| CN | 101043893 A | 9/2007 |
| CN | 101611046 A | 12/2009 |
| CN | 102906102 A | 1/2013 |
| CN | 111265532 | 6/2020 |
| EA | 201071170 A1 | 8/2011 |
| EA | 201171417 A1 | 5/2012 |
| EA | 201200525 A1 | 9/2012 |
| EP | 2480559 B1 | 8/2012 |
| EP | 2396340 B1 | 12/2013 |
| JP | 41017629 | 10/1966 |
| JP | 2004520367 A | 7/2004 |
| JP | 2008502685 A | 1/2008 |
| JP | 2008518934 A | 6/2008 |
| TW | 1401084 B | 7/2013 |
| WO | WO-1991/019721 A1 | 12/1991 |
| WO | WO-2000/56734 A1 | 9/2000 |
| WO | WO-200075157 A1 | 12/2000 |
| WO | WO-2001/32153 A2 | 5/2001 |
| WO | WO-2001/60315 A2 | 8/2001 |
| WO | WO-2001/90121 A2 | 11/2001 |
| WO | WO-2002/008241 | 1/2002 |
| WO | WO-2002/18404 A2 | 3/2002 |
| WO | WO-2002/32920 A2 | 4/2002 |
| WO | WO-2002/057287 A2 | 7/2002 |
| WO | WO-2002/057425 A2 | 7/2002 |
| WO | WO-2003/093272 A1 | 11/2003 |
| WO | WO-2003/093273 A1 | 11/2003 |
| WO | WO-2003/100009 A2 | 12/2003 |
| WO | WO-2004/046331 A2 | 6/2004 |
| WO | WO2004112687 | 12/2004 |
| WO | WO-2005/009418 A2 | 2/2005 |
| WO | WO2005092877 | 10/2005 |
| WO | WO-2005/123087 A2 | 12/2005 |
| WO | WO-2006/031725 A2 | 3/2006 |
| WO | WO-2006/050161 A2 | 5/2006 |
| WO | WO-2006/064033 A2 | 6/2006 |
| WO | WO-2006/065335 A2 | 6/2006 |
| WO | WO-2006/121820 A1 | 11/2006 |
| WO | WO2006135978 | 12/2006 |
| WO | WO-2007/027248 A2 | 3/2007 |
| WO | WO-2007/056170 A2 | 5/2007 |
| WO | WO-2007/064883 A2 | 6/2007 |
| WO | WO-2007/064931 A2 | 6/2007 |
| WO | WO-2007/065289 A2 | 6/2007 |
| WO | WO-2007/065829 A1 | 6/2007 |
| WO | WO-2007/097991 A2 | 8/2007 |
| WO | WO2007113294 | 10/2007 |
| WO | WO-2007/135134 A1 | 11/2007 |
| WO | WO-2008/005542 A2 | 1/2008 |
| WO | WO-2008/055870 A1 | 5/2008 |
| WO | WO-2008/79206 A1 | 7/2008 |
| WO | WO-2008/082601 A2 | 7/2008 |
| WO | WO-2008/085508 A2 | 7/2008 |
| WO | WO-2008/089105 A2 | 7/2008 |
| WO | WO-2008/116064 A2 | 9/2008 |
| WO | WO-2008/121634 A2 | 10/2008 |
| WO | WO-2008/141079 A1 | 11/2008 |
| WO | WO-2009/009951 A1 | 1/2009 |
| WO | WO2009018609 | 2/2009 |
| WO | WO-2009/131926 A1 | 10/2009 |
| WO | WO-2009/132123 A1 | 10/2009 |
| WO | WO-2009/132135 A1 | 10/2009 |
| WO | WO-2010/002877 A2 | 1/2010 |
| WO | WO-2010/036407 A2 | 4/2010 |
| WO | WO-2010/093608 A1 | 8/2010 |
| WO | WO-2010/099458 A1 | 9/2010 |
| WO | WO-2010/135569 A1 | 11/2010 |
| WO | WO-2011/011303 A1 | 1/2011 |
| WO | WO-2011/111381 A3 | 3/2011 |
| WO | WO-2011/035231 A1 | 3/2011 |
| WO | WO-2011/035250 A1 | 3/2011 |
| WO | WO2011080568 | 7/2011 |
| WO | WO-2011/123645 A2 | 10/2011 |
| WO | WO 2011/123668 | 10/2011 |
| WO | WO-2011/123672 A1 | 10/2011 |
| WO | WO-2011/150288 A1 | 12/2011 |
| WO | WO-2012/012465 A1 | 1/2012 |
| WO | WO-2012/012776 A1 | 1/2012 |
| WO | WO-2012/039787 A1 | 3/2012 |
| WO | WO-2012/039791 A1 | 3/2012 |
| WO | WO-2012/051570 A1 | 4/2012 |
| WO | WO2012040127 | 5/2012 |
| WO | WO 2012/142523 | 10/2012 |
| WO | 2012158643 A1 | 11/2012 |
| WO | WO-2013/084165 A1 | 6/2013 |
| WO | WO 2014/033617 | 3/2014 |
| WO | WO-2014/042433 A2 | 3/2014 |
| WO | WO 2014/078463 | 5/2014 |
| WO | WO-2014/078778 A2 | 5/2014 |
| WO | WO-2014/116755 A1 | 7/2014 |
| WO | WO 2014/169280 | 10/2014 |
| WO | WO2016107833 | 12/2014 |
| WO | WO-2015/069939 A1 | 5/2015 |
| WO | WO2015173164 | 11/2015 |
| WO | WO2016012470 | 1/2016 |
| WO | WO2016023877 | 2/2016 |
| WO | WO-2016/069825 A1 | 5/2016 |
| WO | WO-2016/069826 A1 | 5/2016 |
| WO | WO-2016/069827 A1 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO-2017/049060 A1 | 3/2017 |
| WO | WO2017049060 | 3/2017 |
| WO | WO-2017/184668 A1 | 10/2017 |
| WO | WO2018145148 | 8/2018 |
| WO | WO-2018204198 A1 | 11/2018 |
| WO | WO2019014247 | 1/2019 |

OTHER PUBLICATIONS

Ali, et al., "Quantitative structure-activity relationships (QSAR) of two series of O-aryl or N-acyl O-ethyl phosphoramidate and phosphorodiamidate fungicides incorporating amino acid ethyl esters," Bulletin of Environmental Contamination and Toxicology, 65(4):415-420, 2000.

Arimilli, M.N., et al., "Synthesis, In Vitro Biological Evaluation and Oral Bioavailability of 9-[2-(phosphonomethoxy)propyl]adenine (PMPA) Prodrugs," Antiviral Chemistry & Chemotherapy, vol. 8, No. 6, ; pp. 557-564 (1997).

(56) References Cited

OTHER PUBLICATIONS

ARIPO Form 21 and Substantive Examination Report (in English) for AP Application No. AP/P/2010/005439, dated Mar. 18, 2014.
Asbun, et al., "Synthesis of 5-substituted Pyrimidines. II," Journal of Organic Chemistry, 31:140-142, 1968.
Ballini, et al., "Enantioselective Synthesis of the Lactone Moiety of the Mevinic Acids using D-Xylose as a Chiral Precursor," Journal of the Chemical Society, Perkin Transactions 1, pp. 490-491, 1991.
Bandini, et al., "Indium tribromide: a highly effective catalyst for the addition of trimethylsilyl cyanide to α-hetero-substituted ketone," Tetrahedron Letters, 42:3041-3043, 2001.
Barker, et al., "2,3,5-Tri-O-benzyl-D-ribosyl and -L-arabinosyl Bromides," Journal of Organic Chemistry, 26(11):4605-4609, 1961.
Belokon, et al., "Optimized catalysts for the asymmetric addition of trimethylsilyl cyanide to aldehydes and ketones," Tetrahedron, 57:771-779, 2001.
Benksim, et al., "A Novel Stereospecific Synthesis of Glycosyl Cyanides from 1,2-O-sulfinyl Derivatives," Organic Letters, 6(22):3913-3915, 2004.
Benzaria, et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., vol. 39, No. 25, pp. 4958-4965 (1996).
Bio, et al., "Practical Synthesis of a Potent Hepatitis C Virus RNA Replication Inhibitor," J. Org. Chem., vol. 69, No. 19, pp. 6257-6266 (2004).
Bobeck, et al., "Advances in Nucleoside Monophosphate Prodrugs as Anti-HCV Agents," Antiviral Therapy, vol. 15, pp. 935-950 (2010).
Bojack, et al., "Design and Synthesis of Inhibitors of Adenosine and AMP Deaminases," Org. Lett., vol. 3, ; No. 6, pp. 839-842 (2001).
Boyer, et al., "Pathogenesis, diagnosis and management of hepatitis C," Journal of Hepatology, 32:98-112, 2000.
Brown, "Progress towards improving antiviral therapy for hepatitis C virus polymerase inhibitors. Part O: Nucleoside analogues," Expert Opinion, 18:709-725, 2009.
Butora, et al., "Synthesis and HCV inhibitory properties of 9-deaza- and 7,9-dideaza-7-oxa-2'-C-methyladenosine," Bioorganic & Medicinal Chemistry, 15(15)5219-5229, 2007.
Cabirol, et al., "robust and Efficient, yet Uncatalyzed, Synthesis of Triarylsilyl-protected Cyanohydrins from Ketones," Journal of Organic Chemistry, 73:2446-2449, 2008.
Calisher, et al., "Antigenic Relationships between Flaviviruses as Determined by Cross-neutralization Tests with Polyclonal Antisera," Journal of General Virology, 70:37-43, 1989.
Calès, et al., "Treatment of liver fibrosis: clinical aspects," Gastroéntérologie Clinique et Biologique, 33(10-11):958-966, 2009.
Camps, "Studies on Structurally Simple-αβ-butenolides-II," Tetrahedron, 38(15):2395-2402, 1982.
Carroll, "Robust Antiviral Efficacy upon Administration of a Nucleoside Analog to Hepatitis C Virus-Infected Chimpanzees," Antimicrobial Agents and Chemotherapy, 53(3):926-934, 2009.
Chapman, et al., "RSV604, a Novel Inhibitor of Respiratory Syncytial Virus Replication," Antimicrobial Agents and Chemotherapy, 51(9):3346-53, 2007.
Cho, A. et al., (2012), "Synthesis and antiviral activity of a series of 1'-substituted 4-aza-7,9-dideazaadenosine C-nucleosides", *Bioorg Med Chem Lett*, 22:2705-7.
Cihlar, et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 52(2):655-65, 2008.
Clark, et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 48(17):5504-5508, 2005.
Colacino, et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 22(11):2013-2026, 2003.
Communication pursuant to Article 94(3) EPC for EP Patent Application No. 10763083.2, dated May 2, 2014.
Communication pursuant to Article 94(3) EPC for EP Patent Application No. 11715792.5, dated Feb. 14, 2014.
Communication under 161/162 for EP Patent Application No. 10704068.5, dated Sep. 6, 2011.
Communication under 161/162 for EP Patent Application No. 10763083.2, dated May 11, 2012.
Communication under 161/162 for EP Patent Application No. 11715792.5, dated Apr. 26, 2013.
Communication under 161/162 for EP Patent Application No. 11743400.1, dated Feb. 26, 2013.
Communication under 161/162 for EP Patent Application No. 11743709.5, dated Mar. 1, 2013.
Dai, et al., "Synthesis of 2'-C-β-Fluoromethyluridine," Organic Letters, 5(6):807-810, 2003.
De Clercq, "Antiviral Drugs: Current State of the Art," J. Clin. Virol., vol. 22, No. 1, pp. 73-89 (2001).
De Clercq, "Molecular Targets for Antiviral Agents," The Journal of Pharmacology and Experimental Therapeutics, vol. 297, No. 1, pp. 1-10 (2001).
De Francesco, et al., "Approaching a New Era for Hepatitis C Virus Therapy: Inhibitors of the NS3-4A Serine Protease and the NS5B RNA-Dependent RNA Polymerase," Antiviral Research, vol. 58, No. 1, pp. 1-16 (2003).
De Las Heras, "Synthesis of Ribosyl and Arabinosyl Cyanides by Reaction of 1-O-Acyl Sugars with Trimethylsilyl Cyanide," *Journal of the Chemical Society, Perkin Transactions* 1, 1982:903-907, 1982.
De Lombaert, et al., "N-Phosphonomethyl Dipeptides and Their Phosphonate Prodrugs, a New Generation of Neutral Endopeptidase (NEP, EC 3.4.24.11) Inhibitors," J. Med. Chem., vol. 37, No. 4, ; pp. 498-511 (1994).
Di Bisceglie, et al., "The Unmet Challenges of Hepatitis C," Scientific American, Oct. 1999:80-85, 1999.
Dolzhenko, et al., "Pyrazolo[1,5-a][1,3,5]Triazines(5-Aza-9-Deazapurines): Synthesis and Biological Activity," Heterocycles, vol. 75, No. 7, pp. 1575-1622 (2008).
Domingo, et al., "The quasispecies (extremely heterogeneous) nature of viral RNA genome populations: biological relevance—a review," Gene, 40:1-8, 1985.
Dondoni, et al., "Thiazole-Based Synthesis of Formyl C-Glycosides," Journal of Organic Chemistry, 59:6404-6414, 1994.
Dudfield, et al., "Synthesis of C-ribosyl 1,2,4-triazolo[3,4-f][1,2,4]triazines as Inhibitors of Adenosine and AMP Deaminasses," J. Chem. Soc., Perkin Trans. 1, pp. 2937-2942 (1999).
Dudfield, et al., "Synthesis of C-ribosyl Imidazo[2,1-f][1,2,4]triazines as Inhibitors of Adenosine and AMP Deaminases," J. Chem. Soc., Perkin Trans. 1, pp. 2929-2936 (1999).
Dymock, et al., "Novel approaches to the treatment of hepatitis C virus infection," Antiviral Chemistry & Chemotherapy, 11(2):79-96, 2000.
El Safadi, et al., "5-Modified-2'-dU and 2'-dC as Mutagenic Anti HIV-1 Proliferation Agents: Synthesis and Activity," Journal of Medicinal Chemistry, 53(4):1534-1545, 2010.
English translation of Office Action for MX Application No. MX/a/2013/003179, dated Feb. 25, 2014.
Extended European Search Report for EP Application No. 13194605.5, dated Mar. 13, 2014.
Farquhar, et al., "Biologically Reversible Phosphate-Protective Groups," Journal of Pharmaceutical Sciences, vol. 72, No. 3, pp. 324-325 (1983).
Final Rejection dated Aug. 21, 2014 for U.S. Appl. No. 12/886,248.
First Examination Report (in English) for CO Patent Application No. 10-131479, dated Oct. 23, 2012.
First Examination Report (in English) for MX Patent Application No. MX/a/2010/011661, dated Oct. 26, 2011.
First Examination Report for AU Patent Application No. 2009240630, dated Jun. 14, 2012.
First Examination Report for AU Patent Application No. 2009240642, dated Aug. 2, 2012.

(56) References Cited

OTHER PUBLICATIONS

First Examination Report for CN Patent Application No. 200980120218.8, dated Nov. 13, 2012 ; (with English translation).
First Examination Report for CO Patent Application No. 10-121513-5, dated Dec. 10, 2012 ; (with English translation).
First Examination Report for EA Patent Application No. 201071128, dated Apr. 25, 2012 ; (with English translation).
First Examination Report for EA Patent Application No. 201071170, dated Apr. 25, 2012 (with English translation).
First Examination Report for ID Patent Application No. W00 2010 03923, dated Apr. 5, 2013 ; (with English translation).
First Examination Report for ID Patent Application No. W00 2010 03957, dated Apr. 25, 2013 ; (with English translation).
First Examination Report for IL Patent Application No. 208515, dated Jan. 6, 2013 (English translation).
First Examination Report for IL Patent Application No. 208701, dated Jan. 13, 2013 (English translation).
First Examination Report for JP Patent Application No. 2011-506429, dated Aug. 22, 2013 ; (with English translation).
First Examination Report for JP Patent Application No. 2011-506435, dated Aug. 22, 2013 ; (with English translation).
First Examination Report for NZ Patent Application No. 588400, dated Apr. 11, 2011.
First Examination Report for NZ Patent Application No. 588670, dated Apr. 8, 2011.
First Examination Report for NZ Patent Application No. 608070, dated Nov. 7, 2013.
First Examination Report for TW Patent Application No. 098113324, dated Oct. 30, 2012 ; (English translation).
First Examination Report for UA Patent Application No. 2010 13030, dated Mar. 2, 2013 ; (with English translation).
First Examination Report for VN Patent Application No. Jan. 2010-02653, dated Apr. 26, 2012 ; (with English translation).
First Examination Report for VN Patent Application No. Jan. 2010-02939, dated Apr. 19, 2012 ; (with English translation).
First Office Action for CL Patent Application No. 1906-2011, dated May 7, 2013 (with English translation).
First Office Action for CN Patent Application No. 201080011960.0, dated Jun. 8, 2013 (with English translation).
First Office Action for EA Patent Application No. 201190110/28, dated Apr. 26, 2012 (with English translation).
First Office Action for EA Patent Application No. 201390141/28, with English translation, dated Aug. 14, 2014.
First Office Action for EP Patent Application No. 10704068.5, dated Jun. 18, 2012.
First Office Action for IL Patent Application No. 214396, dated Jul. 8, 2013 (English translation).
First Office Action for UA Application No. A 2011 10568, dated Apr. 7, 2014 (with English translation).
First Office Action for VN Patent Application No. 1-2012-03895, dated Feb. 8, 2013 (and English translation).
Form 21 for AP Patent Application No. AP/P/2011/005818, dated Sep. 19, 2013.
Fukumoto, et al., "Viral Dynamics of Hepatiis C Early After Orthotopic Liver Transplantation: Evidence for Rapid Turnover of Serum Virions," Hepatology, 24:1351-1354, 1996.
Further Examination Report for NZ Application No. 594370, dated Oct. 8, 2013.
Garcia, et al., "Synthesis of (2,3,4,6-tetra-O-acetyl-alpha-D-glycopyranosyl)thiophene derivatives as new C-nucleoside analogues," J. Carbohydrate Chemistry 20(7/8)681-687, 2001.
Gardelli, et al., "Phosphoramidate Prodrugs of 2'-C-Methylcytidine for Therapy of Hepatitis C Virus Infection," Journal of Medicinal Chemistry, 52(17):5394-5407, 2009.
Gleeson, et al., "Prediction of the Potency of Inhibitors of Adenosine Deaminase by QM/MM Calculations," Chem. Commun., pp. 2180-2181 (2003).
Gordon, et al., "Control of Hepatitis C: A Medicinal Chemistry Perspective," J. Med. Chem., vol. 48, No. 1, ; pp. 1-20 (2005).
Greene, Protective Groups in Organic Synthesis (John Wiley & Sons, New York, 1991), 15pgs.
Gudmundsson, et al., "Synthesis of imidazo[1,2-a]pyridine C-Nucleosides with an Unexpected Site of Ribosylation," Journal of Organic Chemistry, 62:3453-3459, 1997.
Gudmundsson, et al., "The Condensation of 2,6-dichloroimidazo[1,2-a]pyridine C-nucleoside with an Unexpected Site of Ribosylation," Tetrahedron Letters, 37(14):2365-2368, 1996.
Gunic, et al.., "Cyclic monophosphate prodrugs of base-modified 2'-C-methyl ribonucleosides as potent inhibitors of hepatitis C virus RNA replication," Bioorganic & Medicinal Chemistry Letters, 17:2452-2455, 2007.
Hamann, et al., "Synthesis and antiviral evaluation of 7,9-dideaza-8-thiapurine C-nucleoside derivatives," Collection Symposium Series, 10:347-349, 2008.
Hamann, et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 17:2321-2326, 2009.
Han, et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 22(19):2815-2822, 1992.
Haraguchi, et al., "Stereoselective Synthesis of 1'-C-Branched Uracil Nucleosides From Uridine," Nucleosides & Nucleotides, vol. 14, No. 3-5, pp. 417-420 (1995).
Harki, et al., "Synthesis and Antiviral Activity of 5-Substituted Cytidine Analogues: Identification of Potent Inhibitor of Viral RNA-Dependent RNA Polymerases," Journal of Medicinal Chemistry, 49(21):6166-6169, 2006.
Hayashi, et al., "C-Nucleosides. 17. A Synthesis of 2-Substituted 7-(B-D-Ribofuranosyl)-Pyrrolo[2,1-f]-1,2,4-Triazines. A New Type of "Purine Like" C-Nucleoside," Heterocycles, vol. 34, No. 3, pp. 569-574 (1992).
Hecker, et al., "Liver Targeted Prodrugs of 2'-C-Methyladenosine for Therapy of Hepatitis C Virus Infection," J. Med. Chem., vol. 50, No. 16, pp. 3891-3896 (2007).
Hoffman, et al., "When, in the Context of Drug Design, Can a Fluorine Atom Successfully Substitute a Hydroxyl Group?," International Journal of Quantum Chemistry, 89:419-427, 2002.
International Preliminary Report on Patentability and Written Opinion for PCT International Application No. PCT/US2009/041432, dated Oct. 26, 2010 (7 pages).
International Preliminary Report on Patentability and Written Opinion for PCT International Application No. PCT/US2010/049471, dated Mar. 27, 2012 (7 pages).
International Preliminary Report on Patentability and Written Opinion for PCT International Application No. PCT/US2010/049508, dated Mar. 27, 2012 (6 pages).
International Preliminary Report on Patentability and Written Opinion for PCT International Application No. PCT/US2011/038253, dated Dec. 4, 2012 (6 pages).
International Preliminary Report on Patentability and Written Opinion for PCT International Application No. PCT/US2011/044581, dated Jan. 22, 2013 (7 pages).
International Preliminary Report on Patentability for PCT International Application No. PCT/US2009/041447, dated Oct. 26, 2010 (7 pages).
International Preliminary Report on Patentability for PCT International Application No. PCT/US2010/023586, dated Aug. 16, 2011 (6 pages).
International Preliminary Report on Patentability for PCT International Application No. PCT/US2011/028897, dated Mar. 26, 2013 (7 pages).
International Preliminary Report on Patentability for PCT International Application No. PCT/US2011/029441, dated Mar. 26, 2013 (7 pages).
International Preliminary Report on Patentability for PCT International Application No. PCT/US2011/045102, dated Jan. 22, 2013 (5 pages).
International Preliminary Report on Patentability for PCT International Application No. PCT/US2015/057932, dated May 2, 2017, (11 pages).

(56) References Cited

OTHER PUBLICATIONS

International Preliminary Report on Patentability for PCT International Application No. PCT/US2015/057933, dated May 2, 2017 (7 pages).
International Preliminary Report on Patentability for PCT International Application No. PCT/US2015/057934, dated May 2, 2017 (14 pages).
International Search Report for PCT International Application No. PCT/US2010/023586, dated Aug. 4, 2010 (4 pages).
International Search Report for PCT International Application No. PCT/US2011/038253, dated Jul. 29, 2011 ; (4 pages).
International Search Report for PCT International Application No. PCT/US2011/044581, dated Nov. 7, 2011 (4 pages).
International Search Report for PCT International Application No. PCT/US2009/041432, dated Aug. 11, 2009 (5 pages).
International Search Report issued in International Application No. PCT/US2009/041447, dated Aug. 7, 2009 (5 pages).
International Search Report issued in International Application No. PCT/US2010/049471, dated Nov. 18, 2010 (5 pages).
International Search Report issued in International Application No. PCT/US2010/049508, dated Nov. 5, 2010 (4 pages).
International Search Report issued in International Application No. PCT/US2011/028897, dated Aug. 1, 2011 (6 pages).
International Search Report issued in International Application No. PCT/US2011/029441, dated Aug. 1, 2011 (5 pages).
International Search Report issued in International Application No. PCT/US2011/045102, dated Nov. 9, 2011 (4 pages).
Itoh, et al., "Divergent and Stereocontrolled Approach to the Synthesis of Uracil Nucleosides Branched at the Anomeric Position," J. Org. Chem., vol. 60, No. 3, pp. 656-662 (1995).
Jasko, et al., "5'-Phosphonates of Ribonucleosides and 2'-Deoxyribonucleosides: Synthesis and Antiviral Activity," Nucleosides & Nucleotides, 12(8):879-893, 1993.
Kabat, et al., "Nucleosides, CXLVIII, Synthesis of 6-(β-D-Ribofuranosyl)picolinamide: A Novel C-Nucleoside from D-Ribonolactone," Chemical & Pharmaceutical Bulletin, 36(2):634-640, 1988.
Khamnei, et al., "Neighboring Group Catalysis in the Design of Nucleotide Prodrugs," J. Med. Chem., vol. 39, No. 20, pp. 4109-4115 (1996).
Klumpp, et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 281(7):3793-3799, 2006.
Knutsen, et al., "Synthesis of Imidazo-fused Bridgehead-nitrogen 2'-Deoxyribo-C-nucleosides: Coupling-Elimination Reactions of 2,5-Anhydro-3,4,6-tri-O-benzoyl-o-allonic Acid," J. Chem. Soc., Perkin Trans. 1, ; pp. 621-630 (1985).
Knutsen, et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc., Perkin Trans 1, pp. 229-238 (1984).
Kobe, et al., "Use of Distance Geometry Approach for the In Vitro Antiviral Activity Evaluation of N-bridgehead C-nucleosides," European J. Med. Chem., vol. 27, No. 3, pp. 259-266 (1992).
Lefebvre, et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 38(20):3941-3950, 1995.
Lefebvre, et al., "Synthesis, Decomposition Pathways and 'In Vitro' Evaluation of Bioreversible Phosphotriesters of Azt," Nucleosides, Nucleotides & Nucleic Acids, 14(3-5):763-766, 1995.
Lindell, et al., "Synthesis and Biochemical Testing of 3-(Carboxyphenylethypimidazo[2,1-f][1,2,4]triazines as Inhibitors of AMP Deaminase," ACS Medicinal Chemistry Letters, 1(6):286-289, 2010.
Lovelette, C.A., "1,2,4-Triazines. Synthesis of selected members of the s-triazolo[3,4-f][1,2,4]triazine and tetrazolo[1,5-f][1,2,4]triazine ring systems," *Journal of Heterocyclic Chemistry*, 16:555-560, 1979.

Martell, et al., "Hepatitis C Virus (HCV) Circulates as a Population of Different but Closely Related Genomes: Quasispecies Nature of HCV Genome Distribution," Journal of Virology, 6695:3225-3229, 1992.
Mason, et al., "Polyadenylation-dependent screening assay for respiratory syncytial virus RNA transcriptase activity and identification of an inhibitor," Nucleic Acids Research, 32(16):4758-4767, 2004.
Matulic-Adamic, et al., "Synthesis of 3-(β-D-Ribofuranosyl)-2-Fluoropyridine and 3-(β-D-Ribofuranosyl)-Pyridin-2-one," Tetrahedron Letters, 38(2):203-206, 1997.
Matulic-Adamic, et al., "Synthesis of 5-(β-D-Ribofuranosyl)-Pyridin-2-one: a 'Deletion-Modified' Analogue of Uridine," Tetrahedron Letters, 38(10):1669-1672, 1997.
McGuigan, C., et al., "Intracellular Delivery of Bioactive AZT Nucleotides by Aryl Phosphate Derivatives of AZT," J. Med. Chem., vol. 36, No. 8, pp. 1048-1052 (1993).
Meppen, et al., "Cyclic phosphoramidates as prodrugs of 2'-C-methylcytidine," European Journal of Medicinal Chemistry, 44(9):3765-3770, 2009.
Meppen, et al., "Medi-404—A Prodrug Approach for the Treatment of HCV Infection," Abstracts of papers, 236th ACS National Meeting, Philadelphia, PA, United States, Aug. 17-21, 2008.
Metobo, S., et al., (2011), "Practical synthesis of 10-substituted Tubercidin C-nucleoside analogs", *Tetrahedron Letters*, 53:484-6.
Migliaccio, et al., "Characterization of Resistance to Non-obligate Chain-terminating Ribonucleoside Analogs That Inhibit Hepatitis C Virus Replication in vitro," The Journal of Biological Chemistry, 278(49):49164-49170, 2003.
Mitchell, et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, pp. 2345-2353 (1992).
Mitchell, et al., "Synthesis of C-Nucleoside Isosteres of 9-(2-Hydroxyethoxymethyl)guanine (Acyclovir),"; J. Het. Chem., vol. 21, No. 3, pp. 697-699 (1984).
Moennig, et al., "The Pestiviruses," Advances in Virus Research, vol. 41, pp. 53-98 (1992).
Moradpour, et al., "Replication of hepatitis C virus," Nature Reviews Microbiology, 5(6):453-463, 2007.
Moscow, et al., "Reduced Folate Carrier Gene (RFC1) Expression and Anti-Folate Resistance in Transfected and Non-Selected Cell Lines," International Journal of Cancer, 72:184-190, 1997.
Murakami, et al., "Mechanism of Activation of Beta-D-2'-Fluoro-2'-C-Methylcytidine and Inhibition of Hepatitis C Virus NS5B RNA Polymerase," Antimicrob Agents Chemother. 51(2):503-509, Feb. 2007.
Neumann, et al., "Hepatitis C Viral Dynamics in Vivo and the Antiviral Efficacy of Interferon-α Therapy," Science, 282:103-107, 1998.
Nishimura, et al., "Synthesis of pyrrolo[2,1-f ][1,2,4]triazine C-nucleosides, Isosteres of sangivamycin, tubercidin, and toyocamycin," Carbohydrate Research, vol. 331, No. 1, pp. 77-82 (2001).
Notice of Allowance dated Apr. 12, 2011 for U.S. Appl. No. 12/428,176.
Notice of Allowance dated Apr. 26, 2011 for U.S. Appl. No. 12/702,957.
Notice of Allowance dated Apr. 7, 2011 for U.S. Appl. No. 12/428,234.
Notice of Allowance dated Aug. 10, 2012 for U.S. Appl. No. 13/117,060.
Notice of Allowance dated Feb. 13, 2014 for U.S. Appl. No. 13/649,511.
Notice of Allowance dated Feb. 17, 2011 for U.S. Appl. No. 12/885,917.
Notice of Allowance dated Jan. 31, 2013 for U.S. Appl. No. 13/050,820.
Notice of Allowance dated Jan. 6, 2011 for U.S. Appl. No. 12/428,176.
Notice of Allowance dated Jul. 16, 2012 for U.S. Appl. No. 13/196,117.
Notice of Allowance dated Jun. 3, 2014 for U.S. Appl. No. 13/649,511.
Notice of Allowance dated Mar. 27, 2012 for U.S. Appl. No. 13/196,117.

(56) References Cited

OTHER PUBLICATIONS

Notice of Allowance dated Nov. 28, 2012 for U.S. Appl. No. 13/117,060.
Notice of Reasons for Rejection for JP Application No. 2011-549324, dated Jul. 28, 2014 ; (with English translation).
Notice of Reasons for Rejection for JP Application No. 2011-549324, dated Mar. 26, 2014 ; (with English translation).
Notification of Defects for IL Patent Application No. 208515, dated Aug. 25, 2014 (English translation).
Notification of Defects for IL Patent Application No. 214396, dated Nov. 11, 2013 (English translation).
Notification of Defects for IL Patent Application No. 218599, dated Aug. 25, 2014 (English translation).
Notification of Defects for IL Patent Applicaton No. 208701, dated Aug. 25, 2014 (English translation).
Notification of Reasons for Rejection for JP Patent Application No. 2012-529958, dated Aug. 5, 2014.
Notification of Reasons for Rejection for JP Patent Application No. 2012-529963, dated Aug. 2014 ; (with English translation).
Notification of Reexamination for CN Patent Application No. 200980120218.8, dated Sep. 1, 2014 ; (with English translation).
Notification of the First Office Action and Search Report for CN Patent Application No. 201080041902.X, dated Nov. 12, 2013 (with English translation).
Notification of the First Office Action for CN Patent Application No. 201080041946.2, dated Dec. 18, 2013 ; with Search Report (+ English translation).
Notification of the First Office Action for CN Patent Application No. 201180035776.1, dated Feb. 27, 2014 ; (with English translation).
Notification of the Second Office Action & Search Report for CN Patent Application No. 201080011690.0, dated Jan. 8, 2014 (with English translation).
Notification of the Third Office Action for CN Patent Application No. 201080011690.0, dated Jul. 29, 2014 ; (with English translation).
Notification Prior to Examination for IL Patent Application No. 218599, dated Nov. 13, 2012 ; (English translation).
Notification Prior to Examination for IL Patent Application No. 218752, dated Jan. 20, 2014 (English translation (3 pages)).
Office Action (Restriction Requirement) dated Sep. 14, 2012 for U.S. Appl. No. 12/886,248.
Office Action dated Jul. 21, 2016 for U.S. Appl. No. 14/613,719.
Office Action dated Nov. 4, 2016 for U.S. Appl. No. 14/613,719.
Office Action dated Sep. 24, 2014 for U.S. Appl. No. 13/813,886.
Office Action for CA Patent Application No. 2,773,772, dated Aug. 12, 2014.
Office Action for CN Patent Application No. 200980114224.2, dated Aug. 19, 2013 (with English translation).
Office Action for CN Patent Application No. 200980114224.2, dated Nov. 30, 2012 (with English translation).
Office Action for CO Application No. 13 004212, dated Dec. 4, 2013 (+ English translation).
Office Action for CO Patent Application No. 11-109.501 dated Nov. 27, 2012 (English translation).
Office Action for CO Patent Application No. 13-235103-1 dated Aug. 27, 2014 (English translation).
Office Action for EA Patent Application No. 201390152, dated Apr. 14, 2014 (and English translation).
Office Action for MX Application No. MX/a/2011/008409, dated Mar. 25, 2014 (with English translation).
Office Action for MX Application No. MX/a/2013/000656, dated Apr. 22, 2014 (+ English translation).
Office Action for MX Application No. MX/a/2013/000656, dated Aug. 4, 2014 (and English translation).
Office Action for MX Application No. MX/a/2013/000744, dated Apr. 22, 2014 (and English translation).
Office Action in PE Application No. 1464 dated Sep. 12, 2013 (with English translation).
Office Action dated Aug. 15, 2013 for U.S. Appl. No. 13/649,511.
Office Action dated Dec. 23, 2010 for U.S. Appl. No. 12/428,234.
Office Action dated Dec. 23, 2010 for U.S. Appl. No. 12/702,957.
Office Action dated Jan. 22, 2013 for U.S. Appl. No. 13/649,511.
Office Action dated Mar. 27, 2012 for U.S. Appl. No. 13/050,820.
Office Action dated Mar. 4, 2013 for U.S. Appl. No. 12/886,248.
Office Action dated Nov. 6, 2012 for U.S. Appl. No. 12/886,248.
Office Action dated Oct. 16, 2012 for U.S. Appl. No. 13/050,820.
Office Action dated Sep. 23, 2011 for U.S. Appl. No. 13/196,117.
Office Action No. 425 for CO Patent Application No. 12 050 579, dated Jan. 21, 2014 ; (with English translation).
Office Action with Search Report for TW Patent Application No. 099131868, dated May 22, 2014 ; (with English translation).
Office Action with Search Report for TW Patent Application No. 102115415, dated May 15, 2014 ; (with English translation).
Office Action with Search Report, dated Jun. 27, 2014 for CN Patent Application No. 201180035281.9 (with English translation).
Official Action (ARIPO Form No. 18) with Substantive Search and Examination Report for AP Application No. AP/P/2010/005414, dated Mar. 14, 2014 (6 pages).
Official Action for EA Patent Application No. 201390133, dated Mar. 27, 2014 (and English translation).
Official Action for SV National Phase Entry of International Application No. PCT/US2010/049471, dated Nov. 6, 2013 (with English translation).
Ogura, et al., "Reaction of Ethynyl Compounds with Lactones," Journal of Organic Chemistry, 37(1):72-75, 1972.
Opposition filed Against CL Patent Application 00076-2013, dated Jun. 18, 2014, with English translation.
Opposition for CL Patent Application No. 727-2013, dated Oct. 15, 2013 with English translation.
Opposition for EC Patent Application No. SP-13-12451, date of Notification Apr. 23, 2014 ; (and English translation).
Opposition for EC Patent Application No. SP-2012-11817, dated May 27, 2013.
Otter, et al., "Conformational Properties of Purine-Like C-Nucleosides," Nucleosides & Nucleotides, vol. 15, No. 1-3, pp. 793-807 (1996).
Pankiewicz, et al., "C-Nucleoside Analogues of Nicotinamide Mononucleotide (NMN)," Nucleosides and Nucleotides, 7(5&6):589-593, 1988.
Pankiewicz, et al., "Efficient Synthesis of 5-(β-D-Ribofuranosyl)nicotinamide and its α-Isomer," Journal of Organic Chemistry, 53:3473-3479, 1988.
Patent Examination Report No. 1 for AU Application No. 2011280910, dated Jun. 10, 2014.
Patent Examination Report No. 1 for AU Application No. 2011306066, dated Nov. 21, 2013.
Patent Examination Report No. 1 for AU Patent Application No. 2010213873, Jun. 4, 2014.
Patent Examination Report No. 1 for AU Patent Application No. 2010295392, dated Sep. 16, 2014.
Patent Examination Report No. 1 for AU Patent Application No. 2011282241, dated Jul. 9, 2014.
Patil, et al., "4-Aza-7,9-Dideazaadenosine, A New Cytotoxic Synthetic C-Nucleoside Analogue of Adenosine," Tet. Lett., vol. 35, pp. 5339-5342 (1994).
Patil, et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 9(7):937-956, 1990.
Patil, et al., "Synthesis of Pyrrolo[2,1-f][1,2,4]triazine Congeners of Nucleic Acid Purines via the N-Amination of 2-Substituted Pyrroles," J. Het. Chem., vol. 31, pp. 781-786 (1994).
Patil, et al., "Synthesis of some new thieno[3,4-d]pyrimidines and their C-nucleosides," Journal of Heterocyclic Chemistry, 30(2):509-515, 1993.
Perrone, et al., "Application of the Phosphoramidate ProTide Approach to 4'-Azidouridine Confers Sub-micromolar Potency versus Hepatitis C Virus on an Inactive Nucleoside," Journal of Medicinal Chemistry, 50(8):1840-1849, 2007.
Piccirilli, et al., "A Direct Route to 3-(D-Ribofuranosyl)pyridine Nucleosides," Helvetica Chimica Acta, 74:397-406, 1991.

(56) References Cited

OTHER PUBLICATIONS

Pierra, et al., "Synthesis and Pharmacokinetics of Valopicitabine (NM283), and Efficient Prodrug of the Potent Anti-HCV Agent 2'-C-Methylcytidine," Journal of Medicinal Chemistry, 49(22):6614-6620, 2006.
Poduch, et al., "Design of Inhibitors of Orotidine Monophosphate Decarboxylase Using Bioisosteric Replacement and Determination of Inhibition Kinetics," Journal of Medicinal Chemistry, 49(16):4937-4945, 2006.
Pre-Appeal Brief Dated Feb. 6, 2017 for U.S. Appl. No. 14/613,719.
Pre-Appeal Decision Dated Mar. 14, 2017 for U.S. Appl. No. 14/613,719.
Puech, et al., "Intracellular Delivery of Nucleoside Monophosphates through a Reductase-mediated Activation Process," Antiviral Research, vol. 22, No. 4, pp. 155-174 (1993).
Ramasamy, et al., "Synthesis and Antitumor Activity of Certain 3-B-D-Ribofuranosy1-1,2,4-triazolo[3,4-f]-1,2,4-Triazines Related to Formycin Prepared via Ring Closure of a 1,2,4-Triazine Precursor," J. Med. Chem., vol. 29, No. 11, pp. 2231-2235 (1986).
Rao, et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, ; 29(29):3537-3540, 1988.
Reddy, et al., "Stereoselective Synthesis of Nucleoside Monophosphate HepDirectTM Prodrugs," Tet. Lett., vol. 46, pp. 4321-4324 (2005).
Rejection Decision for CN Patent Application No. 200980120218.8, dated Feb. 7, 2014 ; (with English translation).
Resolution No. 56673 for CO Patent Application No. 10-131479, dated Sep. 27, 2013 with ; English translation.
Resolution No. 72986 for CO Patent Application No. 10-121513-5, dated Dec. 23, 2013) (12 pages) ; (English translation).
Schul, et al., "A Dengue Fever Viremia Model in Mice Shows Reduction in Viral Replication and Suppression of the Inflammatory Response after Treatment with Antiviral Drugs," Journal of Infectious Diseases, vol. 195, pp. 665-674 (2007).
Schultz, "Prodrugs of Biologically Active Phosphate Esters," Bioorganic & Medicinal Chemistry, ; 11:885-898, 2003.
Scott, et al., "Interferon-a-2b Plus Ribavirin: A Review of its Use in the Management of Chronic Hepatitis C," Drugs, vol. 62, No. 3, pp. 507-556 (2002).
Search and Exam Report for AP Application No. AP/P/2012/006189, dated Jun. 26, 2014.
Search Report for AP Patent Application No. AP/P/2011/005818, dated Sep. 19, 2013.
Second Examination Report (in English) for CO Patent Application No. 10-131479, dated Jun. 20, 2013.
Second Examination Report and Notice of Acceptance for NZ Patent Application No. 588400 dated Jul. 27, 2012.
Second Examination Report for CN Patent Application No. 200980120218.8, dated Jun. 21, 2013 ; (with English translation).
Second Examination Report for EA Patent Application No. 201071128, dated Oct. 24, 2012 ; (with English translation).
Second Examination Report for EA Patent Application No. 201071170, dated Oct. 25, 2012 ; (with English translation).
Second Examination Report for VN Patent Application No. 1-2010-02939, dated Jul. 26, 2012 ; (with English translation).
Second Office Action for CL Patent Application No. 1906-2011, dated Oct. 16, 2013 (with English translation).
Second Office Action for EA Patent Application No. 201190110/28, dated Jan. 28, 2013 ; (with English translation).
Second Office Action for UA Patent Application No. 2011 10568, dated Aug. 11, 2014 (and English translation).
Shekunov, et al., "Crystallization processes in pharmaceutical technology and drug delivery design", ; Journal of Crystal Growth, 211:122-136 (2000).
Silverman et al., *The Organic Chemistry of Drug Design and Drug Action*, 19-23, 1992.
Silverman, "The Organic Chemistry of Drug Design and Drug Action," 2nd Ed., pp. 29-34 (2004).
Srivastav, et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 53(19):7156-7166, 2010.
Statement of Opposition, Mar. 31, 2011, with English translation, for EC Patent Application No. SP-10-10609.
Substantive Examination Report Stage 1 (with English translation) for ID Application No. W-00201103126, dated Jun. 10, 2014.
Supplement to First Examination Report for IL Patent Application No. 208515, dated Jan. 15, 2013 ; (English translation).
Tapia, et al., "Combination of a Mutagenic Agent with a Reverse Transcriptase Inhibitor Results in Systematic Inhibition of HIV-1 Infection," Virology, 338:1-8, 2005.
Third Examination Report for EA Patent Application No. 201071128, dated Apr. 29, 2013 ; (with English translation).
Third Examination Report for EA Patent Application No. 201071170, dated Oct. 10, 2013 ; (with English translation).
Third Office Action for EA Application No. 201190110/28, dated Oct. 18, 2013.
Uchiyama, et al., "O-selective Phosphorylation of Nucleosides without N-protection," J. Org. Chem. 58(2), Jan. 1, 1993.
Vaghefi, et al., "Synthesis and Antiviral Activity of Certain Nucleoside 5'-Phosphonoformate Derivatives," Journal of Medicinal Chemistry, 29(8):1389-1393, 1986.
Warren, T. et al., (2016), "Therapeutic efficacy of the small molecule GS-5734 against Ebola virus in rhesus monkeys", Nature, 531:381-5.
Written Opinion and ISR for International Application No. PCTUS2015057933, dated Jan. 21, 2016, 9 pgs.
Written Opinion and ISR for PCT International Application No. PCT/ US2015/057934, dated May 6, 2016, 20pgs.
Written Opinion and ISR for PCT International Application No. PCT/US2015/057932, dated May 6, 2016, 17 pgs.
Written Opinion for PCT International Application No. PCT/US2010/023586, dated Aug. 4, 2010 (5 pages).
Written Opinion for PCT International Application No. PCT/US2011/028897, dated Aug. 1, 2011 (6 pages).
Written Opinion for PCT International Application No. PCT/US2011/029441, dated Aug. 1, 2011 (6 pages).
Written Opinion for PCT International Application No. PCT/US2011/038253, dated Jul. 29, 2011 (5 pages).
Written Opinion for PCT International Application No. PCT/US2011/044581, dated Nov. 7, 2011 (6 pages).
Written Opinion for PCT International Application No. PCT/US2011/045102, dated Nov. 9, 2011 ; (4 pages).
Written Opinion issued in International Application No. PCT/US2009/041447, dated Oct. 26, 2010 (7 pages).
Written Opinion issued in International Application No. PCT/US2010/049471, dated Mar. 27, 2012 (7 pages).
Written Opinion issued in International Application No. PCT/US2010/049508, dated Mar. 27, 2012 (6 pages).
Written Opinion issued in International Application No. PCT/US2011/045102, dated Jan. 22, 2013 (5 pages).
Wu, et al., "Synthetic Methodologies for C-Nucleosides," Synthesis, 10:1533-1553, 2004.
Yamanaka, et al., "Metabolic Studies on BMS-200475, a New Antiviral Compound Active against Hepatitis B Virus," Antimicrobial Agents and Chemotherapy, 43(1):190, 1999.
Yoshimura, et al., "Synthesis and Biological Evaluation of 1'-C-Cyano-Pyrimidine Nucleosides," Nucleosides & Nucleotides, vol. 15, No. 1-3, pp. 305-324 (1996).
Zhang, et al., "A Practical Synthesis of (2R)-3,5-di-O-benzoyl-2-fluoro-2-C-methyl-D-ribono-y-lactone," Tetrahedron: Asymmetry, 20:305-312, 2009.
International Preliminary Report on Patentability for PCT International Application No. PCT/US2015/057934, dated May 11, 2017 (14 pages).
Barl, et al., The halogen/magnesium-exchange using iPrMgCl•LiCl and related exchange reagents, Heterocycles, Jan. 2014, pp. 827-844, vol. 88, No. 2.

(56) References Cited

OTHER PUBLICATIONS

Balzarini, et al., Inhibition of feline (FIPV) and human (SARS) coronavirus by semisynthetic derivatives of glycopeptide antibiotics, Antiviral Research, Mar. 14, 2006, pp. 20-33, vol. 72.
Bozza, Zika Outbreak, Brazil 2015, ISARIC, 2015, 28 pages.
Bullard-Feibelman, et al., The FDA-approved drug Sofosbuvir inhibits Zika Virus infection, Antiviral Res., Jan. 1, 2018, pp. 134-140, vol. 137.
Burns, A glimmer of hope for a fatal feline disease, American Veterinary Medical Association, Dec. 15, 2017, 5 pages.
Caira, Crystalline Polymorphism of Organic Compounds, Topics in Current Chemistry, 1998, pp. 163-208, vol. 198.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Clarke, et al., Discovery of [beta]-d-2'-deoxy-2'-[alpha]-fluoro-4'[alpha]-cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.
European Patent Office, International Search Report for PCT International Application No. PCT/US2016/052092, dated Nov. 10, 2016, 11 pages.
European Patent Office, International Search Report and Written Opinion for PCT International Application No. PCT/US2017/028243, dated Aug. 29, 2017, 12 pages.
European Patent Office, International Search Report and Written Opinion for PCT International Application No. PCT/US2017/028251, dated Oct. 16, 2017, 22 pages.
European Patent Office, International Search Report and Written Opinion for PCT International Application No. PCT/US2018/022166, dated Jun. 11, 2018, 13 pages.
European Patent Office, International Search Report and Written Opinion for PCT International Application No. PCT/US2018/029974, dated Sep. 18, 2018, 17 pages.
Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.
Murphy, et al., The nucleoside analog GS-441524 strongly inhibits feline infections peritonitis (FIP) virus in tissue culture and experimental cat infection studies, Veterinary Microbiology, ND, pp. 226-233, vol. 219.
Sacramento, et al., The clinically approved antiviral drug Sofosbuvir inhibits Zika Virus replication, Nature, Jan. 18, 2017.
Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Jan. 26 2017, 51 pages.
Knaggs, et al. A QSAR Study Investigating the Effect of L-Alanine Ester Variation on the Anti-HIV Activity of Some Phosphoramidate Derivatives of d4T, 2000, pp. 2075-2078.
Lu, Chengping, Veterinary Microbiology 5th edition, Jan. 31, 2013, p. 431, China Agriculure Press (No English Translation available).
McGuigan, et al. Application of Phosphoramidate ProTide Technology Significantly Improves Antiviral Potency of Carbocyclic Adenosine Derivatives, 2006, pp. 7215-7226.
Porter, et al., Zika virus, drug discovery, and student projects, ScienceBlogs, Mar. 9, 2016, 7 pages.
Venkatachalam, et al. Effect of change in nucleoside structure on the activation and antiviral activity of phosphoramidate derivatives, 2005, pp. 5408-5423.
Ross, et al., Synthesis of. Diastereomerically Pure Nucleotide and Phosphoramidates, Journal of Organic Chemistry, 2011, pp. 8311-8319, vol. 76.
Siegel, et al., Supporting Information Discovery and Synthesis of a Phosphoramidate Prodrug of a Pyrrol[2,1-f][triazin-4- amino] Adenine C-Nucleoside (GS-5734) for the Treatment of Ebola and Emerging Viruses Contents, J. Med. Chem., 2017, 26 pages.
Towner, et al., Newly Discovered Ebola Virus Associated with Hemorrhagic Fever Outbreak in Uganda, PLoS Pathogens, 2008, 6 pages, vol. 4, Issue 11.
Harcort, et al., Molecular Characterization of the Polymerase Gene and Genomic Termini of Nipah Virus, Virology, 2001, pp. 192-201, vol. 287.
McGuigan, et al., Aryl Phosphoramidate Derivatives of d4T Have Improved Anti-HIV Efficacy in Tissue Culture and May Act by the Generation of a Novel Intracellular Metabolite, J. Med. Chem., 1996, pp. 1748-1753, vol. 39.
Mehellou, et. al., Aryloxy Phosphoramidate Triesters: a Technology for Delivering Monophosphorylated Nucleosides and Sugarsinto Cells, ChemMedChem, 2009, pp. 1779-1791, vol. 4.
Peterson, et al., Prodrug approaches to improving the oral absorption of antiviral nucleotide analogues, Expert Opinion, Drug Deliv., 2009, pp. 405-420, vol. 6, No. 4.
Murakami, et al., Mechanism of Activation of PSI-7851 and Its Diastereoisomer PSI-7977, The Journal of Biological Chemistry, Nov. 5, 2010, pp. 34337-34347, vol. 285, No. 45.
ARIPO Patent Office, Official Action (ARIPO Form No. 18) with Substantive Search and Examination Report for AP Application No. AP/P/2010/005414, dated Mar. 14, 2014, 6 pages.
ARIPO Patent Office, Search and Exam Report for AP Application No. AP/P/2012/006189, dated Jun. 26, 2014, 6 pages.
ARIPO Patent Office, Search Report for AP Patent Application No. AP/P/2011/005818, dated Sep. 19, 2013, 1 page.
Brazil Patent Office, Third part submission for BR 11 2013 001267-6, dated Jan. 15, 2019, 30 pages.
Brazilian Office Action in BR Appln. No. 12 2020 018569 4, dated Dec. 28, 2020, 21 pages.
Brazilian Office Action in BR Appln. No. 12 2020 019211 9, dated Jan. 19, 2021, 21 pages.
Chinese Patent Office, Notification of the First Office Action and Search Report for CN Patent Application No. 201080041902.X, dated Nov. 12, 2013, 21 pages.
Chinese Patent Office, Notification of the First Office Action, with Search Report, for CN Patent Application No. 201080041946.2, dated Dec. 18, 2013, 11 pages.
Chinese Patent Office, Notification of the Second Office Action & Search Report for CN Patent Application No. 201080011690.0, dated Jan. 8, 2014, 16 pages.
Chinese Patent Office, Office Action with Search Report for CN Patent Application No. 201180035281.9, dated Jun. 27, 2014, 23 pages.
Costa Rican Office Action in CR Appln. No. 2017-0165, dated Dec. 30, 2020, 17 pages (with English translation).
European Office Action in EP Appln. No. 16770866.8, dated Dec. 23, 2020, 4 pages.
Franchetti et al., Antitumor Activity of C-Methyl-β-D-ribofuranosyladenine Nuceoside Ribonuceotide Reductase Inhibitors, J. Med. Chem. 2005, pp. 4983-4989, vol. 48.
Japanese Office Action in JP Appln. No. 2019-559276, dated Oct. 7, 2020, 6 pages (English translation only).
Lo et al., "GS-5734 and its parent nucleoside analog inhibit Filo-, Pneumo-, and Paramyxoviruses," Scientific Reports, 2017, 7(43395):1-7.
Murakami, et al., Mechanism of Activiation of PSI-7851 and Its Diastereoisomer PSI-7977, The Journal of Biological Chemistry, 2010, pp. 34337-34347, vol. 285, No. 45.
Siegel, et al., Discovery and Synthesis of a Phosphoramidate Prodrug of a Pyrrolo[2,1-f][triazin-4-amino] Adenine C-Nucleoside (GS-5734) for the Treatment of Ebola and Emerging Viruses, J. Med. Chem., 2017, 60, 5, 1648-1661 Supplementary Material.
Taiwan Patent Office, Office Action with Search Report for TW Patent Application No. 099131868, dated May 22, 2014, 23 pages.
Taiwan Patent Office, Office Action with Search Report for TW Patent Application No. 102115415, dated May 15, 2014, 10 pages.
United States Patent and Trademark Office, Notice of Allowance for U.S. Appl. No. 13/649,511, dated Feb. 13, 2014, 7 pages.
United States Patent and Trademark Office, Notice of Allowance for U.S. Appl. No. 12/428,176, dated Apr. 12, 2011, 7 pages.
United States Patent and Trademark Office, Notice of Allowance for U.S. Appl. No. 12/428,234, dated Apr. 7, 2011, 8 pages.

(56) References Cited

OTHER PUBLICATIONS

United States Patent and Trademark Office, Notice of Allowance for U.S. Appl. No. 12/885,917, dated Feb. 17, 2011, 7 pages.
United States Patent and Trademark Office, Notice of Allowance for U.S. Appl. No. 13/117,060, dated Aug. 10, 2012, 8 pages.
United States Patent and Trademark Office, Notice of Allowance for U.S. Appl. No. 13/196,117, dated Jul. 16, 2012, 9 pages.
United States Patent and Trademark Office, Office Action (Restriction Requirement) for U.S. Appl. No. 12/886,248, dated Sep. 14, 2012, 9 pages.
United States Patent and Trademark Office, Office Action for U.S. Appl. No. 14/613,719, dated Nov. 4, 2016, 9 pages.
United States Patent and Trademark Office, Office Action for U.S. Appl. No. 12/702,957, dated Dec. 23, 2010, 9 pages.
United States Patent and Trademark Office, Office Action for U.S. Appl. No. 12/886,248, dated Nov. 6, 2012, 19 pages.
United States Patent and Trademark Office, Office Action for U.S. Appl. No. 13/050,820, dated Oct. 16, 2012, 6 pages.
United States Patent and Trademark Office, Office Action for U.S. Appl. No. 13/649,511, dated Aug. 15, 2013, 8 pages.
United States Patent and Trademark Office, Office Action for U.S. Appl. No. 13/813,886, dated Sep. 24, 2014, 9 pages.
United States Patent and Trademark Office, Pre-Appeal Decision for U.S. Appl. No. 14/613,719, dated Mar. 14, 2017, 2 pages.
Uruguayan Office Action in UY Appln. No. 36.376, dated Jan. 11, 2021, 9 pages (with English translation).
Vietnam Patent Office, Second Examination Report for VN Patent Application No. 1-2010-02939, dated Jul. 26, 2012, 2 pages.
Brittain, Polymorphism in Pharmaceutical Solids, 2nd Edition, 2009, pp. 183-226, Informa Healthcare USA, Inc.
Warren et al., "Protection against filovirus diseases by a novel broad-spectrum nucleoside analogue BCX4430", Nature, Apr. 2014, 508(7496):402-405.
Chinese Office Action in Patent Application No. 201580059613.5, dated Apr. 6, 2021, 11 pages (with English translation).
PCT International Preliminary Report on Patentability for PCT International Application No. PCT/US2015/057932, May 2, 2017, 11 pages.
PCT International Preliminary Report on Patentability for PCT International Application No. PCT/US2015/057933, May 2, 2017, 7 pages.
PCT International Preliminary Report on Patentability for PCT International Application No. PCT/US2015/057934, May 2, 2017, 14 pages.
PCT International Preliminary Report on Patentability for PCT International Application No. PCT/US2018/022166, Sep. 26, 2019, 8 pages.
PCT International Search Report and Written Opinion for PCT International Application No. PCT/US2009/041432, Aug. 11, 2009, 11 pages.
PCT International Search Report and Written Opinion for PCT International Application No. PCT/US2009/041447, Aug. 7, 2009, 11 pages.
PCT International Search Report and Written Opinion for PCT International Application No. PCT/US2010/049508, Nov. 5, 2010, 9 pages.
PCT International Search Report and Written Opinion for PCT International Application No. PCT/US2015/057932, May 6, 2016, 17 pages.
PCT International Search Report and Written Opinion for PCT International Application No. PCT/US2015/057934, Mar. 18, 2016, 20 pages.
PCT International Search Report and Written Opinion for PCT International Application No. PCT/US2017/028251, Sep. 13, 2017, 22 pages.
PCT International Search Report and Written Opinion for PCT International Application No. PCT/US2018/022166, May 25, 2018, 13 pages.
PCT International Search Report for PCT International Application No. PCT/US2016/052092, Oct. 11, 2016, 11 pages.
PCT International Search Report and Written Opinion for PCT International Application No. PCT/US2010/049471, Nov. 18, 2010, 11 pages.
CHINA First Request For Invalidation to China Patent Application No. 201180035776.1, filed Jun. 1, 2020, 57 pages.
CHINA Second Request For Invalidation to China Patent Application No. 201180035776.1, filed Jun. 11, 2020, 28 pages.
NDIA Opposition Notice to India Patent Patent Application No. 1328/CHENP/2013 (India Patent No. 319927), filed Jun. 30, 2020, 259 p. (part 1, pp. 1-129).
NDIA Opposition Notice to India Patent Patent Application No. 1328/CHENP/2013 (India Patent No. 319927), filed Jun. 30, 2020, 259 p. (part 2, pp. 130-259).
NDIA Notice of Post-Grant Opposition in India Patent Application No. 201727012821 (India Patent No. 332280, filed Jun. 30, 2020, 639 pages.
PAKISTAN Notice of Opposition to the Grant of Patent On Pakistan Application No. 684/2015 (Pakistan Patent No. 143378), mailed Aug. 5, 2020, 9 pages.
TAIWAN Cancellation Brief and Exhibits to Taiwan Patent No. 1687432, dated Jul. 17, 2020, 536 p. (part 1, pp. 1-233).
TAIWAN Cancellation Brief and Exhibits to Taiwan Patent No. 1687432, dated Jul. 17, 2020, 536 p. (part 2, pp. 234-536).
Canadian Office Action in CA Appln. No. 2963907, dated Dec. 7, 2020, 6 pages.
Chinese Office Action in CN Appln. No. 201580059613.5, dated Sep. 16, 2020, 7 pages.
Foster et al., "Deuterium isotope effects in studies of drug metabolism," Trends in Pharmacological Sciences, Jan. 1984, 5:524-7.
George et al., "Preparation of silyl-and germylmetallic compounds," Journal of the American Chemical Society, Jan. 1960, 82(2):403-6.
Kalil et al., "Baricitinib plus Remdesivir for hospitalized adults with Covid-19," New England Journal of Medicine, Dec. 11, 2020, 13 pages.
Metobo, et al., Practical synthesis of 1'-substituted Tubercidin C-nucleoside analogs, Tetrahedron Letters, Feb. 2012, pp. 484-486, vol. 53, No. 5.
Mossel et al., "Exogenous ACE2 expression allows refractory cell lines to support severe acute respiratory syndrome coronavirus replication," Journal of Virology, Mar. 15, 2005, 79(6):3846-50.
Xie et al., "A nanoluciferase SARS-CoV-2 for rapid neutralization testing and screening of anti-infective drugs for COVID-19," Nature Communications, Oct. 15, 2020, 11(1):1-1.
Zhu et al., "A novel coronavirus from patients with pneumonia in China, 2019," New England Journal of Medicine, Jan. 24, 2020, 14 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.
Carryer et al., "The effect of cortisone on bronchial asthma and hay fever occurring in subjects sensitive to ragweed pollen", Journal of Allergy, Jul. 1950, 21(4): 282-287.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Fauquet et al., "Abbreviations for vertebrate virus species names", Archives of Virology, Dec. 31, 1999, pp. 1865-1880.

(56) References Cited

OTHER PUBLICATIONS

Kaewkhao et al., "High sensitivity methods to quantify chloroquine and its metabolite in human blood samples using LC-MS/MS", Bioanalysis, Mar. 2019, 11(5):333-347.
Kuzik et al., "Nebulized Hypertonic Saline in the Treatment of Viral Bronchiolitis in Infants", The Journal of Pediatrics, Sep. 2007, 151(3):266-270.e1.
Morris, "Mechanisms of action and therapeutic role of corticosteroids in asthma", J. Allergy Clin. Immunol., Jan. 1985, 75(1 Pt):1-13.
Munster et al., "Hydroxychloroquine concentration-response relationships in patients with rheumatoid arthritis", Arthritis Rheumatology, Jun. 2002, 46(6)4460-1469.
Walker et al., "Plasma chloroquine and desethylchloroquine concentrations in children during and after chloroquine treatment for malaria.", British Journal Clinical Pharmacology, Dec. 1983, 16(6):701-705.
Wang et al., "Remdesivir and chloroquine effectively inhibit the recently emerged novel coronavirus (2019-nCoV) in vitro", Cell Research, 2020, 30:269-271.
Brazilian Office Action in BR Patent Application No. 1120170076365, dated Jul. 6, 2021, 8 pages (with English translation).
Canadian Office Action in CA Patent Application No. 2,963,907, dated Jul. 16, 2021, 4 page.
Indian Notice of Hearing in IN Patent Application No. 201717012502, dated Aug. 4, 2021, 3 pages.
Japanese Office Action in JP Application No. JP 2020-38878, dated Aug. 20, 2021, 5 pages (with English translation).
Brands et al., "Crystallization-Induced Diastereomer Transformations," Chem. Rev., 2006, 106(7): 2711-2733.
Brotschi et al., "Bipyridyl and biphenyl DNA: A recognition motif based on interstrand aromatic stacking," Chemistiy-A European Journal, 2005, 11(6):1911-1923.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
McGuigan et al., "Design, synthesis and biological evaluation of phosphorodiamidate prodrugs of antiviral and anticancer nucleosides," European Journal of Medical Chemistry, 2013, 70:326-340.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Argentinian Office Action in AG Appln. No. 20150103506, dated Sep. 17, 2021, 8 pages (with English translation).
Argentinian Opposition in AG Appln. No. 20150103506, dated Jun. 22, 2021, 87 pages (with English translation).
Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.

\* cited by examiner

METHODS FOR THE PREPARATION OF RIBOSIDES

CROSS-REFERENCES TO RELATED APPLICATIONS

This patent application claims the benefit under 35 U.S.C. § 119(e) of U.S. Provisional Patent Application No. 62/072,331, filed Oct. 29, 2014, and U.S. Provisional Patent Application No. 62/105,619, filed Jan. 20, 2015. The foregoing patent applications are incorporated herein by reference in their entireties. U.S. patent application Ser. No. 15/902,690, claims priority to U.S. patent application Ser. No. 15/246,240, now U.S. Pat. No. 9,949,994, issued on Apr. 24, 2018, which claims priority to U.S. patent application Ser. No. 14/926,062, now U.S. Pat. No. 9,724,360, issued on Aug. 8, 2017, which claims the benefit under 35 U.S.C. § 119(e) of U.S. Provisional Patent Application No. 62/072,331, filed on Oct. 29, 2014, and U.S. Provisional Patent Application No. 62/105,619, filed Jan. 20, 2015.

FIELD OF THE INVENTION

The invention relates generally to methods and compounds for treating Filoviridae virus infections, particularly methods and nucleosides for treating Ebola virus, Marburg virus and Cueva virus.

BACKGROUND OF THE INVENTION

Filoviruses (e.g., Ebola virus (EBOV) and Marburg virus (MARV)) are among the most lethal and destructive viruses. They cause severe, often fatal viral hemorrhagic fevers in humans and nonhuman primates (e.g., monkeys, gorillas, and chimpanzees). Filoviruses are of particular concern as possible biological weapons since they have the potential for aerosol dissemination and weaponization.

The incubation period for Filovirus infection ranges from 2 to 21 days. The onset of illness is abrupt and is characterized by high fever, headaches, joint and muscle aches, sore throat, fatigue, diarrhea, vomiting, and stomach pain. A rash, red eyes, hiccups and internal and external bleeding may be seen in some patients. Within one week of becoming infected with the virus, most patients experience chest pains and multiple organ failure, go into shock, and die. Some patients also experience blindness and extensive bleeding before dying.

Filoviridae are a family of RNA viruses. Two members of the Filoviridae family have been identified: EBOV and MARV. Two key pathogenic types of the Filoviridae family have been identified: Ebolavirus and MARV. There is one identified variant of MARV and five identified species of ebolavirus: Zaire (i.e. Ebola virus, EBOV), Sudan, Tai Forest, Bundibugyo, and Reston. The exact origin, locations, and natural habitat of Filoviridae are unknown. However, on the basis of available evidence and the nature of similar viruses, it is postulated that Filoviridae are zoonotic (i.e., animal-borne) and are normally maintained in an animal host that is native to the African continent.

For more than 30 years, ebolaviruses have been associated with periodic episodes of hemorrhagic fever in Central Africa that produce severe disease in infected patients. Mortality rates in outbreaks have ranged from 50% for the Sudan species of ebolavirus (SEBOV) to up to 90% for the Zaire species of ebolavirus (EBOV, ZEBOV) (Sanchez et al., Filoviridae: Marburg and Ebola Viruses, in *Fields Virology* (eds. Knipe, D. M. & Howley, P. M.) 1409-1448 (Lippincott Williams & Wilkins, Philadelphia)). An outbreak late in 2007 caused by an apparently new species of ebolavirus in Uganda resulted in a fatality rate of about 25% (Towner et al., *PLoS Pathog.*, 4:e1000212 (2008)). ZEBOV has also decimated populations of wild apes in this same region of Africa (Walsh et al., *Nature*, 422:611-614 (2003)).

Prevention and treatment of filovirus infections, including ebolaviruses (i.e. EBOV) presents many challenges. In fact, there are no vaccines or post exposure treatment modalities available for preventing or managing EBOV infections. Patients instead receive supportive therapy, i.e., electrolyte and fluid balancing, oxygen, blood pressure maintenance, and treatment for any secondary infections.

In view of the importance of novel therapeutics for treating filoviridae infections, new efficient methods of producing ribosides, riboside phosphates and prodrugs are needed.

SUMMARY OF THE INVENTION

In some embodiments, the present invention provides a method of preparing a compound of Formula V:

Formula (V)

The method of making the compound of Formula V includes forming a reaction mixture having a coupling agent, a halo-silane, a compound of Formula VI:

Formula (VI)

and a compound of Formula VII:

Formula (VII)

under conditions suitable to prepare the compound of Formula V, wherein each PG is independently a hydroxy protecting group, alternatively, two PG groups on adjacent carbons can be combined to form a —$C(R^{19})_2$— group, $R^{10}$ is H or a silyl group, and $R^{19}$ is H, $C_1$-$C_8$ alkyl, phenyl or substituted phenyl.

In some embodiments, the present invention provides a method of preparing a compound of Formula V-a or V-b:

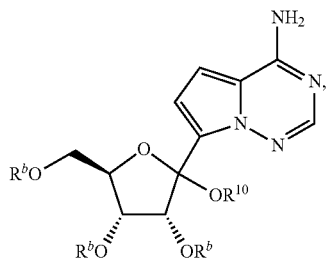
Formula (V-a)

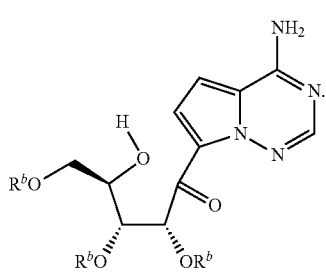
Formula (V-b)

The method of making the compound of Formula V-a or Formula V-b comprises forming a reaction mixture having a deprotonating agent, a silylating agent, a coupling agent, an additive, a compound of Formula VI-a:

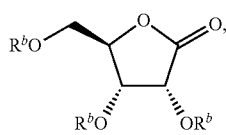
Formula (VI-a)

and a compound of Formula VII:

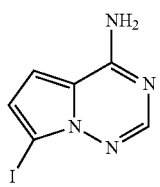
Formula (VII)

under conditions suitable to prepare the compound of Formula V-a or Formula V-b, wherein each $R^b$ is independently a hydroxy protecting group, alternatively, two $R^b$ groups on adjacent carbons can be combined to form a —$C(R^{19})_2$— group, $R^{10}$ is H or a silyl group, and $R^{19}$ is H, $C_1$-$C_8$ alkyl, phenyl or substituted phenyl.

In some embodiments, the present invention provides a method of preparing a compound of Formula XI:

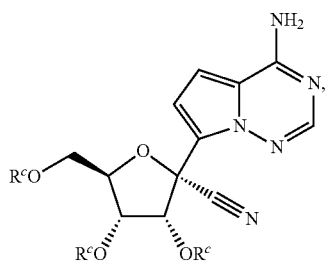
Formula (XI)

wherein $R^c$ is H or a hydroxy protecting group, or two $R^c$ on adjacent carbons can be combined to form a —$C(R^{19})_2$— group, and $R^{19}$ is H or $C_1$-$C_8$ alkyl.

In some embodiments, the present invention provides a method of preparing a compound of Formula XI-a:

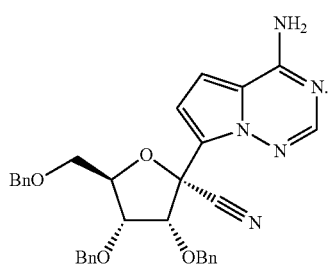
Formula (XI-a)

wherein the method comprises forming a reaction mixture having a cyanating agent, a Lewis Acid, a Broenstedt acid, a solvent, and the compound of Formula V or V-b:

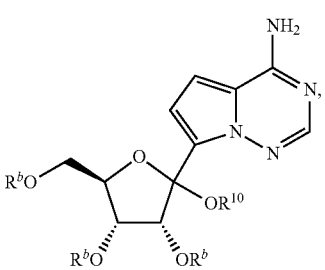
Formula (V-a)

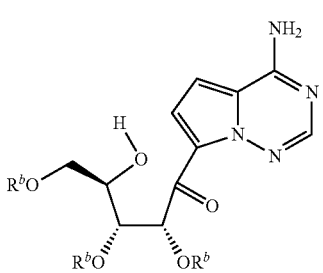
Formula (V-b)

under conditions suitable to prepare the compound of Formula XI, wherein $R^b$ is independently a hydroxy protecting group, alternatively, two $R^b$ groups on adjacent carbons can be combined to form a —$C(R^{19})_2$ group, $R^{10}$ is H or a silyl group, and $R^{19}$ is H, $C_1$-$C_8$ alkyl, phenyl or substituted phenyl.

In some embodiments, the present invention provides a method of preparing a compound of Formula XI-b:

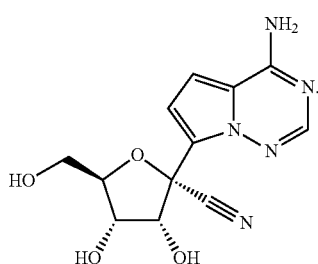

Formula (XI-b)

wherein the method comprises forming a reaction mixture having a Lewis Acid, a base, a solvent, a filtering agent, and the compound of Formula XI-a

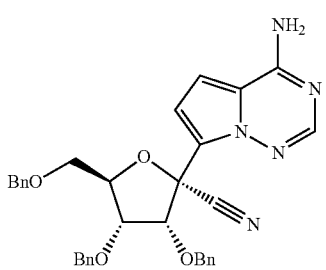

Formula (XI-a)

under conditions suitable to prepare the compound of Formula XI-b.

In some embodiments, the present invention provides a method of preparing a compound of Formula XI-c:

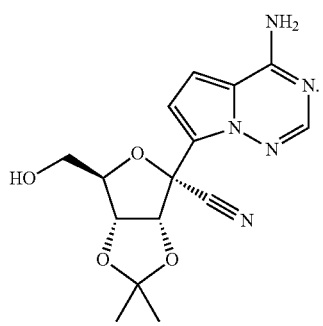

Formula (XI-c)

wherein the method comprises forming a reaction mixture having a solvent, a reagent, and the compound of Formula XI-b

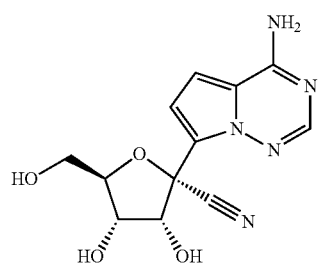

Formula (XI-b)

under conditions suitable to prepare the compound of Formula XI-c.

In some embodiments, the present invention provides a method of preparing a compound of Formula VIII:

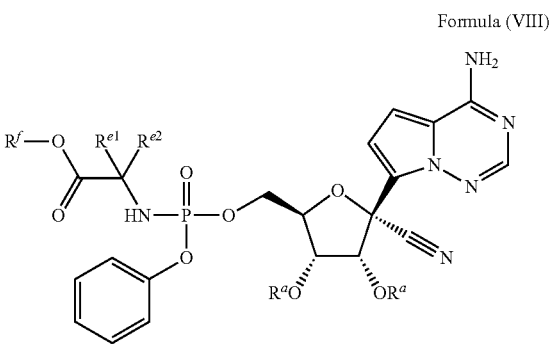

Formula (VIII)

wherein the method includes forming a reaction mixture including a coupling agent, a non-nucleophilic base, a compound of Formula IX:

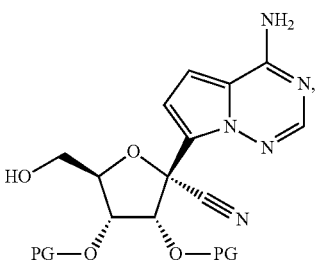

Formula (IX)

and a compound of Formula X:

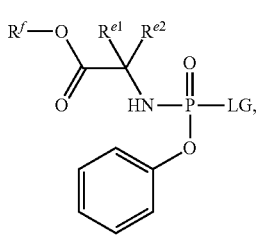

Formula (X)

under conditions suitable to form the compound of Formula VIII, wherein each $R^a$ is H or PG, each PG group is a hydroxy protecting group, or both PG groups are combined to form —$C(R^{19})_2$—, $R^{e1}$ and $R^{e2}$ are each independently H, $C_1$-$C_6$ alkyl or benzyl, $R^f$ is H, $C_1$-$C_8$ alkyl, benzyl, $C_3$-$C_6$ cycloalkyl, or —$CH_2$—$C_3$-$C_6$ cycloalkyl, $R^{19}$ is H, $C_1$-$C_8$ alkyl, phenyl or substituted phenyl, and LG is a leaving group.

In some embodiments, the present invention provides a method of preparing a compound of Formula VIII:

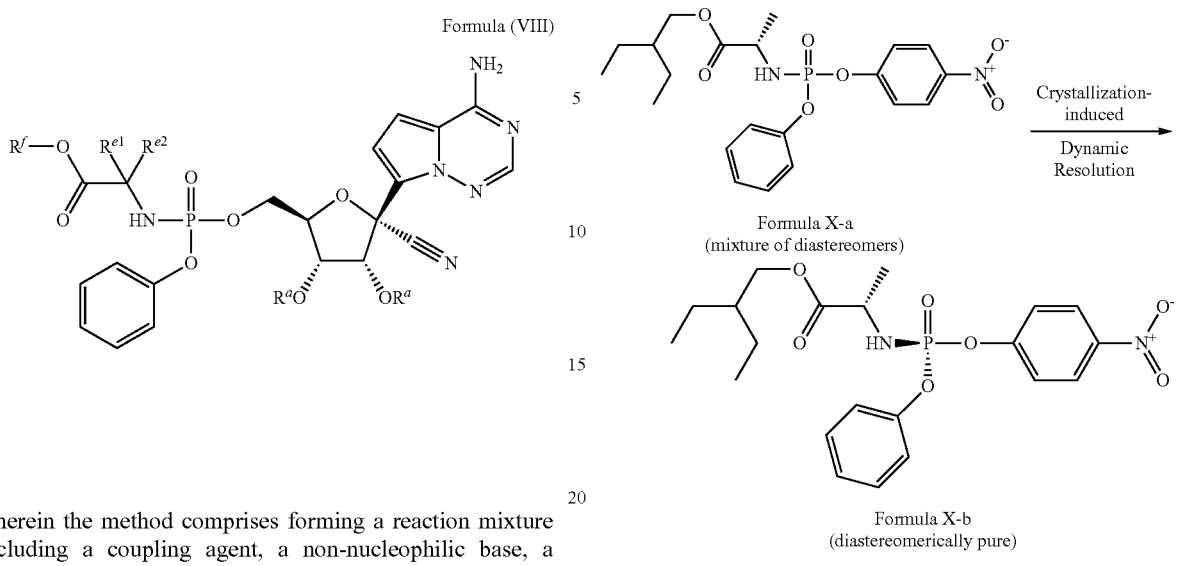

Formula (VIII)

wherein the method comprises forming a reaction mixture including a coupling agent, a non-nucleophilic base, a compound of Formula IX-a:

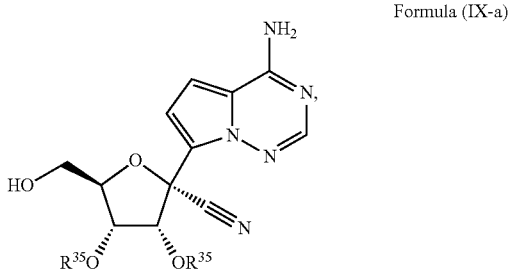

Formula (IX-a)

and a compound of Formula X:

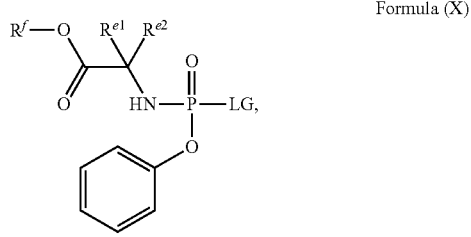

Formula (X)

under conditions suitable to form the compound of Formula VIII, wherein $R^a$ is independently H or a hydroxy protecting group, or two $R^a$ on adjacent carbons can be combined to form a $-C(R^{19})_2-$ group, $R^{35}$ is independently H or a hydroxy protecting group, or two $R^{35}$ on adjacent carbons can be combined to form a $-C(R^{19})_2-$ group, $R^{19}$ is H or $C_1$-$C_8$ alkyl, $R^{e1}$ and $R^{e2}$ are each independently H, $C_1$-$C_6$ alkyl or benzyl, $R^f$ is H, $C_1$-$C_8$ alkyl, benzyl, $C_3$-$C_6$ cycloalkyl, or $-CH_2-C_3$-$C_6$ cycloalkyl, $R^{19}$ is H, $C_1$-$C_8$ alkyl, phenyl or substituted phenyl, and LG is a leaving group.

In one embodiment, there is provided a method for the crystallization-induced dynamic resolution of (2S)-2-ethylbutyl 2-(((4-nitrophenoxy)(phenoxy)phosphoryl)amino) propanoate (Formula X-a):

to provide (Formula X-b).

DETAILED DESCRIPTION OF THE INVENTION

I. Definitions

Unless stated otherwise, the following terms and phrases as used herein are intended to have the following meanings:

When trade names are used herein, applicants intend to independently include the trade name product and the active pharmaceutical ingredient(s) of the trade name product.

As used herein, "a compound of the invention" or "a compound of Formula V" means a compound of Formula V or a pharmaceutically acceptable salt or cocrystal, thereof. In some embodiments, "a compound of the invention" or "a compound of Formula V" means a compound of Formula V or a pharmaceutically acceptable salt, thereof. Similarly, with respect to isolatable intermediates, the phrase "a compound of Formula (number)" means a compound of that formula and pharmaceutically acceptable salts or cocrystals, thereof. In some embodiments, with respect to isolatable intermediates, the phrase "a compound of Formula (number)" means a compound of that formula and pharmaceutically acceptable salts, thereof "Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —CF$_3$, —CHF$_2$, —CFH$_2$, —CH$_2$CF$_3$, and the like.

"Alkenyl" is a hydrocarbon containing normal, secondary, tertiary or cyclic carbon atoms with at least one site of unsaturation, i.e. a carbon-carbon, sp$^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^3$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like. Further typical aryl groups include, but are not limited to, phenyl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. The term "substituted phenyl" means phenyl, in which one or more hydrogen atoms are each independently replaced with a non-hydrogen substituent. Typical substituents include, but are not limited to, —X, —$R^b$, —$O^-$, =O, —$OR^b$, —$SR^b$, —$S^-$, —$NR^b_2$, —$N^+R^b_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b_2$, —S(=O)$_2$—, —S(=O)$_2$OH, —S(=O)$_2R^b$, —OS(=O)$_2OR^b$, —S(=O)$_2NR^b_2$, —S(=O)$R^b$, —OP(=O)(O$R^b$)$_2$, —P(=O)(O$R^b$)$_2$, —P(=O)(O$^-$)$_2$, —P(=O)(OH)$_2$, —P(O)(O$R^b$)(O$^-$), —C(=O)$R^b$, —C(=O)X, —C(S)$R^b$, —C(O)O$R^b$, —C(O)O—, —C(S)O$R^b$, —C(O)S$R^b$, —C(S)S$R^b$, —C(O)NR$^b_2$, —C(S)NR$^b_2$, —C(=NR$^b$)NR$^b_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

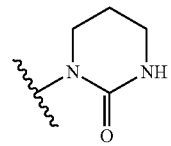 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

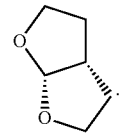

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene- moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene- moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene- moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I-IV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-IV (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

Certain Q and Q$^1$ alternatives are nitrogen oxides such as $^+$N(O)(R) or $^+$N(O)(OR). These nitrogen oxides, as shown here attached to a carbon atom, can also be represented by charge separated groups such as

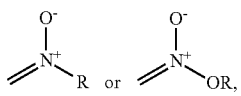

respectively, and are intended to be equivalent to the aforementioned representations for the purposes of describing this invention.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

In some embodiments of the compounds of Formula I-IV, one or more of Z$^1$ or Z$^2$ are independently a radical of a nitrogen-linked naturally occurring α-amino acid ester. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substituent R, particularly those in which R is optionally substituted (C$_1$-C$_8$)alkyl.

The term "purine" or "pyrimidine" base comprises, but is not limited to, adenine, N$^6$-alkylpurines, N$^6$-acylpurines (wherein acyl is C(O)(alkyl, aryl, alkylaryl, or arylalkyl), N$^6$-benzylpurine, N$^6$-halopurine, N$^6$-vinylpurine, N$^6$-acetylenic purine, N$^6$-acyl purine, N$^6$-hydroxyalkyl purine, N$^6$-allylaminopurine, N$^6$-thioallyl purine, N$^2$-alkylpurines, N$^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-5-iodopyrimidine, C$^6$-iodo-pyrimidine, C$^5$—Br-vinyl pyrimidine, C$^6$—Br-vinyl pyrimidine, C$^5$-nitropyrimidine, C$^5$-amino-pyrimidine, N$^2$-alkylpurines, N$^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. The purine and pyrimidine bases are linked to the ribose sugar, or analog thereof, through a nitrogen atom of the base. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

Unless otherwise specified, the carbon atoms of the compounds of Formula I-IV are intended to have a valence of four. In some chemical structure representations where carbon atoms do not have a sufficient number of variables attached to produce a valence of four, the remaining carbon substituents needed to provide a valence of four should be assumed to be hydrogen. For example,

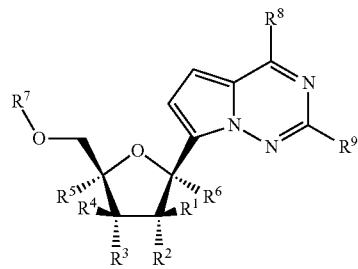

has the same meaning as

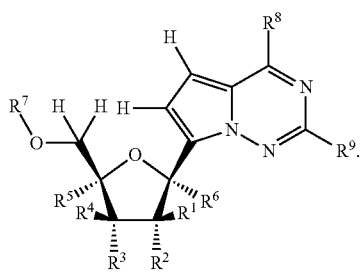

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. See also *Protective Groups in Organic Chemistry*, Peter G. M. Wuts and Theodora W. Greene, 4th Ed., 2006. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive. "Hydroxy protecting groups" refers to those protecting groups useful for protecting hydroxy groups (—OH).

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-IV may have a chiral phosphorus atom when $R^7$ is

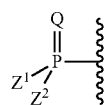

and $Z^1$ and $Z^2$ are different. When at least one of either $Z^1$ or $Z^2$ also has a chiral center, for example with $Z^1$ or $Z^2$ is a nitrogen-linked, chiral, naturally occurring α-amino acid ester, then the compound of Formula I-IV will exists as diastereomers because there are two centers of chirality in the molecule. All such diastereomers and their uses described herein are encompassed by the instant invention. Mixtures of diastereomers may be separate under high resolution analytical procedures such as electrophoresis, crystallization and/or chromatography. Diastereomers may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula I-IV present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I-IV, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Coupling agent" refers to an agent capable of coupling two disparate compounds. Coupling agents can be catalytic or stoichiometric. For example, the coupling agents can be a lithium based coupling agent or a magnesium based coupling agent such as a Grignard reagent.

Exemplary coupling agents include, but are not limited to, n-BuLi, $MgCl_2$, iPrMgCl, tBuMgCl, PhMgCl or combinations thereof.

"Silane" refers to a silicon containing group having the formula $SiR_4$, where each R group can be alkyl, alkenyl, cycloalkyl, phenyl, or other silicon containing groups. When the silane is linked to another compound, the silane is referred to as a "silyl" and has the formula —$SiR_3$.

"Halo-silane" refers to a silane having at least one halogen group linked to the silicon atom. Representative halo-silanes have the formula Halo-$SiR_3$, where each R group can be alkyl, alkenyl, cycloalkyl, phenyl, or other silicon containing groups. Specific halo-silanes include Cl—Si(CH₃)₃, and Cl—Si(CH₃)₂CH₂CH₂Si(CH₃)₂—Cl.

"Non-nucleophilic base" refers to an electron donor, a Lewis base, such as nitrogen bases including triethylamine, diisopropylethyl amine, N,N-diethylaniline, pyridine, 2,6-lutidine, 2,4,6-collidine, 4-dimethylaminopyridine, and quinuclidine.

"Leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, mesylate, tosylate, triflate, 4-nitrobenzenesulfonate, 4-chlorobenzenesulfonate, 4-nitrophenoxy, pentafluorophenoxy, etc. One of skill in the art will recognize other leaving groups useful in the present invention.

"Deprotection agent" refers to any agent capable of removing a protecting group. The deprotection agent will depend on the type of protecting group used. Representative deprotection agents are known in the art and can be found in *Protective Groups in Organic Chemistry*, Peter G. M. Wuts and Theodora W. Greene, 4th Ed., 2006.

II. Preparation of Compounds

The compounds of the present invention can be prepared by a variety of means. For example, protected nucleosides of Formula V can be prepared by reaction of a protected lactone with an iodo-substituted base under suitable coupling conditions. The nucleosides can then be modified with a prodrug moiety by reaction of a partially protected nucleoside with a suitable prodrug moiety, following be removal of the protecting groups, to afford the compounds of the present invention.

A. Preparation of Nucleosides Via Iodo-Base

In one embodiment, the present invention provides a method of preparing a compound of Formula V:

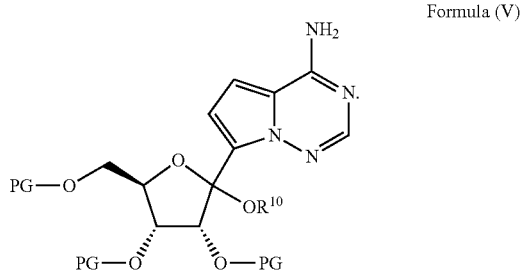

Formula (V)

The method of making the compound of Formula V includes forming a reaction mixture having a coupling agent, a halo-silane, a compound of Formula VI:

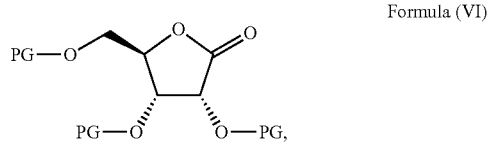

Formula (VI)

and a compound of Formula VII:

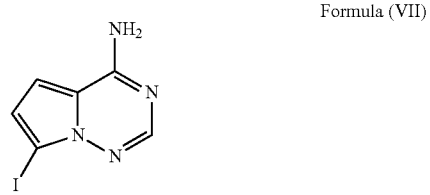 [SMILES: Nc1ncnn2c(I)ccc12]

Formula (VII)

under conditions suitable to prepare the compound of Formula V, wherein each PG is independently a hydroxy protecting group, alternatively, two PG groups on adjacent carbons can be combined to form a —C($R^{19}$)₂— group, $R^{10}$ is H or a silyl group, and $R^{19}$ is H, $C_1$-$C_8$ alkyl, phenyl or substituted phenyl.

Any suitable coupling agent can be used in the method of making the compound of Formula V. The coupling agent can be a lithium coupling agent, a sodium coupling agent, a magnesium coupling agent, or others. For example, the coupling agent can be a deprotonating agent such as n-butyl lithium (n-BuLi), sodium hydride (NaH), lithium aluminum hydride (LAH or LiAlH₄), and others. The coupling agent can also be a magnesium based coupling agent such as, but not limited to, MgCl₂, iPrMgCl, tBuMgCl, PhMgCl, or combinations thereof. In some embodiments, the coupling agent can be a lithium coupling agent or a magnesium coupling agent. In some embodiments, the coupling agent can be n-BuLi, MgCl₂, iPrMgCl, tBuMgCl, PhMgCl, or combinations thereof. In some embodiments, the coupling agent can be n-BuLi. In some embodiments, the coupling agent can be PhMgCl and iPrMgCl.

The coupling agent can be present in any suitable amount. For example, the coupling agent can be present in an amount of at least 1.0 eq. (mol/mol) to the compound of Formula V, such as about 1.0, 2, 3, 4, 5, 6, 7, 8, 9, or about 10.0 eq. (mol/mol). The coupling agent can also be present in an amount of from about 1.0 to about 10.0 eq. (mol/mol) to the compound of Formula V, such as of from about 1.0 to about 5.0 eq. (mol/mol), or of from about 1.0 to about 2.0 eq. (mol/mol). In some embodiments, the coupling agent can be present in an amount of from about 1.0 to about 5.0 eq. (mol/mol) to the compound of Formula V. In some embodiments, the coupling agent can be present in an amount of from about 1.0 to about 2.0 eq. (mol/mol) to the compound of Formula V.

Any suitable halo-silane can be used in the method of making the compound of Formula V. For example, the halo-silane can be a fluoro-silane, a chloro-silane, a bromo-silane or an iodo-silane. The silane portion can have any suitable substituents, such as alkyl, alkenyl, alkynyl, cycloalkyl, or phenyl. Exemplary halo-silanes include, but are not limited to, Cl—Si(CH₃)₃, or Cl—Si(CH₃)₂CH₂CH₂Si(CH₃)₂—Cl. In some embodiments, the halo-silane can be a chloro-silane. In some embodiments, the halo-silane can be Cl—Si(CH₃)₃, or Cl—Si(CH₃)₂CH₂CH₂Si(CH₃)₂—Cl. In some embodiments, the halo-silane can be TMSCl.

The silyl group of $R^{10}$ can be any suitable group, but can depend on the choice of the halo-silane. For example, when the halo-silane is TMSCl, the silyl group can be trimethylsilyl.

The halo-silane can be present in any suitable amount. For example, the halo-silane can be present in an amount of at least 1.0 eq. (mol/mol) to the compound of Formula V, such as about 1.0, 2, 3, 4, 5, 6, 7, 8, 9, or about 10.0 eq. (mol/mol). The halo-silane can also be present in an amount of from about 1.0 to about 10.0 eq. (mol/mol) to the compound of Formula V, such as of from about 1.0 to about 5.0 eq. (mol/mol), or of from about 1.0 to about 2.0 eq. (mol/mol). In some embodiments, the halo-silane can be present in an amount of from about 1.0 to about 5.0 eq. (mol/mol) to the compound of Formula V. In some embodiments, the halo-silane can be present in an amount of from about 1.0 to about 2.0 eq. (mol/mol) to the compound of Formula V.

The hydroxy protecting group can be any protecting group suitable for a hydroxy functional group. Representative hydroxy protecting groups include, but are not limited to, silanes such as trimethyl silane (TMS), t-butyl dimethyl silane (TBDMS), or t-butyl diphenyl silane (TBDPS), ethers such as methyl-methoxy (MOM), tetrahydropyran (THP), t-butyl, allyl, or benzyl, and esters such as acetyl, pivaloyl, or benzoyl. In some embodiments, the hydroxy protecting group can be trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be benzyl.

Hydroxy groups on adjacent carbons, referred to as 1,2-hydroxy groups, can form a cyclic protecting group called an acetonide by reaction with a ketone of di-ether. Exemplary acetonides include, but are not limited to acetonide and benzylidene acetal. In some embodiments, the hydroxy protecting groups of hydroxy groups on adjacent carbons can be combined to form acetonide.

When the $R^{19}$ group is $C_1$-$C_8$ alkyl, $R^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^{19}$ group can be methyl.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran, or combinations thereof. In some embodiments, the solvent can be tetrahydrofuran.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula V in any suitable yield. For example, the compound of Formula V can be prepared in a yield of at least about 50%, 55, 60, 65, 70, 75, 80, 85, 90 or at least about 95%.

The method of the present invention can provide the compound of Formula V in any suitable purity. For example, the compound of Formula V can be prepared in a purity of at least about 90, 95, 96, 97, 98 or at least about 99%. In some embodiments, the compound of Formula V can be prepared in at least 95% purity. In some embodiments, the compound of Formula V can be prepared in at least 98% purity. In some embodiments, the compound of Formula V can be prepared in at least 99% purity.

In some embodiments, the method including preparing the compound of Formula V:

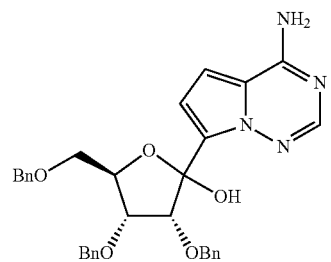 [SMILES: Nc1ncnn2c(C3(O)O[C@H](COCc4ccccc4)[C@@H](OCc4ccccc4)[C@H]3OCc3ccccc3)ccc12]

wherein the method includes forming the reaction mixture having TMSCl, PhMgCl, iPrMgCl, the compound of Formula VI:

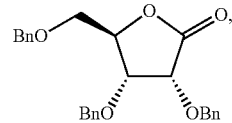 [SMILES: O=C1O[C@H](COCc2ccccc2)[C@@H](OCc2ccccc2)[C@H]1OCc1ccccc1]

and the compound of Formula VII:

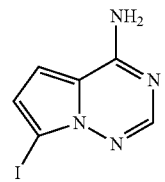

under conditions suitable to prepare the compound of Formula V.

In some embodiments, the present invention provides the compound:

In some embodiments, the present invention provides a method of preparing a compound of Formula V-a or V-b:

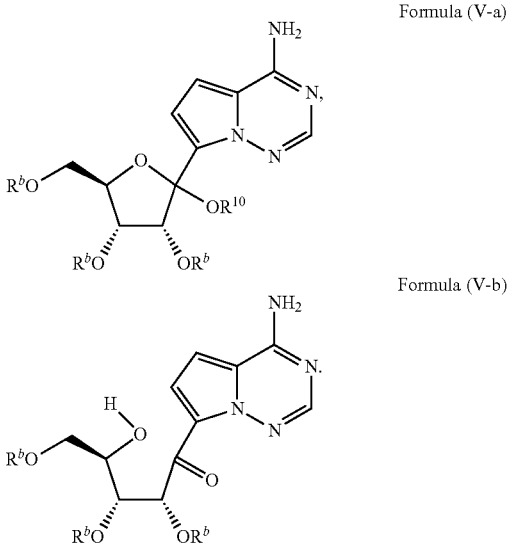

Formula (V-a)

Formula (V-b)

The method of making the compound of Formula V-a or Formula V-b comprises forming a reaction mixture having a deprotonating agent, a silylating agent, a coupling agent, an additive, a compound of Formula VI-a:

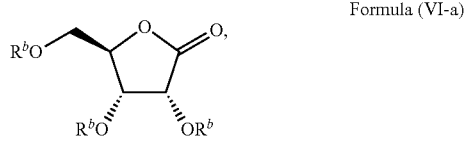

Formula (VI-a)

and a compound of Formula VII:

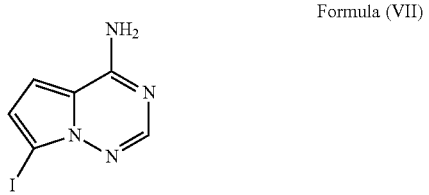 [SMILES: Nc1ncnn2c(I)ccc12]

Formula (VII)

under conditions suitable to prepare the compound of Formula V-a or Formula V-b, wherein each $R^b$ is independently a hydroxy protecting group, alternatively, two $R^b$ groups on adjacent carbons can be combined to form a —$C(R^{19})_2$— group, $R^{10}$ is H or a silyl group, and $R^{19}$ is H, $C_1$-$C_8$ alkyl, phenyl or substituted phenyl.

Any suitable deprotonating agent can be used in the method of making the compound of Formula V-a or Formula V-b. The deprotonating agent can be a sodium deprotonating agent, a magnesium based deprotonating agent, lithium based deprotonating agent, potassium based deprotonating agent, or others. For example, the deprotonating agent can be sodium hydride (NaH), isopropylmagnesium chloride (iPrMgCl), tert-butylmagnesium chloride (tBuMgCl), phenylmagnesium chloride (PhMgCl), phenylmagnesium bromide (PhMgBr), butyllithium (BuLi), methyllithium (MeLi), methylmagnesium chloride (MeMgCl), methylmagnesium bromide (MeMgBr), tert-butyllithium (tBuLi), isopropyllithium (iPrLi), phenyllithium (PhLi), lithium hydride (LiH), potassium hydride (KH), ethyllithium (EtLi), ethylmagnesium bromide (EtMgBr), ethylmagnesium chloride (EtMgCl), propyllithium (PrLi), propylmagnesium bromide (PrMgBr), propylmagnesium chloride (PrMgCl), cyclohexanelithium (cyHexLi), cyclohexanemagnesium bromide (cyHexMgBr), cyclohexanemagnesium chloride (cyHexMgCl), or combinations thereof. In some embodiments, the deprotonating agent can be PhMgCl.

The deprotonating agent can be present in any suitable amount. For example, the deprotonating agent can be present in an amount of at least 0.1 eq. (mol/mol) to the compound of Formula VII, such as about 0.1, 0.5, 1.0, 2, 3, 4, 5, 6, 7, 8, 9, or about 10.0 eq. (mol/mol). The deprotonating agent can also be present in an amount of from about 0.1 to about 10.0 eq. (mol/mol) to the compound of Formula VII, such as of from about 0.1 to about 3.0 eq. (mol/mol), or of from about 1.0 to about 2.0 eq. (mol/mol). In some embodiments, the deprotonating agent can be present in an amount from about 0.1 to 1.0 eq. (mol/mol) to the compound of Formula VII. In some embodiments, the deprotonating agent can be present in an amount of from about 1.0 to about 2.0 eq. (mol/mol) to the compound of Formula VII.

Any suitable silylating agent can be used in the method of making the compound of Formula V-a or Formula V-b. For example, the silylating agent can be a fluoro-silane, a chloro-silane, a bromo-silane or an iodo-silane. For example, the silylating agent can be a tri-substituted silyl chloride, a tri-substituted silyl bromide, a tri-substituted silyl iodide, or a tri-substituted silyl fluoride. The silyl portion can have any suitable substituents, such as alkyl, alkenyl, alkynyl, cycloalkyl, or phenyl. Exemplary silylating agents include, but are not limited to, Cl—Si(CH$_3$)$_3$, Cl—Si(CH$_3$)$_2$CH$_2$CH$_2$Si(CH$_3$)$_2$—Cl, or tert-butyldiphenylsilyl (TBDPS). In some embodiments, the silylating agent can be a chloro-silane. In some embodiments, the silylating agent can be Cl—Si(CH$_3$)$_3$, or Cl—Si(CH$_3$)$_2$CH$_2$CH$_2$Si(CH$_3$)$_2$—Cl. In some embodiments, the silylating agent can be TMSCl.

The silyl group of $R^{10}$ can be any suitable group, but can depend on the choice of the silylating agent. For example, when the silylating agent is TMSCl, the silyl group can be trimethylsilyl.

The silylating agent can be present in any suitable amount. For example, the silylating agent can be present in an amount of at least 0.0 eq. (mol/mol) to the compound of Formula VII, such as about 0.0, 0.1, 0.5, 1.0, 2, 3, 4, 5, 6, 7, 8, 9, or about 10.0 eq. (mol/mol). The silylating agent can also be present in an amount of from about 0.0 to about 10.0 eq. (mol/mol) to the compound of Formula VII, such as of from about 0.0 to about 3.0 eq. (mol/mol), or of from about 1.0 to about 2.0 eq. (mol/mol). In some embodiments, the silylating agent can be present in an amount from about 0.0 to 1.0 eq. (mol/mol) to the compound of Formula VII. In some embodiments, the silylating agent can be present in an amount of from about 1.0 to about 2.0 eq. (mol/mol) to the compound of Formula VII.

Any suitable coupling agent can be used in the method of making the compound of Formula V-a or Formula V-b. The coupling agent can be a lithium coupling agent, a magnesium based deprotonating agent, or others. For example, the coupling agent can be n-butyllithium (nBuLi), magnesium chloride (MgCl$_2$), isopropylmagnesium chloride (iPrMgCl), isopropylmagnesium chloride-lithium chloride (iPrMgCl—LiCl), tert-butylmagnesium chloride (tBuMgCl), phenylmagnesium chloride (PhMgCl), methyllithium (MeLi), methylmagnesium chloride (MeMgCl), methylmagnesium bromide (MeMgBr), tert-butyllithium (tBuLi), isopropyllithium (iPrLi), phenyllithium (PhLi), lithium hydride (LiH), potassium hydride (KH), sodium hydride (NaH), ethyllithium (EtLi), ethylmagnesium bromide (EtMgBr), ethylmagnesium chloride (EtMgCl), propyllithium (PrLi), propylmagnesium bromide (PrMgBr), propylmagnesium chloride (PrMgCl), cyclohexanelithium (cyHexLi), cyclohexanemagnesium bromide (cyHexMgBr), cyclohexanemagnesium chloride (cyHexMgCl), or combinations thereof. In some embodiments, the coupling agent can be iPrMgCl.

The coupling agent can be present in any suitable amount. For example, the coupling agent can be present in an amount of at least 0.1 eq. (mol/mol) to the compound of Formula VII, such as about 0.1, 0.5, 1.0, 2, 3, 4, 5, 6, 7, 8, 9, or about 10.0 eq. (mol/mol). The coupling agent can also be present in an amount of from about 0.1 to about 10.0 eq. (mol/mol) to the compound of Formula VII, such as of from about 0.1 to about 3.0 eq. (mol/mol), or of from about 1.0 to about 2.0 eq. (mol/mol). In some embodiments, the coupling agent can be present in an amount from about 0.1 to 1.0 eq. (mol/mol) to the compound of Formula VII. In some embodiments, the coupling agent can be present in an amount of from about 1.0 to about 2.0 eq. (mol/mol) to the compound of Formula VII.

Any suitable additive can be used in the method of making the compound of Formula V-a of Formula V-b. In some embodiments, the additive is a Lewis Acid. In some embodiments, the additive can be $BF_3$—$OEt_2$, $SmOTf)_3$, $Sc(OTf)_3$, $FeCl_3$, LiCl, LiBr, $TiCl(OiPr)_3$, $ScCl_3$, $Bu_4NBr$+ $LaCl_3$-2LiCl, $nLaCl_3$+mLiCl, wherein m is 0.5 to 50, n is 1 to 100, $LaCl_3$+2LiCl, $Sm(OTf)_3$+LiCl, $SmCl_3$, Bis[2-(N,N-dimethylamino)ethyl]ether, TMEDA, $NdCl_3$, $NdCl_3$+CsCl, $nNdCl_3$+mLiCl, wherein m is 0.5 to 50, n is 1 to 100, $NdCl_3$+2LiCl, $NdCl_3$+LiBr, $NdCl_3$+LiI, $NdBr_3$, $NdBr_3$+ CsCl, $nNdBr_3$+mLiCl, wherein m is 0.5 to 50, n is 1 to 100, $NdBr_3$+2LiCl, $NdBr_3$+LiBr, $NdBr_3$+LiI, $Nd(OTf)_3$, $CeCl_3$, $CeCl_3$+CsCl, $nCeCl_3$+mLiCl, wherein m is 0.5 to 50, n is 1 to 100, $CeCl_3$+2LiCl, $CeCl_3$+LiBr, $CeCl_3$+LiI, $CeBr_3$, $Ce(OTf)_3$, $YCl_3$, $YCl_3$+CsCl, $nYCl_3$+mLiCl, wherein m is 0.5 to 50, n is 1 to 100, $YCl_3$+2LiCl, $YCl_3$+LiBr, $YCl_3$+LiI, $YBr_3$, $YBr_3$+CsCl, $nYBr_3$+mLiCl, wherein m is 0.5 to 50, n is 1 to 100, $YBr_3$+2LiCl, $YBr_3$+LiBr, $YBr_3$+LiI, $Y(OTf)_3$, $LaCl_3$, $La(OTf)_3$, $MgCl_2$, $TiCl_4$, $SnCl_4$, $AlCl_3$, $Bu_4NCl$, Diethyleneglycol diethylether (DGDE), DGDE+$Bu_4NCl$, DGDE+$Bu_4NBr$, DGDE+$Bu_4NI$, $CaCl_2$, $CaBr_2$, $CaI_2$, $Ca(OTf)_2$, $YCl_3$, $YCl_3$-2LiCl, $YCl_3$—LiCl or a combination thereof. In some embodiments, the additive can be LiCl, $Ca(OTf)_2$, $CaCl_2$ and $MgCl_2$, $CeCl_3$, $LaCl_3$, or a combination thereof. In some embodiments, the additive can be $YCl_3$, $CeCl_3$, $NdCl_3$, $LaCl_3$, or a combination thereof.

The additive can be present in any suitable amount. For example, the additive can be present in an amount of at least 0.1 eq. (mol/mol) to the compound of Formula VII, such as about 0.1, 0.5, 1.0, 2, 3, 4, 5, 6, 7, 8, 9, or about 10.0 eq. (mol/mol). The additive can also be present in an amount of from about 0.1 to about 10.0 eq. (mol/mol) to the compound of Formula VII, such as of from about 0.1 to about 3.0 eq. (mol/mol), or of from about 1.0 to about 2.0 eq. (mol/mol). In some embodiments, the additive can be present in an amount from about 0.1 to 1.0 eq. (mol/mol) to the compound of Formula VII. In some embodiments, the additive can be present in an amount of from about 1.0 to about 2.0 eq. (mol/mol) to the compound of Formula VII.

In some embodiments, the additive is $LaCl_3$-2LiCl and is present in an amount of at least 0.1 eq. (mol/mol) to the compound of Formula VII, such as about 0, 0.1, 0.3, 0.5, 1.0, 2, or about 2.0 eq. (mol/mol). In some embodiments, the additive is $LaCl_3$-2LiCl and is present in an amount of from about 0 to about 2.0 eq. (mol/mol) to the compound of Formula VII, such as of from about 0 to about 0.3 eq. (mol/mol), or of from about 0 to about 0.5 eq. (mol/mol). In some embodiments, the additive is $LaCl_3$-2LiCl and is present in an amount from about 0 to 0.5 eq. (mol/mol) to the compound of Formula VII. In some embodiments, the additive is $LaCl_3$-2LiCl and is present in an amount of about 0.5 eq. (mol/mol) to the compound of Formula VII.

In some embodiments, the additive is $CeCl_3$ and is present in an amount of at least 0.1 eq. (mol/mol) to the compound of Formula VII, such as about 0, 0.1, 0.3, 0.5, 1.0, 2, or about 2.0 eq. (mol/mol). In some embodiments, the additive is $CeCl_3$ and is present in an amount of from about 0 to about 2.0 eq. (mol/mol) to the compound of Formula VII, such as of from about 0 to about 0.3 eq. (mol/mol), or of from about 0 to about 0.5 eq. (mol/mol). In some embodiments, the additive is $CeCl_3$ and is present in an amount from about 0 to 0.5 eq. (mol/mol) to the compound of Formula VII. In some embodiments, the additive is $CeCl_3$ and is present in an amount of about 0.5 eq. (mol/mol) to the compound of Formula VII.

In some embodiments, the additive is $NdCl_3$ and is present in an amount of at least 0.1 eq. (mol/mol) to the compound of Formula VII, such as about 0, 0.1, 0.3, 0.5, 1.0, 2, or about 2.0 eq. (mol/mol). In some embodiments, the additive is $NdCl_3$ and is present in an amount of from about 0 to about 2.0 eq. (mol/mol) to the compound of Formula VII, such as of from about 0 to about 0.3 eq. (mol/mol), or of from about 0 to about 0.5 eq. (mol/mol). In some embodiments, the additive is $NdCl_3$ and is present in an amount from about 0 to 0.5 eq. (mol/mol) to the compound of Formula VII. In some embodiments, the additive is $NdCl_3$ and is present in an amount of about 0.5 eq. (mol/mol) to the compound of Formula VII.

In some embodiments, the additive is $YCl_3$ and is present in an amount of at least 0.1 eq. (mol/mol) to the compound of Formula VII, such as about 0, 0.1, 0.3, 0.5, 1.0, 2, or about 2.0 eq. (mol/mol). In some embodiments, the additive is $YCl_3$ and is present in an amount of from about 0 to about 2.0 eq. (mol/mol) to the compound of Formula VII, such as of from about 0 to about 0.3 eq. (mol/mol), or of from about 0 to about 0.5 eq. (mol/mol). In some embodiments, the additive is $YCl_3$ and is present in an amount from about 0 to 0.5 eq. (mol/mol) to the compound of Formula VII. In some embodiments, the additive is $YCl_3$ and is present in an amount of about 0.5 eq. (mol/mol) to the compound of Formula VII.

When the $R^{19}$ group is $C_1$-$C_8$ alkyl, $R^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^{19}$ group can be methyl.

When the $R^b$ group is a hydroxy protecting group, $R^b$ can be any example protecting group described in *Protective Groups in Organic Chemistry*, Peter G. M. Wuts and Theodora W. Greene, 4th Ed., 2006. In some embodiments, the $R^b$ group can be benzyl. In some embodiments, the $R^b$ group can be TBS.

The hydroxy protecting group can be any protecting group suitable for a hydroxy functional group. Representative hydroxy protecting groups include, but are not limited to, silanes, ethers, esters, or others. Representative hydroxy protecting groups include, but are not limited to trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be benzyl. In some embodiments, the hydroxy protecting group can be TBS.

Hydroxy groups on adjacent carbons, referred to as 1,2-hydroxy groups, can form a cyclic protecting group called an acetal or a ketal by reaction with an aldehyde, an acetale, aketoneor a ketal. Exemplary acetals and ketals include, but are not limited to a, benzylidene acetal and an acetonide. In some embodiments, the hydroxy protecting groups of hydroxy groups on adjacent carbons can be combined to form acetonide.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, dichloromethane, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran (THF), 2-methyltetrahydrofuran, dibutyl ether, diisopropyl ether, methyl tert-butyl ether, dimethoxyethane, dioxanes (1,4 dioxane), N-methyl pyrrolidinone (NMP), diisopropyl ether, or combinations thereof. In certain embodiments, the solvent can be THF, MeTHF, toluene, THF+dioxane, THF+pyridine, or THF+DCM, or combinations thereof. In some embodiments, the solvent can be THF.

The reaction mixture of the method can be at any suitable temperature. For example, the temperature of the reaction mixture can be from about −78° C. to about 100° C., or from about −50° C. to about 100° C., or from about −25° C. to about 50° C., or from about −10° C. to about 25° C., or from about 0° C. to about 20° C. In some embodiments, the temperature of the reaction mixture can be from about 0° C. to about 20° C. In some embodiments, the temperature of the reaction mixture can be from about −30° C. to about −10° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula V-a or Formula V-b in any suitable yield. For example, the compound of Formula V-a or Formula V-b can be prepared in a yield of at least about 50%, 55, 60, 65, 70, 75, 80, 85, 90 or at least about 95%.

The method of the present invention can provide the compound of Formula V-a or Formula V-b in any suitable purity. For example, the compound of Formula V-a or Formula V-b can be prepared in a purity of at least about 90, 95, 96, 97, 98 or at least about 99%. In some embodiments, the compound of Formula V-a or Formula V-b can be prepared in at least 95% purity. In some embodiments, the compound of Formula V-a or Formula V-b can be prepared in at least 98% purity. In some embodiments, the compound of Formula V-a or Formula V-b can be prepared in at least 99% purity.

In some embodiments, the method comprises preparing the compound of Formula V-a or Formula V-b:

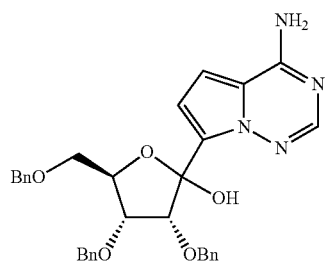

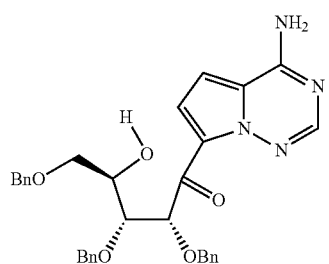

wherein the method comprises forming the reaction mixture having TMSCl, PhMgCl, iPrMgCl, LaCl$_3$-2LiCl the compound of Formula VI:

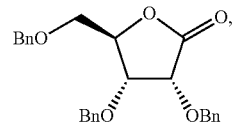

and the compound of Formula VII:

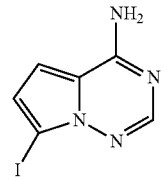

under conditions suitable to prepare the compound of Formula V-a or Formula V-b.

In some embodiments, the method comprises preparing the compound of Formula V-a or Formula V-b:

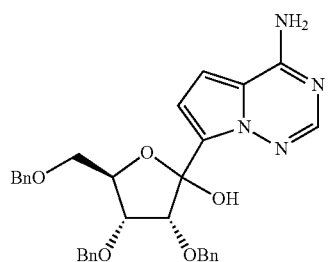

-continued

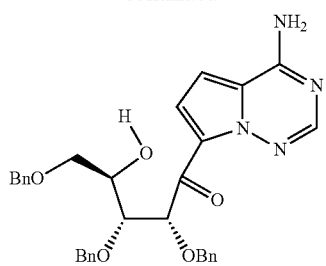

wherein the method comprises forming the reaction mixture having TMSCl, PhMgCl, iPrMgCl, CeCl₃ the compound of Formula VI:

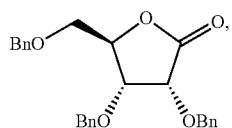 [SMILES: O=C1O[C@H](COCc2ccccc2)[C@@H](OCc2ccccc2)[C@H]1OCc1ccccc1]

and the compound of Formula VII:

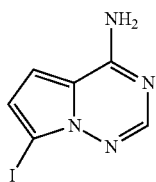 [SMILES: Nc1ncnn2c(I)ccc12]

under conditions suitable to prepare the compound of Formula V-a or Formula V-b.

In some embodiments, the method comprises preparing the compound of Formula V-a or Formula V-b:

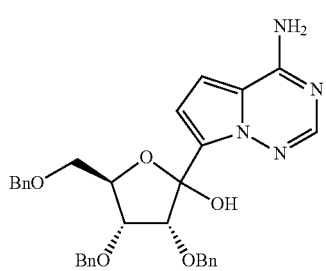

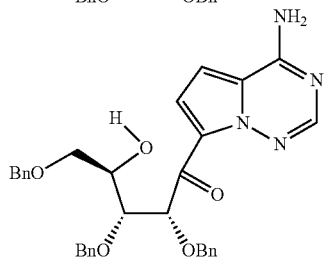

wherein the method comprises forming the reaction mixture having TMSCl, PhMgCl, iPrMgCl, NdCl₃ the compound of Formula VI:

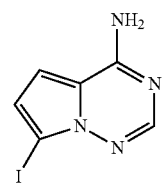

and the compound of Formula VII:

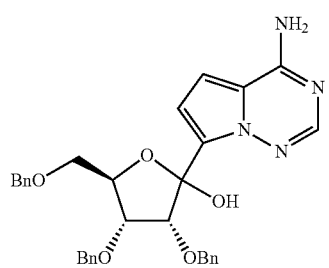

under conditions suitable to prepare the compound of Formula V-a or Formula V-b.

In some embodiments, the method comprises preparing the compound of Formula V-a or Formula V-b:

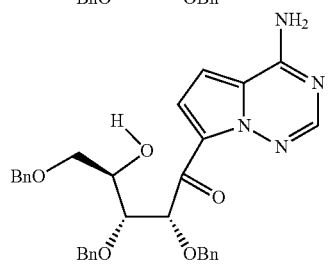

wherein the method comprises forming the reaction mixture having TMSCl, PhMgCl, iPrMgCl, YCl₃ the compound of Formula VI:

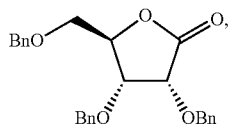 [SMILES: O=C1O[C@H](COCc2ccccc2)[C@@H](OCc2ccccc2)[C@H]1OCc1ccccc1]

and the compound of Formula VII:

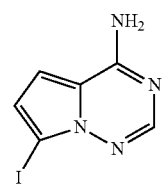 [SMILES: Nc1ncnn2c(I)ccc12]

under conditions suitable to prepare the compound of Formula V-a or Formula V-b.

In some embodiments, the method comprises preparing the compound of Formula V-a:

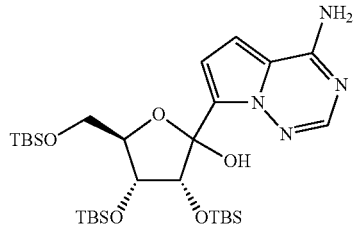 [SMILES: CC(C)(C)[Si](C)(C)OC[C@H]1OC(O)(c2ccc3c(N)ncnn23)[C@H](O[Si](C)(C)C(C)(C)C)[C@@H]1O[Si](C)(C)C(C)(C)C]

wherein the method comprises forming the reaction mixture having TMSCl, PhMgCl, iPrMgCl—LiCl, LaCl$_3$-2LiCl the compound of Formula VI:

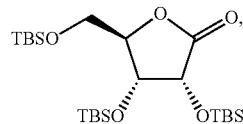 [SMILES: CC(C)(C)[Si](C)(C)OC[C@H]1OC(=O)[C@H](O[Si](C)(C)C(C)(C)C)[C@@H]1O[Si](C)(C)C(C)(C)C]

and the compound of Formula VII:

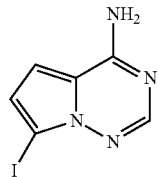 [SMILES: Nc1ncnn2c(I)ccc12]

under conditions suitable to prepare the compound of Formula V-a.

B. Preparation of Cyano Nucleosides

In some embodiments, the present invention provides a method of preparing a compound of Formula XI:

Formula (XI)

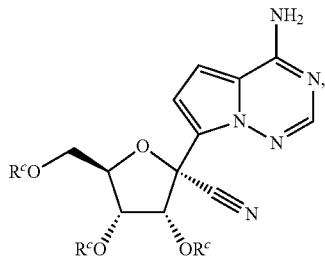

wherein $R^c$ is H or a hydroxy protecting group, or two $R^c$ on adjacent carbons can be combined to form a —C($R^{19}$)$_2$— group, and $R^{19}$ is H or $C_1$-$C_8$ alkyl.

When the $R^{19}$ group is $C_1$-$C_8$ alkyl, $R^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^{19}$ group can be methyl.

When the $R^c$ group is a hydroxy protecting group, the hydroxy protecting group can be any protecting group suitable for a hydroxy functional group. Representative hydroxy protecting groups include, but are not limited to, silanes, ethers, esters, or others. Representative hydroxy protecting groups include, but are not limited to trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be trimethyl silane (TMS), t-butyl dimethyl silane (TBDMS), t-butyl diphenyl silane (TBDPS), methyl-methoxy (MOM), tetrahydropyran (THP), t-butyl, allyl, benzyl, acetyl, pivaloyl, or benzoyl. In some embodiments, the hydroxy protecting group can be benzyl. In some embodiments, the hydroxy protecting group can be TBS Hydroxy groups on adjacent carbons, referred to as 1,2-hydroxy groups, can form a cyclic protecting group called an acetal or a ketal by reaction with an aldehyde, an acetale, aketoneor a ketal. Exemplary acetals and ketals include, but are not limited to a, benzylidene acetal and an acetonide. In some embodiments, the hydroxy protecting groups of hydroxy groups on adjacent carbons can be combined to form acetonide.

In some embodiments, the present invention provides a method of preparing a compound of Formula XI-a:

Formula (XI-a)

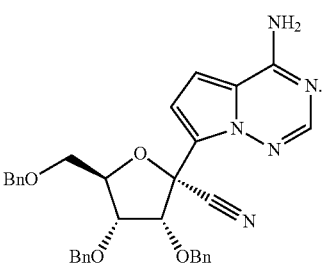

wherein the method comprises forming a reaction mixture having a cyanating agent, a Lewis Acid, a Broenstedt acid, a solvent, and the compound of Formula V-a or V-b:

Formula (V-a)

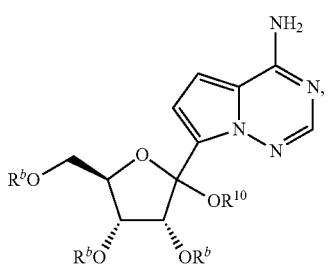

Formula (V-b)

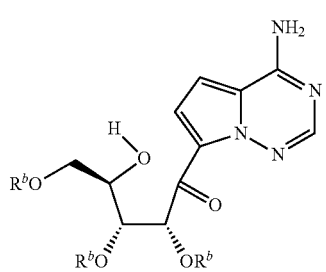

under conditions suitable to prepare the compound of Formula XI-a, wherein $R^b$ is independently a hydroxy protecting group, alternatively, two $R^b$ groups on adjacent carbons can be combined to form a —C($R^{19}$)$_2$ group, $R^{10}$ is H or a silyl group, and $R^{19}$ is H, $C_1$-$C_8$ alkyl, phenyl or substituted phenyl.

Any suitable cyanating agent can be used in the method of making the compound of Formula XI-a. For example, the cyanating agent can be TMSCN, TBSCN, TESCN, HCN, KCN, NaCN, 4-toluenesulfonyl cyanide, CuCN, CuCn*LiCl, LiCN, Zn(CN)$_2$, K4[Fe(CN)$_6$], tetrabutylammonium cyanide, tetrmethylammonium cyanide, tetraethylammonium cyanide, tetrabutylammonium cyanide, (including tetraalkylammonium cyanide with alkyl independently being Me, Et, Pr, iPr, Bu, iBu, tertBu, Pent, Hex), tributyltn cyanide, trimethyltin cyanide, triethyltin cyanide, tripropyltin cyanide, (including trialkyltin cyanide cyanide with alkyl independently being Me, Et, Pr, iPr, Bu, iBu, tertBu, Pent, Hex), 2-hydroxy-2-methylpropanenitrile; or combinations thereof. In some embodiments, the cyanating agent can be TMSCN.

The cyanating agent can be present in any suitable amount. For example, the cyanating agent can be present in an amount of at least 0.1 eq. (mol/mol) to the compound of Formula V-a or Formula V-b, such as about 0.1, 0.5, 1.0, 2, 3, 4, 5, 6, 7, 8, 9, or about 10.0 eq. (mol/mol). The cyanating agent can also be present in an amount of from about 0.1 to about 10.0 eq. (mol/mol) to the compound of Formula V-a or Formula V-b, such as of from about 0.1 to about 3.0 eq. (mol/mol), or of from about 1.0 to about 2.0 eq. (mol/mol). In some embodiments, the cyanating agent can be present in an amount from about 0.1 to 1.0 eq. (mol/mol) to the compound of Formula V-a or Formula V-b. In some embodiments, the cyanating agent can be present in an amount of from about 1.0 to about 2.0 eq. (mol/mol) to the compound of Formula V-a or Formula V-b.

Any suitable Lewis Acid can be used in the method of making the compound of Formula XI-a. For example, the Lewis Acid can be TMSOTf, TMSOTf, TBSOTf, TESOTf, $BF_3$, $BF_3$—$OEt_2$, $BCl_3$, $BF_3$-THF, $MgCl_2$, $MgI_2$, $MgBr_2$, $MgBr_2$—$OEt_2$, $ZnCl_2$, $ZnBr_2$, $ZnI_2$, LiCl, LiBr, LiI, $AlCl_3$, $AlBr_3$, $AlI_3$, $Me_2Si(OTf)_2$, $Et_2Si(OTf)_2$, $Pr_2Si(OTf)_2$, $iPr_2Si(OTf)_2$, $(tBu)_2Si(OTf)_2$, $(C_6F_5)_3B$, $MeSiCl_3$, $Me_2SiCl_2$, $SiCl_4$, TMSCl, TMSI, TMSVr, TBSCl, TBSBr, TBSI, TESCl, TESBr, TESI, $SmCl_3$, $SmBr_3$, $SmI_2$, $SmI_3$, $ScI_3$, $ScBr_3$, $ScI_3$, $Sm(OTf)_3$, $Sc(OTf)_3$, $TiCl_4$, $Ti(OiPr)_4$, $Ti(OiPr)_3Cl$, $Ti(OiPr)_2Cl_2$, $Ti(OiPr)Cl_3$, $Zn(BF_4)_2$, $LiBF_4$, $Mg(BF_4)_2$, $ZrCl_4$, $FeCl_2$, $FeCl_3$, $FeBr_2$, $FeBr_3$, $FeI_2$, $FeI_3$, Cu(OTf), $Cu(OTf)_2$, 4-toluenesulfonylchoride, benzenesulfonylchlopride, 4-toluenesulfonyl triflate, benzenesulfonyl triflate, methylsulfonyl chloride, methylsulfonic anhydrate, $InCl_3$, $InBr_3$, $InI_3$, $In(OTf)_3$, $Mg(SO_4)_2$, $NaSO_4$; or combinations thereof. In some embodiments, the Lewis Acid can be TMSOTf. In some embodiments, the following may be used in the method of making the compound of Formula XI-a instead of a Lewis Acid: dicyclohexylcarbodiimide, 1-Ethyl-3-(3-dimethylaminopropyl)carbodiimide, benzenesulfonic acid, HCl, 4-toluenesulfonic acid, triflic acid, trifluoroacetic acid, 4-nitrobenzolic acid, methylsoulfonic acid, sulfuric acid, phosphoric acid, HBr, acetic acid, formic acid, HI; or combinations thereof.

The Lewis Acid can be present in any suitable amount. For example, the Lewis Acid can be present in an amount of at least 0.0 eq. (mol/mol) to the compound of Formula V-a or Formula V-b, such as about 0.0, 0.5, 1.0, 2, 3, 4, 5, 6, 7, 8, 9, or about 10.0 eq. (mol/mol). The Lewis Acid can also be present in an amount of from about 0.0 to about 10.0 eq. (mol/mol) to the compound of Formula V-a or Formula V-b, such as of from about 0.0 to about 3.0 eq. (mol/mol), or of from about 1.0 to about 2.0 eq. (mol/mol). In some embodiments, the Lewis Acid can be present in an amount from about 0.0 to 1.0 eq. (mol/mol) to the compound of Formula V-a or Formula V-b. In some embodiments, the Lewis Acid can be present in an amount of from about 1.0 to about 2.0 eq. (mol/mol) to the compound of Formula V-a or Formula V-b.

Any suitable Broenstedt acid can be used in the method of making the compound of Formula XI-a. For example, the Broenstedt acid can be TFA, benzenesulfonic acid, HCl, 4-toluenesulfonic acid, triflic acid, trifluoroacetic acid, 4-nitrobenzoic acid, methylsoulfonic acid, sulfuric acid, phosphoric acid, HBr, acetic acid, formic acid, HI, trifluoromethylsulfonic acid, 4-fluorobenzoic acid, pivalic acid, $HBF_4$, nitric acid, 4-chloro-benzoic acid, pentafluorophenol, $HPF_6$, Camphorsulfonic acid; or combinations thereof. In some embodiments, the Broenstedt acid can be TFA.

The Broenstedt acid can be present in any suitable amount. For example, the Broenstedt acid can be present in an amount of at least about 0.0 eq. (mol/mol) to the compound of Formula V-a or Formula V-b, such as about 0.0, 0.5, 1.0, 2, 3, 4, 5, 6, 7, 8, 9, or about 10.0 eq. (mol/mol). The Broenstedt acid can also be present in an amount of from about 0.0 to about 10.0 eq. (mol/mol) to the compound of Formula V-a or Formula V-b, such as of from about 0.0 to about 3.0 eq. (mol/mol), or of from about 1.0 to about 2.0 eq. (mol/mol). In some embodiments, the Broenstedt acid can be present in an amount from about 0.0 to about 1.0 eq. (mol/mol) to the compound of Formula V-a or Formula V-b. In some embodiments, the Broenstedt acid can be present in an amount of from about 1.0 to about 2.0 eq. (mol/mol) to the compound of Formula V-a or Formula V-b.

Any suitable solvent can be used in the method of making the compound of Formula XI-a. For example, the solvent can be DCM, THF, MeTHF, $Et_2O$, MeCN, EtCN, toluene, benzene, chlorobenzene, nitrobenzene, flurorbenzene, methanol, ethanol, 2-propanol, propanol, butanol, MTBE, EtOAc, iPrOAc, Me2O, (TMS)2O, acetone, 2-butanone, chloroform, 1,2-dichloroethane, diglyme, dioxane, acetic acid, formic acid, trifluoroacetic acid, methylisobutylketone, DMAc, DMF, NMP, DMSO; or combinations thereof. In some embodiments, the solvent can be DCM.

The solvent can be present in any suitable amount. For example, the solvent can be present in an amount of at least 0.0 eq. (mol/mol) to the compound of Formula V-a or Formula V-b, such as about 0.0, 0.1, 0.5, 1.0, 2, 3, 4, 5, 6, 7, 8, 9, or about 10.0 eq. (mol/mol). The solvent can also be present in an amount of from about 0.0 to about 10.0 eq. (mol/mol) to the compound of Formula V-a or Formula V-b, such as of from about 0.0 to about 3.0 eq. (mol/mol), or of from about 1.0 to about 2.0 eq. (mol/mol). In some embodiments, the solvent can be present in an amount from about 0.1 to about 1.0 eq. (mol/mol) to the compound of Formula V-a or Formula V-b. In some embodiments, the solvent can be present in an amount of from about 1.0 to about 2.0 eq. (mol/mol) to the compound of Formula V-a or Formula V-b.

The reaction mixture of the method can be at any suitable temperature. For example, the temperature of the reaction mixture can be of from about −150° C. to about 0° C., or of from about −120° C. to about 0° C., or of from about −100° C. to about 0° C., or of from about −100° C. to about −50° C., or of from about −100° C. to about −70° C. In some embodiments, the temperature of the reaction mixture can be of from about −120° C. to about −70° C. In some embodiments, the temperature of the reaction mixture can be of from about −120° C. to about −100° C. In some embodiments, the temperature of the reaction mixture can be of from about −80° C. to about −30° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula XI-a in any suitable yield. For example, the compound of Formula XI-a can be prepared in a yield of at least about 50%, 55, 60, 65, 70, 75, 80, 85, 90 or at least about 95%.

The method of the present invention can provide the compound of Formula XI-a in any suitable purity. For example, the compound of Formula XI-a can be prepared in a purity of at least about 90, 95, 96, 97, 98 or at least about 99%. In some embodiments, the compound of Formula XI-a can be prepared in at least about 95% purity. In some embodiments, the compound of Formula XI-a can be prepared in at least about 98% purity. In some embodiments, the compound of Formula XI-a can be prepared in at least about 99% purity.

In some embodiments, the method of the present invention can be performed as a batch mode process. In some embodiments, the method of the present invention can be performed as a flow process.

In some embodiments, the method comprises preparing the compound of Formula XI-a:

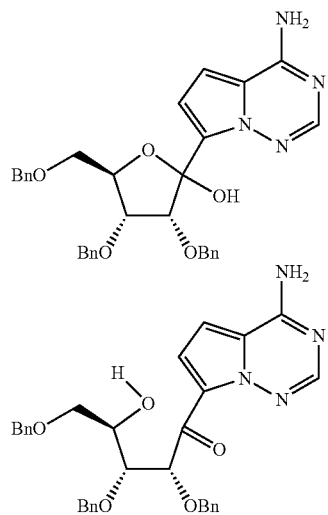

wherein the method comprises forming the reaction mixture having TFA, TMSCN, TMSOTf and the compound of Formula Va or Formula V-b:

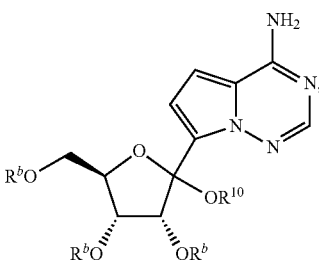

under conditions suitable to prepare the compound of Formula XI-a. In certain embodiments, the method of preparing Formula XI-a is performed between about −120° C. and about 20° C. In another embodiment, the method of preparing Formula XI-a is performed between about −120° C. and about 0° C. In another embodiment, the method of preparing Formula XI-a is performed between about −40° C. and about −20° C.

In some embodiments, the present invention provides a method of preparing a compound of Formula XI-a$^2$:

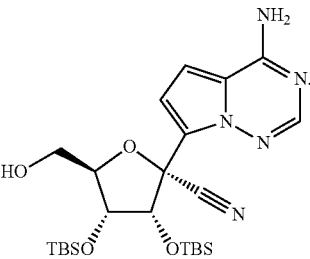

Formula (XI-a$^2$)

wherein the method comprises forming a reaction mixture having a cyanating agent, a Lewis Acid, a Broenstedt acid, solvent, and the compound of Formula V-a:

Formula (V-a)

under conditions suitable to prepare the compound of Formula XI-a$^2$, wherein R$^b$ is independently a hydroxy protecting group, alternatively, two R$^b$ groups on adjacent carbons can be combined to form a —C(R$^{19}$)$_2$ group, R$^{10}$ is H or a silyl group, and R$^{19}$ is H, C$_1$-C$_8$ alkyl, phenyl or substituted phenyl.

Any suitable cyanating agent can be used in the method of making the compound of Formula XI-a$^2$. For example, the cyanating agent can be TMSCN, TBSCN, TESCN, HCN, KCN, NaCN, 4-toluenesulfonyl cyanide, CuCN, CuCn*LiCl, LiCN, Zn(CN)$_2$, K4[Fe(CN)$_6$], tetrabutylammonium cyanide, tetrmethylammonium cyanide, tetraethylammonium cyanide, tetrabutylammonium cyanide, (including tetraalkylammonium cyanide with alkyl independently being Me, Et, Pr, iPr, Bu, iBu, tertBu, Pent, Hex), tributyltn cyanide, trimethyltin cyanide, triethyltin cyanide, tripropyltin cyanide, (including trialkyltin cyanide cyanide with alkyl independently being Me, Et, Pr, iPr, Bu, iBu, tertBu, Pent, Hex), 2-hydroxy-2-methylpropanenitrile; or combinations thereof. In some embodiments, the cyanating agent can be TMSCN.

The cyanating agent can be present in any suitable amount. For example, the cyanating agent can be present in an amount of at least 0.1 eq. (mol/mol) to the compound of Formula V-a, such as about 0.1, 0.5, 1.0, 2, 3, 4, 5, 6, 7, 8, 9, or about 10.0 eq. (mol/mol). The cyanating agent can also be present in an amount of from about 0.1 to about 10.0 eq. (mol/mol) to the compound of Formula V-a, such as of from about 0.1 to about 3.0 eq. (mol/mol), or of from about 1.0 to about 2.0 eq. (mol/mol). In some embodiments, the cyanating agent can be present in an amount from about 0.1 to 1.0 eq. (mol/mol) to the compound of Formula V-a. In some embodiments, the cyanating agent can be present in an amount of from about 1.0 to about 2.0 eq. (mol/mol) to the compound of Formula V-a.

Any suitable Lewis Acid can be used in the method of making the compound of Formula XI-a$^2$. For example, the Lewis Acid can be TMSOTf, TMSOTf, TBSOTf, TESOTf, $BF_3$, $BF_3$—$OEt_2$, $BCl_3$, $BF_3$-THF, $MgCl_2$, $MgI_2$, $MgBr_2$, $MgBr_2$—$OEt_2$, $ZnCl_2$, $ZnBr_2$, $ZnI_2$, LiCl, LiBr, LiI, $AlCl_3$, $AlBr_3$, $AlI_3$, $Me_2Si(OTf)_2$, $Et_2Si(OTf)_2$, $Pr_2Si(OTf)_2$, $iPr_2Si(OTf)_2$, $(tBu)_2Si(OTf)_2$, $(C_6F_5)_3B$, $MeSiCl_3$, $Me_2SiCl_2$, $SiCl_4$, TMSCl, TMSI, TMSVr, TBSCl, TBSBr, TBSI, TESCl, TESBr, TESI, $SmCl_3$, $SmBr_3$, $SmI_2$, $SmI_3$, $ScI_3$, $ScBr_3$, $ScI_3$, $Sm(OTf)_3$, $Sc(OTf)_3$, $TiCl_4$, $Ti(OiPr)_4$, $Ti(OiPr)_3Cl$, $Ti(OiPr)_2Cl_2$, $Ti(OiPr)Cl_3$, $Zn(BF_4)_2$, $LiBF_4$, $Mg(BF4)_2$, $ZrCl_4$, $FeCl_2$, $FeCl_3$, $FeBr_2$, $FeBr_3$, $FeI_2$, $FeI_3$, Cu(OTf), $Cu(OTf)_2$, 4-toluenesulfonylchoride, benzenesulfonylchlopride, 4-toluenesulfonyl triflate, benzenesulfonyl triflate, methylsulfonyl chloride, methylsulfonic anhydrate, $InCl_3$, $InBr_3$, $InI_3$, $In(OTf)_3$, $Mg(SO_4)_2$, $NaSO_4$; or combinations thereof. In some embodiments, the Lewis Acid can be TMSOTf. In some embodiments, the following may be used in the method of making the compound of Formula XI-a$^2$ instead of a Lewis Acid: dicyclohexylcarbodiimide, 1-Ethyl-3-(3-dimethylaminopropyl)carbodiimide, benzenesulfonic acid, HCl, 4-toluenesulfonic acid, triflic acid, trifluoroacetic acid, 4-nitrobenzolic acid, methylsoulfonic acid, sulfuric acid, phosphoric acid, HBr, acetic acid, formic acid, HI; or combinations thereof.

The Lewis Acid can be present in any suitable amount. For example, the Lewis Acid can be present in an amount of at least 0.1 eq. (mol/mol) to the compound of Formula V-a, such as about 0.1, 0.5, 1.0, 2, 3, 4, 5, 6, 7, 8, 9, or about 10.0 eq. (mol/mol). The Lewis Acid can also be present in an amount of from about 0.1 to about 10.0 eq. (mol/mol) to the compound of Formula V-a, such as of from about 0.1 to about 3.0 eq. (mol/mol), or of from about 1.0 to about 2.0 eq. (mol/mol). In some embodiments, the Lewis Acid can be present in an amount from about 0.1 to 1.0 eq. (mol/mol) to the compound of Formula V-a. In some embodiments, the Lewis Acid can be present in an amount of from about 1.0 to about 2.0 eq. (mol/mol) to the compound of Formula V-a.

Any suitable Broenstedt acid can be used in the method of making the compound of Formula XI-a$^2$. For example, the Broenstedt acid can be TFA, benzenesulfonic acid, HCl, 4-toluenesulfonic acid, triflic acid, trifluoroacetic acid, 4-nitrobenzoic acid, methylsoulfonic acid, sulfuric acid, phosphoric acid, HBr, acetic acid, formic acid, HI, trifluoromethylsulfonic acid, 4-fluorobenzoic acid, pivalic acid, $HBF_4$, nitric acid, 4-chloro-benzoic acid, pentafluorophenol, $HPF_6$, Camphorsulfonic acid; or combinations thereof. In some embodiments, the Broenstedt acid can be TFA.

The Broenstedt acid can be present in any suitable amount. For example, the Broenstedt acid can be present in an amount of at least about 0.1 eq. (mol/mol) to the compound of Formula V-a, such as about 0.1, 0.5, 1.0, 2, 3, 4, 5, 6, 7, 8, 9, or about 10.0 eq. (mol/mol). The Broenstedt acid can also be present in an amount of from about 0.1 to about 10.0 eq. (mol/mol) to the compound of Formula V-a, such as of from about 0.1 to about 3.0 eq. (mol/mol), or of from about 1.0 to about 2.0 eq. (mol/mol). In some embodiments, the Broenstedt acid can be present in an amount from about 0.1 to about 1.0 eq. (mol/mol) to the compound of Formula V-a. In some embodiments, the Broenstedt acid can be present in an amount of from about 1.0 to about 2.0 eq. (mol/mol) to the compound of Formula V-a.

Any suitable solvent can be used in the method of making the compound of Formula XI or XI-a$^2$. For example, the solvent can be DCM, THF, MeTHF, $Et_2O$, MeCN, EtCN, toluene, benzene, chlorobenzene, nitrobenzene, flurorbenzene, methanol, ethanol, 2-propanol, propanol, butanol, MTBE, EtOAc, iPrOAc, Me2O, (TMS)2O, acetone, 2-butanone, chloroform, 1,2-dichloroethane, diglyme, dioxane, acetic acid, formic acid, trifluoroacetic acid, methylisobutylketone, DMAc, DMF, NMP, DMSO; or combinations thereof. In some embodiments, the solvent can be DCM.

The solvent can be present in any suitable amount. For example, the solvent can be present in an amount of at least 0.0 eq. (mol/mol) to the compound of Formula V-a, such as about 0.0, 0.1, 0.5, 1.0, 2, 3, 4, 5, 6, 7, 8, 9, or about 10.0 eq. (mol/mol). The solvent can also be present in an amount of from about 0.0 to about 10.0 eq. (mol/mol) to the compound of Formula V-a, such as of from about 0.0 to about 3.0 eq. (mol/mol), or of from about 1.0 to about 2.0 eq. (mol/mol). In some embodiments, the solvent can be present in an amount from about 0.1 to about 1.0 eq. (mol/mol) to the compound of Formula V-a. In some embodiments, the solvent can be present in an amount of from about 1.0 to about 2.0 eq. (mol/mol) to the compound of Formula V-a.

The reaction mixture of the method can be at any suitable temperature. For example, the temperature of the reaction mixture can be of from about −150° C. to about 0° C., or of from about −120° C. to about 0° C., or of from about −100° C. to about 0° C., or of from about −100° C. to about −50° C., or of from about −100° C. to about −70° C. In some embodiments, the temperature of the reaction mixture can be of from about −120° C. to about −70° C. In some embodiments, the temperature of the reaction mixture can be of from about −120° C. to about −100° C. In some embodiments, the temperature of the reaction mixture can be of from about −80° C. to about −30° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula XI-a$^2$ in any suitable yield. For example, the compound of Formula XI-a$^2$ can be prepared in a yield of at least about 50%, 55, 60, 65, 70, 75, 80, 85, 90 or at least about 95%.

The method of the present invention can provide the compound of Formula XI-a$^2$ in any suitable purity. For example, the compound of Formula XI-a$^2$ can be prepared in a purity of at least about 90, 95, 96, 97, 98 or at least about 99%. In some embodiments, the compound of Formula XI-a$^2$ can be prepared in at least about 95% purity. In some embodiments, the compound of Formula XI-a$^2$ can be prepared in at least about 98% purity. In some embodiments, the compound of Formula XI-a$^2$ can be prepared in at least about 99% purity.

In some embodiments, the method of the present invention can be performed as a batch mode process. In some embodiments, the method of the present invention can be performed as a flow process.

In some embodiments, the method comprises preparing the compound of Formula XI-a$^2$:

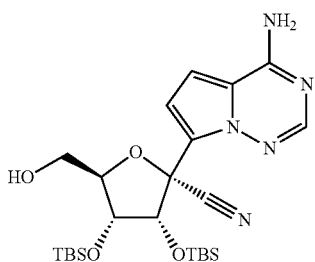

wherein the method comprises forming the reaction mixture having TFA, TMSCN, TMSOTf and the compound of Formula Va:

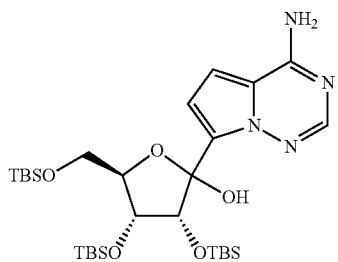

under conditions suitable to prepare the compound of Formula XI-a². In certain embodiments, the method of preparing Formula XI-a² is performed between about −120° C. and about 20° C. In another embodiment, the method of preparing Formula XI-a² is performed between about −120° C. and about 0° C. In another embodiment, the method of preparing Formula XI-a² is performed between about −40° C. and about −20° C.

In some embodiments, the present invention provides a method of preparing a compound of Formula XI-b:

Formula (XI-b)

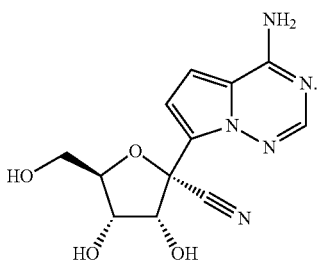

wherein the method comprises forming a reaction mixture having a Lewis Acid, a base, a solvent, a filtering agent, and the compound of Formula XI-a Formula (XI-a)

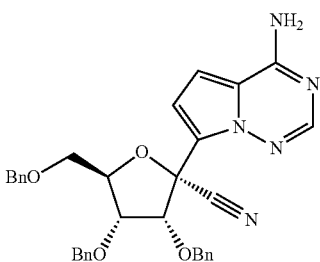

under conditions suitable to prepare the compound of Formula XI-b.

Any suitable Lewis Acid can be used in the method of making the compound of Formula XI-b. For example, the Lewis Acid can be TMSOTf, TMSOTf, TBSOTf, TESOTf, $BF_3$, $BF_3$—$OEt_2$, $BCl_3$, $BF_3$-THF, $MgCl_2$, $MgI_2$, $MgBr_2$, $MgBr_2$—$OEt_2$, $ZnCl_2$, $ZnBr_2$, $ZnI_2$, LiCl, LiBr, Li, $AlCl_3$, $AlBr_3$, $AlI_3$, $Me_2Si(OTf)_2$, $Et_2Si(OTf)_2$, $Pr_2Si(OTf)_2$, $iPr_2Si(OTf)_2$, $(tBu)_2Si(OTf)_2$, $(C_6F_5)_3B$, $MeSiCl_3$, $Me_2SiCl_2$, $SiCl_4$, TMSCl, TMSI, TMSVr, TBSCl, TBSBr, TBSI, TESCl, TESBr, TESI, $SmCl_3$, $SmBr_3$, $SmI_2$, $SmI_3$, $ScI_3$, $ScBr_3$, $ScI_3$, $Sm(OTf)_3$, $Sc(OTf)_3$, $TiCl_4$, $Ti(OiPr)_4$, $Ti(OiPr)_3Cl$, $Ti(OiPr)_2Cl_2$, $Ti(OiPr)Cl_3$, $Zn(BF_4)_2$, $LiBF_4$, $Mg(BF4)_2$, $ZrCl_4$, $FeCl_2$, $FeCl_3$, $FeBr_2$, $FeBr_3$, $FeI_2$, $FeI_3$, Cu(OTf), $Cu(OTf)_2$, 4-toluenesulfonylchoride, benzenesulfonylchlopride, 4-toluenesulfonyl triflate, benzenesulfonyl triflate, methylsulfonyl chloride, methylsulfonic anhydrate, $InCl_3$, $InBr_3$, $InI_3$, $In(OTf)_3$, $Mg(SO_4)_2$, $NaSO_4$; or combinations thereof. In some embodiments, the Lewis Acid can be $BCL_3$. In some embodiments, the following may be used in the method of making the compound of Formula XI-b instead of a Lewis Acid: dicyclohexylcarbodiimide, 1-Ethyl-3-(3-dimethylaminopropyl)carbodiimide, benzenesulfonic acid, HCl, 4-toluenesulfonic acid, triflic acid, trifluoroacetic acid, 4-nitrobenzolic acid, methylsoulfonic acid, sulfuric acid, phosphoric acid, HBr, acetic acid, formic acid, HI; or combinations thereof.

The Lewis Acid can be present in any suitable amount. For example, the Lewis Acid can be present in an amount of at least 0.1 eq. (mol/mol) to the compound of Formula XI-a, such as about 0.1, 0.5, 1.0, 2, 3, 4, 5, 6, 7, 8, 9, or about 10.0 eq. (mol/mol). The Lewis Acid can also be present in an amount of from about 0.1 to about 10.0 eq. (mol/mol) to the compound of Formula XI-a, such as of from about 0.1 to about 3.0 eq. (mol/mol), or of from about 1.0 to about 2.0 eq. (mol/mol). In some embodiments, the Lewis Acid can be present in an amount from about 0.1 to 1.0 eq. (mol/mol) to the compound of Formula XI-a. In some embodiments, the Lewis Acid can be present in an amount of from about 1.0 to about 2.0 eq. (mol/mol) to the compound of Formula XI-a.

Any suitable base can be used in the method of making the compound of Formula XI-b. For example, the base can be $(C_{1-8}Alkyl)_3N$. In some embodiments, the base can be $Et_3N$.

The base can be present in any suitable amount. For example, the base can be present in an amount of at least 0.1 eq. (mol/mol) to the compound of Formula XI-a, such as about 0.1, 0.5, 1.0, 2, 3, 4, 5, 6, 7, 8, 9, or about 10.0 eq. (mol/mol). The base can also be present in an amount of from about 0.1 to about 10.0 eq. (mol/mol) to the compound of Formula XI-a, such as of from about 0.1 to about 3.0 eq. (mol/mol), or of from about 1.0 to about 2.0 eq. (mol/mol). In some embodiments, the base can be present in an amount from about 0.1 to 1.0 eq. (mol/mol) to the compound of Formula XI-a. In some embodiments, the base can be present in an amount of from about 1.0 to about 2.0 eq. (mol/mol) to the compound of Formula XI-a.

Any suitable solvent can be used in the method of making the compound of Formula XI-b. For example, the solvent can be MeOH, DCM, THF, MeTHF, $Et_2O$, MeCN, EtCN, toluene, benzene, chlorobenzene, nitrobenzene, flurorbenzene, methanol, ethanol, 2-propanol, propanol, butanol, MTBE, EtOAc, iPrOAc, Me2O, (TMS)2O, acetone, 2-butanone, chloroform, 1,2-dichloroethane, diglyme, dioxane, acetic acid, formic acid, trifluoroacetic acid, methylisobutylketone, DMAc, DMF, NMP, DMSO; or combinations thereof. In some embodiments, the solvent can be MeOH.

The solvent can be present in any suitable amount. For example, the solvent can be present in an amount of at least 0.1 eq. (mol/mol) to the compound of Formula XI-a, such as about 0.1, 0.5, 1.0, 2, 3, 4, 5, 6, 7, 8, 9, or about 10.0 eq. (mol/mol). The solvent can also be present in an amount of from about 0.1 to about 10.0 eq. (mol/mol) to the compound of Formula XI-a, such as of from about 0.1 to about 3.0 eq. (mol/mol), or of from about 1.0 to about 2.0 eq. (mol/mol). In some embodiments, the solvent can be present in an amount from about 0.1 to about 1.0 eq. (mol/mol) to the compound of Formula XI-a. In some embodiments, the solvent can be present in an amount of from about 1.0 to about 2.0 eq. (mol/mol) to the compound of Formula XI-a.

Any suitable filtering agent can be used in the method of making the compound of Formula XI-b. For example, the filtering agent can be silica gel, Celite® or combinations thereof. In some embodiments, the filtering agent can be Celite®.

The filtering agent can be present in any suitable amount. For example, the filtering agent can be present in an amount of at least 0.1 eq. (mol/mol) to the compound of Formula XI-a, such as about 0.1, 0.5, 1.0, 2, 3, 4, 5, 6, 7, 8, 9, or about 10.0 eq. (mol/mol). The filtering agent can also be present in an amount of from about 0.1 to about 10.0 eq. (mol/mol) to the compound of Formula XI-a, such as of from about 0.1 to about 3.0 eq. (mol/mol), or of from about 1.0 to about 2.0 eq. (mol/mol). In some embodiments, the filtering agent can be present in an amount from about 0.1 to about 1.0 eq. (mol/mol) to the compound of Formula XI-a. In some embodiments, the filtering agent can be present in an amount of from about 1.0 to about 2.0 eq. (mol/mol) to the compound of Formula XI-a.

The reaction mixture of the method can be at any suitable temperature. For example, the temperature of the reaction mixture can be of from about −50° C. to about 0° C., or of from about −40° C. to about 0° C., or of from about −30° C. to about 0° C., or of from about −20° C. to about 0° C., or of from about −20° C. to about −10° C. In some embodiments, the temperature of the reaction mixture can be of from about −30° C. to about 0° C. In some embodiments, the temperature of the reaction mixture can be of from about −20° C. to about −10° C. In some embodiments, the temperature of the reaction mixture can be of from about −25° C. to about −15° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula XI-b in any suitable yield. For example, the compound of Formula XI-b can be prepared in a yield of at least about 50%, 55, 60, 65, 70, 75, 80, 85, 90 or at least about 95%.

The method of the present invention can provide the compound of Formula XI-b in any suitable purity. For example, the compound of Formula XI-b can be prepared in a purity of at least about 90, 95, 96, 97, 98 or at least about 99%. In some embodiments, the compound of Formula XI-b can be prepared in at least about 95% purity. In some embodiments, the compound of Formula XI-b can be prepared in at least about 98% purity. In some embodiments, the compound of Formula XI-b can be prepared in at least about 99% purity.

In some embodiments, the present invention provides a method of preparing a compound of Formula XI-b:

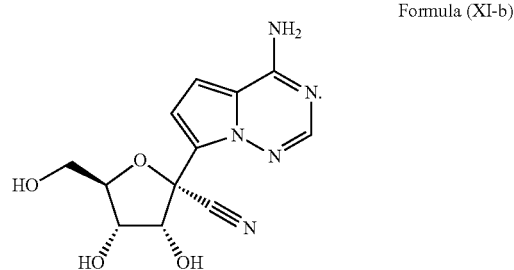

Formula (XI-b)

wherein the method comprises forming a reaction mixture having BCL$_3$, Et$_2$N, MeOH, Celite®, and the compound of Formula XI-a

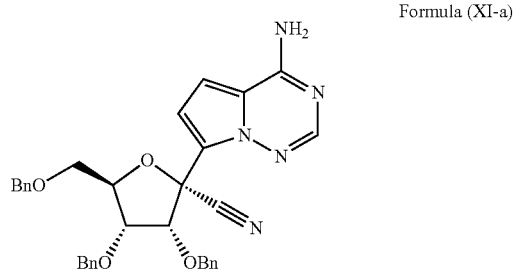

Formula (XI-a)

under conditions suitable to prepare the compound of Formula XI-b. In certain embodiments, the method of preparing Formula XI-b is performed between about −30° C. and about 0° C. In another embodiment, the method of preparing Formula XI is performed between about −20° C. and about 0° C.

In some embodiments, the present invention provides a method of preparing a compound of Formula XI-c:

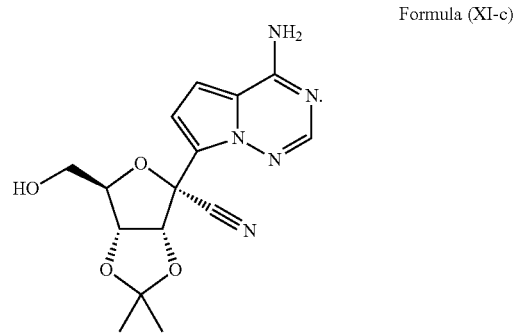 [SMILES: CC1(C)O[C@H]2[C@@H](O1)[C@](C#N)(c1ccc3c(N)ncnn13)O[C@@H]2CO]

Formula (XI-c)

wherein the method comprises forming a reaction mixture having a solvent, a reagent, an acid, and the compound of Formula XI-b

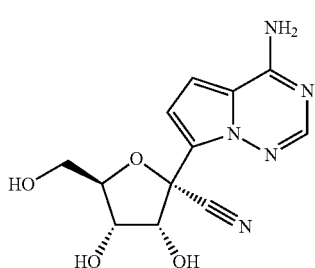

Formula (XI-b)

under conditions suitable to prepare the compound of Formula XI-c.

Any suitable solvent can be used in the method of making the compound of Formula XI-c. For example, the solvent can be acetone, MeOH, DCM, THF, MeTHF, Et₂O, MeCN, EtCN, toluene, benzene, chlorobenzene, nitrobenzene, flurorbenzene, methanol, ethanol, 2-propanol, propanol, butanol, MTBE, EtOAc, iPrOAc, Me2O, (TMS)2O, acetone, 2-butanone, chloroform, 1,2-dichloroethane, diglyme, dioxane, acetic acid, formic acid, trifluoroacetic acid, methylisobutylketone, DMAc, DMF, NMP, DMSO; or combinations thereof. In some embodiments, the solvent can be acetone.

The solvent can be present in any suitable amount. For example, the solvent can be present in an amount of at least 0.1 eq. (mol/mol) to the compound of Formula XI-b, such as about 0.1, 0.5, 1.0, 2, 3, 4, 5, 6, 7, 8, 9, or about 10.0 eq. (mol/mol). The solvent can also be present in an amount of from about 0.1 to about 10.0 eq. (mol/mol) to the compound of Formula XI-b, such as of from about 0.1 to about 3.0 eq. (mol/mol), or of from about 1.0 to about 2.0 eq. (mol/mol). In some embodiments, the solvent can be present in an amount from about 0.1 to 1.0 eq. (mol/mol) to the compound of Formula XI-b. In some embodiments, the solvent can be present in an amount of from about 1.0 to about 2.0 eq. (mol/mol) to the compound of Formula XI-b.

Any suitable reagent can be used in the method of making the compound of Formula XI-c. For example, the reagent can be 2,2-dimethoxypropane, acetone, 2-methoxypropene, 2,2-diethylpropane, 2-ethoxypropene, 2,2-dimethyl-1,3-dioxolane, 2,2-dimethyl-1,3-dioxane; or combinations thereof. In some embodiments, the reagent can be 2,2-dimethoxypropane.

The reagent can be present in any suitable amount. For example, the reagent can be present in an amount of at least 0.1 eq. (mol/mol) to the compound of Formula XI-b, such as about 0.1, 0.5, 1.0, 2, 3, 4, 5, 6, 7, 8, 9, or about 10.0 eq. (mol/mol). The reagent can also be present in an amount of from about 0.1 to about 10.0 eq. (mol/mol) to the compound of Formula XI-b, such as of from about 0.1 to about 3.0 eq. (mol/mol), or of from about 1.0 to about 2.0 eq. (mol/mol). In some embodiments, the reagent can be present in an amount from about 0.1 to 1.0 eq. (mol/mol) to the compound of Formula XI-b. In some embodiments, the reagent can be present in an amount of from about 1.0 to about 2.0 eq. (mol/mol) to the compound of Formula XI-b.

Any suitable acid can be used in the method of making the compound of Formula XI-c. For example, the acid can be TMSOTf, TMSOTf, TBSOTf, TESOTf, BF₃, BF₃—OEt₂, BCl₃, BF₃-THF, MgCl₂, MgI₂, MgBr₂, MgBr₂—OEt₂, ZnCl₂, ZnBr₂, ZnI₂, LiCl, LiBr, LiI, AlCl₃, AlBr₃, AlI₃, Me₂Si(OTf)₂, Et₂Si(OTf)₂, Pr₂Si(OTf)₂, iPr₂Si(OTf)₂, (tBu)₂Si(OTf)₂, (C₆F₅)₃B, MeSiCl₃, Me₂SiCl₂, SiCl₄, TMSCl, TMSI, TMSVr, TBSCl, TBSBr, TBSI, TESCl, TESBr, TESI, SmCl₃, SmBr₃, SmI₂, SmI₃, ScI₃, ScBr₃, ScI₃, Sm(OTf)₃, Sc(OTf)₃, TiCl₄, Ti(OiPr)₄, Ti(OiPr)₃Cl, Ti(OiPr)₂Cl₂, Ti(OiPr)Cl₃, Zn(BF₄)₂, LiBF₄, Mg(BF4)₂, ZrCl₄, FeCl₂, FeCl₃, FeBr₂, FeBr₃, FeI₂, FeI₃, Cu(OTf), Cu(OTf)₂, 4-toluenesulfonylchoride, benzenesulfonylchlopride, 4-toluenesulfonyl triflate, benzenesulfonyl triflate, methylsulfonyl chloride, methylsulfonic anhydride, InCl₃, InBr₃, InI₃, In(OTf)₃, Mg(SO₄)₂, NaSO₄, dicyclohexylcarbodiimide, 1-Ethyl-3-(3-dimethylaminopropyl)carbodiimide, benzenesulfonic acid, HCl, 4-toluenesulfonic acid, triflic acid, trifluoroacetic acid, 4-nitrobenzolic acid, methylsoulfonic acid, sulfuric acid, phosphoric acid, HBr, acetic acid, formic acid, HI, TFA, benzenesulfonic acid, HCl, 4-toluenesulfonic acid, triflic acid, trifluoroacetic acid, 4-nitrobenzoic acid, methylsoulfonic acid, sulfuric acid, phosphoric acid, HBr, acetic acid, formic acid, HI, trifluoromethylsulfonic acid, 4-fluorobenzoic acid, pivalic acid, HBF₄, nitric acid, 4-chloro-benzoic acid, pentafluorophenol, HPF₆, Camphorsulfonic acid; or combinations thereof. In some embodiments, the acid can be sulfuric acid.

The acid can be present in any suitable amount. For example, the acid can be present in an amount of at least 0.0 eq. (mol/mol) to the compound of Formula XI-b, such as about 0.0, 0.5, 1.0, 2, 3, 4, 5, 6, 7, 8, 9, or about 10.0 eq. (mol/mol). The acid can also be present in an amount of from about 0.0 to about 10.0 eq. (mol/mol) to the compound of Formula XI-b, such as of from about 0.0 to about 3.0 eq. (mol/mol), or of from about 1.0 to about 2.0 eq. (mol/mol). In some embodiments, the acid can be present in an amount from about 0.0 to 1.0 eq. (mol/mol) to the compound of Formula XI-b. In some embodiments, the acid can be present in an amount of from about 1.0 to about 2.0 eq. (mol/mol) to the compound of Formula XI-b.

The reaction mixture of the method can be at any suitable temperature. For example, the temperature of the reaction mixture can be of from about −50° C. to about 50° C., or of from about 0° C. to about 50° C., or of from about 0° C. to about 40° C., or of from about 0° C. to about 30° C., or of from about 0° C. to about 25° C. In some embodiments, the temperature of the reaction mixture can be of from about 0° C. to about 23° C. In some embodiments, the temperature of the reaction mixture can be of from about 0° C. to about 25° C. In some embodiments, the temperature of the reaction mixture can be of from about 0° C. to about 30° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula XI-c in any suitable yield. For example, the compound of Formula XI-c can be prepared in a yield of at least about 50%, 55, 60, 65, 70, 75, 80, 85, 90 or at least about 95%.

The method of the present invention can provide the compound of Formula XI-c in any suitable purity. For example, the compound of Formula XI-c can be prepared in a purity of at least about 90, 95, 96, 97, 98 or at least about 99%. In some embodiments, the compound of Formula XI-b can be prepared in at least about 95% purity. In some embodiments, the compound of Formula XI-b can be prepared in at least about 98% purity. In some embodiments, the compound of Formula XI-b can be prepared in at least about 99% purity.

In some embodiments, the method comprises preparing the compound of Formula XI-c:

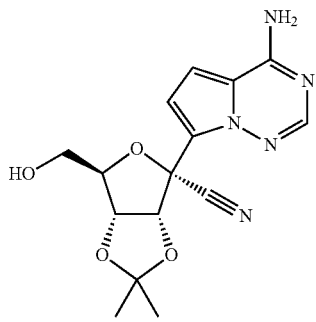 [SMILES: CC1(C)O[C@H]2[C@@H](O1)[C@](C#N)(c1ccc3c(N)ncnn13)O[C@@H]2CO]

wherein the method comprises forming a reaction mixture having acetone, 2,2-dimethoxypropane, sulfuric acid, and the compound of Formula XI-b

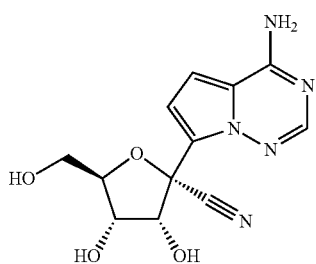 [SMILES: N#C[C@@]1(c2ccc3c(N)ncnn23)O[C@H](CO)[C@@H](O)[C@H]1O]

under conditions suitable to prepare the compound of Formula XI-c. In certain embodiments, the method of preparing Formula XI-c is performed between about 0° C. and about 30° C. In another embodiment, the method of preparing Formula XI is performed between about 10° C. and about 30 C.

C. Addition of Prodrug Moiety

The present invention also provides a method of coupling a prodrug moiety to a nucleoside to provide a compound of the present invention. In some embodiments, the present invention provides a method of preparing a compound of Formula VIII:

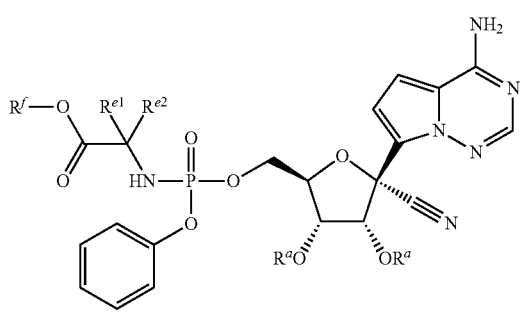

Formula (VIII)

wherein the method includes forming a reaction mixture including a coupling agent, a non-nucleophilic base, a compound of Formula IX:

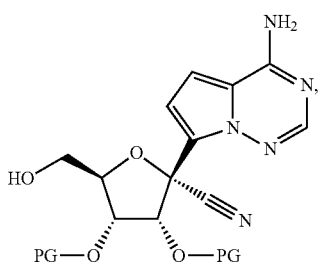

Formula (IX)

and a compound of Formula X:

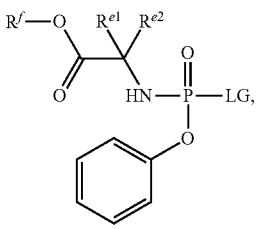

Formula (X)

under conditions suitable to form the compound of Formula VIII, wherein each $R^a$ is H or PG, each PG group is a hydroxy protecting group, or both PG groups are combined to form —C($R^{19}$)$_2$—, $R^{e1}$ and $R^{e2}$ are each independently H, $C_1$-$C_6$ alkyl or benzyl, $R^f$ is H, $C_1$-$C_8$ alkyl, benzyl, $C_3$-$C_6$ cycloalkyl, or —CH$_2$—$C_3$-$C_6$ cycloalkyl, $R^{19}$ is H, $C_1$-$C_8$ alkyl, phenyl or substituted phenyl, and LG is a leaving group.

Any suitable coupling agent can be used in the method of making the compound of Formula VIII, as described above for the method of making the compound of Formula V. In some embodiments, the coupling agent can be a magnesium coupling agent. In some embodiments, the coupling agent can be MgCl$_2$, iPrMgCl, tBuMgCl, PhMgCl, or combinations thereof. In some embodiments, the coupling agent can be MgCl$_2$.

Any suitable non-nucleophilic base can be used in the method of making the compound of Formula VIII. Representative non-nucleophilic bases include, but are not limited to, triethylamine, diisopropylethyl amine, N,N-diethylaniline, pyridine, 2,6-lutidine, 2,4,6-collidine, 4-dimethylaminopyridine, and quinuclidine. In some embodiments, the non-nucleophilic base can be di-isopropyl ethyl amine (DIPEA).

The protecting groups PG can be any suitable hydroxy protecting groups, as described above for the method of making the compound of Formula V. Exemplary protecting groups PG can be benzyl, or the PG groups can be combined to form an acetonide. Exemplary acetonides include, but are not limited to, acetonide and benzylidene acetal. In some embodiments, the hydroxy protecting groups of hydroxy groups on adjacent carbons can be combined to form acetonide. In some embodiments, the PG groups are combined to form —C($R^{19}$)$_2$—. In some embodiments, each $R^a$ is the protecting group PG where the PG groups are combined to form —C(Me)$_2$-.

When the $R^e$ group is $C_1$-$C_8$ alkyl, each $R^e$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, each $R^e$ group can be methyl.

When the $R^f$ group is $C_1$-$C_8$ alkyl, $R^f$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^f$ group can be methyl, ethyl, isopropyl, t-butyl, or iso-hexyl. When the $R^f$ group is $C_3$-$C_6$ cycloalkyl, $R^f$ can be cyclopropyl, cyclobutyl, cyclopentyl or cyclohexyl. In some embodiments, $R^f$ can be cyclobutyl, cyclopentyl or cyclohexyl.

When the $R^{19}$ group is $C_1$-$C_8$ alkyl, $R^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the $R^{19}$ group can be methyl.

The leaving group can be any suitable leaving group. Suitable leaving groups LG include, but are not limited to, chloride, bromide, mesylate, tosylate, triflate, 4-nitrobenzenesulfonate, 4-chlorobenzenesulfonate, 4-nitrophenoxy, pentafluorophenoxy, etc. In some embodiments, the leaving group LG can be 4-nitrophenoxy or pentafluorophenoxy. In some embodiments, the leaving group LG can be 4-nitrophenoxy.

In some embodiments, each $R^a$ is PG where the PG groups are combined to form $-C(R^{19})_2-$, $R^f$ is $C_1$-$C_8$ alkyl, $R^{19}$ is $C_1$-$C_8$ alkyl, and the leaving group LG is 4-nitrophenoxy or pentafluorophenoxy.

In some embodiments, the coupling agent is $MgCl_2$, and the non-nucleophilic base is di-isopropyl ethyl amine.

In some embodiments, the compound of Formula VIII can be

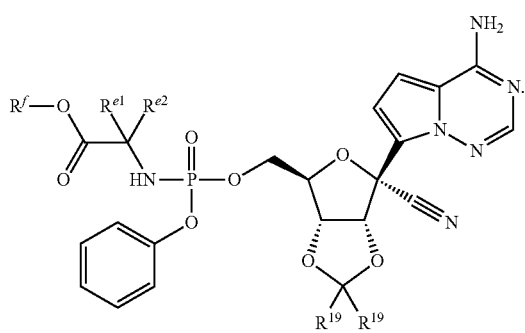

In some embodiments, the compound of Formula VIII can be

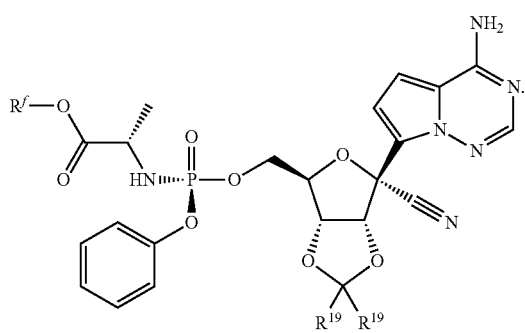

In some embodiments, the compound of Formula VIII can be

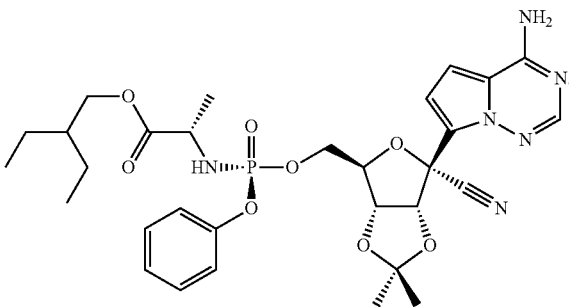

In some embodiments, the method of making the compound Formula VIII includes forming the reaction mixture including $MgCl_2$, DIPEA, the compound of Formula IX:

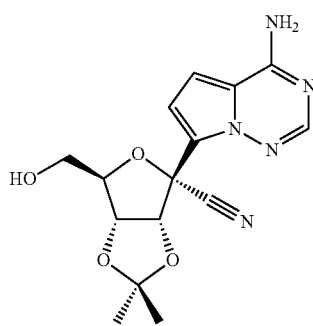

and the compound of Formula X:

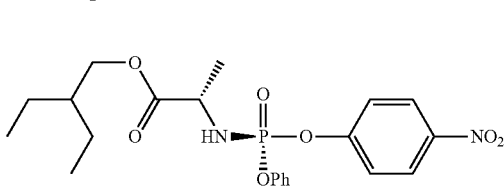

under conditions suitable to form the compound of Formula VIII:

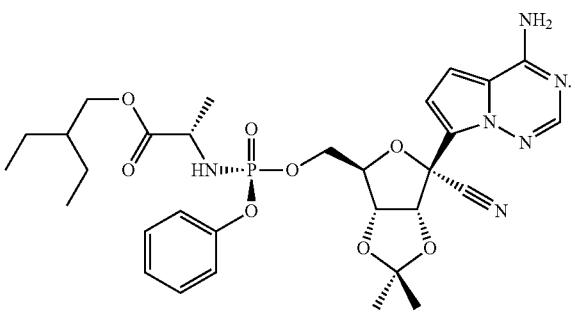

When the $R^a$ groups of the compound of Formula VIII are the hydroxy protecting groups PG, the method can include the additional step of removing the protecting groups to form the compound of Formula VIII where each $R^a$ is H. In some embodiments, the method of preparing the compound of Formula VIII includes forming a second reaction mixture including a deprotection agent and the compound Formula VIII wherein each $R^a$ group is the protecting group PG, under suitable conditions to form the compound of Formula VIII where each $R^a$ is H. The deprotection agent can be any suitable agent to remove the protecting groups PG such as hydrogen and a hydrogenation catalyst, or acid. For example, if the protecting group PG is benzyl, the deprotection agent can be hydrogen and platinum on carbon. Alternatively, when the protecting group PG is an acetonide, the deprotection agent can be an acid. Representative acids include, but are not limited to, acetic acid, glacial acetic acid, trifluoroacetic acid (TFA), hydrochloric acid, concentrated hydrochloric acid, and others. In some embodiments, the method of preparing the compound of Formula VIII includes forming a second reaction mixture including an acid and the compound Formula VIII wherein the $R^a$ groups are combined to form —$C(R^{19})_2$—, under suitable conditions to form the compound of Formula VIII where each $R^a$ is H. In some embodiments, the acid can be hydrochloric acid.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran, acetonitrile, or combinations thereof. In some embodiments, the solvent can be acetonitrile.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula VIII in any suitable yield. For example, the compound of Formula VIII can be prepared in a yield of at least about 50%, 55, 60, 65, 70, 75, 80, 85, 90 or at least about 95%.

The method of the present invention can provide the compound of Formula VIII in any suitable purity. For example, the compound of Formula VIII can be prepared in a purity of at least about 90, 95, 96, 97, 98 or at least about 99%. In some embodiments, the compound of Formula VIII can be prepared in at least 95% purity. In some embodiments, the compound of Formula VIII can be prepared in at least 98% purity. In some embodiments, the compound of Formula VIII can be prepared in at least 99% purity.

In some embodiments, the present invention provides the compound

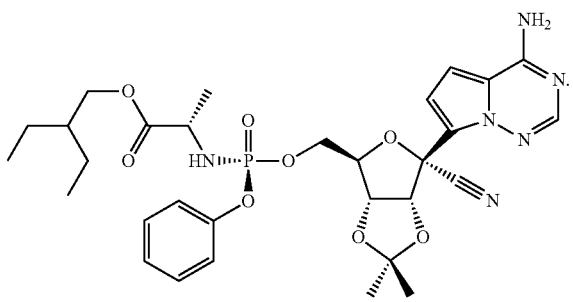

In some embodiments, the present invention provides a method of preparing a compound of Formula VIII:

Formula (VIII)

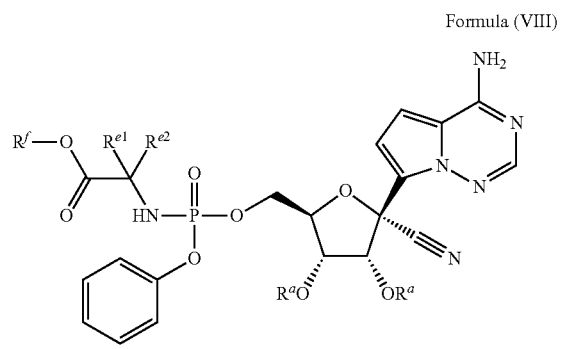

wherein the method comprises forming a reaction mixture including a coupling agent, a non-nucleophilic base, a compound of Formula IX-a:

Formula (IX-a)

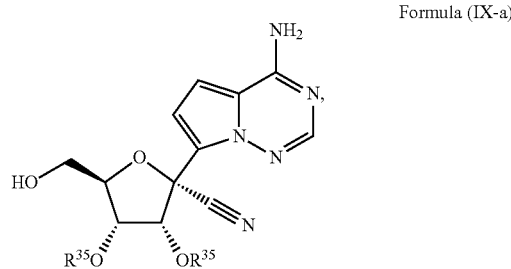

and a compound of Formula X:

Formula (X)

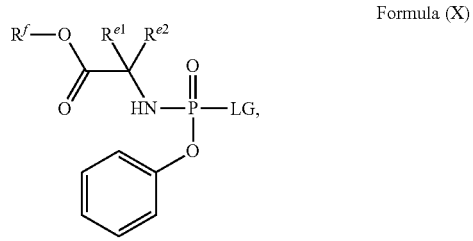

under conditions suitable to form the compound of Formula VIII, wherein $R^a$ is independently H or a hydroxy protecting group, or two $R^a$ on adjacent carbons can be combined to form a —$C(R^{19})_2$— group, $R^{35}$ is independently H or a hydroxy protecting group, or two $R^{35}$ on adjacent carbons can be combined to form a —C(R$^{19}$)$_2$— group, R$^{19}$ is H or C$_1$-C$_8$ alkyl, R$^{e1}$ and R$^{e2}$ are each independently H, C$_1$-C$_6$ alkyl or benzyl, R$^f$ is H, C$_1$-C$_8$ alkyl, benzyl, C$_3$-C$_6$ cycloalkyl, or —CH$_2$—C$_3$-C$_6$ cycloalkyl, R$^{19}$ is H, C$_1$-C$_8$ alkyl, phenyl or substituted phenyl, and LG is a leaving group.

Any suitable coupling agent can be used in the method of making the compound of Formula VIII, as described above for the method of making the compound of Formula V. In some embodiments, the coupling agent can be a magnesium coupling agent. In some embodiments, the coupling agent can be MgCl$_2$, iPrMgCl, tBuMgCl, PhMgCl, or combinations thereof. In some embodiments, the coupling agent can be MgCl$_2$.

Any suitable non-nucleophilic base can be used in the method of making the compound of Formula VIII. Representative non-nucleophilic bases include, but are not limited to, triethylamine, diisopropylethyl amine, N,N-diethylaniline, pyridine, 2,6-lutidine, 2,4,6-collidine, 4-dimethylaminopyridine, and quinuclidine. In some embodiments, the non-nucleophilic base can be di-isopropyl ethyl amine (DIPEA).

The hydroxy protecting groups, as described above for the method of making the compound of Formula V. Exemplary hydroxy protecting group can be benzyl, SiR$_3$, wherein each R group can be hydrogen, alkyl, alkenyl, cycloalkyl, phenyl, or other silicon containing groups, or the PG groups can be combined to form an acetonide. Exemplary silanes include, but are not limited to tert-butyldimethylsilyl (TBS). Exemplary acetonides include, but are not limited to acetonide and benzylidene acetal. In some embodiments, the hydroxy protecting groups of hydroxy groups on adjacent carbons can be combined to form acetonide. In some embodiments, the PG groups are combined to form —C(R$^{19}$)$_2$—. In some embodiments, each R$^a$ is the protecting group PG where the PG groups are combined to form —C(Me)$_2$-. In other embodiments, PG is a SiR$_3$. In other embodiments, PG is tert-butyldimethylsilyl (TBS).

When the R$^e$ group is C$_1$-C$_8$ alkyl, each R$^e$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, each R$^e$ group can be methyl.

When the R$^f$ group is C$_1$-C$_8$ alkyl, R$^f$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the R$^f$ group can be methyl, ethyl, isopropyl, t-butyl, or iso-hexyl. When the R$^f$ group is C$_3$-C$_6$ cycloalkyl, R$^f$ can be cyclopropyl, cyclobutyl, cyclopentyl or cyclohexyl. In some embodiments, R$^f$ can be cyclobutyl, cyclopentyl or cyclohexyl.

When the R$^{19}$ group is C$_1$-C$_8$ alkyl, R$^{19}$ can be methyl, ethyl, propyl, isopropyl, butyl, iso-butyl, sec-buty, t-butyl, pentyl, iso-pentyl, neo-pentyl, hexyl, isohexyl, neohexyl, septyl or octyl. In some embodiments, the R$^{19}$ group can be methyl.

When the R$^{35}$ group is a hydroxy protecting group, R$^{35}$ can be any example protecting group described in *Protective Groups in Organic Chemistry*, Peter G. M. Wuts and Theodora W. Greene, 4th Ed., 2006. In some embodiments, the R$^{35}$ group can be benzyl. In some embodiments, the R$^{35}$ group can be TBS.

The leaving group can be any suitable leaving group. Suitable leaving groups LG include, but are not limited to, chloride, bromide, mesylate, tosylate, triflate, 4-nitrobenzenesulfonate, 4-chlorobenzenesulfonate, 4-nitrophenoxy, pentafluorophenoxy, etc.

In some embodiments, the leaving group LG can be 4-nitrophenoxy or pentafluorophenoxy. In some embodiments, the leaving group LG can be 4-nitrophenoxy.

In some embodiments, each R$^a$ is PG where the PG groups are combined to form —C(R$^{19}$)$_2$—, R$^f$ is C$_1$-C$_8$ alkyl, R$^{19}$ is C$_1$-C$_8$ alkyl, and the leaving group LG is 4-nitrophenoxy or pentafluorophenoxy.

In some embodiments, the coupling agent is MgCl$_2$, and the non-nucleophilic base is di-isopropyl ethyl amine.

In some embodiments, the compound of Formula VIII can be

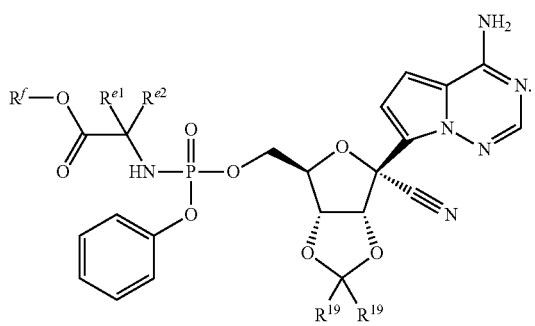

In some embodiments, the compound of Formula VIII can be

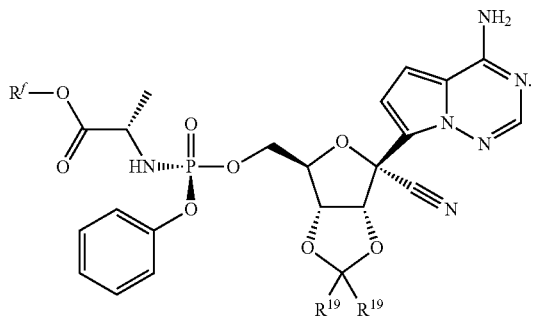

In some embodiments, the compound of Formula VIII can be

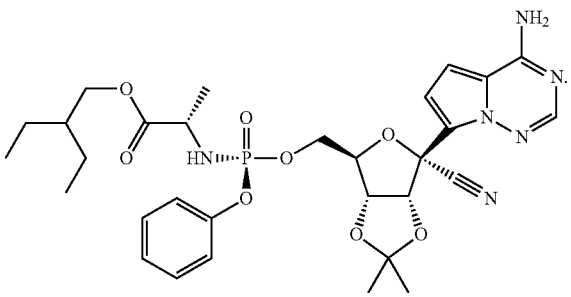 [SMILES: CCC(CC)COC(=O)[C@H](C)N[P@](=O)(OC[C@H]1O[C@@](C#N)(c2ccc3c(N)ncnn23)[C@@H]2OC(C)(C)O[C@@H]21)Oc1ccccc1]

In some embodiments, the method of making the compound Formula VIII comprises forming the reaction mixture including MgCl$_2$, DIPEA, the compound of Formula IX:

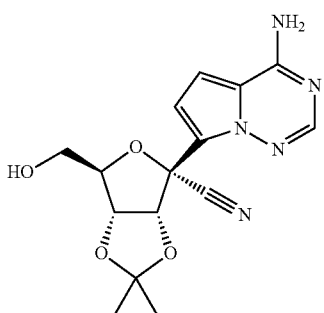 [SMILES: CC1(C)O[C@H]2[C@@H](O1)[C@](C#N)(c1ccc3c(N)ncnn13)O[C@@H]2CO]

and the compound of Formula X:

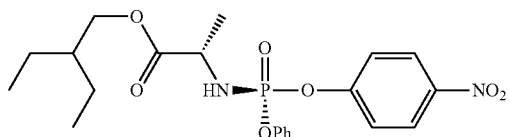

under conditions suitable to form the compound of Formula VIII:

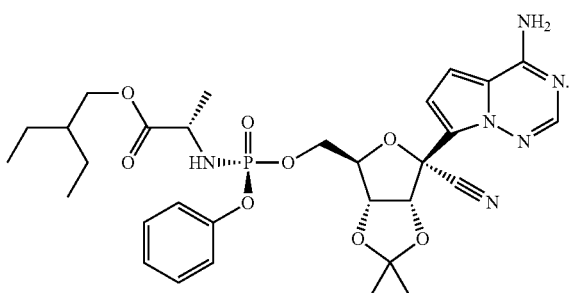

When the $R^a$ groups of the compound of Formula VIII are the hydroxy protecting groups PG, the method can include the additional step of removing the protecting groups to form the compound of Formula VIII where each $R^a$ is H. In some embodiments, the method of preparing the compound of Formula VIII comprises forming a second reaction mixture including a deprotection agent and the compound Formula VIII wherein each $R^a$ group is the protecting group PG, under suitable conditions to form the compound of Formula VIII where each $R^a$ is H. The deprotection agent can be any suitable agent to remove the protecting groups PG such as hydrogen and a hydrogenation catalyst, or acid. For example, if the protecting group PG is benzyl, the deprotection agent can be hydrogen and platinum on carbon. Alternatively, when the protecting group PG is an acetonide, the deprotection agent can be an acid. Representative acids include, but are not limited to, acetic acid, glacial acetic acid, trifluoroacetic acid (TFA), hydrochloric acid, concentrated hydrochloric acid, formic acids, toluenesulfonic acid, sulfuric acid, and others. Additional representative acids include, but are not limited to those found in Greene, T. W.; Wuts, P. G. M. *Protective Groups In Organic Synthesis*, 4th Ed., John Wiley & Sons: New York, 2006. In some embodiments, the method of preparing the compound of Formula VIII comprises forming a second reaction mixture including an acid and the compound Formula VIII wherein the $R^a$ groups are combined to form —$C(R^{19})_2$—, under suitable conditions to form the compound of Formula VIII where each $R^a$ is H. In some embodiments, the acid can be hydrochloric acid. Alternatively, when the protecting group PG is $SiR_3$, the deprotection agent can be TBAF, pyridine HF, HCl, TsOH, camphor sulfonic acid, AcCl in MeOH, $BF^3OEt^2$, TFA, AcOG, Formic Acid, HBr, F, HF, $Et_3N$—HF, KF—$H_2O$, $KHF_2$, NaF, LiF, LiCl, LiBr, LiI, and others.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, acetone, ethyl acetate, diethyl ether, tetrahydrofuran, acetonitrile, or combinations thereof. In some embodiments, the solvent can be acetonitrile. In some embodiments, the solvent can be MeCN. In some embodiments, the solvent can be tetrahydrofuran.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can also be exposed to any suitable environment, such as atmospheric gasses, or inert gasses such as nitrogen or argon.

The method of the present invention can provide the compound of Formula VIII in any suitable yield. For example, the compound of Formula VIII can be prepared in a yield of at least about 50%, 55, 60, 65, 70, 75, 80, 85, 90 or at least about 95%.

The method of the present invention can provide the compound of Formula VIII in any suitable purity. For example, the compound of Formula VIII can be prepared in a purity of at least about 90, 95, 96, 97, 98 or at least about 99%. In some embodiments, the compound of Formula VIII can be prepared in at least about 95% purity. In some embodiments, the compound of Formula VIII can be prepared in at least about 98% purity. In some embodiments, the compound of Formula VIII can be prepared in at least about 99% purity.

In some embodiments, the compound of Formula VIII can be

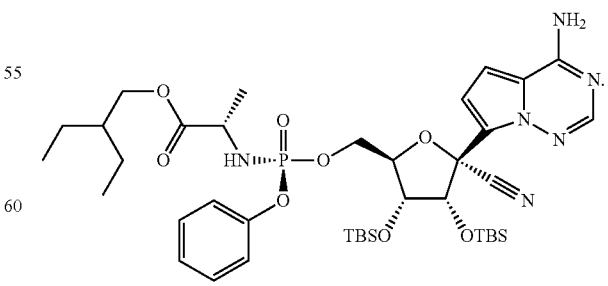

In some embodiments, the method of making the compound Formula VIII comprises forming the reaction mixture including $MgCl_2$, DIPEA, the compound of Formula IX-$a^2$:

(Formula IX-a²)

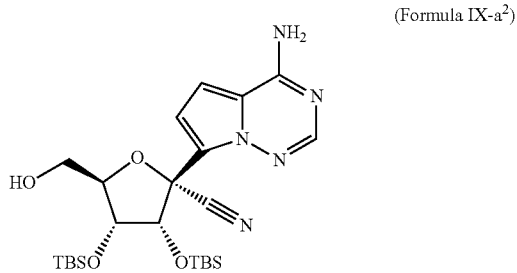 [SMILES: CC(C)(C)[Si](C)(C)O[C@H]1[C@@H](O[Si](C)(C)C(C)(C)C)[C@](C#N)(c2ccc3c(N)ncnn23)O[C@@H]1CO]

and the compound of Formula X:

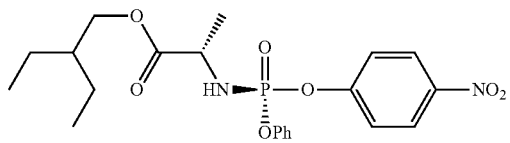 [SMILES: CCC(CC)COC(=O)[C@H](C)N[P@](=O)(Oc1ccccc1)Oc1ccc([N+](=O)[O-])cc1]

under conditions suitable to form the compound of Formula VIII:

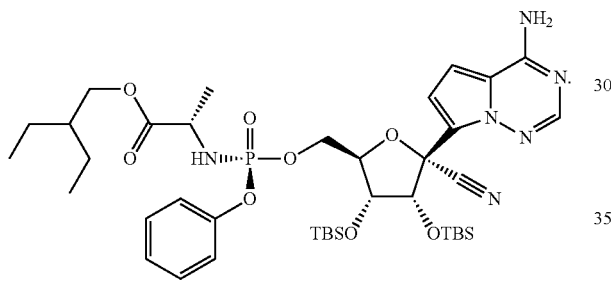

The method can include the additional step of removing the protecting groups to form the compound of Formula VIII where each TBS is H.

The reaction mixture of the method can be at any suitable temperature. For example, the temperature of the reaction mixture can be of from about −78° C. to about 100° C., or of from about −50° C. to about 100° C., or of from about −25° C. to about 50° C., or of from about −10° C. to about 25° C., or of from about 0° C. to about 20° C. In some embodiments, the temperature of the reaction mixture can be of from about 0° C. to about 20° C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula VIII in any suitable yield. For example, the compound of Formula VIII can be prepared in a yield of at least about 50%, 55, 60, 65, 70, 75, 80, 85, 90 or at least about 95%.

The method of the present invention can provide the compound of Formula VIII in any suitable purity. For example, the compound of Formula VIII can be prepared in a purity of at least about 90, 95, 96, 97, 98 or at least about 99%. In some embodiments, the compound of Formula VIII can be prepared in at least about 95% purity. In some embodiments, the compound of Formula VIII can be prepared in at least about 98% purity. In some embodiments, the compound of Formula VIII can be prepared in at least about 99% purity.

D. Preparation of Formula X-b by Crystallization-Induced Dynamic Resolution

In one embodiment, there is provided a method for the crystallization-induced dynamic resolution of (2S)-2-ethylbutyl 2-(((4-nitrophenoxy)(phenoxy)phosphoryl)amino) propanoate (Formula X-a):

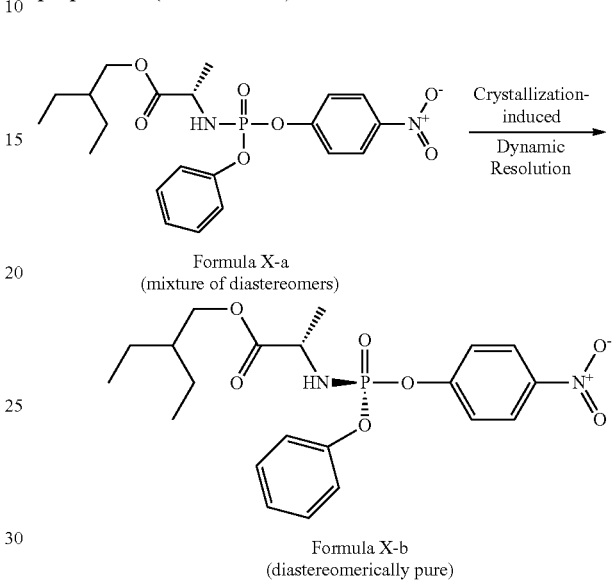

to provide (S)-2-ethylbutyl 2-(((S)-(4-nitrophenoxy)(phenoxy)phosphoryl)amino)propanoate (Formula X-b). The method comprises subjecting a solution comprising: a) a suitable solvent; b) a suitable base; c) (2S)-2-ethylbutyl 2-(((4-nitrophenoxy)(phenoxy)phosphoryl)amino)propanoate; and, optionally, d) one or more seed crystals of (S)-2-ethylbutyl 2-(((S)-(4-nitrophenoxy)(phenoxy)phosphoryl) amino)propanoate, to conditions that provide for the epimerization of the phosphorus center, under conditions that also provide selective crystallization of (S)-2-ethylbutyl 2-(((S)-(4-nitrophenoxy)(phenoxy)phosphoryl)amino)propanoate.

The crystallization can be carried out in any suitable solvent. For example, it can be carried out in an aprotic organic solvent, or in a mixture thereof. For example, the aprotic organic solvent may comprise ethyl acetate, methyl acetate, propyl acetate, isopropyl acetate, diethyl ether, diisopropyl ether, tetrahydrofuran, dichloromethane, acetone, methyl ethyl ketone, methyl tert-butylether, toluene, or acetonitrile, or a mixture thereof. In one embodiment, the solvent comprises acetonitrile.

The resolution can be carried out in the presence of any suitable base. For example, the resolution can be carried out in the presence of a base selected from 1,5-diazobicyclo [4.3.0]non-5-ene (DBN), 1,8-diazabicyclo[5.4.0]undec-7-ene (DBU), 7-methyl-1,5,7-triazabicyclo[4.4.0]dec-5-ene (MTBD), triethylamine (Et$_3$N), Hunig's Base (iPr$_2$NEt), tetramethylguanidine, a Verkade base (e.g., 2,8,9-triisopropyl-2,5,8,9-tetraaza-1-phosphabicyclo[3.3.3]undecane, and 2,8,9-triisobutyl-2,5,8,9-tetraaza-1-phosphabicyclo[3.3.3] undecane), a metal carbonate (e.g., M$_x$CO$_3$), a metal phenoxide (M$^+$ $^-$OPh), and PhOTMS in combination with a fluoride ion source (e.g., R$_4$N$^+$ $^-$F, TASF (tris(dimethylamino) sulfonium difluorotrimethylsilicate), or TBAT (tetrabutylammonium triphenyldifluorosilicate), and mixtures thereof, wherein each M is a suitable metal such as an alkali metal or an alkaline earth metal, and each R is, for example, a ($C_1$-$C_6$) alkyl. In one specific embodiment, the base is DBU.

The resolution can also be carried out at any suitable temperature, for example, a temperature in the range of from about 0° C. to about 50° C. In one specific embodiment, the resolution is carried out at a temperature of about 0° C.

In one specific embodiment, the resolution is carried out in the presence of phenol.

The percentage of (S)-2-ethylbutyl 2-(((S)-(4-nitrophenoxy)(phenoxy)phosphoryl)amino)propanoate in the starting diastereomeric mixture can be anywhere in the range from about 0% to about 99%. In one embodiment of the invention, the percentage of (S)-2-ethylbutyl 2-(((S)-(4-nitrophenoxy)(phenoxy)phosphoryl)amino)propanoate in the starting diastereomeric mixture is in the range from about 0% to about 20%. In one embodiment, the percentage of Compound (S)-2-ethylbutyl 2-(((S)-(4-nitrophenoxy)(phenoxy)phosphoryl)amino)propanoate in the starting diastereomeric mixture is in the range from about 20% to about 99%. In one embodiment, the percentage of Compound (S)-2-ethylbutyl 2-(((S)-(4-nitrophenoxy)(phenoxy)phosphoryl)amino)propanoate in the starting diastereomeric mixture is in the range from about 50% to about 99%. In one embodiment, the final Compound (S)-2-ethylbutyl 2-(((S)-(4-nitrophenoxy)(phenoxy)phosphoryl)amino)propanoate is at least about 90%, about 95%, about 97%, or about 99% diastereomerically pure. In one embodiment, the final Compound (S)-2-ethylbutyl 2-(((S)-(4-nitrophenoxy)(phenoxy)phosphoryl)amino)propanoate contains less than 1% of any diastereomeric impurities. In one embodiment, the final Compound (S)-2-ethylbutyl 2-(((S)-(4-nitrophenoxy)(phenoxy)phosphoryl)amino)propanoate is free of any detectable diastereomeric impurities.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| $Ac_2O$ | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |

TABLE 1-continued

List of abbreviations and acronyms.

| Abbreviation | Meaning |
|---|---|
| ESI | electrospray ionization |
| EtOAc | ethyl acetate |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| MTBE | tert-butylmethyl ether |
| NBS | N-bromosuccinimide |
| Ph | phenyl |
| rt or r.t. | room temperature |
| TBAF | tetrabutylammonium fluoride |
| THF | tetrahydrofuran |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

E. Preparation of Compounds

Example 1

(2S)-ethyl 2-(chloro(phenoxy)phosphorylamino)propanoate (Chloridate A)

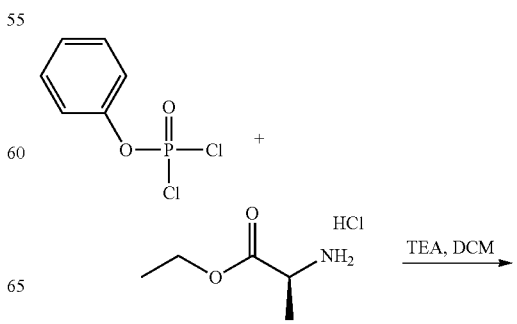

-continued

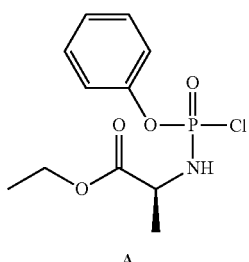

A

Ethyl alanine ester hydrochloride salt (1.69 g, 11 mmol) was dissolved in anhydrous $CH_2Cl_2$ (10 mL) and the mixture stirred with cooling to 0° C. under $N_2(g)$. Phenyl dichlorophosphate (1.49 mL, 10 mmol) was added followed by dropwise addition of $Et_3N$ over about 10 min. The reaction mixture was then slowly warmed to RT and stirred for about 12 h. Anhydrous $Et_2O$ (50 mL) was added and the mixture stirred for about 30 min. The solid that formed was removed by filtration, and the filtrate concentrated under reduced pressure. The residue was subjected to silica gel chromatography eluting with 0-50% EtOAc in hexanes to provide intermediate A. $^1$H NMR (300 MHz, $CDCl_3$) δ 7.39-7.27 (m, 5H), 4.27 (m, 3H), 1.52 (m, 3H), 1.32 (m, 3H). $^{31}$P NMR (121.4 MHz, $CDCl_3$) δ 8.2, 7.8.

Example 2

(2S)-2-ethylbutyl 2-(chloro(phenoxy)phosphorylamino)propanoate (Chloridate B)

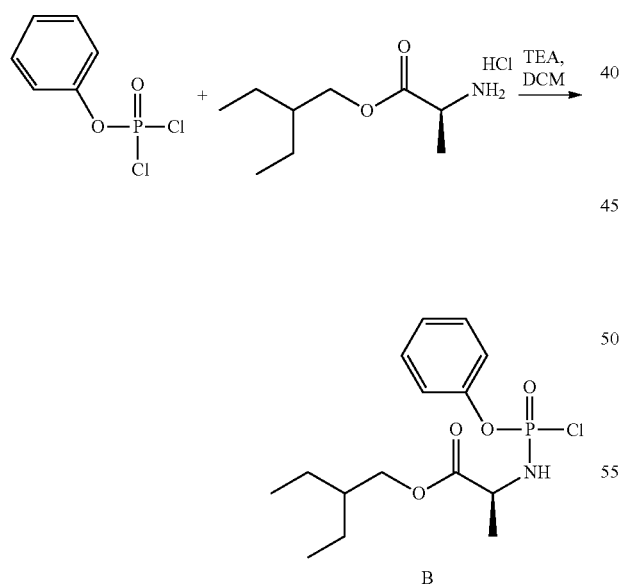

The 2-ethylbutyl alanine chlorophosphoramidate ester B was prepared using the same procedure as chloridate A except substituting 2-ethylbutyl alanine ester for ethyl alanine ester. The material is used crude in the next reaction. Treatment with methanol or ethanol forms the displaced product with the requisite LCMS signal.

Example 3

(2S)-isopropyl 2-(chloro(phenoxy)phosphorylamino)propanoate (Chloridate C)

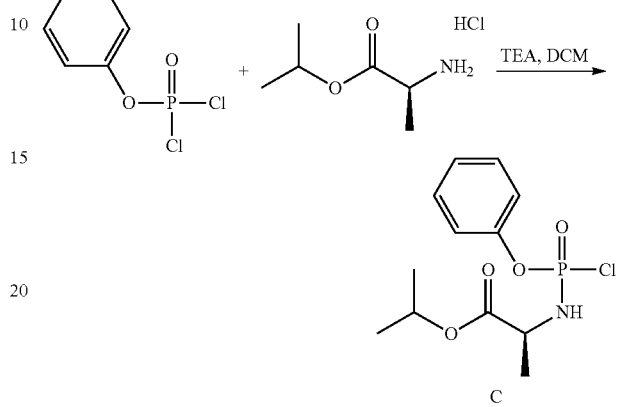

The isopropyl alanine chlorophosphoramidate ester C was prepared using the same procedure as chloridate A except substituting isopropyl alanine ester for the ethyl alanine ester. The material is used crude in the next reaction. Treatment with methanol or ethanol forms the displaced product with the requisite LCMS signal.

Example 4

(2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile (Compound 1)

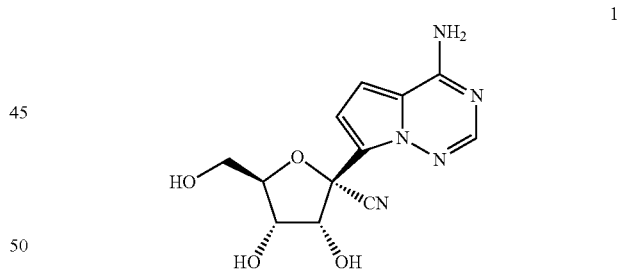

1

The preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile is described below.

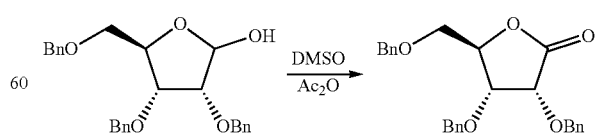

The commercially available lactol (10 g, 23.8 mmol) was dissolved in anhydrous DMSO (30 mL) under $N_2(g)$. $Ac_2O$ (20 mL) was added and the resultant reaction mixture stirred at RT for about 48 h. The reaction mixture was poured onto ice H₂O (500 mL) and the mixture stirred for 20 min. The mixture was extracted with EtOAc (3×200 mL) and the combined organic extracts were then washed with H₂O (3×200 mL). The organic extract was dried over anhydrous MgSO₄, filtered and concentrated under reduced pressure. The residue was dissolved in CH₂Cl₂ and subjected to silica gel chromatography eluting with 25% EtOAc in hexanes to provide the lactone. ¹H NMR (400 MHz, DMSO) δ 7.30-7.34 (m, 13H), 7.19-7.21 (m, 2H), 4.55-4.72 (m, 6H), 4.47 (s, 2H), 4.28 (d, J=3.9 Hz, 1H), 3.66 (m, 2H). LCMS m/z 436.1 [M+H₂O], 435.2 [M+OH]- Tr=2.82 min. HPLC Tr=4.59 [2-98% ACN in H2) over 5 min at 2 mL/min flow.

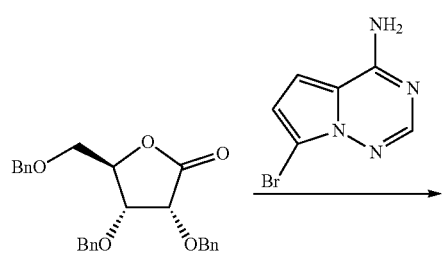

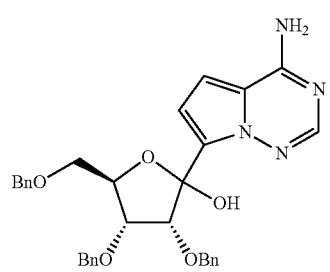

The bromopyrazole (prepared according to WO2009/132135) (0.5 g, 2.4 mmol) was suspended in anhydrous THF (10 mL) under N₂(g). The suspension was stirred and TMSCl (0.67 mL, 5.28 mmol) was added. The mixture was stirred for 20 min. at RT and then cooled to about −78° C. after which time a solution of n-BuLi (6 mL, 1.6 N in hexanes, 9.6 mmol) was added slowly. The reaction mixture was stirred for 10 min. at about −78° C. and then the lactone (1 g, 2.4 mmol) was added via syringe. When the reaction was complete as measured by LCMS, AcOH was added to quench the reaction. The mixture was concentrated under reduced pressure and the residue dissolved in a mixture of CH₂Cl₂ and H₂O (100 mL, 1:1). The organic layer was separated and washed with H₂O (50 mL). The organic layer was then dried over anhydrous MgSO₄, filtered and concentrated under reduced pressure. The residue was subjected to silica gel chromatography eluting with 0-50% EtOAc in hexanes to provide the product as a 1:1 mixture of anomers. LCMS m/z 553 [M+H].

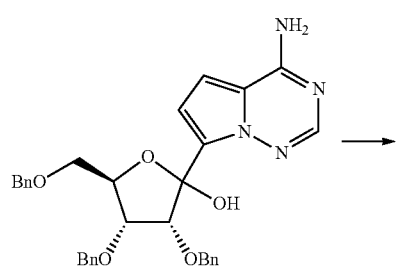

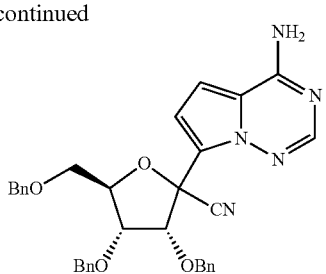

The hydroxy nucleoside (1.1 g, 2.0 mmol) was dissolved in anhydrous CH₂Cl₂ (40 mL) and the solution cooled with stirring to about −78° C. under N₂(g). TMSCN (0.931 mL, 7 mmol) was added and the mixture stirred for a further 10 min. TMSOTf (1.63 mL, 9.0 mmol) was slowly added to the reaction and the mixture stirred for 1 h. The reaction mixture was then diluted with CH₂Cl₂ (120 mL) and aqueous NaHCO₃ (120 mL) was added to quench the reaction. The reaction mixture was stirred for a further 10 min and the organic layer separated. The aqueous layer was extracted with CH₂Cl₂ (150 mL) and the combined organic extracts dried over anhydrous MgSO₄, filtered and concentrated under reduced pressure. The residue was dissolved in a minimal amount of CH₂Cl₂ and subjected to silica gel chromatography eluting with a gradient of 0-75% EtOAc and hexanes to provide the tribenzyl cyano nucleoside as a mixture of anomers. ¹H NMR (300 MHz, CD₃CN) δ 7.94 (s, 0.5H), 7.88 (s, 0.5H), 7.29-7.43 (m, 13H), 7.11-7.19 (m, 1H), 6.82-6.88 (m, 1H), 6.70-6.76 (m, 1H), 6.41 (bs, 2H), 5.10 (d, J=3.9 Hz, 0.5H), 4.96 (d, J=5.1 Hz, 0.5H), 4.31-4.85 (m, 7H), 4.09-4.18 (m, 2H), 3.61-3.90 (m, 2H). LCMS m/z 562 [M+H].

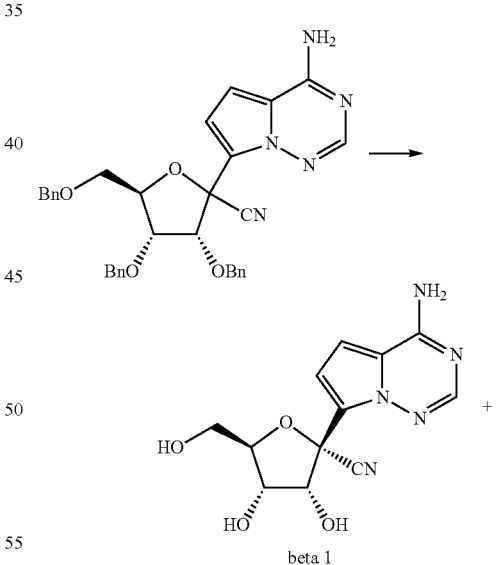

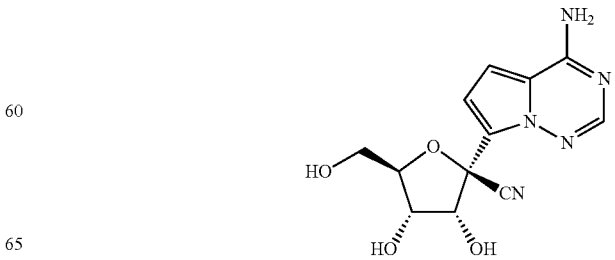

The tribenzyl cyano nucleoside (70 mg, 0.124 mmol) was dissolved in anhydrous CH$_2$Cl$_2$ (2 mL) and cooled to about −20° C. under N$_2$(g). A solution of BCl$_3$ (1N in CH$_2$Cl$_2$, 0.506 mL, 0.506 mmol) was added and the reaction mixture stirred for 1 h. at −78° C. When the reaction was complete by LC/MS, MeOH was added to quench the reaction. The reaction mixture was allowed to warm to RT and the solvent removed under reduced pressure. The residue was subjected to C18 reverse phase HPLC, eluting for 5 min with H$_2$O (0.1% TFA), followed by a gradient of 0-70% MeCN in H$_2$O (0.1% TFA) over 35 min, to elute the α-anomer, and β-anomer 1. (α-anomer) $^1$H NMR (300 MHz, D$_2$O) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H). (β-anomer)$^1$H NMR (400 MHz, DMSO) δ 7.91 (s, 1H), 7.80-8.00 (br s, 2H), 6.85-6.89 (m, 2H), 6.07 (d, J=6.0 Hz, 1H), 5.17 (br s, 1H), 4.90 (br s, 1H), 4.63 (t, J=3.9 Hz, 1H), 4.02-4.06 (m, 1H), 3.94 (br s, 1H), 3.48-3.64 (m, 2H). LCMS m/z 292.2 [M+H], 290.0 [M−H]. Tr=0.35 min. 13C NMR (400 MHZ, DMSO), 156.0, 148.3, 124.3, 117.8, 117.0, 111.2, 101.3, 85.8, 79.0, 74.7, 70.5, 61.4. HPLC Tr=1.32 min Example 4-a (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile (Compound 1)

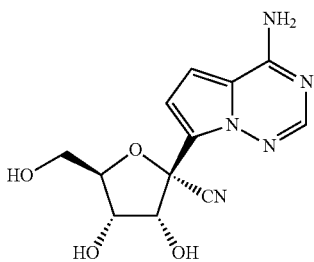

The preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile is described below.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol using LaCl$_3$-2LiCl

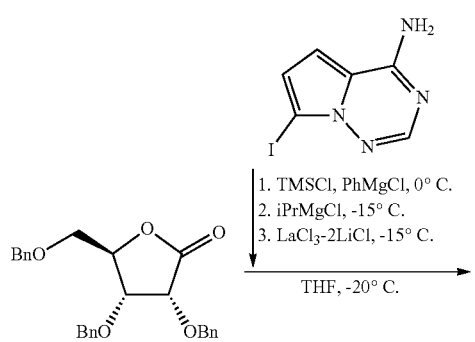

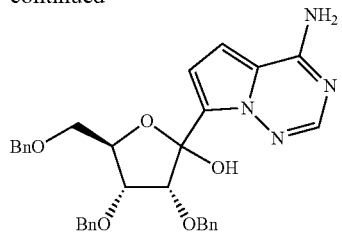

A solution of 7-iodopyrrolo[2,1-f][1,2,4]triazin-4-amine (7.5 g, 28.8 mmol, 1.0 equiv) was prepared in THF (67 mL). The solution was cooled to about 0° C., and TMSCl (3.3 mL, 30.3 mmol, 1.05 equiv) was added. The reaction mixture was stirred for about 30 min, and then PhMgCl (2 M in THF; 28 mL, 56.8 mmol, 1.97 equiv) was added while maintaining an internal temperature below 5° C. The reaction mixture was agitated at about 0° C. for about 35 min, and then cooled to about −15° C. iPrMgCl (2 M in THF, 14 mL, 30.2 mmol, 1.05 equiv) was then added while maintaining an internal temperature below about −10° C. After approximately 15 minutes at about −15° C., LaCl$_3$-2LiCl (0.6 M in THF, 50 mL, 14.4 mmol, 0.5 equiv) was added while maintaining an internal temperature below about −15° C. The reaction mixture was agitated for about 25 min at about −20° C.

In a separate flask, a solution of (3R,4R,5R)-3,4-bis(benzyloxy)-5-((benzyloxy)methyl)dihydrofuran-2(3H)-one (10.0 g, 23.9 mmol, 0.83 equiv) was prepared in THF (45 mL). The solution was cooled to about −20° C., and then transferred to the Grignard solution while maintaining an internal temperature below about −15° C. The resulting reaction mixture was agitated at about −20° C. for about 30 min.

The reaction was quenched with 2 M HCl (53 mL), and the mixture warmed to about 15° C. iPrOAc (38 mL) was added, and the organic and aqueous phases were separated. The bottom aqueous layer was discharged, and the upper organic layer was washed sequentially with 2.5 wt % NaHCO$_3$ (53 mL), 2.5 wt % NaHCO$_3$ (53 mL), and 10 wt % NaCl (53 mL).

The organic phase was concentrated to about 45 mL, and then diluted with iPrOAc (75 mL). The solution was concentrated again to about 45 mL, and then diluted with iPrOAc (23 mL). The solution was concentrated to about 45 mL, and then filtered over a pad of Celite. The filtered solution was concentrated to about 26 mL, and then diluted with MTBE (75 mL). After 2 h, heptane (23 mL) was slowly added and the slurry was stirred at about 25° C. for about 2 h, and was then cooled to about −5° C. over about 8 h. The solids were isolated by filtration, and the filter cake was washed with MTBE/heptane (4:1, 23 mL). The solids were dried in a vacuum oven at no more than about 35° C. to afford (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol using CeCl₃

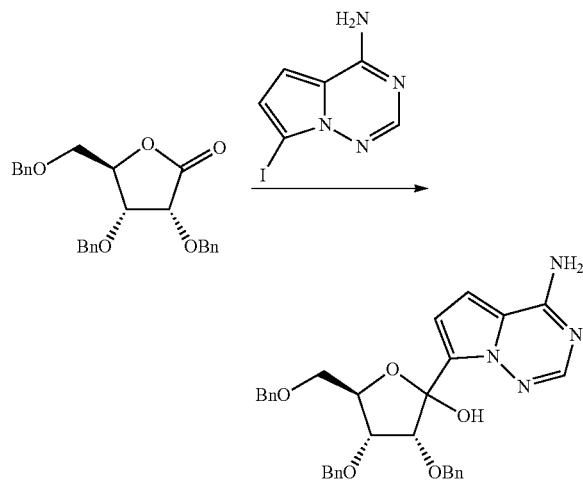

The iodopyrazole (5.02 g, 19.3 mmol) was dissolved in THF (45 g) and the solution was cooled to about 0° C. with stirring. TMSCl (2.04 g, 18.7 mmol) was added, and after about 1 h phenyl magnesium chloride (2.0 M in THF, 19.9 g, 38.2 mmol) was added. The reaction mixture was cooled to about −20° C. and iso-propyl magnesium chloride (2.0 M in THF, 9.99 g, 20.5 mmol) was added slowly. After about 30 min, the reaction mixture was transferred to a mixture of anhydrous cerium chloride (4.75 g, 19.3 mmol) in THF (22 g) at about −20° C. After about 1.5 h a solution of lactone (6.73 g, 16.1 mmol) in THF (22 g) was added slowly, and the resulting reaction mixture was stirred for about 1 h. 2 M HCl (41 g) was added, the mixture was warmed to about 15° C., and iso-propyl acetate (35 g) was added. The layers were separated and the organic layer was washed with 2.5% NaHCO₃ (2×40 g), 10% NaCl (1×35 g) and concentrated to about 30 mL volume. iso-Propyl acetate (44 g) was charged and the solution was concentrated to about 30 mL volume. iso-Propyl acetate (43 g) was charged and the solution was concentrated to about 30 mL volume. The solution was filtered and the filtrate was concentrated to about 18 mL volume. tert-Butylmethyl ether (37 g) was added followed by product seed crystals (10.7 mg). After about 14 h n-heptane (10.5 g) was added and the mixture was cooled to about −5° C. and filtered. The solids were washed with tert-butylmethyl ether (9 g) at about −5° C. and dried under vacuum at about 34° C. for about 15 h to provide the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol Using CeCl₃ and iPrMgCl—LiCl

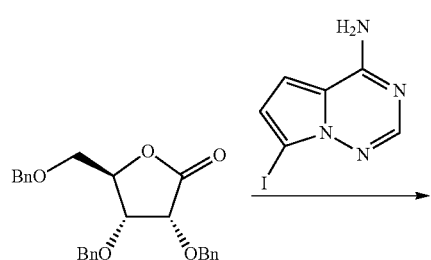

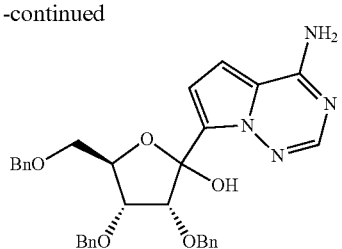

The iodopyrazole (5.03 g, 19.3 mmol) was dissolved in THF (45 g) and the solution was cooled to about 0° C. with stirring under N₂(g). TMSCl (2.06 g, 19.0 mmol) was added, and after about 1 h phenyl magnesium chloride (2.0 M in THF, 20.23 g, 38.8 mmol) was added. The reaction mixture was cooled to about −20° C. and iso-propyl magnesium chloride-lithium chloride complex (2.0 M in THF, 15.37 g, 21.0 mmol) was added slowly. After about 1 h, the reaction mixture was transferred to a mixture of cerium chloride (4.77 g, 19.4 mmol) in THF (22 g) at about −20° C. After about 1 h a solution of lactone (6.75 g, 16.1 mmol) in THF (23 g) was added slowly, and the resulting reaction mixture was stirred for about 1.5 h. 2 M HCl (40 g) was added, the mixture was warmed to about 15° C. and iso-propyl acetate (35 g) was added. The layers were separated and the organic layer was washed with 2.5% NaHCO₃ (2×40 g), 10% NaCl (1×36 g) and concentrated to about 30 mL volume. iso-Propyl acetate (44 g) was added and the solution was concentrated to about 30 mL volume. The solution was filtered and the filtrate was concentrated to about 18 mL volume. tert-Butylmethyl ether (37 g) was added followed by product seed crystals (10.5 mg). After about 14 h n-heptane (11 g) was added and the mixture was cooled to about −5° C. and filtered. The solids were washed with tert-butylmethyl ether (9 g) at about −5° C. and dried under vacuum at about 34° C. for about 15 h to provide the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol Using YCl₃

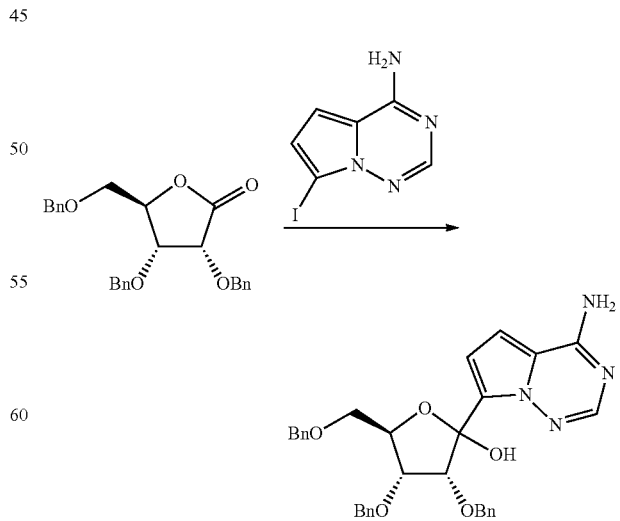

The iodopyrazole (4.99 g, 19.2 mmol) was dissolved in THF (44 g) and the solution was cooled to about 0° C. with stirring. TMSCl (2.45 mL, 19.4 mmol) was added, and after about 30 min phenyl magnesium chloride (2.0 M in THF, 20.29 g, 39.0 mmol) was added. The reaction mixture was cooled to about −20° C. and iso-propyl magnesium chloride (2.0 M in THF, 9.85 g, 20.1 mmol) was added slowly. After about 30 min, the reaction mixture was transferred into a mixture of anhydrous yttrium chloride (3.76 g, 19.3 mmol) and lactone (6.68 g, 16.0 mml) in THF (24 g) at about −20° C. After about 2.5 h 2 M HCl (30 g) was added, the mixture was warmed to about 15° C., and iso-propyl acetate (22 g) was added. The layers were separated and the organic layer was washed with 2.5% NaHCO₃ (2×40 g), 10% NaCl (1×35 g) and concentrated to about 30 mL volume. iso-Propyl acetate (44 g) was charged and the solution was concentrated to about 30 mL volume. iso-Propyl acetate (45 g) was charged and the solution was concentrated to about 30 mL volume. The solution was filtered and the filtrate was concentrated to about 18 mL volume. tert-Butylmethyl ether (37 g) was added followed by product seed crystals (11.5 mg). After about 1 h n-heptane (15 mL) was added and the mixture was cooled to about −5° C. and agitated for about 17 h. The slurry was filtered and the solids were washed with a tert-butylmethyl ether (8 g)/n-heptane (2 g) mixture precooled to about −5° C. The resulting solids were dried under vacuum at about 34° C. for about 22 h to afford the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol Using NdCl₃

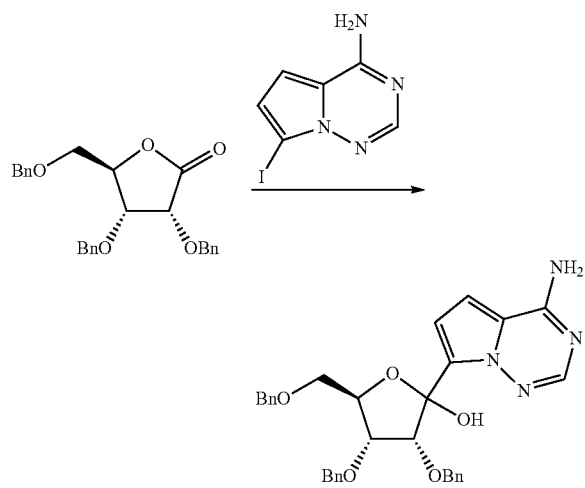

The iodopyrazole (5.02 g, 19.3 mmol) was dissolved in THF (38 g) and the solution was cooled to about 0° C. with stirring under N₂(g). TMSCl (2.45 mL, 19.4 mmol) was added, and after about 1 h phenylmagnesium chloride (2.0 M in THF, 19.75 g, 38.0 mmol) was added. The reaction mixture was cooled to about −20° C. and iso-propylmagnesium chloride (2.0 M in THF, 9.40 g, 19.2 mmol) was added slowly. After about 1.5 h, the reaction mixture was transferred into a mixture of anhydrous neodymium (III) chloride (4.03 g, 16.1 mmol) and lactone (6.70 g, 16.0 mml) in THF (22 g) at about −20° C. After about 1.5 h the reaction mixture was warmed to −10° C. and, after an additional 2 h, 2 M HCl (36 g) was added. The mixture was warmed to about 15° C. and iso-propyl acetate (23 g) was added. The layers were separated and the organic layer was washed with 2.5% NaHCO₃ (2×44 g), 10% NaCl (1×41 g) and concentrated to about 30 mL volume. iso-Propyl acetate (44 g) was charged and the solution was concentrated to about 30 mL volume. iso-Propyl acetate (45 g) was charged and the solution was concentrated to about 30 mL volume. The solution was filtered and the filtrate was concentrated to about 18 mL volume. tert-Butylmethyl ether (37 g) was added followed by product seed crystals (11.9 mg). After about 1 h n-heptane (15 mL) was added and the mixture was cooled to about −5° C. and agitated for about 15 h. The slurry was filtered and the solids were washed with a tert-butylmethyl ether (8 g)/n-heptane (11 g) mixture precooled to about −5° C. The resulting solids were dried under vacuum at about 34° C. for about 25 h to afford the product.

Preparation of (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile

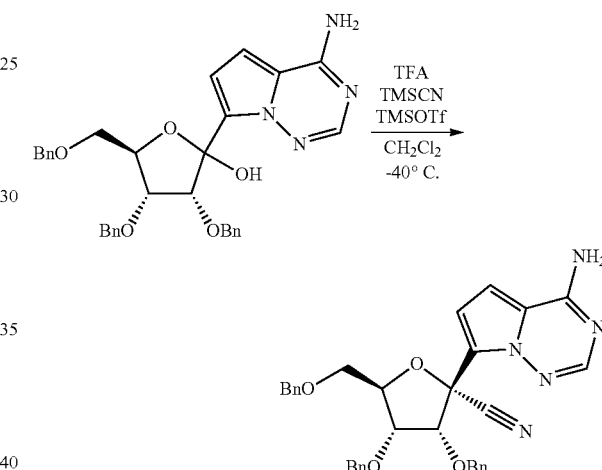

To a pre-cooled (−40° C.) solution of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol (10.0 grams, 18.1 mmols, 1.0 equiv.) in DCM (100 mL) was charged trifluoroacetic acid (6.19 grams, 54.3 mmols, 3.0 equiv.), followed by a pre-cooled (−30° C.) solution of TMSOTf (24.1 grams, 108.6 mmols, 6.0 equiv.) and TMSCN (10.8 grams, 108.6 mmols, 6.0 equiv.) in DCM (50 mL) while maintaining the internal temperature below about −25° C. The reaction mixture was agitated at below about −30° C. for no less than 10 minutes and quenched into a pre-cooled (about −10° C.) solution of 20 wt. % KOH aq. (120 mL). The bi-phasic mixture was warmed to ambient temperature. The organic layer was separated and washed with 10 wt. % NaCl aq. (3×50 mL). The organic phase was filtered, concentrated under vacuum to about 50 mL, re-diluted with toluene (200 mL) and concentrated under vacuum to 140 mL at about 50° C. The solution was seeded with (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile at about 55° C. Agitated at about 55° C. for about an hour and cooled to about 0° C. over about 6 hours. The solids were isolated by filtration and the filter cake was washed with toluene (30 mL). The solids were dried under vacuum at about 50° C.

Preparation of (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile via Flow Chemistry

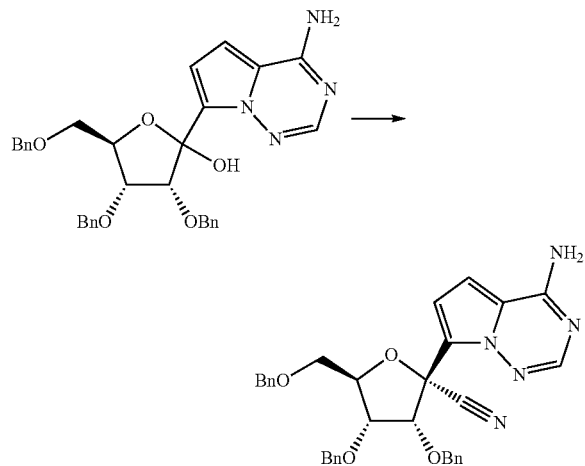

Solutions of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol (23.0 g in 460.07 g of DCM), TMSOTf (55.81 g in 138.07 g of DCM) and TMSCN (25.03 g in 138.10 g of DCM) were sequentially pumped, into a tube reactor at about −40° C. The reaction mixture was collected in a flask, kept in ice bath, containing 20% KOH aqueous solution (46.91 g KOH and 210 g of water). The layers were separated and the organic phase was sequentially washed with 10% KOH aqueous solution (10 g KOH and 90 mL of water) and with 10% brine (2×100 g). The organic phase was concentrated under vacuum to about 4 volumes, isopropyl alcohol was charged (162.89 g) and the mixture was concentrated under vacuum to about 10 volumes. The contents were warmed to about 60° C., then adjusted to about 0° C. over about 6.5 h and agitated at about 0° C. for about 15.5 h. The resulting slurry was filtered, the solids were rinsed with isopropyl alcohol (61.79 g) and then dried at about 50° C. under reduced pressure overnight to afford the product.

Preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile

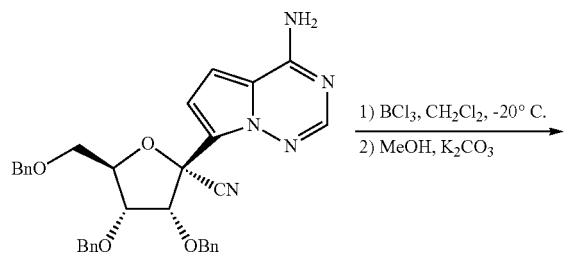

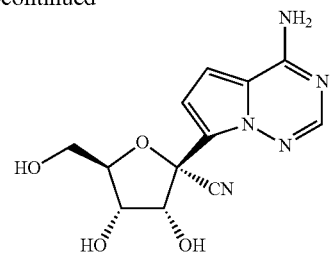

The tribenzyl cyano nucleoside (48.8 g, 86.9 mmol, 1.0 equiv.) was dissolved in anhydrous $CH_2Cl_2$ (244 mL) and cooled to about −20° C. A solution of $BCl_3$ (1M in $CH_2Cl_2$, 295 mL, 295 mmol, 3.4 equiv.) was added dropwise, maintaining the internal temperature below about −15° C. Following addition, the reaction mixture was stirred for 1 h at about −20° C. MeOH (340 ml) was added dropwise, maintaining the internal temperature below −15° C. The resulting solution was distilled to about 250 ml, then refilled with about 250 ml MeOH. The resulting solution was again distilled to about 250 ml, then refilled with about 250 ml MeOH, and finally distilled to about 125 ml. Water (125 ml) was added, followed by $K_2CO_3$ solution (20 wt % in water, 125 ml). The pH was checked, and found to be ~3. $K_2CO_3$ solution was added (20 wt % in water, 50 ml), and the pH was found to be ~8. The resulting slurry was stirred overnight, then filtered and washed with water (50 ml) and MeOH (50 ml). The wet product cake was dried overnight at about 40° C. overnight. $^1$H NMR (300 MHz, $D_2O$) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H).

Example 5

(2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (Compound 2)

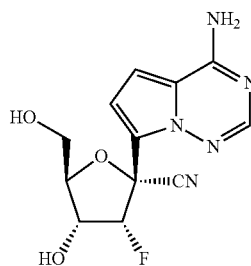

The preparation of (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile is described below.

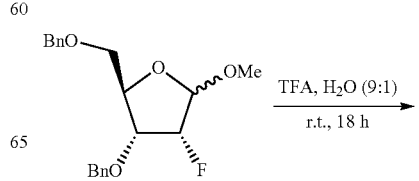

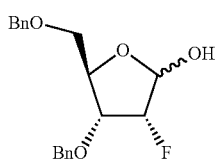

2-Deoxy-2-fluoro-4,5-O,O-dibenzyl-D-arabinose. 1'-Methoxy-2-deoxy-2-fluoro-4,5-O,O-dibenzyl-D-arabinose (1.0 g, 2.88 mmol) in TFA (13.5 mL) was treated with H$_2$O (1.5 mL) and the resultant mixture stirred for 5 h. The mixture was then diluted with EtOAc (100 mL) and treated with saturated NaHCO$_3$ (50 mL). The organic layer was separated and washed with NaCl (50 mL), dried over anhydrous MgSO$_4$, filtered and concentrated under reduced pressure. The residue was subjected to silica gel chromatography (80 g SiO$_2$ Combiflash HP Gold Column) eluting with 0-100% EtOAc in hexanes to afford 2-deoxy-2-fluoro-4,5-O,O-dibenzyl-D-arabinose as a white solid: R$_f$=0.52 (25% EtOAc in hexanes). $^1$H NMR (300 MHz, CDCl$_3$) δ 7.30 (m, 10H), 5.35 (m, 1H), 4.68-4.29 (m, 7H), 3.70 (d, J=10.5 Hz, 1H), 3.50 (d, J=10.5 Hz, 2H). $^{19}$F NMR (282.2 MHz, CDCl$_3$) δ −207 (m), −211 (m). LCMS m/z 350 [M+H$_2$O].

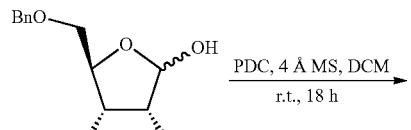

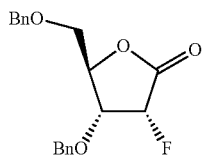

(3R,4R,5R)-4-(benzyloxy)-5-(benzyloxymethyl)-3-fluorodihydrofuran-2(3H)-one. 2-Deoxy-2-fluoro-4,5-O,O-dibenzyl-D-arabinose (4.3 g, 12.8 mmol) was dissolved in CH$_2$Cl$_2$ (85 mL) was treated with 4 Å MS (10 g) and pyridinium dichromate (14.4 g, 38.3 mmol). The resultant mixture was stirred for 24 h and then filtered through a pad of Celite®. The eluant was concentrated under reduced pressure and the residue subjected to silica gel chromatography (120 g SiO$_2$ HP Gold Combiflash Column) eluting with 0-100% EtOAc in hexanes to afford (3R,4R,5R)-4-(benzyloxy)-5-(benzyloxymethyl)-3-fluorodihydrofuran-2(3H)-one as a clear oil (3.5 g, 83%): R$_f$=0.25 (25% EtOAc in hexanes). $^1$H NMR (300 MHz, CDCl$_3$) δ 7.37 (m, 10H), 5.45 (dd, J=49, 5.7, Hz, 1H), 4.85 (d, J=11.7 Hz, 1H), 4.52 (m, 4 H), 4.29 (d, J=5.4 Hz, 1H), 2.08 (dd, J=15.3, 10.2 Hz, 2H). $^{19}$F NMR (282.2 MHz, CDCl$_3$) δ −216. LCMS m/z 348 [M+H$_2$O]. HPLC (6-98% MeCN—H$_2$O gradient, 0.05% TFA modifier) t$_R$=5.29 min. Phenomenex Synergi 4 m Hydro-RP 80 A, 50×4.60 mm, 4 micron; 2 mL/min flow rate

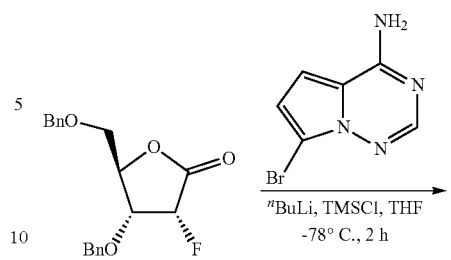

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol. 7-Bromopyrrolo[1,2-f][1,2,4]-triazin-4-amine (68 mg, 0.319 mmol) in THF (1.4 mL) was treated with TMSCl (89 µL, 0.703 mmol) and the mixture stirred for 2 h. The mixture was then cooled to about −78° C. and treated with nBuLi (1.0 M in hexanes, 1.09 mL, 1.09 mmol). The solution was stirred for about 30 min and then treated with (3R,4R,5R)-4-(benzyloxy)-5-(benzyloxymethyl)-3-fluorodihydrofuran-2(3H)-one (106 mg, 0.319 mmol) dropwise in THF (1.4 mL). The resultant mixture was stirred for 30 min and then AcOH (83 µL, 1.44 mmol) in THF (1.0 mL) was added to quench the reaction. The mixture was warmed to RT and then concentrated under reduced pressure. The residue was diluted with EtOAc (100 mL) and washed with saturated NaCl solution (50 mL). The organic layer was dried over anhydrous MgSO$_4$, filtered and concentrated under reduced pressure. The residue was subjected to silica gel chromatography (40 g SiO$_2$ HP Gold Combiflash Column) eluting with 0-100% EtOAc in hexanes followed by a 0-100% gradient of (20% MeOH in EtOAc) in EtOAc to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol as a white solid (68 mg, 44%, 60/40 mixture of α/β isomers). R$_f$=0.32 (EtOAc). $^1$H NMR (300 MHz, CDCl$_3$) δ 8.05 (s, 1H), 7.86 (s, 1H), 7.81 (s, 1H), 7.64 (s, 1H), 7.26 (m, 10H), 6.95 (m, 1H), 6.71 (m, 1H), 6.08 (m, 1H), 5.34 (m, 1H), 4.65 (m, 6H), 4.71 (m, 2H). $^{19}$F NMR (282.2 MHz, CDCl$_3$) δ −211 (m). LCMS m/z 465 [M+H]. HPLC (6-98% MeCN—H$_2$O gradient, 0.05% TFA modifier) t$_R$=4.37 min. (α-isomer), 4.54 min. (β-isomer).

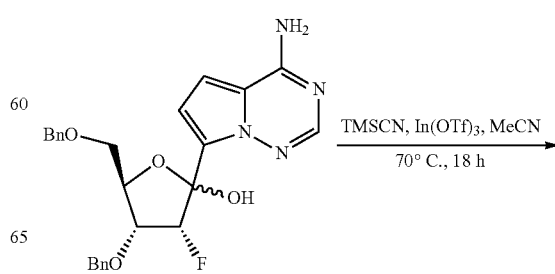

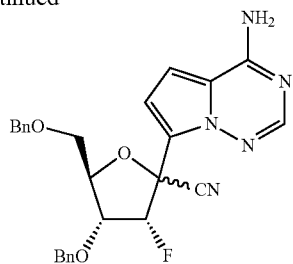

(3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile: (3R,4R,5R)-2-(4-aminopyrrolo[1,2-f][1,2,4]triazin-7-yl)-4-(benzyloxy)-5-(benzyloxymethyl)-3-fluorotetrahydrofuran-2-ol (195 mg, 0.42 mmol) was dissolved in MeCN (1.4 mL) was treated with TMSCN (336 μL, 2.52 mmol) and In(OTf)₃ (708 mg, 1.26 mmol). The solution was stirred at about 70° C. for 18 h and then cooled to about 0° C. The mixture was treated with saturated NaHCO₃ solution (20 drops) then warmed to RT and diluted with EtOAc (100 mL) and H₂O (50 mL). The organic layer was separated and washed with saturated NaCl solution (50 mL), dried over MgSO₄, filtered and concentrated under reduced pressure. The residue was subjected to silica gel chromatography (40 g SiO₂ HP Gold Combiflash Column) eluting with 0-100% EtOAc in hexanes to afford (3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile as a white solid (60/40 mixture of α/β isomers). Data for both isomers: R_f=0.53 (EtOAc). ¹H NMR (300 MHz, CDCl₃) δ 8.01 (s, 1H), 7.94 (s, 1H), 7.30 (m, 10H), 7.00 (d, J=4.5 Hz, 1H), 6.93 (d, J=4.8 Hz, 1H), 6.87 (d, J=5.4 Hz, 1H), 6.70 (d, J=4.8 Hz, 1H), 5.85 (dd, J=52, 3.3 Hz, 1H), 5.55 (dd, J=53, 4.5 Hz, 1H), 4.71 (m, 7H), 3.87 (m, 2H), 3.72 (m, 2H). ¹⁹F NMR (282.2 MHz, CDCl₃) δ −196 (m), −203 (m). LCMS m/z 474 [M+H]. HPLC (6-98% MeCN—H₂O gradient, 0.05% TFA modifier) t_R=4.98 min.

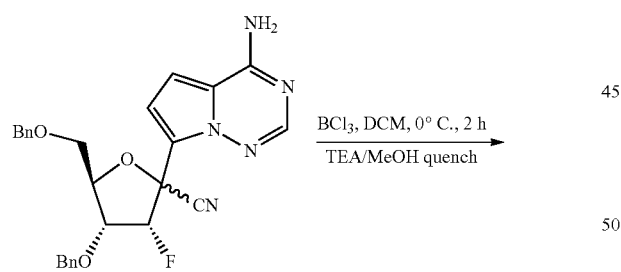

(2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile (2) (3R,4R,5R)-2-(4-aminopyrrolo[1,2-f][1,2,4]triazin-7-yl)-4-(benzyloxy)-5-(benzyloxymethyl)-3-fluorotetrahydrofuran-2-carbonitrile (110 mg, 0.23 mmol) was dissolved in CH₂Cl₂ (1.5 mL) and cooled to about 0° C. The reaction mixture was treated with BCl₃ (1.0 M in CH₂Cl₂, 766 μL, 0.77 mmol) and stirred for 2 h. The mixture was then cooled to about −78° C. and treated with Et₃N (340 μL, 2.44 mmol) followed by MeOH (2 mL) before allowing to warm to RT. The reaction was concentrated under reduced pressure and then co-evaporated with MeOH (3×5 mL). The residue was then suspended in H₂O (5 mL) and treated with NaHCO₃ (1 g). The solution was stirred for 10 min and then concentrated under reduced pressure. The residue was filtered and washed with MeOH (3×10 mL) on a fritted glass funnel (coarse) and the eluant concentrated under reduced pressure. The residue was subjected to reverse phase HPLC (6-98% MeCN in H₂O gradient with 0.05% TFA modifier) to afford (2R,3R,4R,5R)-2-(4-aminopyrrolo[1,2-f][1,2,4]triazin-7-yl)-3-fluoro-4-hydroxy-5-(hydroxymethyl)tetrahydrofuran-2-carbonitrile 2 as a white solid and the α-isomer. Data for the β-isomer: R_f=0.13 (10% MeOH in EtOAc). ¹H NMR (300 MHz, CD₃OD) δ 8.09 (s, 1H), 7.28 (d, J=5.1 Hz, 1H), 7.17 (d, J=5.1 Hz, 1H), 5.42 (dd, J=53, 3.3 Hz, 1H), 4.20 (m, 2H), 3.99 (d, J=3.6 Hz, 1H), 3.77 (d, J=3.6 Hz, 1H). ¹⁹F NMR (282.2 MHz, CDCl₃) δ −197 (m). LCMS m/z 294 [M+H]. HPLC (2-98% MeCN—H₂O gradient, 0.05% TFA modifier) t_R=1.49 min.

Example 6

(2R,3R,4R,5S)-5-(4-aminopyrrolo[1,2-f][1,2,4]triazin-7-yl)-4-fluoro-2-(hydroxymethyl)-5-methyltetrahydrofuran-3-ol (Compound 3)

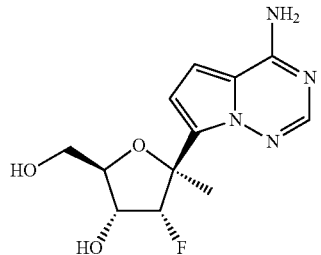

The preparation of (2R,3R,4R,5S)-5-(4-aminopyrrolo[1,2-f][1,2,4]triazin-7-yl)-4-fluoro-2-(hydroxymethyl)-5-methyltetrahydrofuran-3-ol is described below.

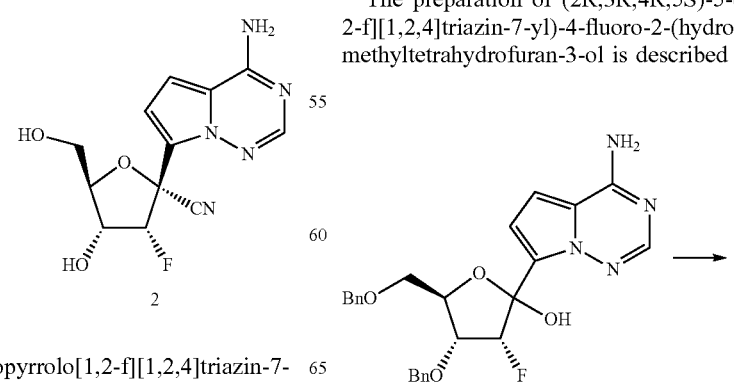

-continued

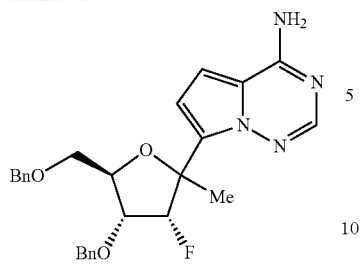

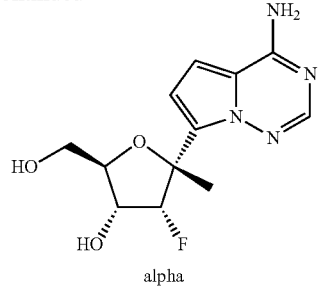
alpha

The starting nucleoside (prepared as described in the synthesis of compound 2) (0.355 g, 0.765 mmol) was dissolved in anhydrous THF (35 mL) and cooled to about 0° C. with stirring under N₂(g). A solution of methyl magnesium chloride (2 mL, 6 mmol) (3N in THF) was added and the resultant mixture stirred overnight. Acetic acid (7 mmol) was added to quench the reaction and then the solvents were removed by rotory under reduced pressure. The residue was re-dissolved in CH₂Cl₂ and the solution subjected to a plug of silica gel to isolate the product (0.355 g) as a crude mixture. LC/MS (m/z: 480, M$^{+1}$). The crude material was dissolved in anhydrous CH₂Cl₂ (20 mL) and placed under N₂(g). The solution was stirred and treated with methanesulfonic acid (0.2 mL, 2.74 mmol). The reaction mixture was stirred for about 12 h at RT and then quenched by the addition of Et₃N (3.5 mmol). The mixture was concentrated under reduced pressure and the residue subjected to silica gel chromatography to provide the methyl substituted nucleoside as a 4:1 mixture of beta- and alpha-anomers respectively. $^1$H NMR (300 MHz, CD₃CN) major anomer δ 7.87 (s, 1H), 7.27-7.40 (m, 10 H), 6.77 (d, J=4.5 HZ, 1H), 6.70 (d, J=4.5 Hz, 1H), 6.23 (br s, 2H), 5.53 (dd, J=55, 3.3 Hz, 1H), 4.42-4.75 (m, 4H), 4.19-4.26 (m, 1H), 3.65-4.00 (m, 3H), 1.74 (d, J=3.9 Hz, 3H). $^{19}$F NMR (282.2 MHz, CD₃CN) major anomer δ −207 (m, 1F). LCMS m/z 463 [M+H].

The benzylated nucleoside material (0.134 g, 0.290 mmol), Degussa catalyst (0.268 g) and AcOH (30 mL) were mixed together. The reaction atmosphere was charged with H₂ (g) and the reaction stirred for about 2 h. The catalyst was removed by filtration and the mixture concentrated under reduced pressure. The residue was dissolved in a minimal amount of H₂O and subjected to reverse phase HPLC (C$^{18}$ hydro RP column) to isolate the β-anomer 3. $^1$H NMR (300 MHz, D₂O) δ 7.87 (s, 1H), 7.22 (d, J=4.8 Hz, 1H), 6.87 (d, J=4.8 Hz, 1H), 5.35 (dd, J=54, 3.6 Hz, 1H), 3.97-4.10 (m, 2H), 3.81 (dd, J=12.6, 2.1 Hz, 1H), 3.64 (dd, J=12.6, 4.8 Hz, 1H), 1.65 (d, J=4.2 Hz, 3H). $^{19}$F NMR (282.2 MHz, CD₃CN) δ −207 (m, 1F).

A small amount of alpha anomer was characterized as follows. $^1$H NMR (300 MHz, D₂O) δ 7.86 (s, 1H), 7.26 (d, J=4.8 Hz, 1H), 6.85 (d, J=4.8 Hz, 1H), 5.31 (dd, J=54, 3.9 Hz, 1H), 4.39 (ddd, J=26.1, 9.9, 3.6 Hz, 2H), 4.00-4.05 (m, 1H), 3.90 (dd, J=12.3, 2.1 Hz, 1H), 3.66 (dd, J=12.6, 4.8, 1H), 1.56 (s, 3H). $^{19}$F NMR (282.2 MHz, CD₃CN) δ −198 (dd, J=54, 26 Hz, 1F).

Example 7

(2S)-isopropyl 2-(((((2R,3R,4R,5S)-5-(4-aminopyrrolo[2,1-f][1,2,4]triazin-7-yl)-4-fluoro-3-hydroxy-5-methyltetrahydrofuran-2-yl)methoxy)(phenoxy)phosphoryl)amino)propanoate (Compound 4)

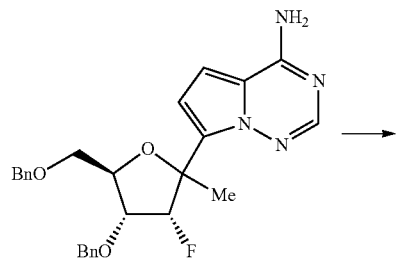

→

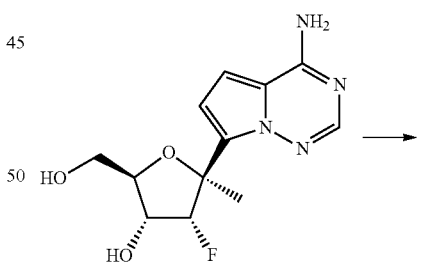
3

→

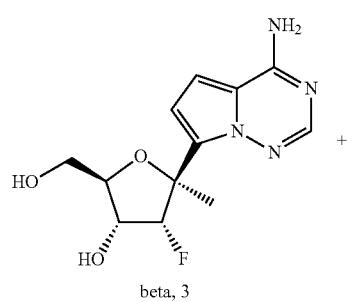
beta, 3

+

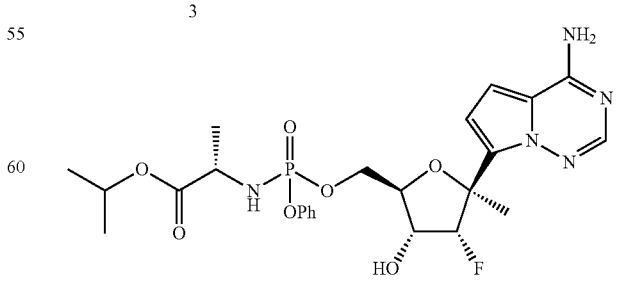
4

The nucleoside 3 (0.011 g, 0.04 mmol) was dissolved in trimethylphosphate (2 mL) and cooled to 0° C. The mixture was stirred under an atmosphere of $N_2(g)$ and 1-Methylimidazole (0.320 mL, 5 mmol) followed by the alaninylmonoisopropyl, monophenol phosphorchloridate C (0.240 mL, 4.4 mmol) was added. The reaction mixture was stirred for 2 h. at 0° C. and then allowed to warm slowly to RT. while monitoring by LC/MS. When complete by LCMS, the reaction mixture was treated with $H_2O$ (5 mL) and then concentrated under reduced pressure. The residue was dissolved in $CH_2Cl_2$ and subjected to silica gel chromatography eluting with 0-100% EtOAc in hexanes. The product fractions were collected and concentrated. The residue was subjected to prep HPLC to yield the alanine isopropyl monoamidate prodrug 4 as a mixture of isomers. $^1$H NMR (300 MHz, CD3CN) δ 7.87 (s, 1H), 7.17-7.44 (m, 5H), 6.71-6.83 (m, 2H), 6.14 (br, s, 2H), 5.38 (dd, J=56, 3.3 Hz, 1H), 4.92-5.01 (m, 1H), 3.86-4.46 (m, 6H), 3.58 (m, 1H), 1.73 (m, 3H), 1.18-1.34 (m, 9H). LCMS m/z 552 [M+H].

Example 8

(2S)-ethyl 2-(((((2R,3R,4R,5S)-5-(4-aminopyrrolo[2,1-f][1,2,4]triazin-7-yl)-4-fluoro-3-hydroxy-5-methyltetrahydrofuran-2-yl)methoxy)(phenoxy)phosphoryl)amino)propanoate (Compound 5)

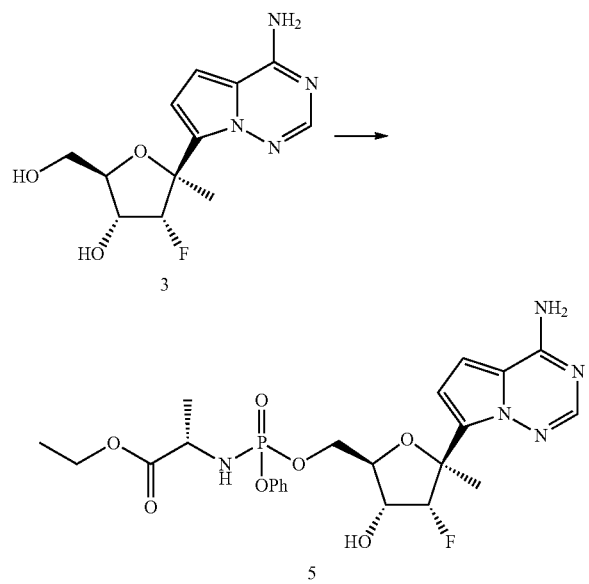

The nucleoside 3 (0.026 g, 0.092 mmol) was dissolved in trimethylphosphate (2 mL) and cooled to 0° C. The mixture was stirred under $N_2(g)$ and 1-methylimidazole (0.062 mL, 0.763 mmol) followed by the chloridate A (0.160 g, 0.552 mmol) were added. The reaction mixture was stirred for 2 h. at 0° C. and then allowed to warm slowly to RT. $H_2O$ (5 mL) was added to quench the reaction and then the mixture concentrated under reduced pressure. The residue was dissolved in $CH_2Cl_2$ and subjected to silica gel chromatography eluting with 0-100% EtOAc in hexanes. The product fractions were collected and concentrated. Crude product was eluted using 0 to 100 percent EtOAc in hexanes. The crude product was collected and concentrated under reduced pressure. The residue was subjected to prep HPLC to yield compound 5. LCMS m/z 538 [M+H].

Example 9

((2R,3R,4R,5S)-5-(4-aminopyrrolo[1,2-f][1,2,4]triazin-7-yl)-4-fluoro-3-hydroxy-5-methyltetrahydrofuran-2-yl)methyl tetrahydrogen triphosphate (Compound 6)

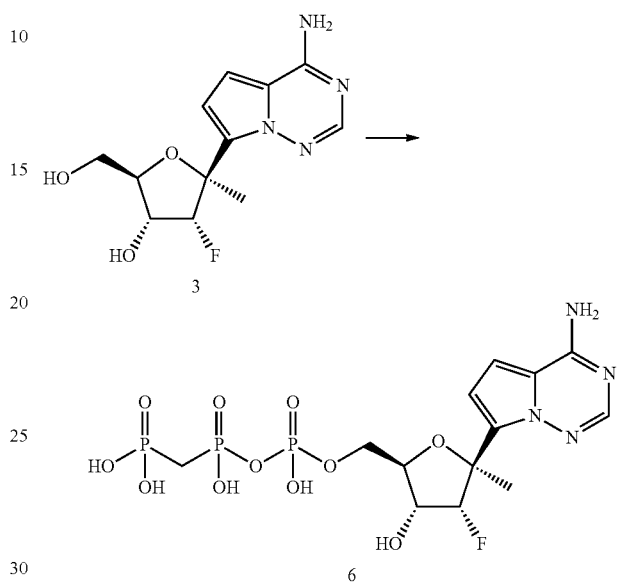

The nucleoside 3 (0.022 g, 0.056 mmol) was dissolved in trimethylphosphate (1 mL) and stirred under $N_2(g)$. Phosphorous oxychloride (0.067 mL, 0.73 mmol) was added and the mixture stirred for about 2 h. Monitoring by analytical ion-exchange column determined the time at which >80 percent of monophosphate was formed. A solution of tributylamine (0.44 mL, 1.85 mmol) and triethylammonium pyrophosphate (0.327 g, 0.72 mmol) dissolved in anhydrous DMF (1 mL) was added. The reaction mixture was stirred for 20 min and then quenched by the addition of 1N triethylammonium bicarbonate solution in $H_2O$ (5 mL). The mixture was concentrated under reduced pressure and the residue re-dissolved in $H_2O$. The solution was subjected to ion exchange chromatography to yield the title product compound 6. LCMS m/z 521 [M-H]. Tr=0.41. HPLC ion exchange TR=9.40 min Example 10

(2R,3R,5S)-2-(4-aminopyrrolo[1,2-f][1,2,4]triazin-7-yl)-3-hydroxy-5-(hydroxymethyl)-tetrahydrofuran-2-carbonitrile (Compound 7)

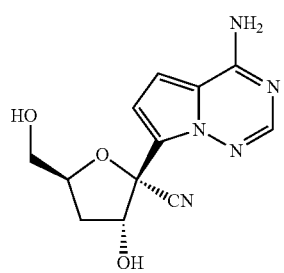

The preparation of (2R,3R,5S)-2-(4-aminopyrrolo[1,2-f][1,2,4]triazin-7-yl)-3-hydroxy-5-(hydroxymethyl)-tetrahydrofuran-2-carbonitrile is described below.

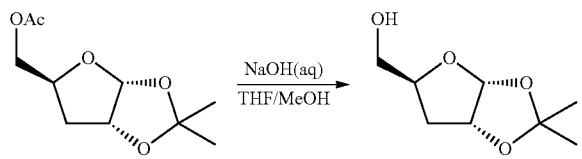

((3αR,5S,6αR)-2,2-dimethyl-tetrahydrofuro[2,3-d][1,3]dioxol-5-yl)methanol. The acetate material (1.2 g, 5.5 mmol) (J. Org. Chem. 1985, 50, 3457, De Bernardo et al) was dissolved in a 1:1 mixture MeOH and THF (10 mL). A 1N solution of NaOH(aq) (10 mL) was added until the pH was 13. The reaction mixture was stirred for about 2 h and then neutralized to pH 8-9 by the addition of AcOH. The mixture was extracted with EtOAc (10×30 mL) and the combined organic extracts dried over anhydrous Na$_2$SO$_4$, filtered and concentrated under reduced pressure. The residue was subjected to silica gel chromatography eluting with 0-70% EtOAc in hexanes to give the desired product (866 mg, 90%). $^1$H NMR (300 MHz, CDCl$_3$) δ 5.84 (d, J=3.6 Hz, 1H), 4.78 (t, J=4.5 Hz, 1H), 4.38 (m, 1H), 3.93-3.54 (m, 2H), 2.04-1.84 (m, 2H), 1.52 (s, 3H), 1.33 (s, 3H).

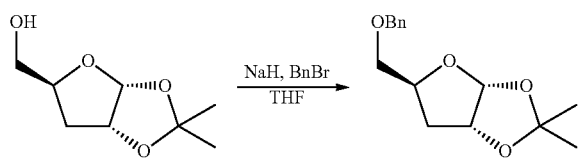 [SMILES: CC1(C)O[C@H]2O[C@H](CO)C[C@H]2O1 ; CC1(C)O[C@H]2O[C@H](COCc3ccccc3)C[C@H]2O1 ; "THF"]

(3αR,5S,6αR)-5-(benzyloxymethyl)-2,2-dimethyl-tetrahydrofuro[2,3-d][1,3]dioxole. Sodium hydride (188 mg, 7.46 mmol) was dissolved in anhydrous THF (5 mL) and stirred under N$_2$(g) at RT. The alcohol (866 mg, 4.97 mmol) was dissolved in anhydrous THF (3 mL) and then added in portions over 5 min. to the sodium hydride mixture. The resultant mixture was stirred for about 20 min. and then benzyl bromide (892 μL, 7.46 mmol) was added. The reaction was stirred for about 2 h and then poured onto a mixture of ice cold aqueous NaHCO$_3$ and EtOAc (30 mL). The organic layer was separated and then the aqueous layer re-extracted with EtOAc (30 mL). The combined organic extracts were dried over anhydrous Na$_2$SO$_4$, filtered and concentrated under reduced pressure. The residue was subjected to silica gel chromatography eluting with 0-40% EtOAc in hexanes to give the benzyl ether product. $^1$H NMR (300 MHz, CDCl$_3$) δ 7.35-7.27 (m, 5H), 5.86 (d, J=3.6 Hz, 1H), 4.74 (t, J=4.2 Hz, 1H), 4.60 (s, 2H), 4.42 (m, 1H), 3.69-3.53 (m, 2H), 2.10-2.04 (m, 1H), 1.83-1.77 (m, 1H), 1.52 (s, 3H), 1.33 (s, 3H).

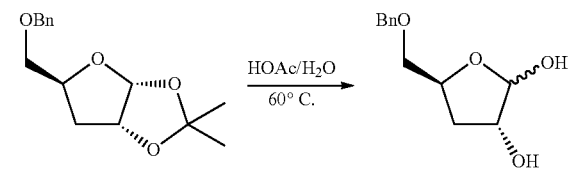 [SMILES: CC1(C)O[C@H]2O[C@H](COCc3ccccc3)C[C@H]2O1 ; OC1O[C@H](COCc2ccccc2)C[C@H]1O]

(3R,5S)-5-(benzyloxymethyl)-tetrahydrofuran-2,3-diol. The benzyl ether (910 mg, 3.44 mmol) was dissolved in a 1:1 AcOH and H$_2$O (20 mL) mixture and stirred at about 60° C. for about 7 h. The mixture was concentrated under reduced pressure and the residue subjected to silica gel chromatography eluting with 0-70% EtOAc in hexanes to give the diol product (705 mg, 91%). $^1$H NMR (300 MHz, CDCl$_3$) δ 7.36-7.27 (m, 5H), 5.40 (d, J=3.9 Hz, 0.5H), 5.17 (s, 0.5H), 4.67-4.56 (m, 3H), 4.33 (m, 0.5H), 4.24 (d, J=4.8 Hz, 0.5H), 3.71-3.67 (m, 1H), 3.56-3.42 (m, 2H), 2.31-2.22 (m, 1H), 2.08-1.89 (m, 2H).

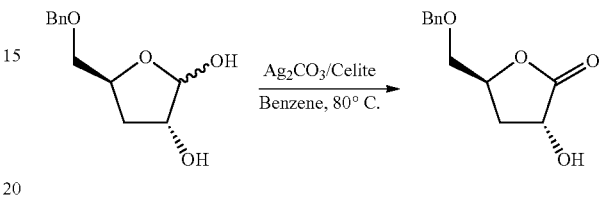

(3R,5S)-5-(benzyloxymethyl)-3-hydroxy-dihydrofuran-2(3H)-one. The diol (705 mg, 3.14 mmol) was dissolved in benzene (30 mL) and treated with a silver carbonate celite mixture (3.46 g, 6.28 mmol). The resultant mixture was stirred at about 80° C. under N$_2$(g) for about 2 h. The mixture was then cooled to RT, filtered and concentrated under reduced pressure. The residue was subjected to silica gel chromatography eluting with 0-70% EtOAc in hexanes to give the lactone product. $^1$H NMR (300 MHz, CDCl$_3$) δ 7.39-7.27 (m, 5H), 4.75-4.68 (m, 1H), 4.60-4.49 (m, 2H), 3.74-3.54 (m, 2H), 2.61-2.35 (m, 2H), 2.38-2.28 (m, 1H).

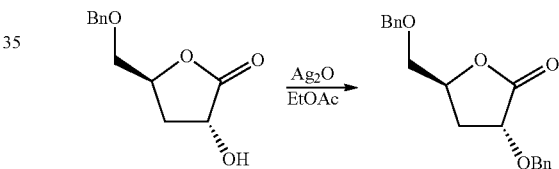

(3R,5S)-3-(benzyloxy)-5-(benzyloxymethyl)-dihydrofuran-2(3H)-one. The lactone (600 mg, 2.7 mmol) was dissolved in EtOAc (30 mL) and treated with silver oxide (626 mg, 2.7 mmol) followed by benzyl bromide (387 μL, 3.24 mmol). The reaction mixture was then stirred at about 50° C. under N$_2$(g) for about 8 h. Additional silver oxide (300 g) was then added and the resultant mixture stirred at about 50° C. for about 16 h. Additional benzyl bromide (50 uL) and silver oxide (150 g) were added and the mixture stirred for an additional about 8 h. The reaction mixture was allowed to cool, filtered and then concentrated under reduced pressure. The residue was subjected to silica gel chromatography eluting with 0-20% EtOAc in hexanes to give the title product. $^1$H NMR (300 MHz, CDCl$_3$) δ 7.39-7.27 (m, 10H), 4.99 (d, J=11.4 Hz, 1H), 4.72 (m, 2H), 4.56 (m, 2H), 4.39 (t, J=8.1 Hz, 1H), 3.72-3.51 (m, 2H), 2.42-2.25 (m, 2H).

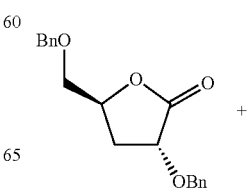

+

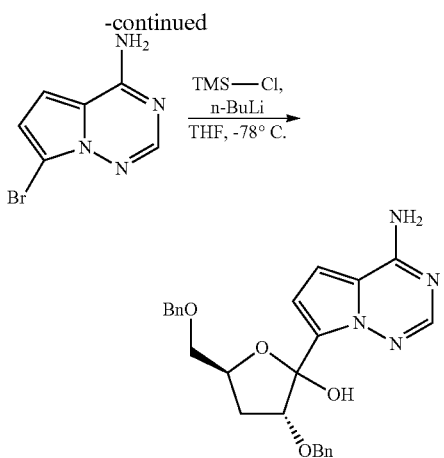

(3R,5S)-2-(4-aminopyrrolo[1,2-f][1,2,4]triazin-7-yl)-3-(benzyloxy)-5-(benzyloxymethyl)-tetrahydrofuran-2-ol.
The 7-bromopyrrolo[1,2-f][1,2,4]triazin-4-amine (607 mg, 2.85 mmol) was dissolved in anhydrous THF (10 mL) and stirred under Ar(g) at RT. TMSCl (1.1 mL, 8.55 mmol) was added dropwise and the mixture stirred for about 2 h. The reaction was concentrated under reduced pressure and then dried under high vacuum. The residue was suspended in THF (20 mL) and stirred under Ar(g) at about −78° C. A 2.5M n-BuLi solution in hexane (2.28 mL, 5.7 mmol) was added dropwise over about 10 min. and the resultant mixture stirred for about 60 min. The lactone (742 mg, 2.37 mmol) dissolved in anhydrous THF (7 mL) was added to the above mixture over about 20 min. The reaction mixture was stirred for about 2 h. and then quenched with AcOH until pH was 5-6. The mixture was allowed to warm to RT and then diluted with EtOAc. The solution was washed with saturated NaHCO₃ solution, saturated NaCl, dried over anhydrous Na₂SO₄ and concentrated under reduced pressure. The residue was subjected to silica gel chromatography eluting with 0-80% EtOAc in hexanes to give the title product. LCMS m/z 447.2 [M+H], 445.1 [M−H].

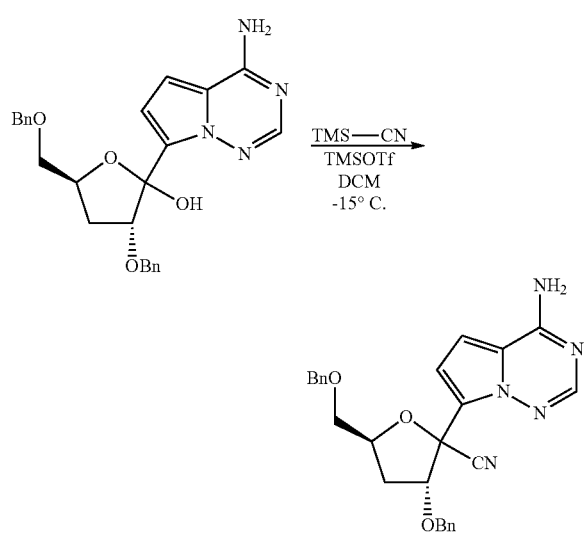

(3R,5S)-2-(4-aminopyrrolo[1,2-f][1,2,4]triazin-7-yl)-3-(benzyloxy)-5-(benzyloxymethyl)-tetrahydrofuran-2-carbonitrile. The alcohol (250 mg, 0.56 mmol) was dissolved in anhydrous CH₂Cl₂ (10 mL) and stirred under Ar(g) at about −15° C. TMSCN (448 μL, 3.36 mmol) was added dropwise and the mixture stirred for about 10 min. TMSOTf (466 μL, 2.58 mmol) was added dropwise over 10 min and the resultant mixture stirred for about 90 min. at about −15° C. Additional TMSCN (224 μL, 3 eq.) and TMSOTf (202 μL, 2 eq.) was added and stirring continued for about 5 h. Saturated aqueous NaHCO₃ solution was added to quench the reaction and the mixture stirred for about 10 min. The organic layer was separated and washed with saturated aqueous NaHCO₃ solution, saturated NaCl solution, dried over anhydrous Na₂SO₄, filtered and concentrated under reduced pressure. The residue was subjected to silica gel chromatography eluting with 0-70% EtOAc in hexanes to give the title product. LCMS m/z 456.3 [M+H], 454.1 [M−H].

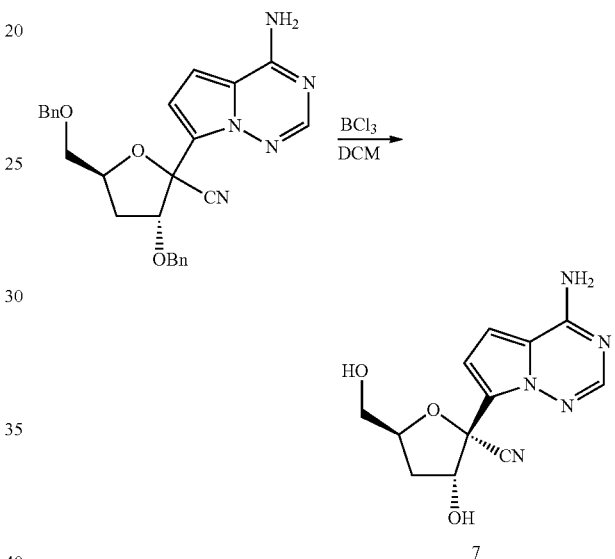

(2R,3R,5S)₂-(4-aminopyrrolo[1,2-f][1,2,4]triazin-7-yl)-3-hydroxy-5-(hydroxymethyl)-tetrahydrofuran-2-carbonitrile (7). The benzyl ether (150 mg, 0.329 mmol) was dissolved in anhydrous CH₂Cl₂ (2 mL) and the mixture stirred under Ar(g) at about −20° C. A 1M BCl₃ solution in CH₂Cl₂ (724 μL, 0.724 mmol) was added dropwise and the resultant mixture stirred for about 2 h. Additional 1M BCl₃ in CH₂Cl₂ (724 μL, 0.724 mmol) was added and stirring continued for 2 h. The mixture was then cooled to about −78° C. and slowly treated with a 2:1 mixture of Et₃N and MeOH (3 mL). The mixture was stirred for about 10 min and then treated with MeOH (10 mL). The reaction was allowed to warm to RT and then concentrated under reduced pressure. The residue was dissolved in MeOH and concentrated under reduced pressure. The residue was dissolved in MeOH again and treated with solid NaHCO₃. The mixture was stirred for about 5 min and then the solid removed by filtration. The solution was concentrated under reduced pressure and subjected to preparative HPLC to provide the desired product 7. ¹H NMR (300 MHz, D₂O) δ 7.71 (s, 1H), 6.75 (d, J=4.5 Hz, 1H), 6.65 (d, J=4.8 Hz, 1H), 4.91 (t, J=6.3 Hz, 1H), 4.57 (m, 1H), 3.67-3.47 (m, 2H), 2.18 (m, 2H). LCMS m/z 276.1 [M+H], 274.0 [M−H].

Example 11

(2S)-isopropyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)-phosphorylamino)propanoate (Compound 8)

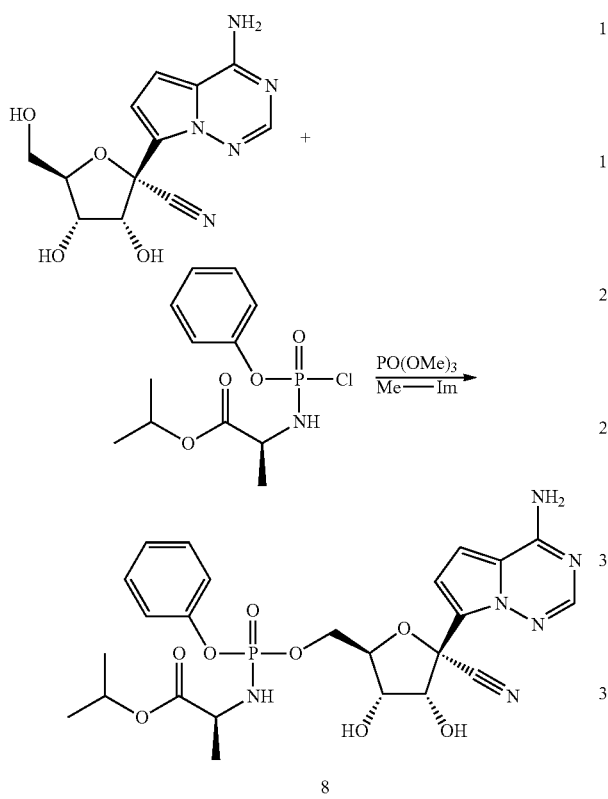

8

The nucleoside 1 (45 mg, 0.15 mmol) was dissolved in anhydrous trimethyl phosphate (0.5 mL) and the solution stirred under N₂(g) at about 0° C. Methyl imidazole (36 µL, 0.45 mmol) was added to the solution. Chlorophosphoramidate C (69 mg, 0.225 mmol) was dissolved in anhydrous THF (0.25 mL) and added dropwise to the nucleoside mixture. When the reaction was complete by LCMS, the reaction mixture was diluted with EtOAc and washed with saturated aqueous NaHCO₃ solution, saturated NaCl, dried over anhydrous Na₂SO₄, filtered and concentrated under reduced pressure. The residue was subjected to silica gel chromatography eluting with 0-5% MeOH in CH₂Cl₂ followed by preparative HPLC to give the product. ¹H NMR (300 MHz, CD₃OD) δ 7.95 (m, 1H), 7.31-6.97 (m, 7H), 4.94 (m, 1H), 4.78 (m, 1H), 4.43 (m, 3H), 4.20 (m, 1H), 3.80 (d, 1H), 1.30-1.18 (m, 9H). ³¹P NMR (121.4 MHz, CD₃OD) δ 3.8. LCMS m/z 561.0 [M+H], 559.0 [M−H].

Example 12

(2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 9)

Compound 9 can be prepared by several methods described below.

Procedure 1

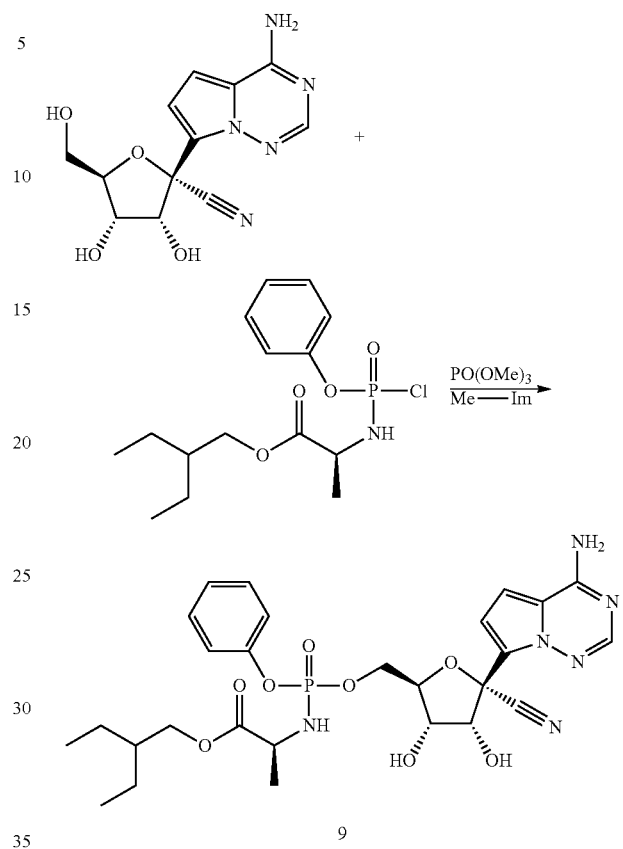

9

Prepared from Compound 1 and chloridate B according to the same method as for the preparation of compound 8. ¹H NMR (300 MHz, CD₃OD) δ 7.87 (m, 1H), 7.31-7.16 (m, 5H), 6.92-6.89 (m, 2H), 4.78 (m, 1H), 4.50-3.80 (m, 7H), 1.45-1.24 (m, 8H), 0.95-0.84 (m, 6H). ³¹P NMR (121.4 MHz, CD₃OD) δ 3.7. LCMS m/z 603.1 [M+H], 601.0 [M−H].

Procedure 2

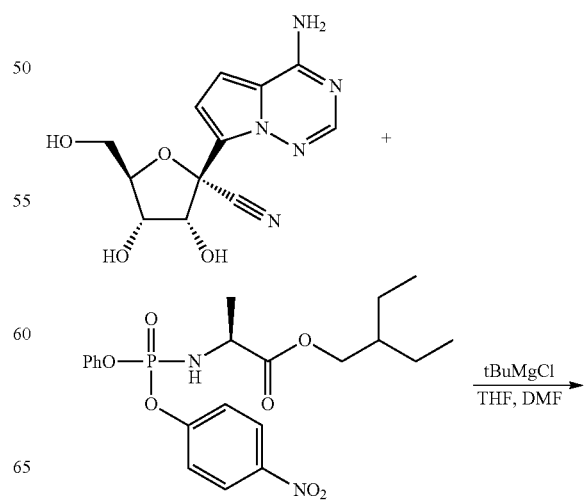

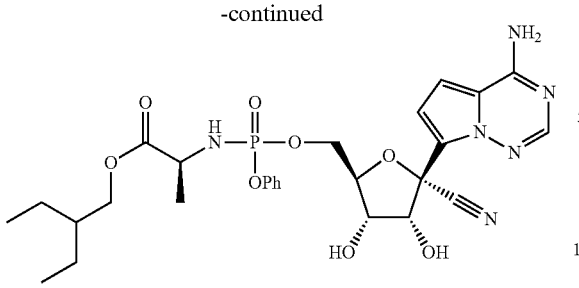

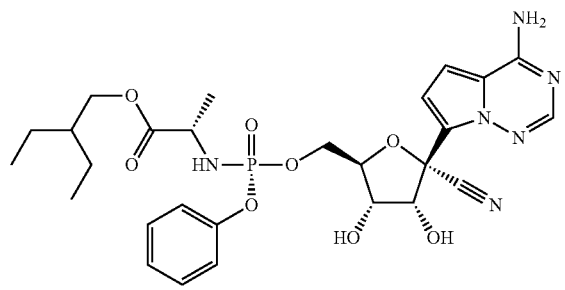 [SMILES: CCC(CC)COC(=O)[C@H](C)N[P@@](=O)(OC[C@H]1O[C@@](C#N)(c2ccc3c(N)ncnn23)[C@H](O)[C@@H]1O)Oc1ccccc1]

¹HNMR (400 MHz, CD₃OD) δ 8.05 (s, 1H), 7.36 (d, J=4.8 Hz, 1H), 7.29 (br t, J=7.8 Hz, 2H), 7.19-7.13 (m, 3H), 7.11 (d, J=4.8 Hz, 1H), 4.73 (d, J=5.2 Hz, 1H), 4.48-4.38 (m, 2H), 4.37-4.28 (m, 1H), 4.17 (t, J=5.6 Hz, 1H), 4.08-3.94 (m, 2H), 3.94-3.80 (m, 1H), 1.48 (sep, J=12.0, 6.1 Hz, 1H), 1.34 (p, J=7.3 Hz, 4H), 1.29 (d, J=7.2 Hz, 3H), 0.87 (t, J=7.4 Hz, 6H). ³¹PNMR (162 MHz, CD₃OD) δ 3.71 (s). HPLC (2-98% MeCN—H₂O gradient with 0.1% TFA modifier over 8.5 min, 1.5 mL/min, Column: Phenomenex Kinetex C18, 2.6 um 100 Å, 4.6×100 mm) $t_R$=5.585 min.

Second Eluting Diastereomer is (S)-2-ethylbutyl 2-(((S)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate

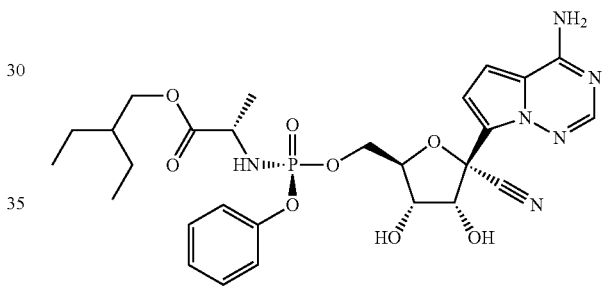

(2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate. (2S)-2-ethylbutyl 2-(((4-nitrophenoxy)(phenoxy)phosphoryl)amino)propanoate (1.08 g, 2.4 mmol) was dissolved in anhydrous DMF (9 mL) and stirred under a nitrogen atmosphere at RT. (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (350 mg, 1.2 mmol) was added to the reaction mixture in one portion. A solution of t-butylmagnesium chloride in THF (1M, 1.8 mL, 1.8 mmol) was then added to the reaction dropwise over about 10 minutes. The reaction was stirred for about 2 h, at which point the reaction mixture was diluted with ethyl acetate (50 mL) and washed with saturated aqueous sodium bicarbonate solution (3×15 mL) followed by saturated aqueous sodium chloride solution (15 mL). The organic layer was dried over anhydrous sodium sulfate and concentrated under reduced pressure. The resulting oil was purified with silica gel column chromatography (0-10% MeOH in DCM) to afford (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (311 mg, 43%, 1:0.4 diastereomeric mixture at phosphorus) as a white solid. ¹H NMR (400 MHz, CD₃OD) δ 7.85 (m, 1H), 7.34-7.23 (m, 2H), 7.21-7.09 (m, 3H), 6.94-6.84 (m, 2H), 4.78 (d, J=5.4 Hz, 1H), 4.46-4.33 (m, 2H), 4.33-4.24 (m, 1H), 4.18 (m, 1H), 4.05-3.80 (m, 3H), 1.52-1.39 (m, 1H), 1.38-1.20 (m, 7H), 0.85 (m, 6H). ³¹P NMR (162 MHz, CD₃OD) δ 3.71, 3.65. LCMS m/z 603.1 [M+H], 600.9 [M−H]. HPLC (2-98% MeCN—H₂O gradient with 0.1% TFA modifier over 8.5 min, 1.5 mL/min, Column: Phenomenex Kinetex C18, 2.6 um 100 Å, 4.6×100 mm) $t_R$=5.544 min, 5.601 min Separation of the (S) and (R) Diastereomers (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate. The resulting solution was loaded onto Lux Cellulose-2 chiral column, equilibrated in acetonitrile, and eluted with isocratic acetonitrile/methanol (95:5 vol/vol). The first eluting diastereomer had a retention time of 17.4 min, and the second eluting diastereomer had a retention time of 25.0 min.

First Eluting Diastereomer is (S)-2-ethylbutyl 2-(((R)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate:

¹HNMR (400 MHz, CD₃OD) δ 8.08 (s, 1H), 7.36-7.28 (m, 3H), 7.23-7.14 (m, 3H), 7.08 (d, J=4.8 Hz, 1H), 4.71 (d, J=5.3 Hz, 1H), 4.45-4.34 (m, 2H), 4.32-4.24 (m, 1H), 4.14 (t, J=5.8 Hz, 1H), 4.08-3.94 (m, 2H), 3.93-3.85 (m, 1H), 1.47 (sep, J=6.2 Hz, 1H), 1.38-1.26 (m, 7H), 0.87 (t, J=7.5 Hz, 6H). ³¹PNMR (162 MHz, CD₃OD) δ 3.73 (s). HPLC (2-98% MeCN—H₂O gradient with 0.1% TFA modifier over 8.5 min, 1.5 mL/min, Column: Phenomenex Kinetex C18, 2.6 um 100 Å, 4.6×100 mm) $t_R$=5.629 min.

Example 13

(2S)-ethyl 2-(((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino)propanoate (Compound 10)

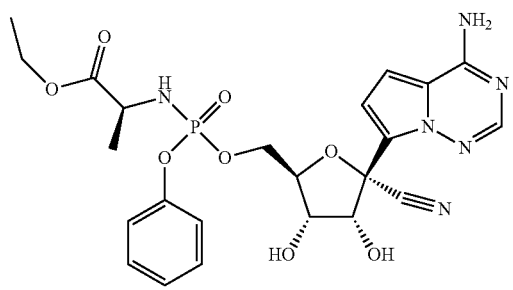 [SMILES: CCOC(=O)[C@H](C)NP(=O)(OC[C@H]1O[C@@](C#N)(c2ccc3c(N)ncnn23)[C@H](O)[C@@H]1O)Oc1ccccc1]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Procedure 1. Preparation Via Chloridate A

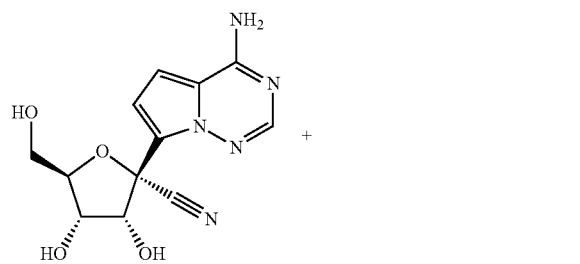

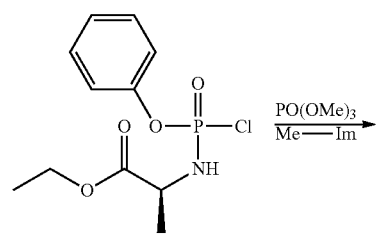

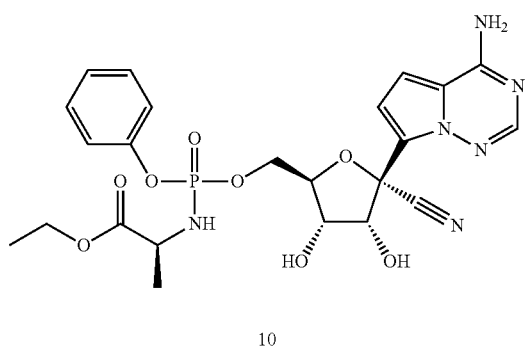

Prepared from Compound 1 and chloridate A using same method as for the preparation of compound 8. $^1$H NMR (300 MHz, CD$_3$OD) δ 7.95 (m, 1H), 7.32-6.97 (m, 7H), 4.78 (m, 1H), 4.43-4.08 (m, 6H), 3.83 (m, 1H), 1.31-1.18 (m, 6H). $^{31}$P NMR (121.4 MHz, CD$_3$OD) δ 3.7. LCMS m/z 547.0 [M+H], 545.0 [M−H].

Procedure 2. Preparation Via Nitro-Benzene Compound L

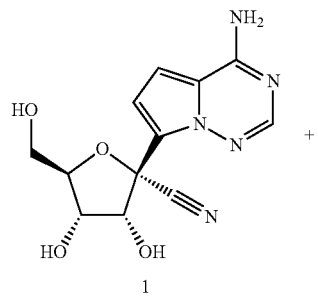

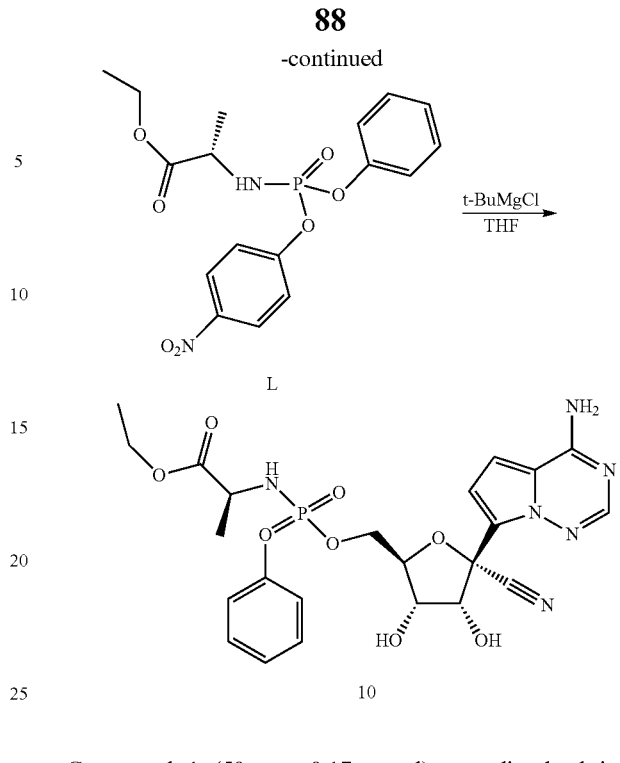

Compound 1 (50 mg, 0.17 mmol) was dissolved in NMP-THF (1:1 mL)) and cooled with ice bath. tBuMgCl (0.257 mL, 0.257 mmol) was then added over about 5 min. The resulting mixture was allowed to warm to RT and was stirred for about 30 min. Then a solution of compound L (Prepared according to US20120009147, 74.6 mg, 0.189 mmol) in THF (2 mL) was added. After about 30 min, the reaction mixture was purified by HPLC (acetonitrile 10 to 80% in water) to give compound 29 as a yellow solid. The solid was further purified with silica gel chromatography (MeOH 0 to 20% DCM) to afford compound 29. $^1$H NMR (400 MHz, CD$_3$OD) δ 7.76 (d, J=6.0 Hz, 1H), 7.25-7.14 (m, 2H), 7.11-6.99 (m, 3H), 6.87-6.72 (m, 2H), 4.70 (d, J=5.4 Hz, 1H), 4.39-4.24 (m, 2H), 4.20 (dddd, J=9.7, 7.9, 5.1, 2.8 Hz, 1H), 4.10 (dt, J=12.8, 5.5 Hz, 1H), 4.06-3.91 (m, 2H), 3.72 (ddq, J=14.3, 9.3, 7.1 Hz, 1H), 1.17 (dd, J=7.1, 1.0 Hz, 1H), 1.14-1.06 (m, 5H). $^{31}$P NMR (162 MHz, CD$_3$OD) δ 3.73, 3.68. MS m/z=547 (M+1)+.

Example 14

(2S)-ethyl 2-((((2R,3R,4R,5R)-5-(4-aminopyrrolo[1,2-f][1,2,4]triazin-7-yl)-5-cyano-4-fluoro-3-hydroxytetrahydrofuran-2-yl)methoxy)(phenoxy)phosphorylamino)propanoate (Compound 11)

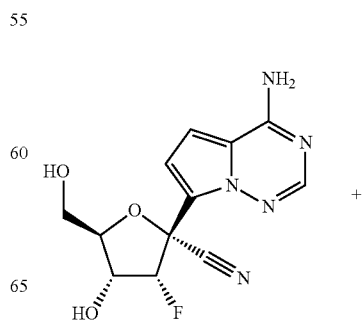

-continued

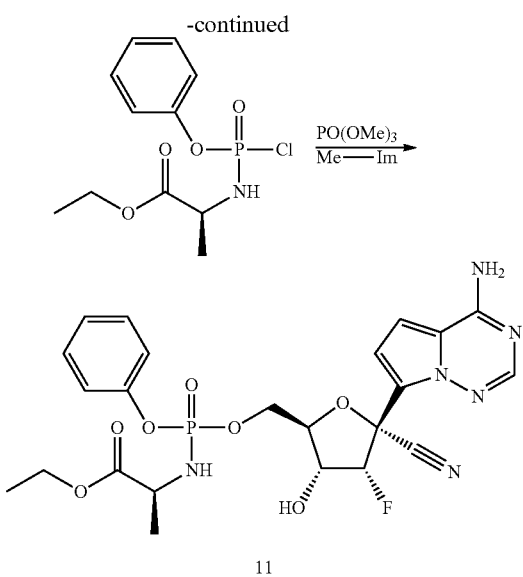

Compound 11 was prepared from Compound 2 and chloridate A using same method as for the preparation of compound 8. $^1$H NMR (300 MHz, CD$_3$OD) δ 7.91 (m, 1H), 7.33-7.16 (m, 5H), 6.98-6.90 (m, 2H), 5.59 (m, 1H), 4.50-4.15 (m, 4H), 4.12-3.90 (m, 3H), 1.33-1.18 (m, 6H). $^{31}$P NMR (121.4 MHz, CD$_3$OD) δ 3.8. LCMS m/z 549.0 [M+H], 547.1 [M−H].

Example 15

(2S,2'S)-diethyl 2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(azanediyl)dipropanoate (Compound 12)

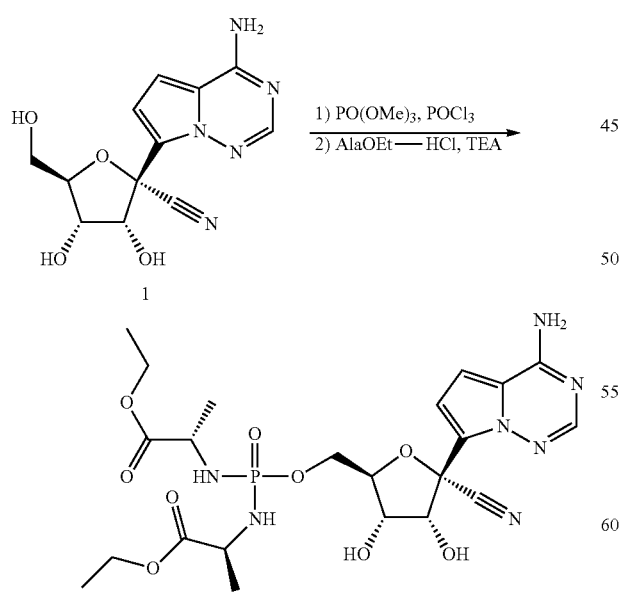

The nucleoside 1 (14.6 g, 0.05 mmol) was dissolved in anhydrous trimethyl phosphate (0.5 mL) and stirred under N$_2$(g) at RT. POCl$_3$ (9.2 μL, 0.1 mmol) was added and the mixture stirred for about 60 min. Alanine ethyl ester hydrochloride (61 mg, 0.4 mmol) and then Et$_3$N (70 μL, 0.5 mmol) was added. The resultant mixture was stirred for about 15 min. and then additional Et$_3$N (70 μl, 0.5 mmol) was added to give a solution pH of 9-10. The mixture was stirred for about 2 h. and then diluted with EtOAc, washed with saturated aqueous NaHCO$_3$ solution followed by saturated aqueous NaCl solution. The organic layer was dried over anhydrous Na$_2$SO$_4$ and concentrated under reduced pressure. The residue was subjected to preparative HPLC (C$_{18}$ column) to yield the product 12. $^1$H NMR (400 MHz, CD$_3$OD) δ 8.13 (s, 1H), 7.41 (d, J=4.8 Hz, 1H), 7.18 (d, J=4.8 Hz, 1H), 4.78 (d, J=5.6 Hz, 1H), 4.36 (m, 1H), 4.25-4.08 (m, 7H), 3.83 (m, 2H), 1.33-1.23 (m, 12H). $^{31}$P NMR (121.4 MHz, CD$_3$OD) δ 13.8. LCMS m/z 570.0 [M+H], 568.0 [M−H].

Example 16

(2S,3R,4S,5R)-2-(4-aminopyrrolo[1,2-f][1,2,4]triazin-7-yl)-2-ethynyl-5-(hydroxymethyl)tetrahydrofuran-3,4-diol (Compound 13)

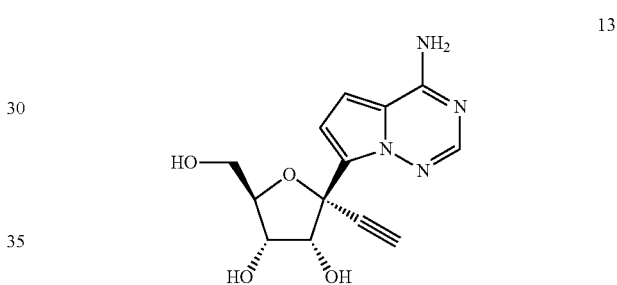

The preparation of (2S,3R,4S,5R)-2-(4-aminopyrrolo[1,2-f][1,2,4]triazin-7-yl)-2-ethynyl-5-(hydroxymethyl)tetrahydrofuran-3,4-diol is described below.

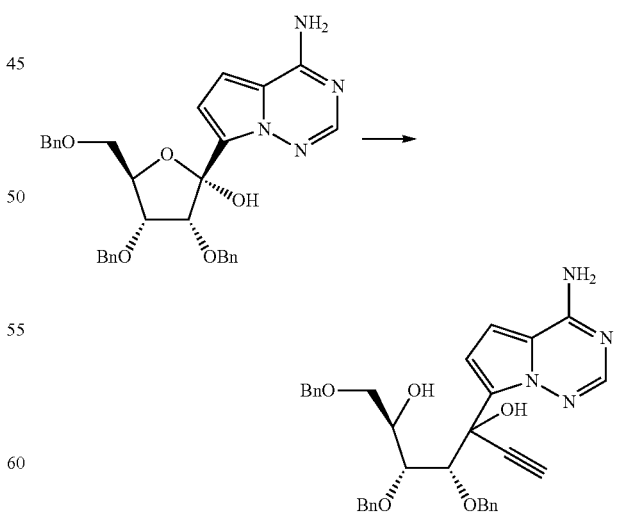

The nucleoside alcohol (0.6 g, 1.08 mmol) (prepared as described in Compound 1 synthesis) was dissolved in anhydrous THF (8 mL) and placed under N$_2$(g). The reaction mixture was stirred and cooled to about 0° C. and then treated with a 0.5N solution of ethynyl magnesium bromide in THF (17.2 mL, 17.2 mmol). The reaction mixture was stirred overnight at RT. AcOH (1.5 mL) was added to quench the reaction. The mixture was concentrated under reduced pressure and the residue redissolved in CH$_2$Cl$_2$. The solution subjected to a plug of silica gel eluting with 0 to 80% EtOAc in Hexanes to provide the title product as a crude mixture. LCMS m/z 579 [M+H].

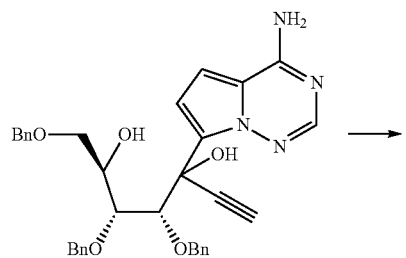

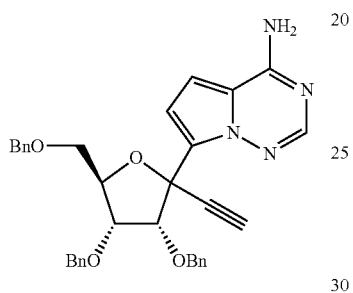

The crude ethynyl alcohol (0.624 g, 1.08 mmol) was dissolved in anhydrous CH$_2$Cl$_2$ (10 mL) and placed under N$_2$(g). The mixture was stirred and sulfonic acid (0.2 mL, 2.74 mmol) was added. The reaction mixture was stirred for about 12 h. at RT. When complete by LCMS, Et$_3$N (0.56 mL) was added to quench the reaction. The reaction was concentrated under reduced pressure and the residue subjected to silica gel chromatography eluting with 0 to 75% EtOAc in Hexanes to yield the ethynyl nucleoside as a mixture of anomers. LCMS m/z 561 [M+H].

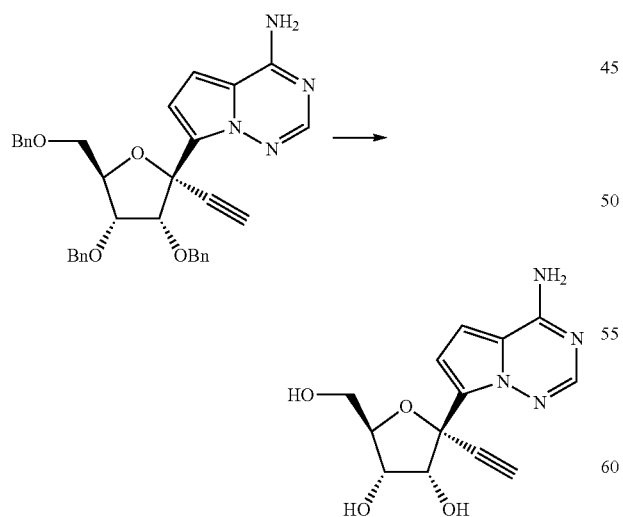

The tribenzyl nucleoside (0.650 g, 1.16 mmol) was dissolved in anhydrous CH$_2$Cl$_2$ (30 mL) and cooled to −78° C. under N$_2$(g). A solution of boron tribromide (1 N in CH$_2$Cl$_2$, 5.5 mL) was added and the reaction mixture stirred for 1 h. at −78° C. A solution of MeOH (10 mL) and pyridine (2 mL) was added to quench the reaction and the mixture was allowed to rise to RT. The mixture was concentrated under reduced pressure and subjected to preparative HPLC to provide the α-anomer (20 g) and β-anomer 13 (110 g). (β-anomer) $^1$H NMR (300 MHz, DMSO) δ 7.81 (s, 1H), 7.76 (br s, 2H), 6.80-6.85 (m, 2H), 5.11 (d, J=7.2 Hz, 1H), 4.90 (d, J=6.0 Hz, 1H), 4.82 (dd, J=7.2, 4.8 Hz, 1H), 4.62 (t, J=6.3 Hz, 1H), 3.95-3.99 (m, 1H), 3.85-3.91 (dd, J=11.4, 5.7 Hz, 1H), 3.61-3.67 (m, 1H), 3.47-3.55 (m, 1H), 3.52 (d, J=0.9 Hz, 1H). (α-anomer) $^1$H NMR (300 MHz, DMSO) δ 7.80 (s, 1H), 7.59 (bs, 2H), 6.80 (d, J=4.5 Hz, 1H), 6.54 (d, J=4.2 Hz, 1H), 5.00 (d, J=7.2 Hz, 1H), 4.89 (d, J=4.8 Hz, 1H), 4.74 (t, J=5.7 Hz, 1H), 4.58 (t, J=4.5 Hz, 1H), 4.27 (m, 1H), 3.88 (m, 1H), 3.64-3.72 (m, 1H), 3.51-3.59 (m, 1H), 3.48 (d, J=0.6 Hz, 1H). LCMS m/z 291 [M+H].

Example 17

(2R,3R,4R)-5-(4-aminopyrrolo[1,2-f][1,2,4]triazin-7-yl)-1,3,4-tris(benzyloxy)hexane-2,5-diol (Compound 14)

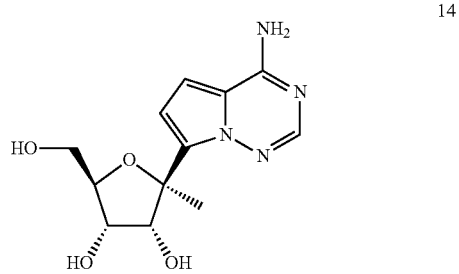 [SMILES: C[C@@]1(c2ccc3c(N)ncnn23)O[C@H](CO)[C@@H](O)[C@H]1O]

The preparation of (2R,3R,4R)-5-(4-aminopyrrolo[1,2-f][1,2,4]triazin-7-yl)-1,3,4-tris(benzyloxy)hexane-2,5-diol is described below.

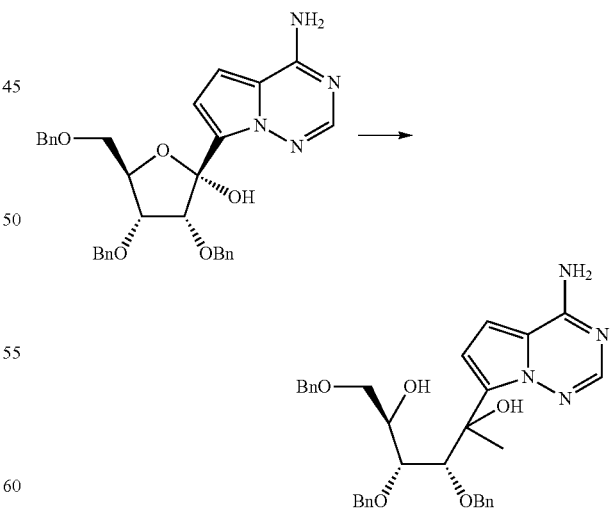

The tribenzyl alcohol from Compound 1 synthesis (0.250 g, 0.453 mmol) was dissolved in anhydrous THF (25 mL) and stirred under N$_2$(g). The reaction mixture was cooled to 0° C. and then a 3.0 N solution of methyl magnesium chloride in THF (1.2 mL, 3.62 mmol) was added. The reaction mixture was stirred overnight at RT. Acetic acid (1.5 mL) was added to quench the reaction and then the mixture was concentrated under reduced pressure. The residue was redissolved in CH$_2$Cl$_2$ and subjected to a plug of silica gel eluting with 0 to 80% EtOAc in hexanes. The crude product (0.452 g) was then used in the next reaction without further purification. LCMS m/z 569 [M+H].

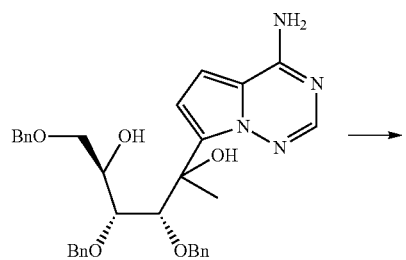

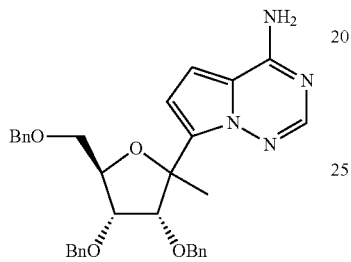

The crude methyl nucleoside (0.452 g, 0.796 mmol) was dissolved in anhydrous CH$_2$Cl$_2$ (20 mL) and stirred under N$_2$(g). Methanesulfonic acid (0.2 mL, 2.78 mmol) was added and the reaction stirred for about 12 hr at RT. Et$_3$N (0.56 mL) was added to quench the reaction and then the mixture concentrated under reduced pressure. The residue was subjected to silica gel chromatography eluting with 0 to 75% EtOAc in Hexanes to yield the product as a mixture of anomers. LCMS m/z 551 [M+H].

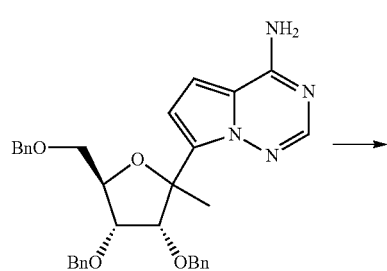

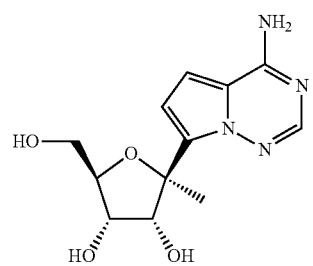

The tribenzyl nucleoside (0.20 g, 0.364 mmol) was dissolved in AcOH (30 mL). and charged with Pd/C (Degussa) (400 g). The stirred mixture was flushed with N$_2$(g) three times and then H$_2$ (g) was introduced, The reaction was stirred under H$_2$ (g) for 2 h. and then the catalyst removed by filtration. The solution was concentrated under reduced pressure and under the residue was re-dissolved in H$_2$O. The solution was subjected to preparative HPLC under neutral conditions to provide the α-anomer and β-anomer 14. (α-anomer)$^1$H NMR (300 MHz, D$_2$O) δ 7.81 (s, 1H), 7.22 (d, 1H), 6.75 (d, 1H), 4.47 (d, 1H), 4.25-4.31 (m, 1H), 3.88-4.95 (m, 1H), 3.58-3.86 (dd, 2H), 1.50 (s, 3H). (β-anomer)$^1$H NMR (300 MHz, D$_2$O) δ 7.91 (s, 1H), 7.26 (d, 1H), 6.90 (d, 1H), 4.61 (d, 1H), 4.00-4.09 (m, 2H), 3.63-3.82 (dd, 2H), 1.67 (s, 3H). LCMS m/z 281 [M+H].

Example 18

S,S'-2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(oxy)bis(ethane-2,1-diyl)bis(2,2-dimethylpropanethioate) (Compound 15)

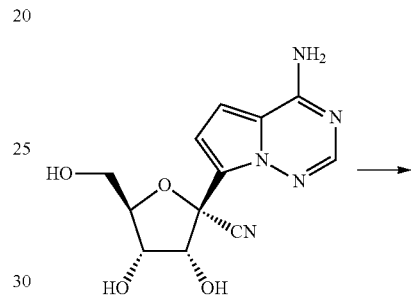

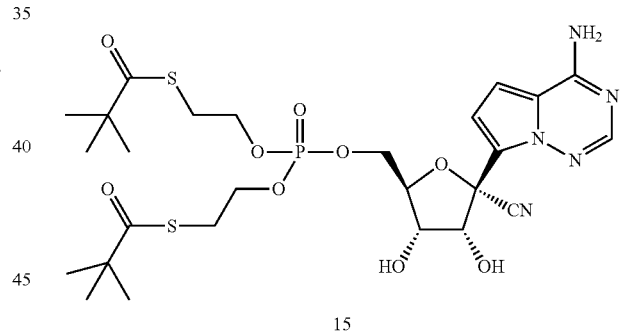

15

The nucleoside 1 (0.028 g, 0.096 mmol) was dissolved in trimethylphosphate (1 mL). The reaction was stirred under N$_2$(g) and then treated with 1H-tetrazole (0.021 g, 0.29 mmol). The reaction mixture was cooled to 0° C. and the phosphane (Nucleoside Nucleotides, Nucleic acids; 14; 3-5; 1995; 763-766. Lefebvre, Isabelle; Pompon, Alain; Perigaud, Christian; Girardet, Jean-Luc; Gosselin, Gilles; et al.) (87 mg, 0.192 mmol) was added. The reaction was stirred for 2 h. and then quenched with 30% hydrogen peroxide (0.120 mL). The mixture was stirred for 30 min at RT and then treated with saturated aqueous sodium thiosulfate (1 mL). The mixture was stirred for 10 min. and then concentrated under reduced pressure. The residue was subjected to preparative HPLC to isolate the title product 15. $^1$H NMR (300 MHz, CD$_3$CN) δ 7.98 (s, 1H), 6.92 (d, 1H), 6.81 (d, 1H), 6.44 (bs, 2H), 4.82 (m, 2H), 4.47 (m, 1H), 4.24 (m, 2H), 4.00 (m, 4H), 3.80 (bs, 1H), 3.11 (m, 4H), 1.24 (s, 9H). $^{31}$P NMR (121.4 MHz, CD$_3$CN) δ −1.85 (s). LCMS m/z 661 [M+H].

Example 19

S,S'-2,2'-(((((2R,3S,4R,5S)-5-(4-aminopyrrolo[1,2-f][1,2,4]triazin-7-yl)-5-ethynyl-3,4-dihydroxytetrahydrofuran-2-yl)methoxy)phosphoryl)bis(oxy)bis(ethane-2,1-diyl)bis(2,2-dimethylpropanethioate) (Compound 16)

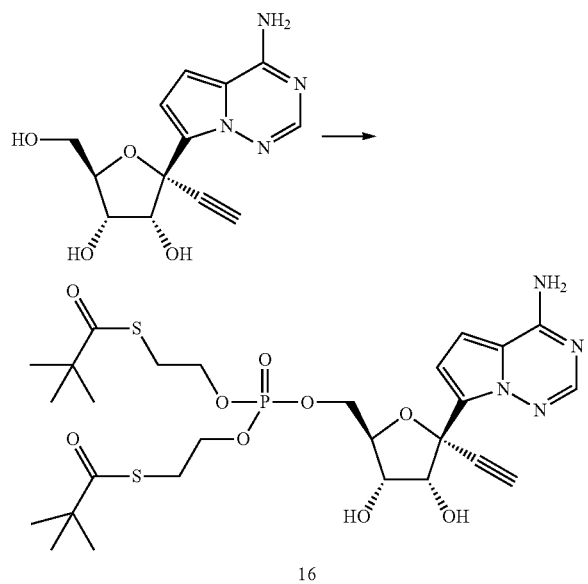

Compound 16 was prepared using the same method as compound 15 except substituting compound 13 as the starting nucleoside. $^1$H NMR (300 MHz, CD$_3$CN) δ 7.91 (s, 1H), 6.86 (d, J=4.8 Hz, 1H), 6.76 (d, J=4.5 Hz, 1H), 6.29 (bs, 2H), 4.69 (t, J=2.7 Hz, 1H), 4.58 (d, J=5.7 Hz, 1H), 4.14-4.33 (m, 5H), 3.99-4.07 (m, 4H), 3.53 (d, J=5.4 Hz, 1H), 3.11 (q, J=5.7 Hz, 4H), 1.22 (s, 18H). LCMS m/z 658.9 [M+]. Tr=2.31

Example 20

((2R,3S,4R,5R)-5-(4-aminopyrrolo[1,2-f][1,2,4]triazin-7-yl)-5-cyano-3,4-dihydroxytetrahydrofuran-2-yl)methyl tetrahydrogen triphosphate (Compound 17)

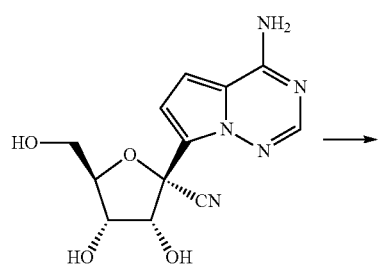

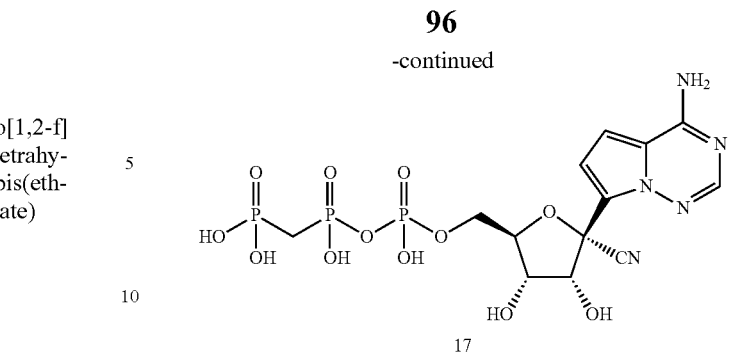

Compound 17 was prepared from compound 1 using a similar procedure to the preparation of compound 6. The product was isolated as the sodium salt. $^1$H NMR (400 MHz, D$_2$O) δ 7.76 (s, 1H), 6.88 (d, J=4.8 Hz, 1H), 6.73 (d, J=4.4 Hz, 1H), 4.86 (d, J=5.2 Hz, 1H), 4.43 (m, 1H), 4.39 (m, 1H), 4.05 (m, 1H), 3.94 (m, 1H). $^{31}$P NMR (121.4 MHz, D$_2$O) δ −5.4 (d, 1P), −10.8 (d, 1P), −21.1 (t, 1P). LCMS m/z 530 [M−H], 531.9 [M+H] Tr=0.22 min. HPLC ion exchange Tr=9.95 min.

Example 21

((2R,3S,4R,5S)-5-(4-aminopyrrolo[1,2-f][1,2,4]triazin-7-yl)-5-ethynyl-3,4-dihydroxytetrahydrofuran-2-yl)methyl tetrahydrogen triphosphate (Compound 18)

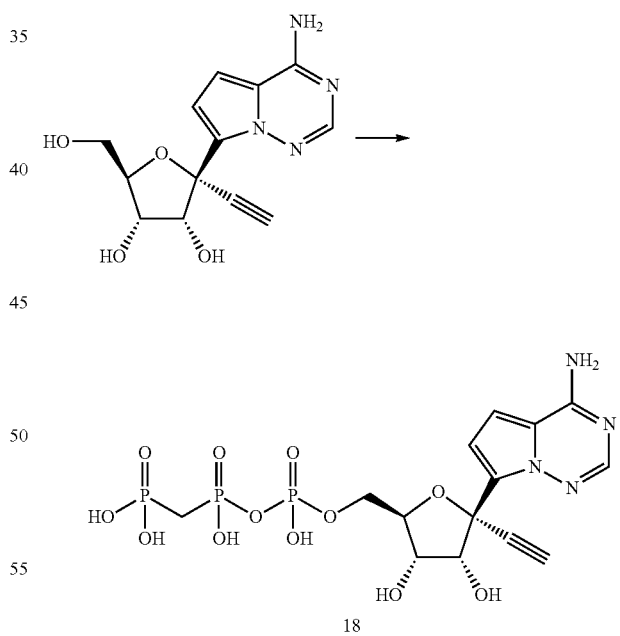

Compound 18 was prepared from compound 13 using a similar procedure to the preparation of compound 6. The product was isolated as the TEA salt. $^1$H NMR (300 MHz, D$_2$O) δ 7.85 (s, 1H), 7.09 (d, J=4.6 Hz, 1H), 6.95 (d, J=4.7 Hz, 1H), 4.23 (m, 2H), 4.08 (m, 2H), 3.06 (q, J=7.4 Hz, 20H), 1.14 (t, J=7.3 Hz, 30H). $^{31}$P NMR (121.4 MHz, D$_2$O) δ −10.8 (d, 1P), −11.2 (d, 1P), −23.2 (t, 1P). LCMS m/z 530.8 [M+H], Tr=0.46. HPLC ion exchange Tr=9.40 min.

Example 22

((2R,3S,4R,5S)-5-(4-aminopyrrolo[1,2-f][1,2,4]tri-azin-7-yl)-3,4-dihydroxy-5-methyltetrahydrofuran-2-yl)methyl tetrahydrogen triphosphate (Compound 19)

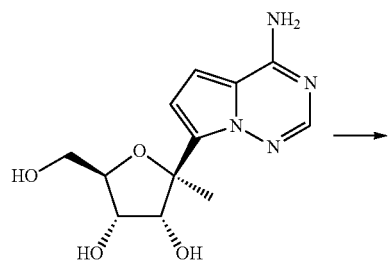

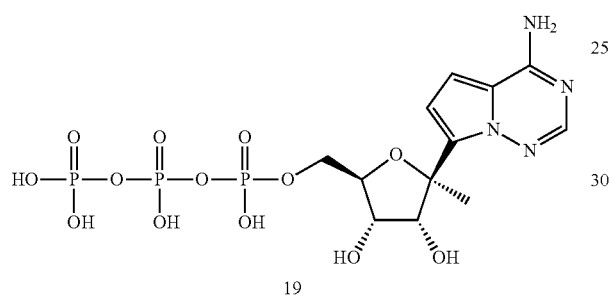

19

Compound 19 was prepared from compound 14 using a similar procedure to the preparation of compound 6. $^1$H NMR (400 MHz, D$_2$O) δ 7.78 (s, 1H), 6.98 (m, 1H), 6.84 (m, 1H), 4.45 (m, 1H), 4.04 (m, 4H), 1.54 (s, 3H). $^{31}$P NMR (161 MHz, D$_2$O) δ −10.6 (m), −23.0 (m). LCMS m/z 521.0 [M+H].

Example 23

((2R,3R,4R,5R)-5-(4-aminopyrrolo[1,2-f][1,2,4] triazin-7-yl)-5-cyano-4-fluoro-3-hydroxytetrahydrofuran-2-yl)methyl tetrahydrogen triphosphate (Compound 20)

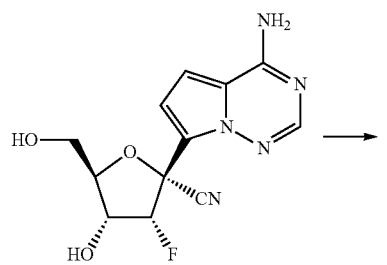

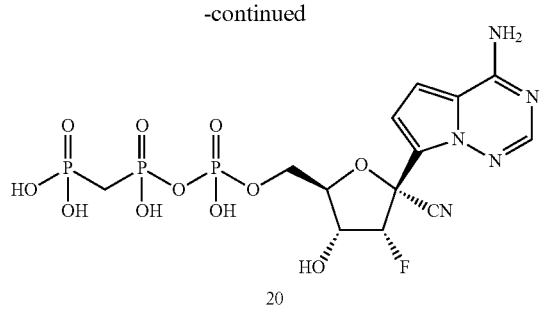

20

Compound 20 was prepared from compound 2 using a similar procedure to the preparation of compound 6. $^1$H NMR (400 MHz, D$_2$O) δ 7.78 (s, 1H), 6.93 (d, J=4.4 Hz, 1H), 6.78 (d, J=4.8 Hz, 1H), 5.45 (dd, J=53, 4.4 Hz, 1H), 4.38-4.50 (m, 2H), 4.13-4.20 (m, 2H). $^{31}$P NMR (161 MHz, D$_2$O) δ −5.7 (d, 1P), −11.0 (d, 1P), −21.5 (t, 1P). LCMS m/z 533.9.0 [M+H], 532.0 [M−H] Tr=1.25 min. HPLC ion exchange Tr=11.0 min.

Example 24

(2S)-ethyl 2-(((((2R,3S,4R,5R)-5-(4-aminopyrrolo [2,1-f][1,2,4]triazin-7-yl)-5-cyano-3,4-dihydroxytetrahydrofuran-2-yl)methoxy)(phenoxy)phosphoryl) amino)-3-phenylpropanoate (21)

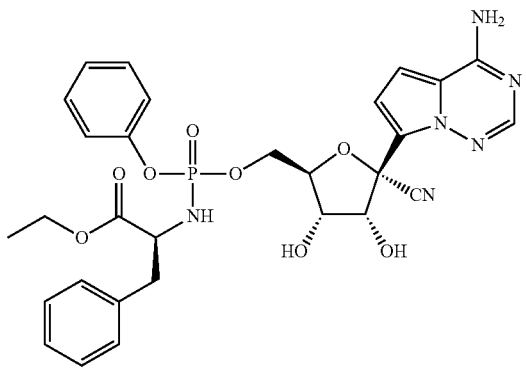 [SMILES: CCOC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)-3-phenylpropanoate is described below.

Preparation of (S)-ethyl 2-amino-3-phenylpropanoate hydrochloride

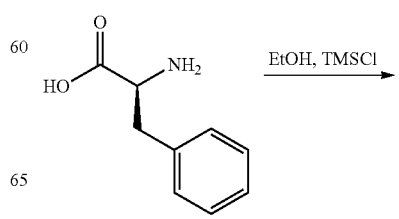

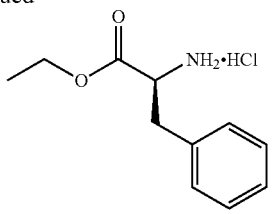

L-Phenylalanine (5 g, 30 mmol) was taken up in EtOH (30 mL). TMSCl (6.915 mL, 54 mmol) was added to the reaction at RT. The reaction vessel was fitted with a reflux condenser and the reaction was placed in an 80° C. bath. The reaction was stirred overnight. The next day the reaction was cooled to RT, concentrated under reduced pressure and the resulting residue was taken up in Et$_2$O. The resulting slurry was filtered and the isolate solids were further washed with Et$_2$O. The washed solids were placed under high vacuum to yield example (S)-ethyl 2-amino-3-phenylpropanoate hydrochloride. $^1$H NMR (400 MHz, DMSO-d$_6$) δ 8.52 (s, 3H), 7.30 (m, 5H), 4.24 (AB<u>X</u>, J$_{AX}$=7.8 Hz, J$_{BX}$=6.2 Hz, 1H), 4.11 (m, 2H), 3.17, 3.05 (A<u>B</u>X, J$_{AB}$=−14 Hz, J$_{BX}$=5.8 Hz, J$_{AX}$=7.6 Hz, 2H), 1.09 (t, J=6.8 Hz, 3H).

Preparation of (2S)-ethyl 2-(((4-nitrophenoxy)(phenoxy)phosphoryl)amino)-3-phenylpropanoate (Compound D)

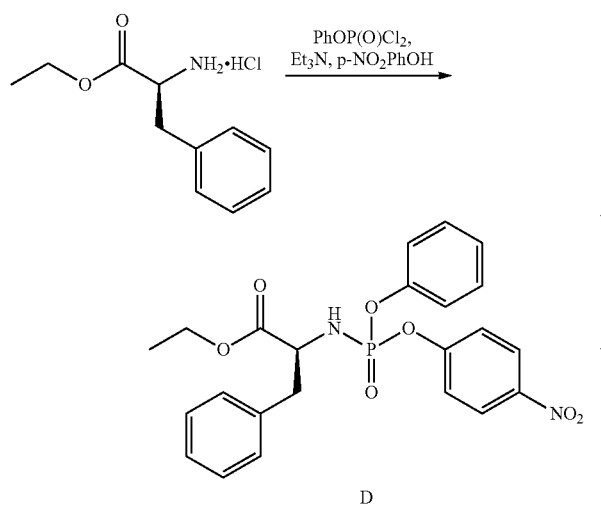

D (S)-ethyl 2-amino-3-phenylpropanoate hydrochloride (1.01 g, 4.41 mmol) was dissolved in DCM (50 mL). This solution was cooled to about 0° C. and PhOP(O)Cl$_2$ (0.656 mL, 4.41 mmol) was added, followed by the slow addition of Et$_3$N (1.62 mL, 11.5 mmol) over 5 min. The cold bath was removed and the reaction was allowed to warm to RT and stir over a period of 80 min. p-NO$_2$PhOH (0.583 g, 4.19 mmol) was added, followed by more Et$_3$N (0.3 mL, 2.1 mmol). The reaction progress was monitored by LC/MS. Upon completion of the reaction, it was diluted with Et$_2$O, and the resulting solids were removed by filtration. The filtrate was concentrated and compound D was isolated by silica gel column chromatography (25 g dry load cartridge, 120 g column; eluent: 100% hexanes ramping to 55% EtOAc in hexanes). $^1$H NMR (400 MHz, CD$_3$OD) δ 8.17 (m, 2H), 7.33 (m, 2H), 7.09-7.25 (m, 10H), 4.17 (m, 1H), 4.07 (m, 2H), 3.08 (m, 1H), 2.84 (m, 1H), 1.14 (m, 3H). $^{31}$P NMR (162 MHz, DMSO-d$_6$) δ −1.479 (s), −1.719 (s). MS m/z=471.01 [M+1].

Preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (Compound 21)

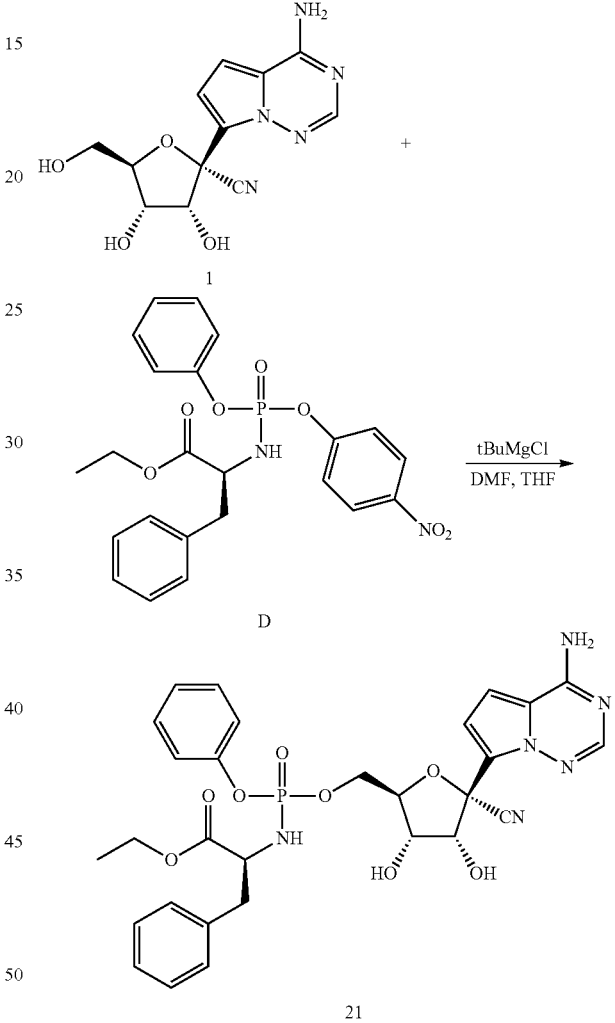

Compound 1 (0.030 g, 0.103 mmol) was dissolved in DMF (1 mL) and then THF (0.5 mL) was added. t-BuMgCl (1M/THF, 154.5 μL, 0.154 μmol) was added to the reaction in a drop-wise manner with vigorous stirring. The resulting white slurry was stirred at RT for about 30 min. A solution of compound D (0.058 g, 0.124 mmol) in THF (1 mL) was added in a drop-wise manner to the reaction at RT. The reaction progress was monitored by LC/MS. When the reaction progressed to 50% conversion, the reaction was cooled in an ice bath and quenched with glacial acetic acid (70 μL). The reaction was concentrated and compound 21 was isolated from the residue by reverse phase HPLC. $^1$H NMR (400 MHz, DMSO-d$_6$) δ 7.91 (d, J=4 Hz, 1H), 7.90 (brs, 2H), 7.09-7.30 (m, 8H), 7.01, (t, J=8.2 Hz, 2H), 6.89 (d, J=4.4 Hz, 1H), 6.82 (t, J=4.4 Hz, 1H), 6.27 (m, 1H), 6.14 (m, 1H), 5.34 (m, 1H), 4.62 (t, J=5.6 Hz, 1H), 4.15 (m, 1H), 3.78-4.01 (m, 6H), 2.92 (m, 1H), 2.78 (m, 1H), 1.04 (m, 3H). $^{31}$P NMR (162 MHz, DMSO-$d_6$) δ 3.69 (s), 3.34 (s). MS m/z=623.0 [M+H].

Example 25

(2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate (22)

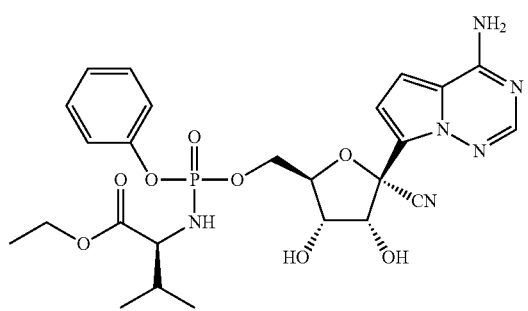 [SMILES: CCOC(=O)[C@@H](NP(=O)(OC[C@H]1O[C@@](C#N)(c2ccc3c(N)ncnn23)[C@H](O)[C@@H]1O)Oc1ccccc1)C(C)C]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate is described below.

Preparation of (2S)-ethyl 3-methyl-2-(((4-nitrophenoxy)(phenoxy)phosphoryl)amino) butanoate (Compound E)

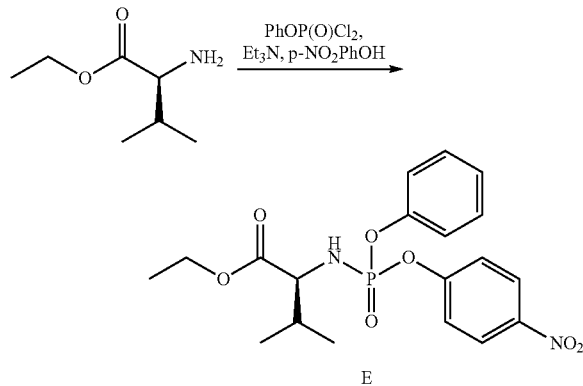

The (S)-ethyl 2-amino-3-methylbutanoate (0.351 g, 1.932 mmol) was dissolved in DCM (17 mL). This solution was cooled in an ice bath and PhOP(O)Cl$_2$ (0.287 mL, 1.932 mmol) was added, followed by the slow addition of Et$_3$N (1.62 mL, 11.4 mmol) over about 5 min. The cold bath was removed and the reaction was allowed to warm to RT and stir over a period of 1 h. p-NO$_2$PhOH (0.255 g, 1.836 mmol) was added, and the reaction progress was monitored by LC/MS. Upon completion of the reaction, the mixture was diluted with Et$_2$O, and the resulting solids were removed by filtration. The filtrate was concentrated and compound E was isolated by silica gel column chromatography (12 g dry load cartridge, 80 g column; eluent: 100% hexanes ramping to 55% EtOAc in hexanes). $^1$H NMR (400 MHz, DMSO-$d_6$) δ 8.30 (d, J=9.2 Hz, 2H), 7.48 (t, J=9.6 Hz, 2H), 7.40 (t, J=7.8 Hz, 2H), 7.20-7.27 (m, 3H), 6.60 (quart, J=11.6 Hz, 1H), 4.01 (m, 2H), 3.61 (m, 1H), 1.93 (m, 1H), 1.11 (m, 3H), 0.79 (m, 6H). $^{31}$P NMR (162 MHz, DMSO-$d_6$) δ −0.342 (s), −0.578 (s). MS m/z=422.9 [M+H].

Preparation of (2S)-ethyl 2-(((((2R,3S,4R,5R)-5-(4-aminopyrrolo[2,1-f][1,2,4]triazin-7-yl-5-cyano-3,4-dihydroxytetrahydrofuran-2-yl)methoxy)(phenoxy)phosphoryl)amino)-3-methylbutanoate (Compound 22)

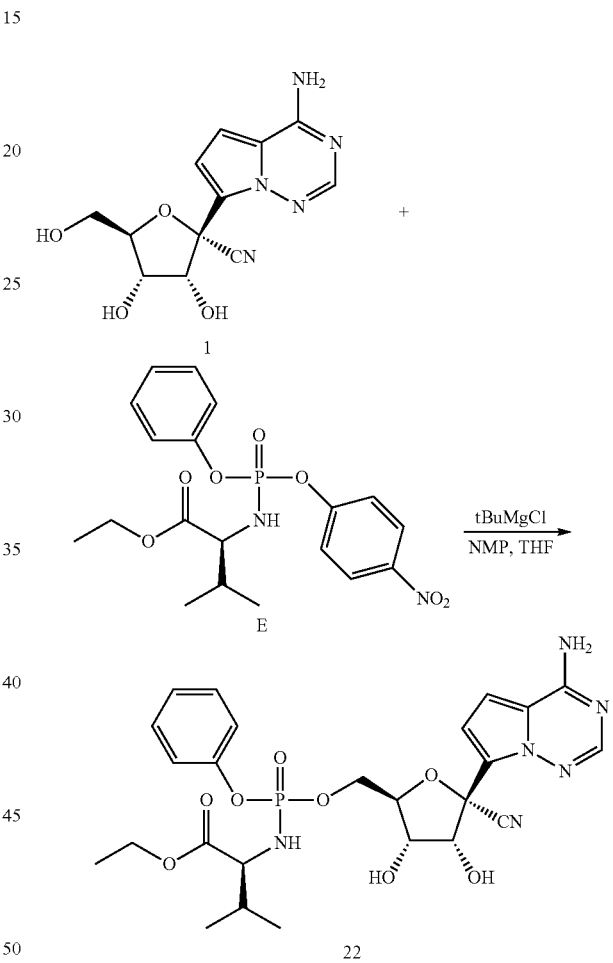

Compound 1 (0.040 g, 0.137 mmol) was dissolved in NMP (1.5 mL) and then THF (0.25 mL) was added. This solution was cooled in an ice bath and t-BuMgCl (1M/THF, 425.7 μL, 0.426 μmol) was added in a drop-wise manner with vigorous stirring. The ice bath was removed and the resulting white slurry was stirred at RT for about 15 min. A solution of compound E (0.081 g, 0.192 mmol) in THF (0.5 mL) was added in a drop-wise manner to the reaction at RT. The reaction progress was monitored by LC/MS. When the reaction progressed to 50% conversion, the reaction was cooled in an ice bath and quenched with glacial acetic acid (70 μL). The reaction was concentrated and compound 22 was semi-purified from the residue by reverse phase HPLC. The semi-pure material was further purified by silica gel column chromatography (12 g dry load cartridge, 40 g column; eluent: 100% EtOAc ramping to 10% MeOH in EtOAc) to yield compound 22. ¹H NMR (400 MHz, DMSO-d₆) δ 7.91 (d, J=1.6 Hz, 1H), 7.88 (brs, 2H), 7.32 (m, 2H), 7.15 (m, 3H), 6.90 (t, J=4.2 Hz, 1H), 6.84 (d, J=4.8 Hz, 1H), 6.26 (dd, J=13.4, 6.2 Hz, 1H), 5.87 (quart. J=11.2 Hz, 1H), 5.35 (m, 1H), 4.64 (m, 1H), 4.25 (m, 2H), 3.93-4.15 (m, 4H), 3.45 (m, 1H), 1.87 (m, 1H), 1.09-1.16 (m, 3H), 0.70-0.83 (m, 6H). ³¹P NMR (162 MHz, DMSO-d₆) δ 4.59 (s), 4.47 (s). MS m/z=575.02 [M+H].

Example 26

(S)-isopropyl 2-(((R)-(((2R,3S,4R,5R)-5-(4-amino-pyrrolo[2,1-f][1,2,4]triazin-7-yl)-5-cyano-3,4-dihy-droxytetrahydrofuran-2-yl)methoxy)(phenoxy)phosphoryl)amino)propanoate (23)

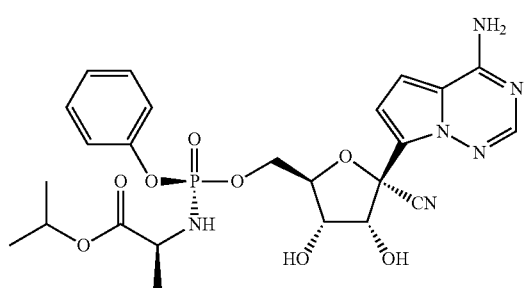 [SMILES: CC(C)OC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-isopropyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

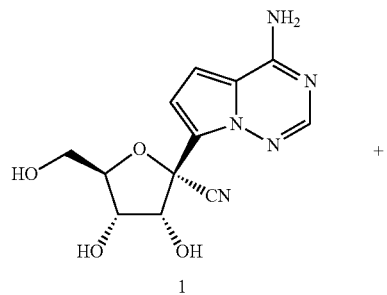

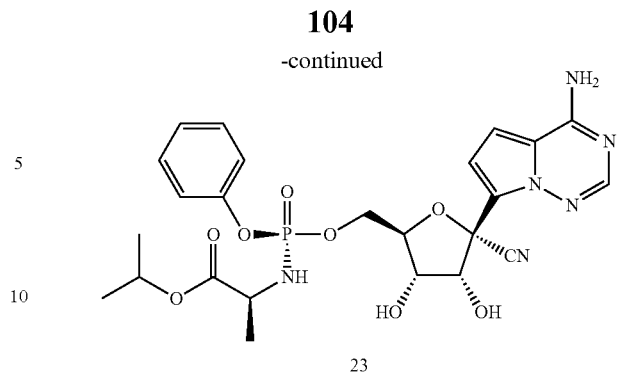

Compound 1 (60.0 mg, 206 µmol) was dissolved in NMP (0.28 mL). THF (0.2 mL) was added followed by tert-butyl magnesium chloride (1.0M solution in tetrahydrofuran, 0.309 mL) at RT under an argon atmosphere. After 20 min, a solution of compound F (Prepared according to Cho, A. et al *J. Med. Chem.* 2014, 57, 1812-1825, 81 mg, 206 µmol) in THF (0.2 mL) was added, and the resulting mixture was warmed to about 50° C. After 3 h, the reaction mixture was allowed to cool to RT and was purified directly by preparatory HPLC (Phenominex Synergi 4u Hydro-RR 80 Å 150×30 mm column, 5-100% acetonitrile/water gradient) to afford compound 23. ¹H NMR (400 MHz, CD₃OD) δ 7.86 (s, 1H), 7.34-7.26 (m, 2H), 7.21-7.12 (m, 3H), 6.91 (d, J=4.6 Hz, 1H), 6.87 (d, J=4.6 Hz, 1H), 4.92 (sept, J=6.3 Hz, 1H), 4.80 (d, J=5.4 Hz, 1H), 4.43-4.34 (m, 1H), 4.33-4.24 (m, 1H), 4.18 (t, J=5.6 Hz, 1H), 3.82 (dq, J=9.7, 7.1 Hz, 2H), 1.27 (dd, J=7.1, 1.0 Hz, 3H), 1.18 (dd, J=6.3, 4.8 Hz, 6H). ³¹P NMR (162 MHz, CD₃OD) δ 3.72 (s). LC/MS: t_R=1.39 min, MS m/z=561.11 [M+H]; LC system: Thermo Accela 1250 UHPLC; MS system: Thermo LCQ Fleet; Column: Kinetex 2.6µ XB-C18 100A, 50×4.6 mm; Solvents: ACN with 0.1% acetic acid, water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min. HPLC: t_R=2.523 min; HPLC system: Agilent 1100 series; Column: Gemini 5µ C18 110A, 50×4.6 mm; Solvents: ACN with 0.1% TFA, Water with 0.1% TFA; Gradient: 0 min-5.0 min 2-98% ACN, 5.0 min-6.0 min 98% ACN at 2 mL/min.

Example 27

(2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (24)

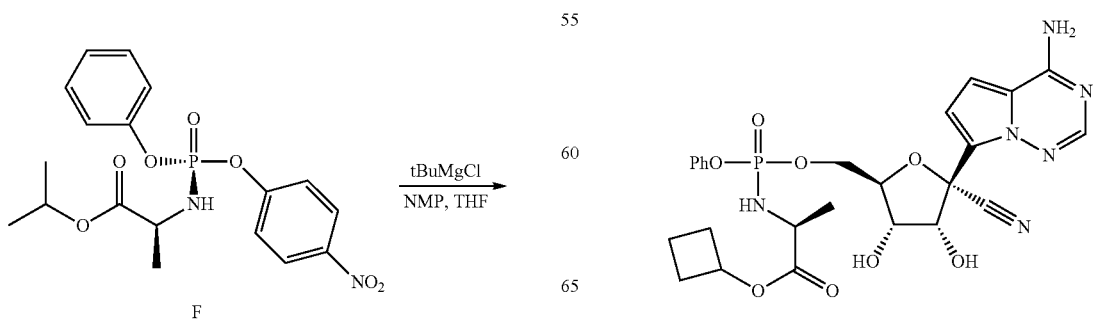

The preparation of (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Preparation of (2S)-cyclobutyl 2-(((4-nitrophenoxy)(phenoxy)phosphoryl)amino)propanoate (Compound G)

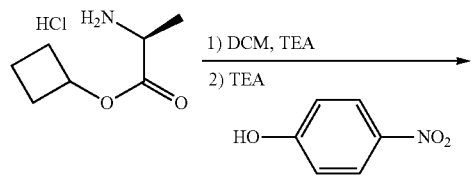

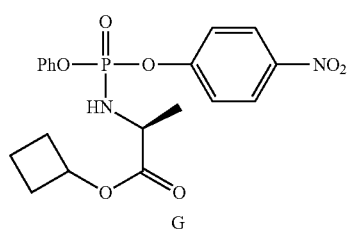

Phenyl dichlorophosphate (1.49 mL, 10 mmol) was dissolved in 10 mL of anhydrous DCM and stirred under atmosphere nitrogen in an ice bath. L-Alanine isobutyl ester hydrochloride (0.9 g, 5 mmol) was added in one portion. Triethylamine (765 µL, 5.5 mmol) was then added dropwise. Reaction stirred for about 1 h. More Triethylamine (765 µL, 5.5 mmol) was added dropwise and the reaction was stirred for about 45 min. p-Nitrophenol (1.25 g, 9 mmol) was added in one portion and stirred for about 30 min. Triethylamine (765 µL, 5.5 mmol) was added and the reaction mixture was stirred for about 2 h. Additional p-nitrophenol (1.25 g, 9 mmol) and triethylamine (765 µL, 5.5 mmol) were then added, and the reaction was stirred for another about 2 h. The reaction mixture was concentrated under reduced pressure. The resulting crude was diluted with EtOAc and washed twice with 5% aqueous citric acid solution, followed with saturated aqueous sodium chloride solution. The organic layer was then dried over anhydrous sodium sulfate and concentrated under reduced pressure. The crude residue was purified with silica gel column (0-20-50% EtOAc in hexanes) to give compound G. $^1$H NMR (400 MHz, CD$_3$OD) δ 8.33-8.23 (m, 2H), 7.52-7.33 (m, 4H), 7.33-7.17 (m, 3H), 4.96-4.85 (m, 1H), 4.07-3.96 (m, 1H), 2.27 (m, 2H), 2.07-1.91 (m, 2H), 1.83-1.70 (m, 1H), 1.70-1.55 (m, 1H), 1.32 (m, 3H). $^{31}$P NMR (162 MHz, CD$_3$OD) δ −1.36, −1.59. MS m/z=420.9 [M+H].

Preparation (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 24)

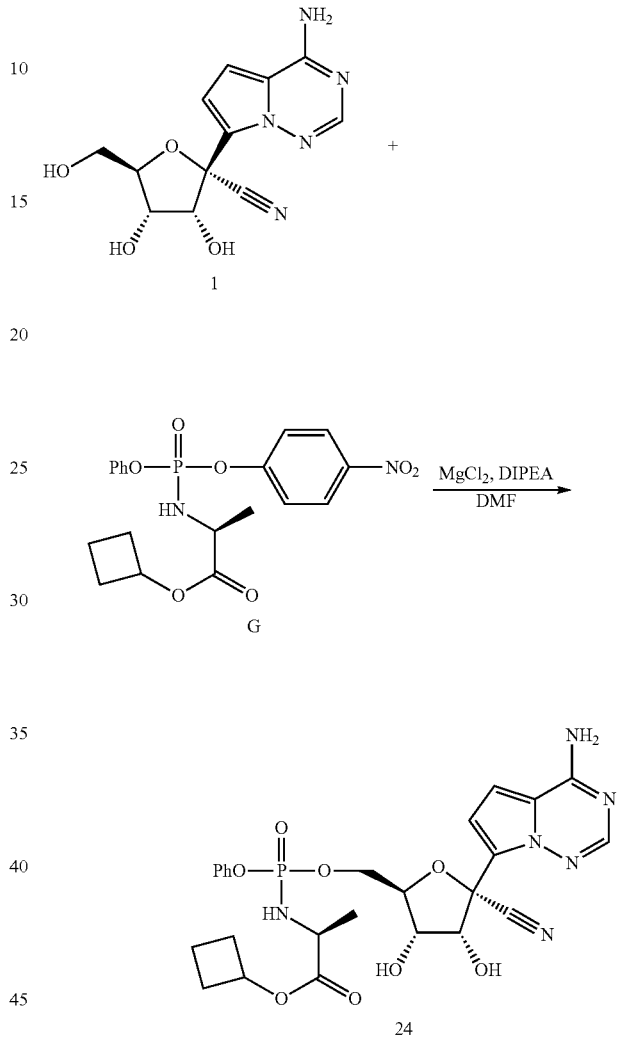

Compound 1 (58 mg, 0.2 mmol) was mixed with compound G (101 mg, 0.24 mmol) in 2 mL of anhydrous DMF. Magnesium chloride (42 mg, 0.44 mmol) was added in one portion. The reaction mixture was heated to about 50° C. DIPEA (87 µL, 0.5 mmol) was added, and the reaction was stirred for about 2 h at about 50° C. The reaction mixture was cooled to room temperature, was diluted with EtOAc and was washed with 5% aqueous citric acid solution followed by saturated aqueous sodium chloride solution. The organic layer was then dried over anhydrous sodium sulfate and concentrated under reduced pressure. The crude residue was purified with silica gel column (0-2-5% MeOH in DCM) to afford compound 24. $^1$H NMR (400 MHz, Methanol-d4) δ 7.85 (m, 1H), 7.34-7.22 (m, 2H), 7.22-7.08 (m, 3H), 6.94-6.84 (m, 2H), 4.95-4.85 (m, 1H), 4.79 (m, 1H), 4.46-4.34 (m, 2H), 4.34-4.24 (m, 1H), 4.19 (m, 1H), 3.81 (m, 1H), 2.27 (m, 2H), 2.01 (m, 2H), 1.84-1.68 (m, 1H), 1.62 (m, 1H), 1.30-1.16 (m, 3H). $^{31}$P NMR (162 MHz, cd$_3$od) δ 3.70, 3.65. MS m/z=573.0 [M+H].

Example 28

(2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (25)

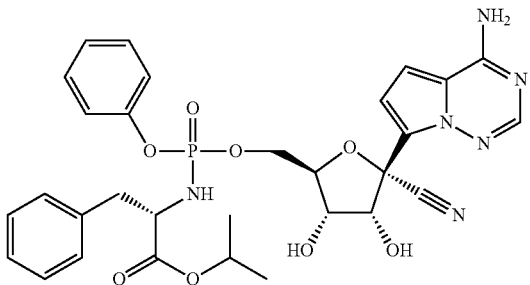 [SMILES: CC(C)OC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate is described below.

Preparation of (2S)-isopropyl 2-(((4-nitrophenoxy)(phenoxy)phosphoryl)amino)-3-phenylpropanoate (Compound H)

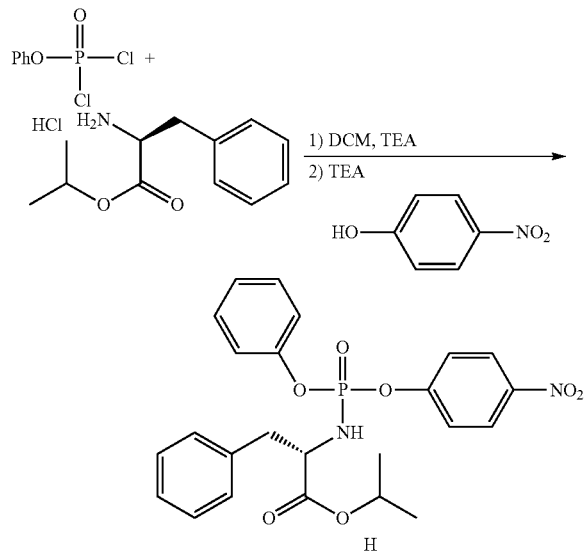

Phenyl dichlorophosphate (718 µL, 4.8 mmol) was dissolved in 10 mL of anhydrous DCM and stirred under a nitrogen atmosphere in an ice bath. L-Phenylalanine isopropyl ester hydrochloride (1 g, 4.1 mmol) was added in one portion. Another 10 mL of anhydrous DCM was added. Triethylamine (736 µL, 5.3 mmol) was added dropwise and the reaction mixture was stirred for about 30 min. More triethylamine (736 µL, 5.3 mmol) was then added dropwise and the reaction mixture was stirred for 30 min. Additional triethylamine (736 µL, 5.3 mmol) was then added dropwise and the reaction mixture was stirred for about 15 min. p-Nitrophenol (600 mg, 4.32 mmol) was then added. The ice bath was then removed and the reaction mixture was allowed to warm to room temperature and stirred for about 2 h. More p-nitrophenol (50 g) and triethylamine (736 µL, 5.3 mmol) were the added and the reaction mixture was stirred for about 1 h.

The reaction mixture was then concentrated under reduced pressure, and was diluted with EtOAc and washed twice with 5% aqueous citric acid solution, followed with saturated aqueous sodium chloride solution. The organic layer was dried over anhydrous sodium sulfate and was concentrated under reduced pressure. The crude was purified with silica gel column (0-15% EtOAc in hexanes) to give compound H. $^1$H NMR (400 MHz, CDCl$_3$) δ 8.17 (m, 2H), 7.38-7.13 (m, 10H), 7.13-7.02 (m, 2H), 4.95 (m, 1H), 4.31 (m, 1H), 3.69 (m, 1H), 3.02 (dd, J=6.1, 1.8 Hz, 2H), 1.21-1.08 (m, 6H). $^{31}$P NMR (162 MHz, cdcl3) δ −2.96, −2.98. MS m/z=485.0 [M+H].

Preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (Compound 25)

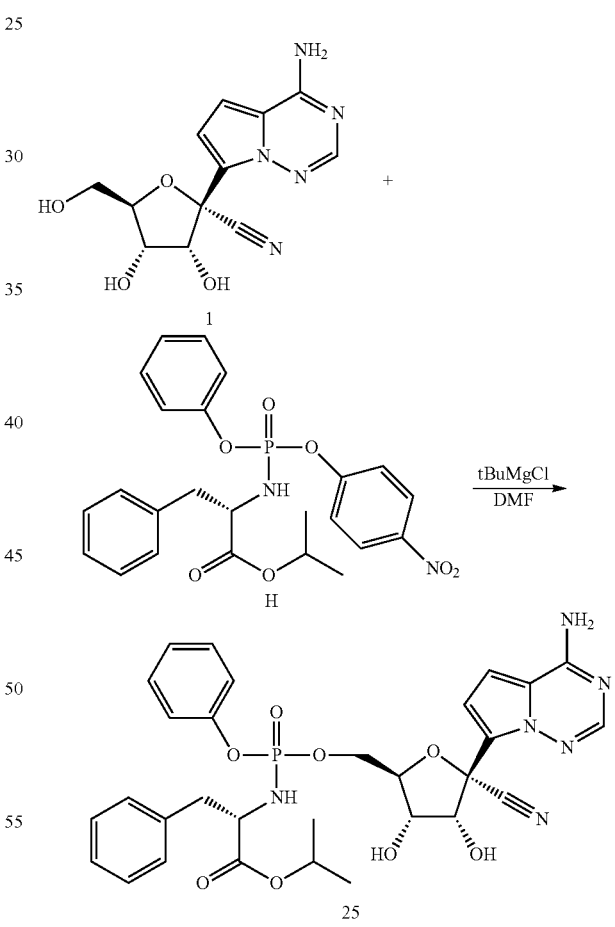

Compound 1 (58 mg, 0.2 mmol) and compound H (116 mg, 0.24 mmol) were mixed and 2 mL of anhydrous DMF was added. The reaction mixture was stirred under a nitrogen atmosphere at room temperature. 1M tBuMgCl in THF (300 µL, 0.3 mmol) was added dropwise over 3 minutes and the reaction mixture was then stirred for about 16 h. The reaction mixture was diluted with EtOAc and washed with 5% aqueous citric acid solution, saturated aqueous sodium bicarbonate solution and then saturated aqueous sodium chloride solution. The organic layer was dried over anhydrous sodium sulfate and concentrated under reduced pressure. The crude residue was purified with silica gel column (0-5% MeOH in DCM) to give compound 25. $^1$H NMR (400 MHz, CD$_3$OD) δ 7.84 (m, 1H), 7.27-7.08 (m, 8H), 7.08-6.97 (m, 2H), 6.88 (m, 2H), 4.91-4.84 (m, 1H), 4.74 (m, 1H), 4.26 (m, 1H), 4.19-4.04 (m, 2H), 4.04-3.91 (m, 2H), 2.97 (m, 1H), 2.82 (m, 1H), 1.14 (m, 3H), 1.06 (m, 3H). $^{31}$P NMR (162 MHz, CD$_3$OD) δ 3.63, 3.25. MS m/z=637.0 [M+H].

Example 29

(S)-methyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (26)

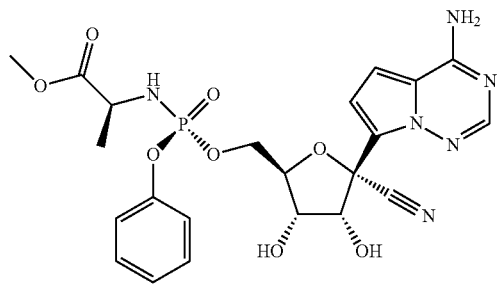 [SMILES: COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-methyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

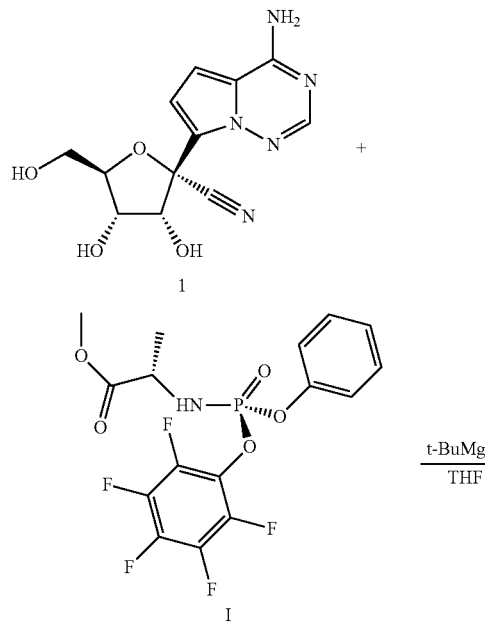

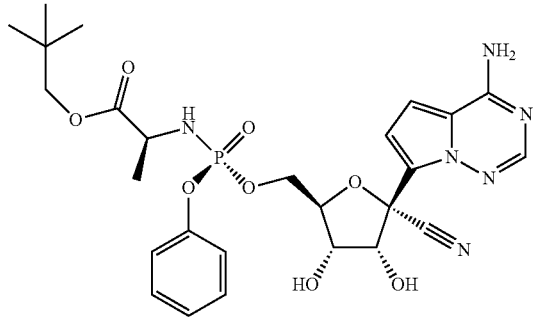 [SMILES: C[C@H](N[P@](=O)(OC[C@H]1O[C@@](C#N)(c2ccc3c(N)ncnn23)[C@H](O)[C@@H]1O)Oc1ccccc1)C(=O)OCC(C)(C)C]

26

Compound 1 (100 mg, 0.34 mmol) was dissolved in THF (2 mL) and cooled with an ice water bath. Then 1M t-BuMgCl (0.52 mL, 0.77 mmol) was added dropwise slowly. The resulting mixture was stirred for about 30 min at room temperature. Then compound I (Prepared according to WO 2012142085, 219 mg, 0.52 mmol) in THF (2 mL) was added over 5 min and the resulting mixture was stirred for about 24 h at room temperature. The reaction mixture was then diluted with EtOAc, cooled under ice-water bath, washed with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give compound 26. $^1$H NMR (400 MHz, CD$_3$OD) δ 7.86 (s, 1H), 7.29 (dd, J=8.6, 7.2 Hz, 2H), 7.21-7.09 (m, 3H), 6.94-6.81 (m, 2H), 4.79 (d, J=5.4 Hz, 1H), 4.38 (ddq, J=10.8, 5.3, 2.7 Hz, 2H), 4.33-4.23 (m, 1H), 4.18 (t, J=5.5 Hz, 1H), 3.86 (dq, J=9.9, 7.1 Hz, 1H), 3.62 (s, 3H), 1.27 (dd, J=7.2, 1.1 Hz, 3H). MS m/z=533 (M+1)$^+$.

Example 30

(S)-neopentyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (27)

The preparation of (S)-neopentyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

111

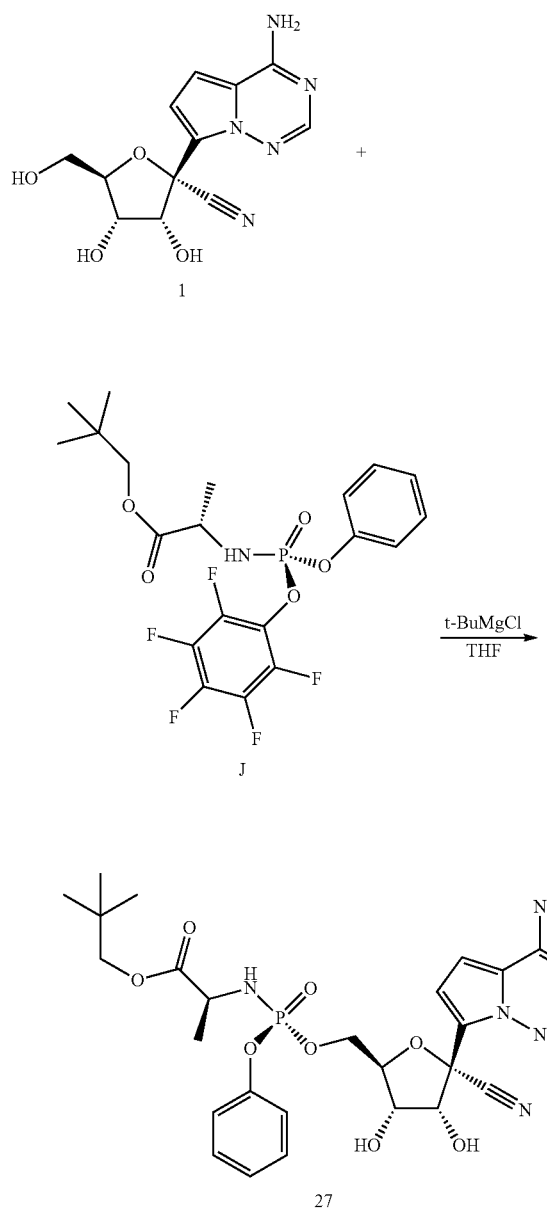

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for about 30 min at room temperature. Then compound J (Prepared according to WO2012075140, 248 mg, 0.52 mmol) was added over about 5 min and the resulting mixture was stirred for about 24 h at room temperature, diluted with EtOAc, cooled under ice-water bath, treated with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give Compound 27. $^1$H NMR (400 MHz, CD$_3$OD) δ 7.86 (s, 1H), 7.36-7.24 (m, 2H), 7.23-7.10 (m, 3H), 6.96-6.85 (m, 2H), 4.78 (d, J=5.4 Hz, 1H), 4.38 (tdd, J=10.0, 4.9, 2.5 Hz, 2H), 4.32-4.24 (m, 1H), 4.17 (t, J=5.6 Hz, 1H), 3.91 (dq, J=9.8, 7.1 Hz, 1H), 3.81 (d, J=10.5 Hz, 1H), 3.69 (d, J=10.5 Hz, 1H), 1.31 (dd, J=7.2, 1.1 Hz, 3H), 0.89 (s, 9H). MS m/z=589 (M+1)$^+$.

112

Example 31

(2S)-cyclopentyl 2-(((((2R,3S,4R,5R)-5-(4-amino-pyrrolo[2,1-f][1,2,4]triazin-7-yl)-5-cyano-3,4-dihydroxytetrahydrofuran-2-yl)methoxy)(phenoxy)phosphoryl)amino)propanoate (28)

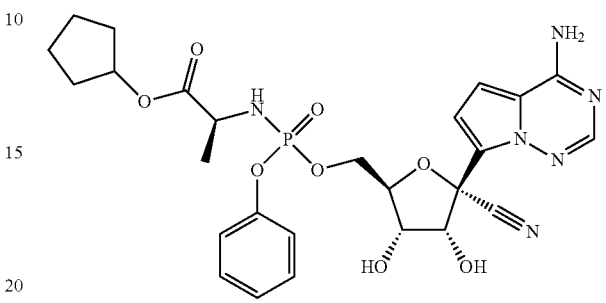

The preparation of (2S)-cyclopentyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

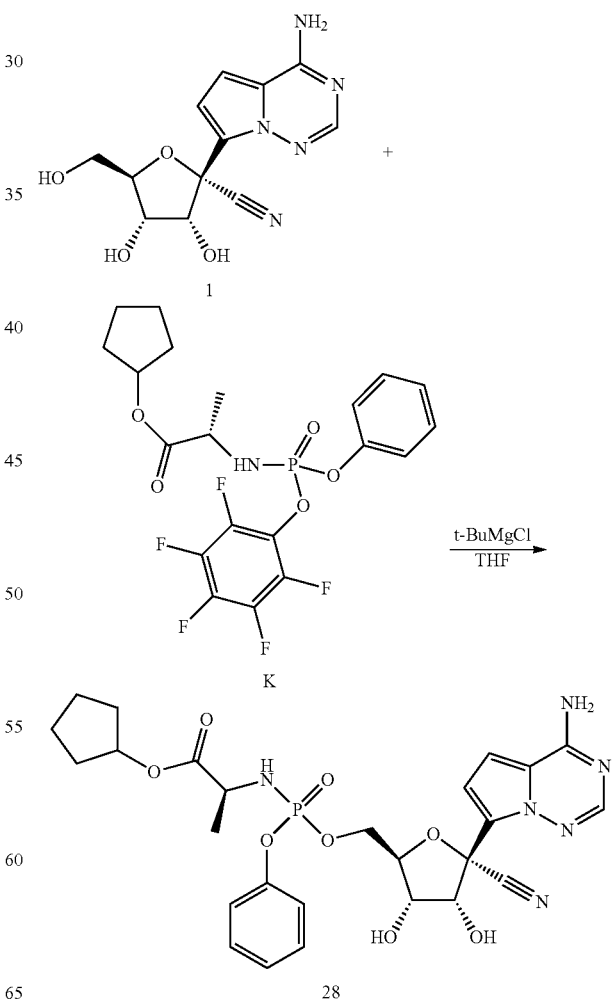

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for about 30 min at room temperature. Then compound K (Prepared according to WO2012075140, 247 mg, 0.52 mmol) in THF (2 mL) was added over about 5 min and the resulting mixture was stirred for about 24 h at room temperature, diluted with EtOAc, cooled under ice-water bath, treated with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give example 28. $^1$H NMR (400 MHz, CD$_3$OD) δ 7.85 (s, 1H), 7.33-7.22 (m, 2H), 7.14 (tdd, J=7.6, 2.1, 1.1 Hz, 3H), 6.95-6.87 (m, 2H), 5.13-5.00 (m, 1H), 4.78 (d, J=5.4 Hz, 1H), 4.48-4.35 (m, 2H), 4.30 (ddd, J=10.6, 5.7, 3.6 Hz, 1H), 4.19 (t, J=5.4 Hz, 1H), 3.78 (dq, J=9.2, 7.1 Hz, 1H), 1.81 (dtd, J=12.5, 5.9, 2.4 Hz, 2H), 1.74-1.49 (m, 6H), 1.21 (dd, J=7.1, 1.2 Hz, 3H). MS m/z=587 (M+1)+.

Example 32

(2S)-cyclohexyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (29)

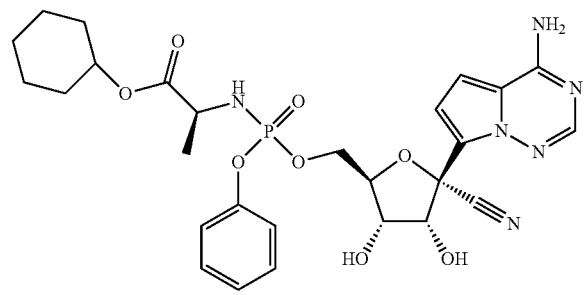 [SMILES: C[C@H](NP(=O)(OC[C@H]1O[C@@](C#N)(c2ccc3c(N)ncnn23)[C@H](O)[C@@H]1O)Oc1ccccc1)C(=O)OC1CCCCC1]

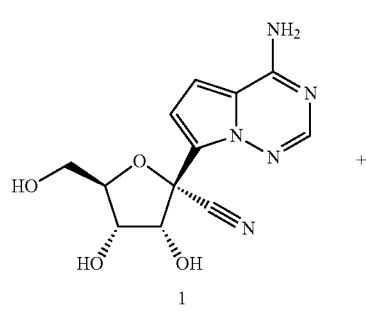

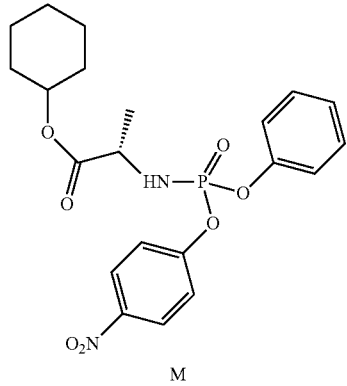

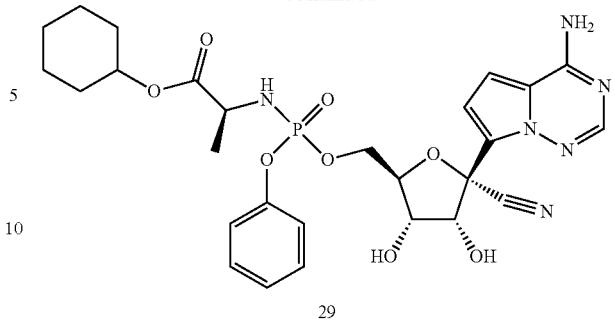

To a mixture of compound 1 (50 mg, 0.343 mmol), compound M (Prepared according to US20130143835, 93 mg, 0.209 mmol), and MgCl$_2$ (24.5 g, 0.257 mmol) in DMF (1 mL) was added diisopropylethylamine (0.075 mL, 0.43 mmol) dropwise over about 5 min at about 0° C. The resulting mixture was stirred at about 50° C. for about 1 h. The reaction mixture was then cooled with an ice-water bath, treated with 1M citric acid (0.5 mL), and was purified directly by prep-HPLC (ACN 0 to 70% in water) to afford compound 29. $^1$H NMR (400 MHz, CD$_3$OD) δ 7.84 (s, 1H), 7.32-7.23 (m, 2H), 7.18-7.10 (m, 3H), 6.93-6.87 (m, 2H), 4.78 (d, J=5.4 Hz, 1H), 4.67 (td, J=8.7, 4.2 Hz, 1H), 4.48-4.35 (m, 2H), 4.30 (ddd, J=10.8, 5.7, 3.7 Hz, 1H), 4.20 (t, J=5.4 Hz, 1H), 3.88-3.71 (m, 1H), 1.83-1.63 (m, 4H), 1.58-1.46 (m, 1H), 1.46-1.24 (m, 5H), 1.24 (s, 3H). $^{31}$P NMR (162 MHz, CD$_3$OD) δ 3.75. MS m/z=601 (M+1)$^+$.

Example 33

Ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (30)

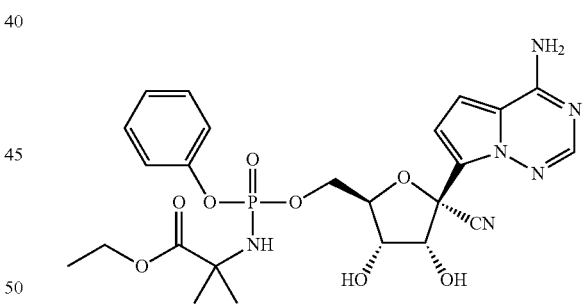

The preparation of ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Ethyl 2-((tert-butoxycarbonyl)amino)-2-methylpropanoate

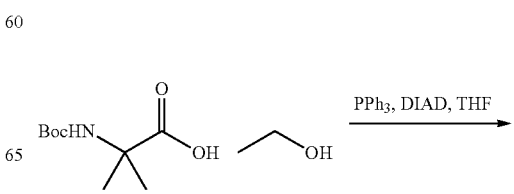

-continued

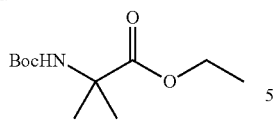

Take up triphenylphosphine (6.18 g, 25.00 mmol) in THF (30 mL). Next charge DIAD (4.92 mL, 25.00 mmol) and stir at room temperature for 10 min. Dissolve 2-((tert-butoxycarbonyl)amino)-2-methylpropanoic acid (5.08 g, 25.00 mmol) in THF (20 mL) and add to the reaction mixture followed by the addition of ethanol (2.19 mL, 37.49 mmol). Allow the reaction to stir at room temperature for about 1 h. The solvents were removed under reduced pressure and the crude was taken up in 1:1 Et$_2$O:Hexanes (120 mL). The solid triphenylphosphine oxide was filtered off and the solvent was removed under reduced pressure. The crude was taken up in minimal CH$_2$Cl$_2$ and purified by silica gel chromatography 0-50% EtOAc/Hex to afford ethyl 2-((tert-butoxycarbonyl)amino)-2-methylpropanoate. $^1$H NMR (400 MHz, Chloroform-d) δ 4.18 (q, J=7.1 Hz, 2H), 1.49 (s, 6H), 1.43 (s, 9H), 1.27 (t, J=7.1 Hz, 3H).

Preparation of Ethyl 2-amino-2-methylpropanoate hydrochloride

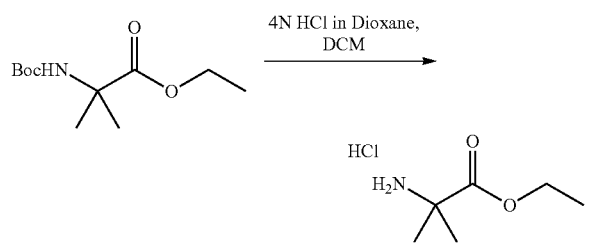

Take up ethyl 2-((tert-butoxycarbonyl)amino)-2-methylpropanoate (2.71 g, 11.72 mmol) in CH$_2$Cl$_2$ (25 mL) and slowly add 4N HCl in dioxane (25 mmol) and stir at room temperature. At 1 h, the reaction was determined to be complete by TLC. The solvents were removed under reduced pressure and the crude was coevaporated with Et$_2$O two times then placed under high vacuum to afford ethyl 2-amino-2-methylpropanoate hydrochloride. $^1$H NMR (400 MHz, DMSO-d$_6$) δ 8.70 (s, 3H), 4.18 (q, J=7.1 Hz, 2H), 1.46 (s, 6H), 1.21 (t, J=7.1 Hz, 3H).

Preparation of Ethyl 2-methyl-2-(((4-nitrophenoxy)(phenoxy)phosphoryl)amino)propanoate (Compound N)

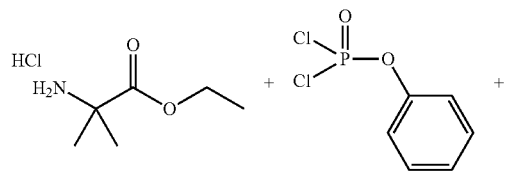

-continued

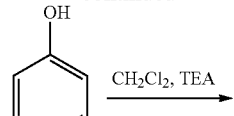

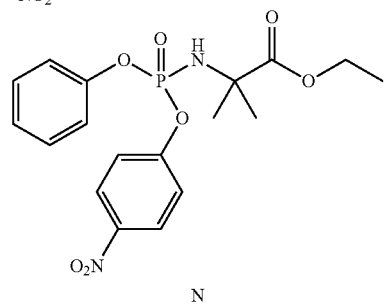

Take up phenyl dichlorophosphate (0.97 mL, 6.50 mmol) and ethyl 2-amino-2-methylpropanoate hydrochloride (1.09 g, 6.50 mmol) in CH$_2$Cl$_2$ (50 mL). Cool the reaction mixture to about 0° C. and slowly add TEA (1.75 mL, 12.45 mmol). Remove the cold bath and allow the reaction mixture to stir at room temperature. After about 2 h, the addition of the amino acid was determined to be complete by $^{31}$P NMR. Charge p-nitrophenol (0.860 g, 6.17 mmol) followed by the addition of TEA (0.87 g, 7.69 mmol). Allow the reaction to stir at room temperature. After about 2 h, the reaction was determined to be complete by LCMS. The reaction was diluted with Et$_2$O and the TEA·HCl salts were filtered off. The crude was concentrated and purified by silica gel chromatography (0-50% EtOAc/Hex) to afford compound N. $^1$H NMR (400 MHz, DMSO-d$_6$) δ 8.37-8.21 (m, 2H), 7.55-7.44 (m, 2H), 7.43-7.33 (m, 2H), 7.30-7.09 (m, 3H), 6.57 (d, J=10.1 Hz, 1H), 3.99 (q, J=7.1 Hz, 2H), 1.39 (s, 6H), 1.08 (t, J=7.1 Hz, 3H). $^{31}$P NMR (162 MHz, DMSO-d$_6$) δ -2.87. LC/MS: t$_R$=1.65 min, MS m/z=408.97 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Preparation of ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 30)

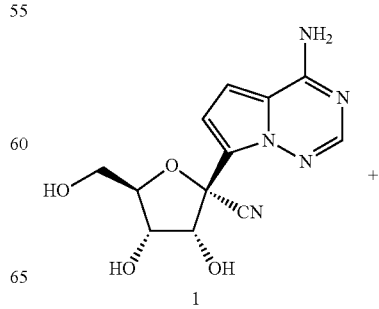

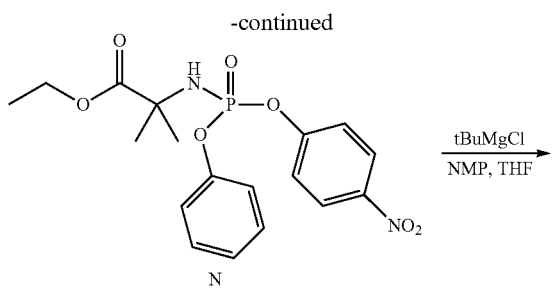

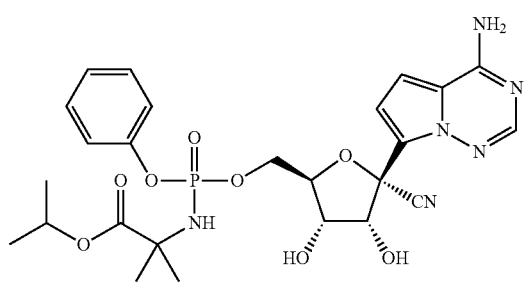 [SMILES: CC(C)OC(=O)C(C)(C)NP(=O)(OC[C@H]1O[C@@](C#N)(c2ccc3c(N)ncnn23)[C@H](O)[C@@H]1O)Oc1ccccc1]

Take up compound 1 (66 mg, 0.23 mmol) in NMP (2.0 mL). Cool the mixture to about 0° C. and slowly add tBuMgCl (1.0M in THF, 0.34 mL, 0.34 mmol). Allow the reaction to stir at about 0° C. for about 30 min, then add a solution of compound N (139 mg, 0.34 mmol) dissolved in THF (1.0 mL). Remove the cold bath and place the reaction in about 50° C. preheated oil bath. After about 2 h, the reaction was cooled to room temperature and quenched with acetic acid and methanol. The crude was concentrated and purified by reverse phase HPLC without modifier to afford compound 30. $^1$H NMR (400 MHz, DMSO-$d_6$) δ 7.89 (m, 3H), 7.31 (q, J=8.1 Hz, 2H), 7.22-7.05 (m, 3H), 6.87 (d, J=4.5, 1H), 6.80 (d, J=4.5 Hz, 1H), 6.27 (d, J=11.7, 1H), 5.81 (d, J=9.7, 1H), 5.35 (d, J=5.6 Hz, 1H), 4.64 (dt, J=9.0, 5.6 Hz, 1H), 4.24 (m, 2H), 4.11 (m, 1H), 4.04-3.90 (m, 3H), 1.39-1.23 (m, 6H), 1.10 (t, J=7.1, 3H). $^{31}$P NMR (162 MHz, DMSO-$d_6$) δ 2.45, 2.41. LC/MS: $t_R$=1.03 min, MS m/z=561.03 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 34

Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (31)

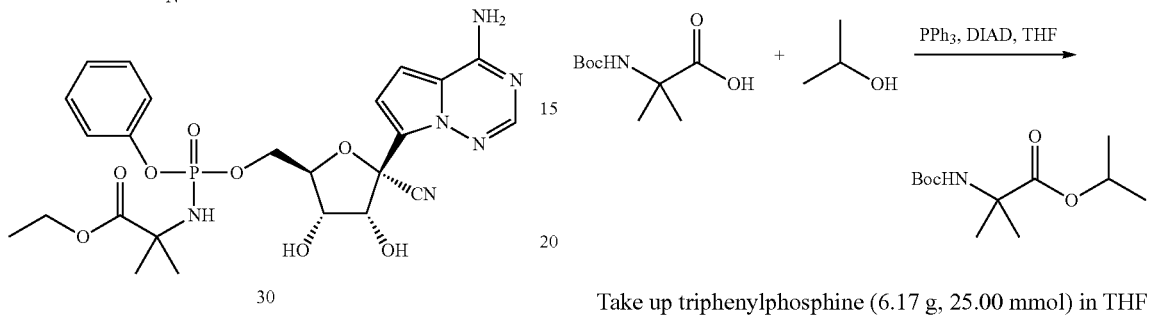

The preparation of Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Isopropyl 2-((tert-butoxycarbonyl)amino)-2-methylpropanoate

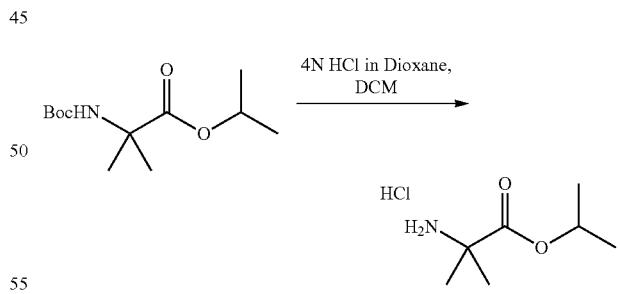

Take up triphenylphosphine (6.17 g, 25.00 mmol) in THF (30 mL). Next charge DIAD (4.92 mL, 25.00 mmol) and stir at room temperature for about 10 min. Dissolve 2-((tert-butoxycarbonyl)amino)-2-methylpropanoic acid (5.07 g, 25.00 mmol) dissolved in THF (20 mL) and add to the reaction mixture followed by the addition of isopropanol (1.91 mL, 25.00 mmol). Allow the reaction to stir at room temperature for about 1 h. The solvents were removed under reduced pressure and the crude was taken up in 1:1 Et$_2$O: Hexanes (120 mL). The solid triphenylphosphine oxide was filtered off and the solvent was removed under reduced pressure. The crude was taken up in minimal CH$_2$Cl$_2$ and purified by silica gel chromatography (0-50% EtOAc/Hex) to afford isopropyl 2-((tert-butoxycarbonyl)amino)-2-methylpropanoate. $^1$H NMR (400 MHz, Chloroform-d) δ 5.03 (p, J=6.2 Hz, 1H), 1.48 (s, 6H), 1.40 (d, J=6.2 Hz, 9H), 1.24 (d, J=6.3 Hz, 6H).

Preparation of Isopropyl 2-amino-2-methylpropanoate hydrochloride

Take up isopropyl 2-((tert-butoxycarbonyl)amino)-2-methylpropanoate (4.09 g, 16.67 mmol) in CH$_2$Cl$_2$ (50 mL) and slowly add 4N HCl in dioxane (50 mmol) and stir at room temperature. At about 1 h, the reaction was determined to be complete by TLC. The solvents were removed under reduced pressure and the crude was coevaporated with Et$_2$O two times then placed under high vacuum to afford isopropyl 2-amino-2-methylpropanoate hydrochloride. $^1$H NMR (400 MHz, DMSO-$d_6$) δ 8.61 (s, 3H), 4.96 (p, J=6.2 Hz, 1H), 1.44 (s, 6H), 1.22 (d, J=6.2 Hz, 6H).

119

Preparation of Isopropyl 2-methyl-2-(((4-nitrophenoxy)(phenoxy)phosphoryl)amino)propanoate (Compound O)

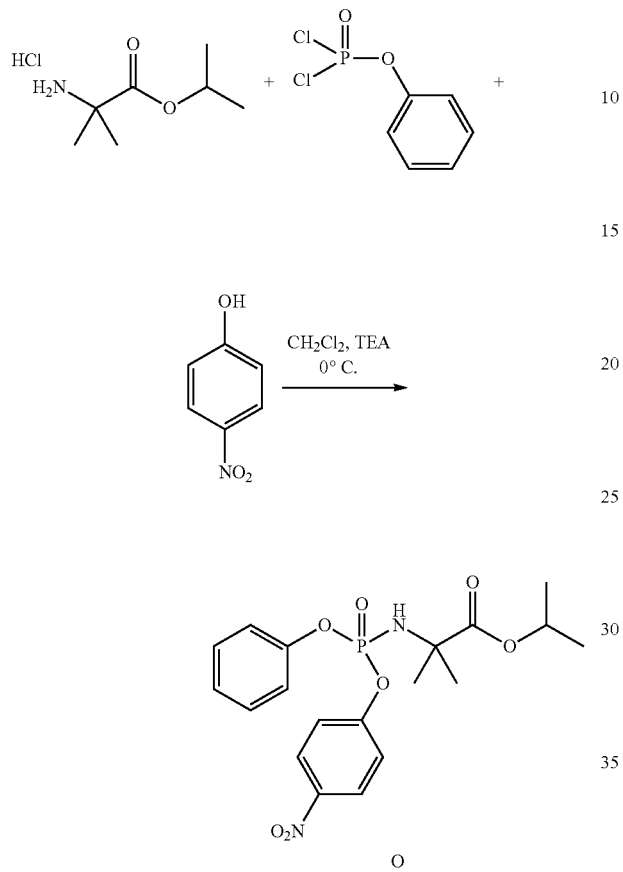

Take up phenyl dichlorophosphate (0.83 mL, 5.58 mmol) and isopropyl 2-amino-2-methylpropanoate hydrochloride (1.01 g, 5.58 mmol) in $CH_2Cl_2$ (50 mL). Cool the reaction mixture to 0° C. and slowly add TEA (1.61 mL, 11.45 mmol). Remove the cold bath and allow the reaction mixture to stir at room temperature. After about 2 h, the addition of the amino acid was determined to be complete by $^{31}P$ NMR. Charge p-nitrophenol (0.74 g, 5.30 mmol) followed by the addition of TEA (0.81, 5.84 mmol). Allow the reaction to stir at room temperature. After about 2 h, the reaction was determined to be complete by LCMS. The reaction was diluted with $Et_2O$ and the TEA·HCl salts were filtered off. The crude was concentrated and purified by silica gel chromatography (0-50% EtOAc/Hex) to afford compound O. $^1H$ NMR (400 MHz, DMSO-$d_6$) δ 8.42-8.19 (m, 2H), 7.55-7.43 (m, 2H), 7.39 (dd, J=8.6, 7.2 Hz, 2H), 7.30-7.12 (m, 3H), 6.53 (d, J=10.1 Hz, 1H), 4.82 (hept, J=6.3 Hz, 1H), 1.38 (s, 6H), 1.09 (d, J=6.3, 6H). $^{31}P$ NMR (162 MHz, DMSO-$d_6$) δ −2.84. LC/MS: $t_R$=1.73 min, MS m/z=422.92 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

120

Preparation of Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 31)

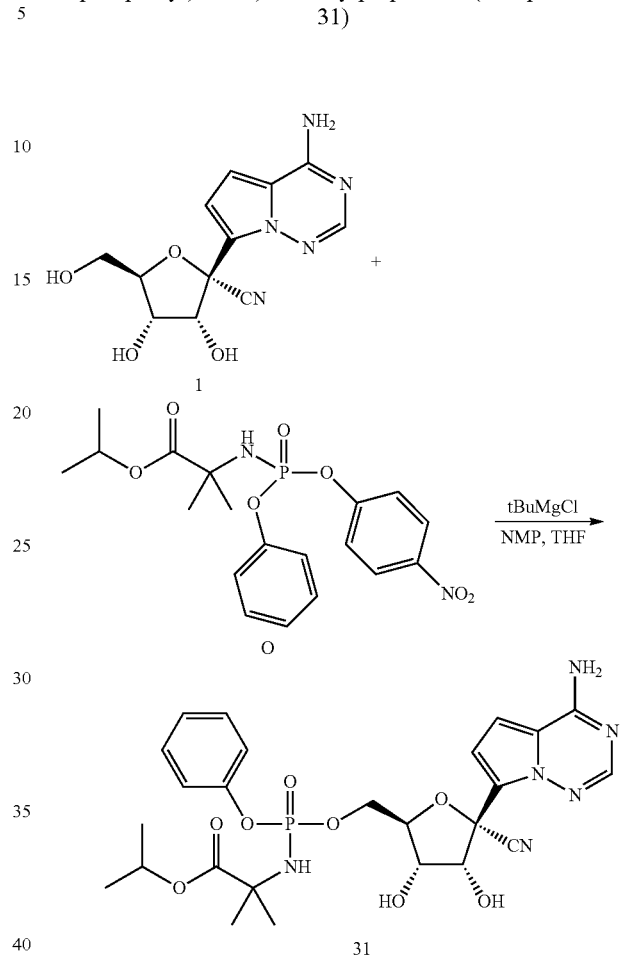

Take up compound 1 (66 mg, 0.23 mmol) in NMP (2.0 mL). Cool the mixture to about 0° C. and slowly add tBuMgCl (1.0M in THF, 0.57 mL, 0.57 mmol). Allow the reaction to stir at about 0° C. for about 30 min, then add a solution of compound O (143 mg, 0.34 mmol) dissolved in THF (1.0 mL). Remove the cold bath and place the reaction in an about 50° C. preheated oil bath. After about 2 h, the reaction was cooled to room temperature and was quenched with acetic acid and methanol. The crude was concentrated and purified by reverse phase HPLC without modifier to afford compound 31. $^1H$ NMR (400 MHz, DMSO-$d_6$) δ 7.88 (m, 3H), 7.30 (td, J=8.5, 7.0 Hz, 2H), 7.20-7.04 (m, 3H), 6.87 (d, J=4.5, 1H), 6.80 (d, J=4.5 Hz, 1H), 6.27 (d, 6.1 Hz, 1H), 5.75 (t, J=9.1 Hz, 1H), 5.34 (d, J=5.7 Hz, 1H), 4.81 (p, J=6.3 Hz, 1H), 4.71-4.50 (m, 1H), 4.23 (m, 2H), 4.11 (m, 1H), 4.03-3.83 (m, 1H), 1.37-1.23 (m, 6H), 1.18-1.04 (m, 6H). $^{31}P$ NMR (162 MHz, DMSO) δ 2.47, 2.43. LC/MS: $t_R$=1.08 min, MS m/z=575.06 [M+1]; LC system: Thermo Accela 1250 UHPLC; MS system: Thermo LCQ Fleet; Column: Kinetex 2.6μ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 35

(S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (32)

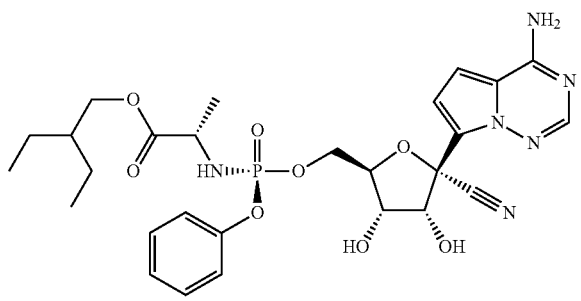 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Preparation of (3R,4R,5R)-3,4-bis(benzyloxy)-5-((benzyloxy)methyl)dihydrofuran-2(3H)-one

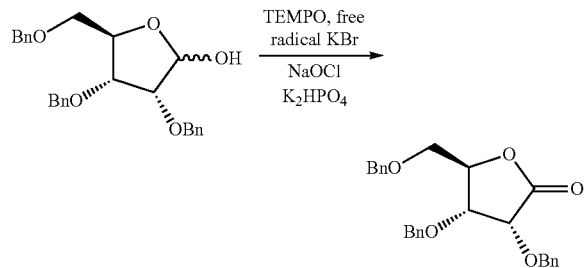

(3R,4R,5R)-3,4-bis(benzyloxy)-5-((benzyloxy)methyl)tetrahydrofuran-2-ol (15.0 g) was combined with MTBE (60.0 mL), KBr (424.5 mg), aqueous K₂HPO₄ solution (2.5M, 14.3 mL), and TEMPO (56 g). This mixture was cooled to about 1° C. Aqueous bleach solution (7.9% wt.) was slowly charged in portions until complete consumption of starting material as indicated through a starch/iodide test. The layers were separated, and the aqueous layer was extracted with MTBE. The combined organic phase was dried over MgSO₄ and concentrated under reduced pressure to yield the product as a solid.

Preparation (4-amino-7-iodopyrrolo[2,1-f][1,2,4]triazine)

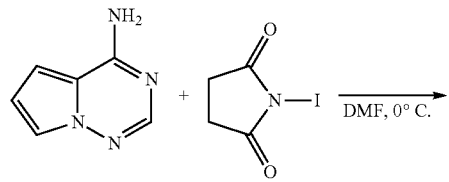

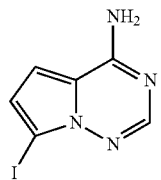

To a cold solution of 4-aminopyrrolo[2,1-f][1,2,4]-triazine (10.03 g; 74.8 mmol) in N,N-dimethylformamide (70.27 g), N-iodosuccinimide (17.01 g; 75.6 mmol) was charged in portions, while keeping the contents at about 0° C. Upon reaction completion (about 3 h at about 0° C.), the reaction mixture was transferred into a 1 M sodium hydroxide aqueous solution (11 g NaOH and 276 mL water) while keeping the contents at about 20-30° C. The resulting slurry was agitated at about 22° C. for 1.5 h and then filtered. The solids are rinsed with water (50 mL) and dried at about 50° C. under vacuum to yield 4-amino-7-iodopyrrolo[2,1-f][1,2,4]triazine as a solid. $^1$H NMR (400 MHz, DMSO-d6) δ 7.90 (s, 1H), 7.78 (br s, 2H), 6.98 (d, J=4.4 Hz, 1H), 6.82 (d, J=4.4 Hz, 1H). $^{13}$C NMR (101 MHz, DMSO-d6) δ 155.7, 149.1, 118.8, 118.1, 104.4, 71.9. MS m/z=260.97 [M+H].

Preparation (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol via (4-amino-7-iodopyrrolo[2,1-f][1,2,4]triazine)

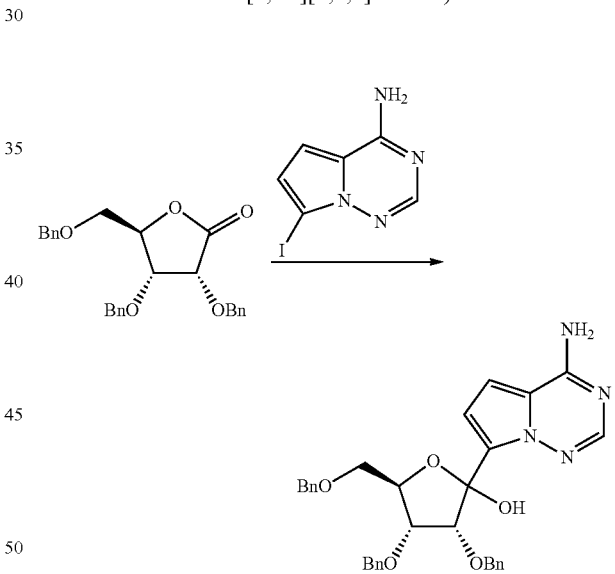

To a reactor under a nitrogen atmosphere was charged iodobase 2 (81 g) and THF (1.6 L). The resulting solution was cooled to about 5° C., and TMSCl (68 g) was charged. PhMgCl (345 mL, 1.8 M in THF) was then charged slowly while maintaining an internal temperature at about <5° C. The reaction mixture was stirred at about 0° C. for 30 min, and then cooled to about −15° C. iPrMgCl—LiCl (311 mL, 1.1 M in THF) was charged slowly while maintaining an internal temperature below about −12° C. After about 10 minutes of stirring at about −15° C., the reaction mixture was cooled to about −20° C., and a solution of lactone 1 (130 g) in THF (400 mL) was charged. The reaction mixture was then agitated at about −20° C. for about 1 h and quenched with AcOH (57 mL). The reaction mixture was warmed to about 0° C. and adjusted to pH 7-8 with aqueous NaHCO₃

(5 wt %, 1300 mL). The reaction mixture was then diluted with EtOAc (1300 mL), and the organic and aqueous layers were separated. The organic layer was washed with 1N HCl (1300 mL), aqueous NaHCO₃ (5 wt %, 1300 mL), and brine (1300 mL), and then dried over anhydrous Na₂SO₄ and concentrated to dryness. Purification by silica gel column chromatography using a gradient consisting of a mixture of MeOH and EtOAc afforded the product.

Preparation ((2S)-2-ethylbutyl 2-(((perfluorophenoxy)(phenoxy)phosphoryl)amino)propanoate) (Mixture of Sp and Rp)

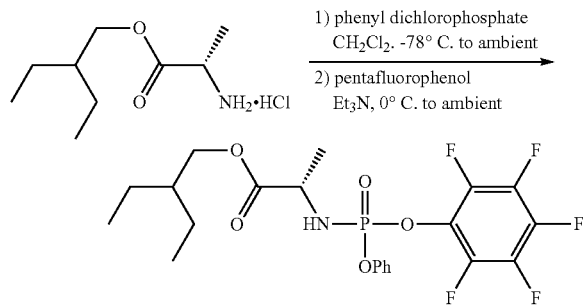

L-Alanine 2-ethylbutyl ester hydrochloride (5.0 g, 23.84 mmol) was combined with methylene chloride (40 mL), cooled to about −78° C., and phenyl dichlorophosphate (3.65 mL, 23.84 mmol) was added. Triethylamine (6.6 mL, 47.68 mmol) was added over about 60 min at about −78° C. and the resulting mixture was stirred at ambient temperature for 3 h. The reaction mixture was cooled to about 0° C. and pentafluorophenol (4.4 g, 23.84 mmol) was added. Triethylamine (3.3 mL, 23.84 mmol) was added over about 60 min. The mixture was stirred for about 3 h at ambient temperature and concentrated under reduced pressure. The residue was dissolved in EtOAc, washed with an aqueous sodium carbonate solution several times, and concentrated under reduced pressure. The residue was purified by silica gel column chromatography using a gradient of EtOAc and hexanes (0 to 30%). Product containing fractions were concentrated under reduced pressure to give (2S)-2-ethylbutyl 2-(((perfluorophenoxy)(phenoxy)phosphoryl)amino) propanoate as a solid. $^1$H NMR (400 MHz, Chloroform-d) δ 7.41-7.32 (m, 4H), 7.30-7.17 (m, 6H), 4.24-4.16 (m, 1H), 4.13-4.03 (m, 4H), 4.01-3.89 (m, 1H), 1.59-1.42 (m, 8H), 1.40-1.31 (m, 8H), 0.88 (t, J=7.5 Hz, 12H). $^{31}$P NMR (162 MHz, Chloroform-d) δ −1.52. $^{19}$F NMR (377 MHz, Chloroform-d) δ −153.63, −153.93 (m), −160.05 (td, J=21.9, 3.6 Hz), −162.65 (qd, J=22.4, 20.5, 4.5 Hz). MS m/z=496 [M+H].

Preparation ((2S)-2-ethylbutyl 2-(((perfluorophenoxy)(phenoxy)phosphoryl)amino)propanoate)

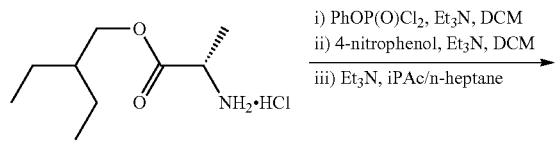

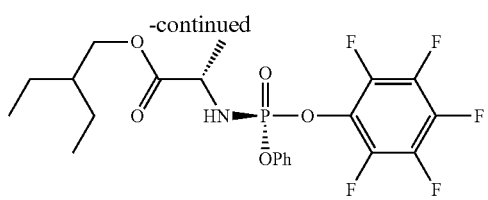

L-alanine-2-ethylbutylester hydrochloride (40.10 g, 0.191 mmol) was dissolved in dichloromethane (533 g) and the solution was cooled with stirring to about −15° C. under N₂(g). Phenyl dichlorophosphate (40.32 g, 0.191 mol) was added followed by slow addition of triethylamine (41.58 g, 0.411 mmol) and the reaction mixture was stirred at about −15° C. for about 1.5 h. Pentafluorophenol (35.14 g, 0.191 mol) was added, followed by triethylamine (19.23 g, 0.190 mol) and the reaction mixture was stirred for about 2 h. The reaction mixture was warmed to about 0° C. and 0.5 M HCl (279.19 g) was added. The mixture was warmed to about 22° C. and the organic layer was separated and washed with 5% KHCO₃ aqueous solution (281 g), then water (281 g). An aliquot of the organic layer (453.10 g of the 604.30 g solution) was concentrated to about 120 mL volume, isopropyl acetate (157 g) was added and the solution was concentrated to dryness. The residue was dissolved in isopropyl acetate (158 g). The resulting solution was concentrated to about 120 mL volume and the temperature was adjusted to about 45° C. n-Heptane (165 g) was added and the mixture was cooled to 22° C. over about 1 h. n-Heptane (167 g) was added and the mixture was cooled to about 0° C. Triethylamine (2.90 g, 0.0287 mol) was added and the mixture was stirred at 0° C. for about 17 h. The mixture was filtered, the solids were rinsed with n-heptane (145 g) and the solids were dried under vacuum at about 40° C. for about 15 h to provide 2-ethylbutyl ((S)-(penthafluorophenoxy)(phenoxy)phosphoryl)-L-alaninate.

Preparation 2-ethylbutyl ((S)-(4-nitrophenoxy)(phenoxy)phosphoryl)-L-alaninate

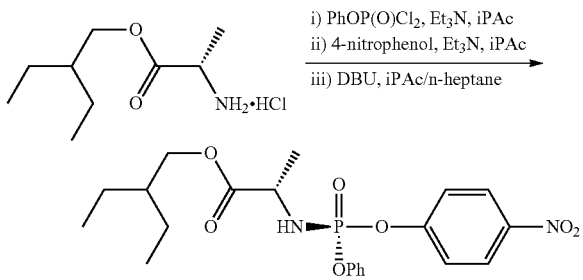

A slurry of L-alanine-2-ethylbutylester hydrochloride (20.08 g, 95.8 mmol) and isopropyl acetate (174 g) was cooled with stirring to about −20° C.). Phenyl dichlorophosphate (20.37 g, 96.5 mmol) was added, followed by slow addition of triethyl amine (20.97 g, 207.2 mmol) and the mixture was stirred at about −20° C. for about 1 h. 4-Nitrophenol (13.23 g, 95.1 mmol) was added, followed by slow addition of triethylamine (10.01 g, 98.8 mmol) and the reaction mixture was stirred for about 1.5 h. The reaction mixture was warmed to about 0° C. and 0.5 M HCl (140 g) was added. The organic layer was separated and washed with 5% Na₂CO₃ (2×100 g) and 10% NaCl (2×100 g). The organic layer was then concentrated to about 80 mL volume and isopropylacetate (4 g) was added, followed by n-heptane (110 g). Product seed crystals (0.100 g) were added followed by a second portion of n-heptane (110 g) and the mixture was cooled to about 0° C. 1,8-Diazabicycloundec-7-ene (1.49 g, 9.79 mmol) was added and the mixture was stirred at about 0° C. for about 21 h. The resultant solids were filtered and washed first with n-heptane (61 g) and then with H₂O (2×100 g). The solids were stirred with H₂O (200 g) for about 1.5 h, filtered, and rinsed with H₂O (3×100 g), then n-heptane (61 g). The obtained solids were dried under vacuum at about 40° C. for about 19 h to provide 2-ethylbutyl ((S)-(4-nitrophenoxy) (phenoxy)phosphoryl)-L-alaninate.

Preparation of Title Compound (Mixture of Sp and Rp)

Preparation of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile

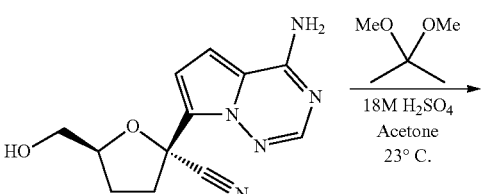

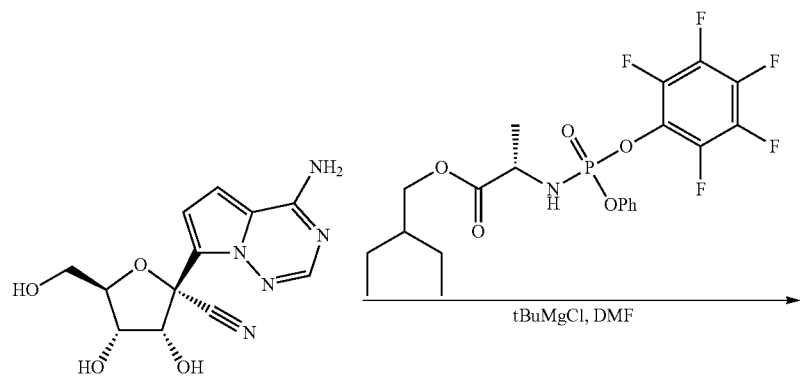

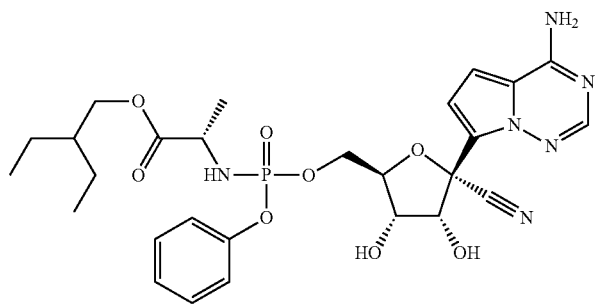

The nucleoside (29 mg, 0.1 mmol) and the phosphonamide (60 mg, 0.12 mmol) and N,N-dimethylformamide (2 mL) were combined at ambient temperature. Tert-Butyl magnesium chloride (1M in THF, 0.15 mL) was slowly added. After about 1 h, the reaction was diluted with ethyl acetate, washed with aqueous citric acid solution (5% wt.), aqueous saturated NaHCO₃ solution and saturated brine solution. The organic phase was dried over Na₂SO₄ and concentrated under reduced pressure. The residue was purified by silica gel column chromatography using a gradient of methanol and CH₂Cl₂ (0 to 5%). Product containing fractions were concentrated under reduced pressure to provide the product.

-continued

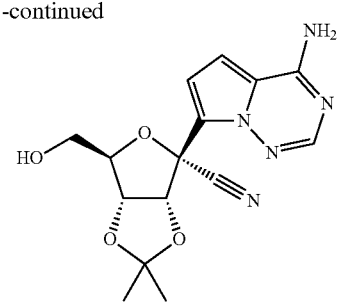

To a mixture of (2R,3R,4S,5R)-2-(4-aminopyrrolo[2,1-f][1,2,4]triazin-7-yl)-3,4-dimethoxypropane (11.59 mL, 0.09 mol) and acetone (145 mL) at ambient temperature was added sulfuric acid (18M, 1.44 mL). The mixture was warmed to about 45° C. After about 30 min, the mixture was cooled to ambient temperature and sodium bicarbonate (5.8 g) and water 5.8 mL) were added. After 15 min, the mixture was concentrated under reduced pressure. The residue was taken up in ethyl acetate (150 mL) and water (50 mL). The aqueous layer was extracted with ethyl acetate (2×50 mL). The combined organic phase was dried over sodium sulfate and concentrated under reduced pressure to give crude (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. $^1$H NMR (400 MHz, CD$_3$OD) δ 7.84 (s, 1H), 6.93 (d, J=4.6 Hz, 1H), 6.89 (d, J=4.6 Hz, 1H), 5.40 (d, J=6.7 Hz, 1H), 5.00 (dd, J=6.7, 3.3 Hz, 1H), 4.48-4.40 (m, 1H), 3.81-3.72 (m, 2H), 1.71 (s, 3H), 1.40 (s, 3H). MS m/z=332.23 [M+1].

Preparation of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile TsOH salt

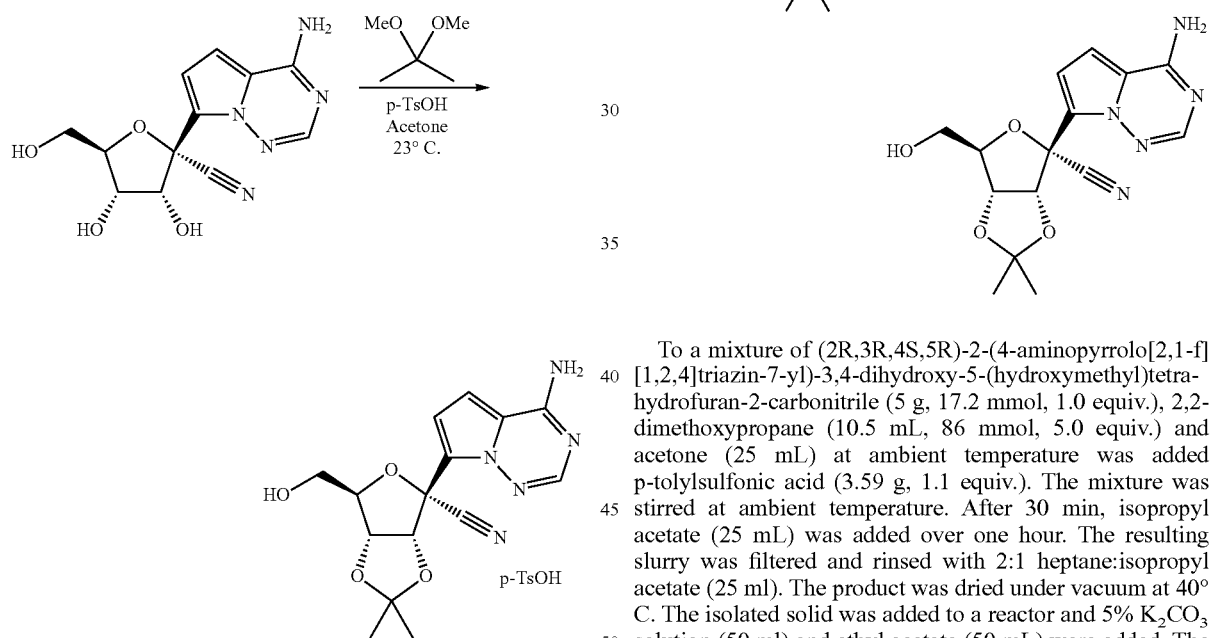

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (5.0 g, 17.2 mmol, 1.0 equiv.), 2,2-dimethoxypropane (10.5 mL, 86 mmol, 5.0 equiv.) and acetone (25 mL) at ambient temperature was added p-tolylsulfonic acid (3.59 g, 1.1 equiv.). The mixture was stirred at ambient temperature. After about 30 min, isopropyl acetate (25 mL) was added over about one hour. The resulting slurry was filtered and rinsed with 2:1 heptane: isopropyl acetate (25 ml). The product was dried under vacuum at about 40° C.

Preparation of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile

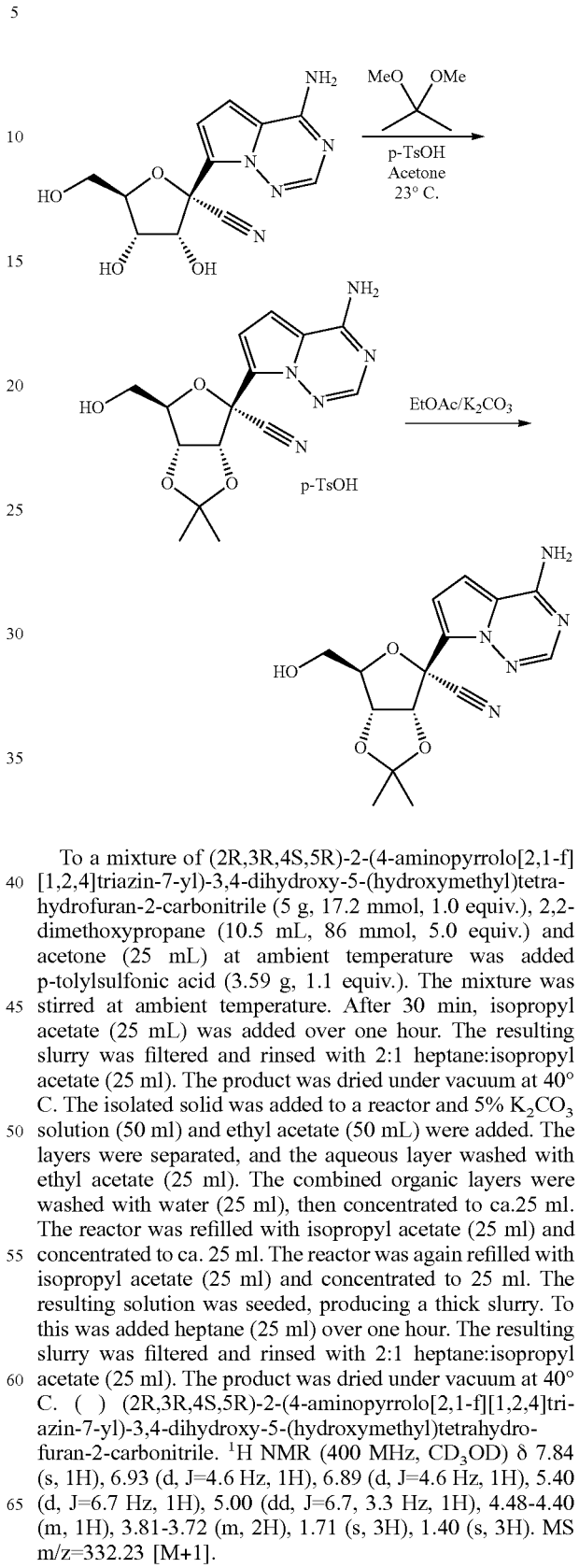

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (5 g, 17.2 mmol, 1.0 equiv.), 2,2-dimethoxypropane (10.5 mL, 86 mmol, 5.0 equiv.) and acetone (25 mL) at ambient temperature was added p-tolylsulfonic acid (3.59 g, 1.1 equiv.). The mixture was stirred at ambient temperature. After 30 min, isopropyl acetate (25 mL) was added over one hour. The resulting slurry was filtered and rinsed with 2:1 heptane:isopropyl acetate (25 ml). The product was dried under vacuum at 40° C. The isolated solid was added to a reactor and 5% K$_2$CO$_3$ solution (50 ml) and ethyl acetate (50 mL) were added. The layers were separated, and the aqueous layer washed with ethyl acetate (25 ml). The combined organic layers were washed with water (25 ml), then concentrated to ca. 25 ml. The reactor was refilled with isopropyl acetate (25 ml) and concentrated to ca. 25 ml. The reactor was again refilled with isopropyl acetate (25 ml) and concentrated to 25 ml. The resulting solution was seeded, producing a thick slurry. To this was added heptane (25 ml) over one hour. The resulting slurry was filtered and rinsed with 2:1 heptane:isopropyl acetate (25 ml). The product was dried under vacuum at 40° C. ( ) (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. $^1$H NMR (400 MHz, CD$_3$OD) δ 7.84 (s, 1H), 6.93 (d, J=4.6 Hz, 1H), 6.89 (d, J=4.6 Hz, 1H), 5.40 (d, J=6.7 Hz, 1H), 5.00 (dd, J=6.7, 3.3 Hz, 1H), 4.48-4.40 (m, 1H), 3.81-3.72 (m, 2H), 1.71 (s, 3H), 1.40 (s, 3H). MS m/z=332.23 [M+1].

Preparation of (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate

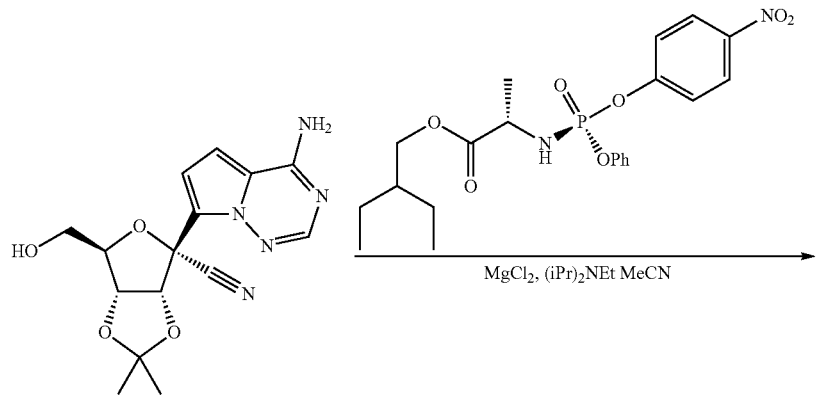

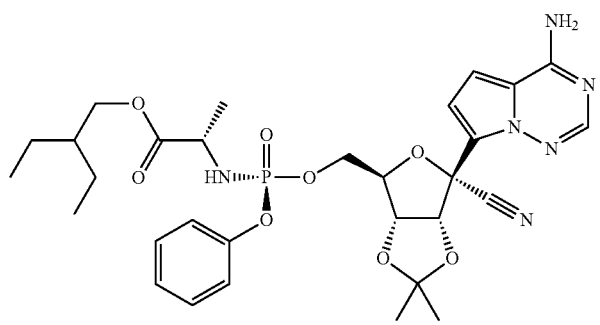

Acetonitrile (100 mL) was combined with (2S)-2-ethylbutyl 2-(((4-nitrophenoxy)(phenoxy)phosphoryl)-amino)propanoate (9.6 g, 21.31 mmol), the substrate alcohol (6.6 g, 0.02 mol), magnesium chloride ((1.9 g, 19.91 mmol) at ambient temperature. The mixture was agitated for about 15 min and N,N-diisopropylethylamine (8.67 mL, 49.78 mmol) was added. After about 4 h, the reaction was diluted with ethyl acetate (100 mL), cooled to about 0° C. and combined with aqueous citric acid solution (5% wt., 100 mL). The organic phase was washed with aqueous citric acid solution (5% wt., 100 mL) and aqueous saturated ammonium chloride solution (40 mL), aqueous potassium carbonate solution (10% wt., 2×100 mL), and aqueous saturated brine solution (100 mL). The organic phase was dried with sodium sulfate and concentrated under reduced pressure to provide crude product. $^1$H NMR (400 MHz, CD$_3$OD) δ 7.86 (s, 1H), 7.31-7.22 (m, 2H), 7.17-7.09 (m, 3H), 6.93-6.84 (m, 2H), 5.34 (d, J=6.7 Hz, 1H), 4.98 (dd, J=6.6, 3.5 Hz, 1H), 4.59-4.50 (m, 1H), 4.36-4.22 (m, 2H), 4.02 (dd, J=10.9, 5.7 Hz, 1H), 3.91 (dd, J=10.9, 5.7 Hz, 1H), 3.83 (dq, J=9.7, 7.1 Hz, 1H), 1.70 (s, 3H), 1.50-1.41 (m, 1H), 1.39 (s, 3H), 1.36-1.21 (m, 7H), 0.86 (t, J=7.4 Hz, 6H). MS m/z=643.21 [M+1].

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 32)

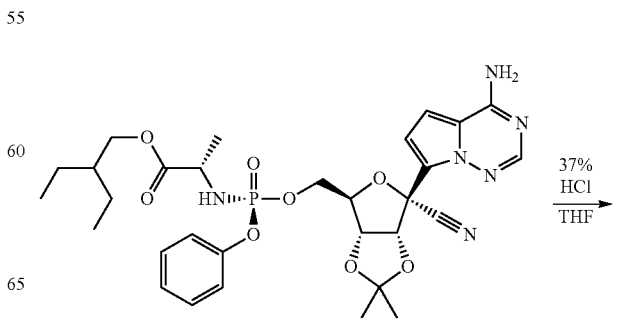

37% HCl / THF

131

-continued

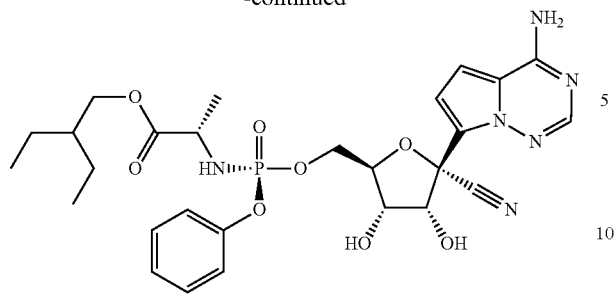

The crude acetonide (12.85 g) was combined with tetrahydrofuran (50 mL) and concentrated under reduced pressure. The residue was taken up in tetrahydrofuran (100 mL), cooled to about 0° C. and concentrated HCl (20 mL) was slowly added. The mixture was allowed to warm to ambient temperature. After consumption of the starting acetonide as indicated by HPLC analysis, water (100 mL) was added followed by aqueous saturated sodium bicarbonate solution (200 mL). The mixture was extracted with ethyl acetate (100 mL), the organic phase washed with aqueous saturated brine solution (50 mL), dried over sodium sulfated and concentrated under reduced pressure. The residue was purified by silica gel column chromatography using a gradient of methanol and ethyl acetate (0 to 20%). Product containing fractions were concentrated under reduced pressure to provide the product.

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 32)

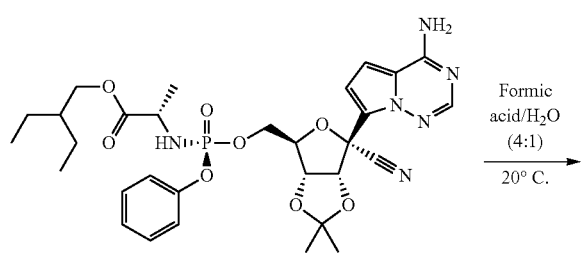

132

-continued

To a vial containing (S)-2-ethylbutyl 2-(((S)-(((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)amino)propanoate (30 mg, 0.05 mmol) was added an 80% aqueous formic acid solution (1.5 mL). After 18 h at about 20° C. complete conversion was confirmed by HPLC and LC-MS. MS (m/z)=603 (M+1)$^+$.

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 32) via Direct Coupling

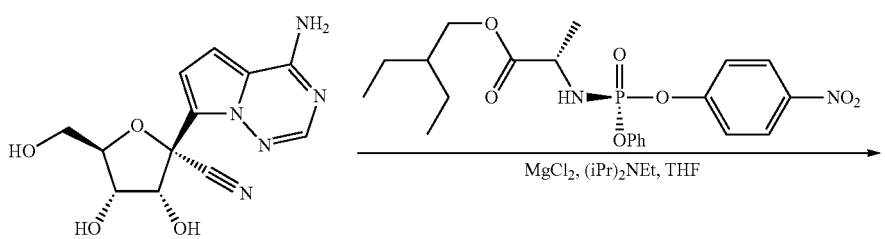

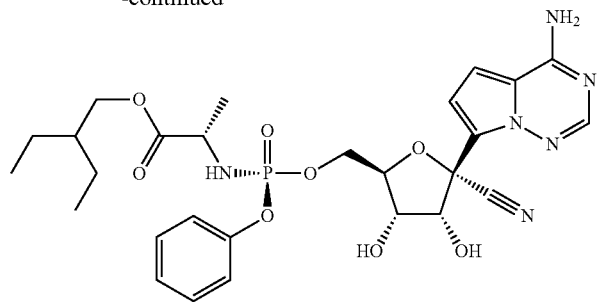

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (0.5 g, 2 mmol), (S)-2-ethylbutyl 2-(((S)-(4-nitrophenoxy)(phenoxy)phosphoryl)amino)propanoate (0.9 g, 2 mmol), and $MgCl_2$ (0.2 g, 2 mmol), was charged N,N-dimethylacetamide (10 mL). The resulting mixture was warmed to about 30° C. with constant stirring. N,N-Diisopropylethylamine (0.7 mL, 4 mmol) was then added slowly, and the reaction mixture was stirred for about 6 h. Water (10 mL) was charged $H_2O$, followed by 2-MeTHF (10 mL), and the organic and aqueous phases were separated. The aqueous layer was then back-extracted with 2-MeTHF (10 mL). The organic layers were combined, and washed with 10 wt % citric acid solution (10 mL), followed by 10 wt % $K_2CO_3$ solution (10 mL), and $H_2O$ (10 mL). A small amount of brine was added to resolve emulsions in the water wash before the layers were separated. The organic layer was evaporated to dryness to afford 0.65 g of a foam. iPrOAc (2.6 mL) was added then added, and the mixture was warmed to about 40° C. to achieve dissolution. The solution was cooled to about 20° C., and the mixture was stirred for about 3 days. The solids were isolated by filtration, and the filter cake was washed with a small amount of iPrOAc. The solids were dried to afford (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate.

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (0.2 g, 0.7 mmol), (S)-2-ethylbutyl 2-(((S)-(perfluorophenoxy)(phenoxy)phosphoryl)amino)propanoate (0.3 g, 0.7 mmol), and $MgCl_2$ (0.1 g, 1 mmol), was charged N,N-dimethylacetamide (4 mL). The resulting mixture was warmed to about 30° C. with constant stirring. N,N-Diisopropylethylamine (0.3 mL, 2 mmol) was then added slowly, and the reaction mixture was stirred for 5 h. Conversion to the product was confirmed through UPLC analysis.

Preparation of (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol

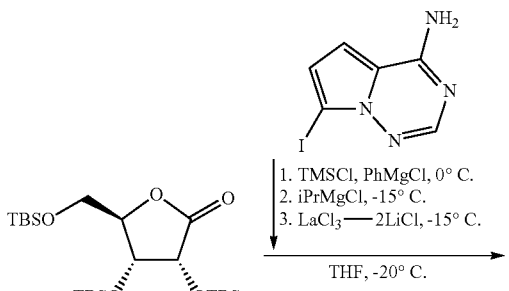

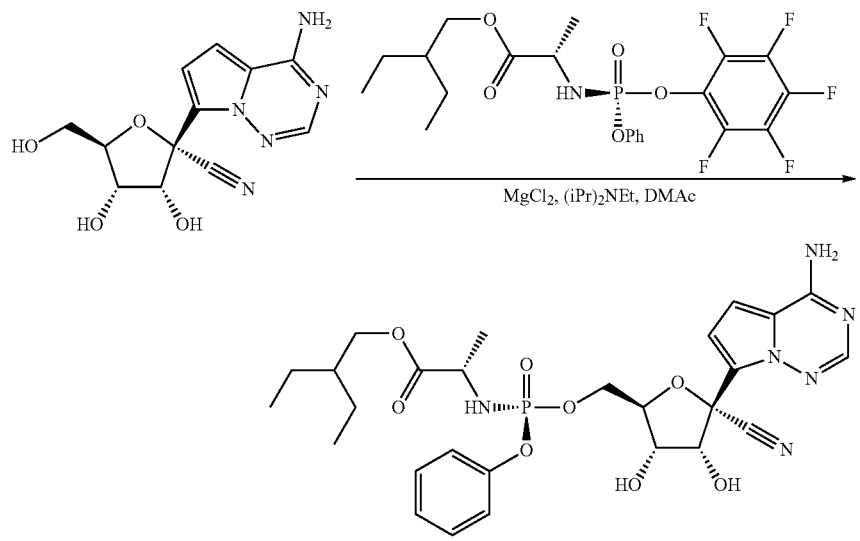

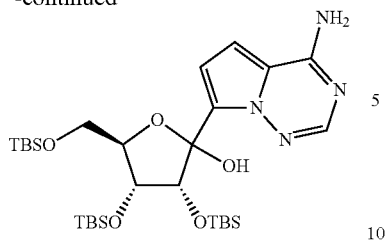

A solution of 7-iodopyrrolo[2,1-f][1,2,4]triazin-4-amine (13.9 g, 53.5 mmol) was prepared in THF (280 mL). The solution was cooled to about 0° C., and TMSCl (13.6 mL, 107 mmol) was added. The reaction mixture was stirred for about 20 min, and then PhMgCl (2 M in THF; 53.5 mL, 56.8 mmol) was added while maintaining an internal temperature below about 5° C. The reaction mixture was agitated at about 0° C. for about 30 min, and then cooled to about −20° C. iPrMgCl—LiCl (1.3 M in THF, 43.1 mL, 56 mmol) was then added while maintaining an internal temperature below about −15° C. The reaction mixture was agitated for about 30 min at about −20° C.

In a separate flask, a solution of (3R,4R,5R)-3,4-bis((tert-butyldimethylsilyl)oxy)-5-(((tert-butyldimethylsilyl)oxy)methyl)dihydrofuran-2(3H)-one (25.0 g, 50.9 mmol, 0.83 equiv) was prepared in LaCl$_3$-2LiCl (0.6 M in THF, 85 mL, 50.9 mmol). The solution was then transferred to the Grignard solution while maintaining an internal temperature below −20° C. The resulting reaction mixture was agitated at about −20° C. for about 4 h.

The reaction was quenched with 1 M HCl (140 mL), and the mixture warmed to ambient temperature. EtOAc (140 mL) was added, and the organic and aqueous phases were separated. The water layer was extracted with EtOAc (200 mL). The combined EtOAc layers were extracted sequentially with saturated aqueous NaHCO$_3$ (2×200 mL), water (200 mL), and brine (200 mL). The organic layer was concentrated, and then purified by silica gel chromatography (30% EtOAc/hexane) to afford (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol. $^1$H NMR (300 MHz, CDCl$_3$) δ 8.15-7.88 (m, 1H), 7.51 (d, J=4.8 Hz, 0.5H), 7.02-6.92 (m, 0.5H), 6.65-6.57 (m, 1H), 5.66-5.24 (m, 3H), 4.49-3.50 (m, 4H), 0.97-0.78 (26H), 0.65 (s, 1.5H), 0.19-0.00 (m, 15.5H), −0.22 (s, 1H), −0.55 (s, 1H). MS m/z=626 (M+H).

Preparation of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile

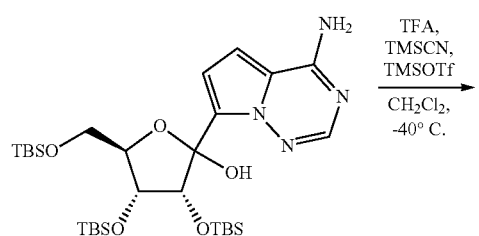

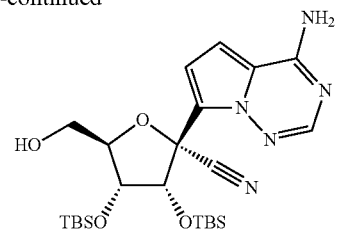

A solution of (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol (1.50 g, 2.40 mmol) in CH$_2$Cl$_2$ (15 mL) was cooled to about −40° C. Trifluoroacetic acid (0.555 mL, 7.20 mmol) was added keeping the temperature below −20° C. In a separate flask, trimethylsilyl trifluoromethanesulfonate (2.60 mL, 14.4 mmol) was added to 5 ml of CH$_2$Cl$_2$ (5 mL) at about 15° C., followed by trimethylsilyl cyanide (1.92 mL, 14.4 mmol), and the solution was cooled to about −30° C. The cooled solution was added to the solution of (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol while keeping the temperature below −25° C. The reaction mixture was stirred for 15 min at about −30° C. The reaction was quenched with triethylamine (3.34 mL, 24.0 mmol) and the mixture was warmed to about 0° C. Water (50 mL) was added while keeping the temperature below about 20° C. When the addition was complete the mixture was stirred for 15 min at room temperature. The layers were separated and the organic layer was washed sequentially with KOH (20 mL), water (20 mL), and brine (20 mL). The organic layer was dried over Na$_2$SO$_4$, concentrated, and then purified by silica gel chromatography (30% EtOAc/hexane) to afford the product as a 3.8:1 mixture of diastereomers). The mixture was purified further by prep-HPLC (ACN 0 to 95% in water) to afford the product as a single diastereomer. $^1$H NMR (400 MHz, DMSO-d6) δ 8.14-7.92 (m, 2H), 7.89 (s, 1H), 6.95 (d, J=4.8 Hz, 1H), 6.88 (d, J=4.4 Hz, 1H), 5.27 (d, J=4.6 Hz, 1H), 5.10 (dd, J=7.7, 4.6 Hz, 1H), 4.31 (dd, J=4.7, 1.4 Hz, 1H), 4.12 (ddd, J=5.9, 4.1, 1.4 Hz, 1H), 3.80-3.69 (m, 1H), 3.56 (td, J=7.8, 3.9 Hz, 1H), 0.93 (s, 9H), 0.75 (s, 9H), 0.11 (s, 3H), 0.09 (s, 3H), −0.15 (s, 3H), −0.62 (s, 3H). MS m/z=520 (M+H).

Preparation of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy)phosphoryl)amino)propanoate

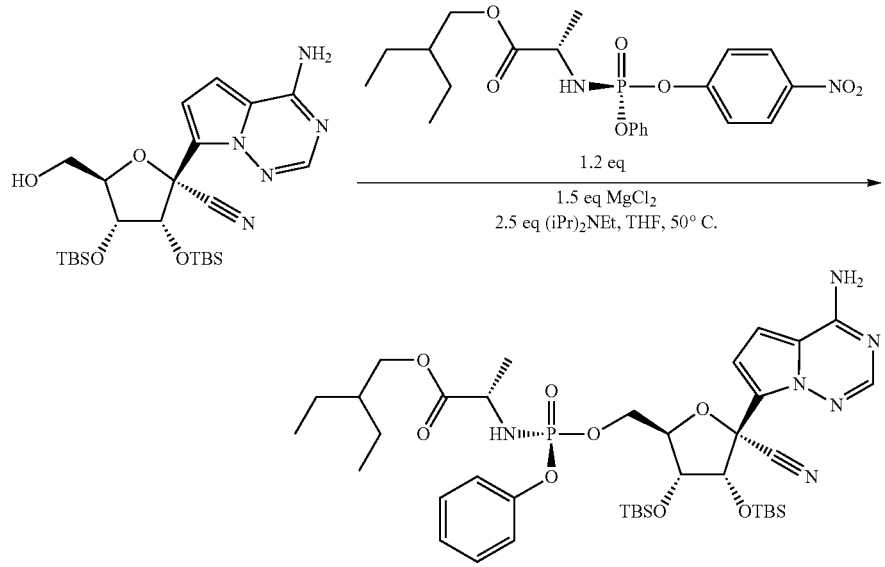

To a mixture of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile (16 mg, 0.03 mmol), (S)-2-ethylbutyl 2-(((S)-(4-nitrophenoxy)(phenoxy)phosphoryl)amino)propanoate (17 mg, 0.04 mmol), and MgCl₂ (4 mg, 0.05 mmol), was charged THF (0.3 mL). The resulting mixture was warmed to about 50° C. with constant stirring. N,N-Diisopropylethylamine (0.013 mL, 0.08 mmol) was then added, and the reaction mixture was stirred for 21 h. Conversion to the product was confirmed through UPLC and LC-MS analysis. MS m/z=831 (M+H).

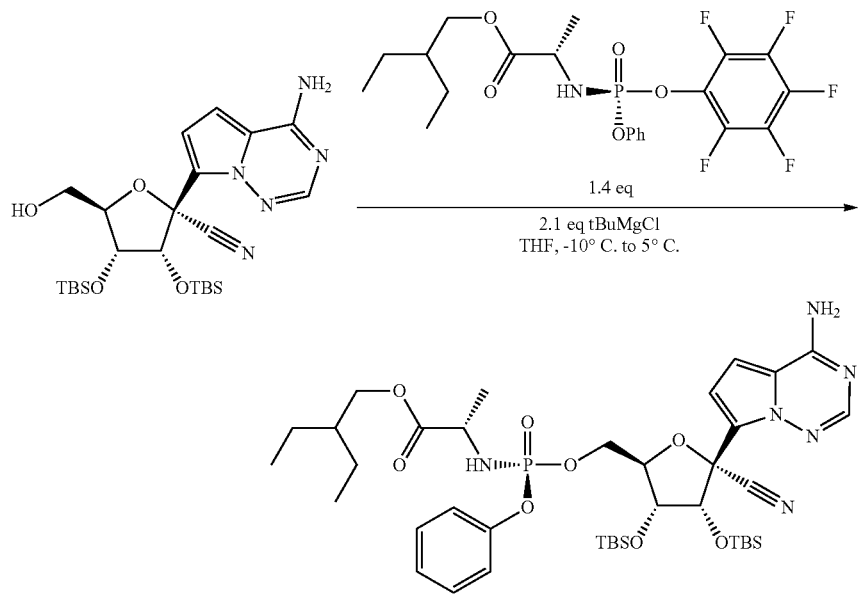

A solution of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile (16 mg, 0.03 mmol) in THF (0.3 mL) was cooled to −10° C. tBuMgCl was added dropwise (0.07 mL, 0.07 mmol), followed by a solution of (S)-2-ethylbutyl 2-(((S)-(perfluorophenoxy)(phenoxy)phosphoryl)amino)propanoate (22 mg, 0.04 mmol) in THF (0.15 mL). The reaction mixture was warmed to 5° C., and stirred for 16 h. The reaction was quenched with MeOH, concentrated, and then purified by silica gel chromatography (EtOAc/hexanes) to afford the product. 1H NMR (400 MHz, CDCl₃) δ 7.97 (s, 1H), 7.38-7.29 (m, 2H), 7.25-7.21 (m, 2H), 7.21-7.13 (m, 1H), 7.11 (d, J=4.6 Hz, 1H), 6.65 (d, J=4.6 Hz, 1H), 5.88 (br s, 2H), 5.35 (d, J=4.4 Hz, 1H), 4.49-4.41 (m, 1H), 4.41-4.35 (m, 1H), 4.32-4.26 (m, 1H), 4.24 (dd, J=4.5, 1.7 Hz, 1H), 4.10-3.99 (m, 2H), 3.96 (dd, J=10.9, 5.7 Hz, 1H), 3.80-3.72 (m, 1H), 1.48 (h, J=6.2 Hz, 1H), 1.39-1.28 (m, 7H), 0.96 (s, 9H), 0.85 (t, J=7.5 Hz, 6H), 0.80 (s, 9H), 0.08 (s, 3H), 0.07 (s, 3H), −0.13 (s, 3H), −0.56 (s, 3H). 31P NMR (162 MHz, CDCl3) δ 2.74 (s). MS m/z=831 (M+H).

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate

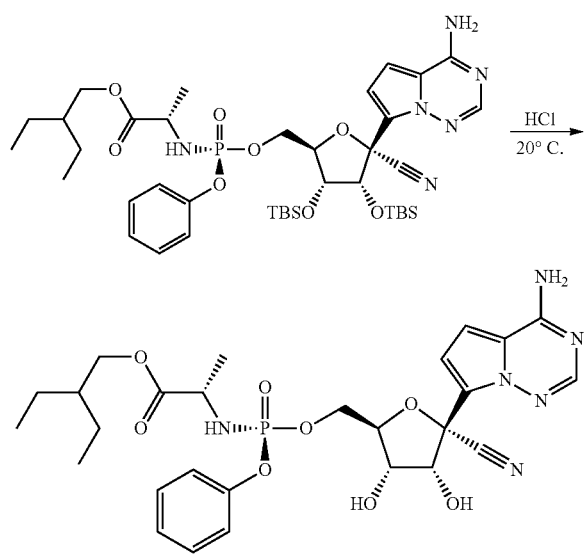

A crude solution of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy)phosphoryl)amino)propanoate was cooled to about 0° C. and conc HCl (0.05 mL, 0.62 mmol) was slowly added. The reaction mixture was stirred for about 72 hours at about 20° C. Conversion to the product was confirmed through UPLC and LC-MS analysis. MS m/z=603 (M+H).

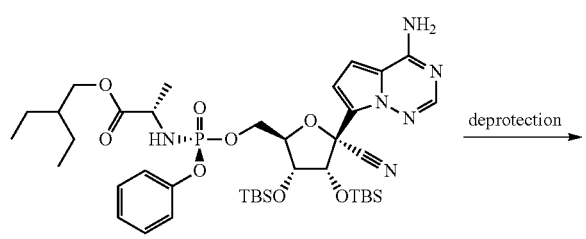

A solution of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy)phosphoryl)amino)propanoate in a fluoride or acid can deprotect to a solution of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate. Representative fluorides include, but are not limited to TBAF, KF, pyridinium hydrofluoride, triethylammonium hydrofluoride, hydrogen fluoride, hydrochloric acid, toluenesulfonic acid, or any other suitable fluoride source. Representative acids include, but are not limited to those found in Greene, T. W.; Wuts, P. G. M. *Protective Groups In Organic Synthesis*, 4th Ed., John Wiley & Sons: New York, 2006.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A method of preparing a compound of Formula (XI-a²)

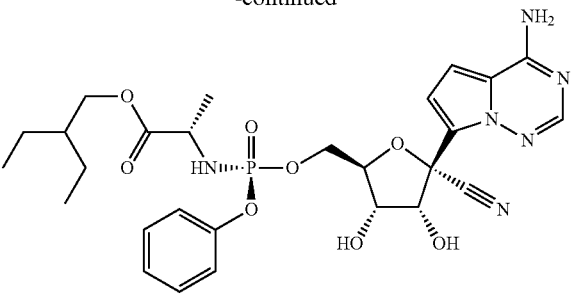

Formula (XI-a²)

Formula (XI-a²), the method comprising:
forming a reaction mixture with a cyanating agent, a Lewis Acid, a Bronsted acid, a solvent, and a compound of Formula (V-a):

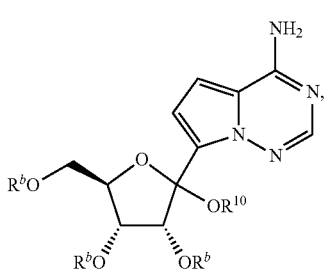

Formula (V-a),
to prepare the compound of Formula (XI-a²),
wherein
each $R^b$ is independently a hydroxy protecting group; alternatively, two $R^b$ groups on adjacent carbons can be combined to form a $-C(R^{19})_2-$ group;
$R^{10o}$ is H or a trialkylsilyl group; and
$R^{19}$ is H, Ci-C8 alkyl, phenyl or substituted phenyl.

2. A method of claim 1 wherein
the cyanating agent is TMSCN;
the Lewis Acid is TMSOTf;
the Brönsted acid is TFA;
the solvent is DCM; and
the hydroxy protecting group is tert-butyldimethylsilyl (TBS).

3. The method of claim 1

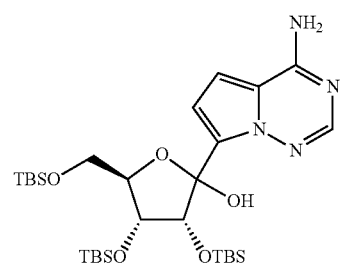

the method comprising:
forming the reaction mixture with TFA, TMSCN, TMSOTf and the compound of Formula
(V-a) having the structure:
to prepare the compound of Formula XI-a².

4. The method of claim 3, further comprising preparing the compound of Formula (V-a) having the structure:

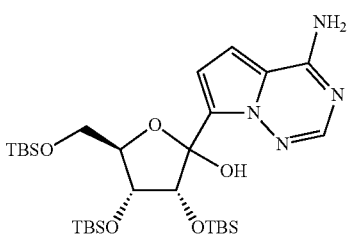

the method comprising:
forming the reaction mixture comprising TMSCl, PhMgCl, iPrMgCl-LiCl, an additive, a compound of Formula (VI-a) having the structure:

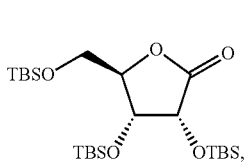

and a compound of Formula (VII):

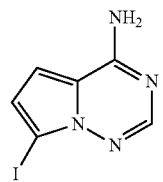

to prepare the compound of Formula (V-a),
wherein
the additive is LaCl3-2LiCl, LaCl₃, CeCl₃, NdCl₃, or YCl3.

5. A method of preparing a compound of Formula VIII:

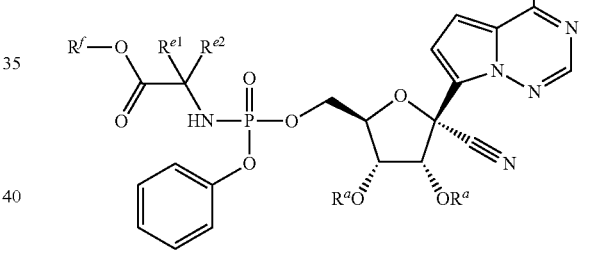

the method comprising:
forming a reaction mixture with MgCl₂, diisopropylethylamine, a compound of Formula IX:

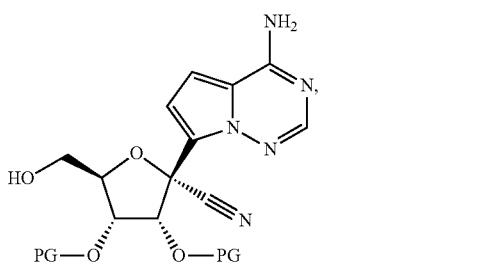

and a compound of Formula (X):

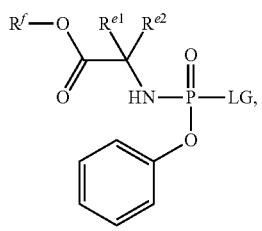

Formula (X)

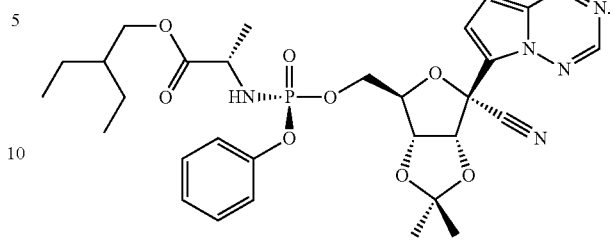

to form the compound of Formula wherein
each $R^a$ is PG;
each PG group is a hydroxy protecting group, or both PG groups are combined to form $-C(R19)_2-$;
$R^{ei}$ and $R^{ei}$ are each independently H, $C_1$-$C_6$ alkyl or benzyl;
$R^f$ is H, $C_1$-$C_8$ alkyl, benzyl, C3-C6 cycloalkyl, or 'CH2-C3-C6 cycloalkyl;
$R^{19}$ is H, $C_1$-$C_8$ alkyl, phenyl or substituted phenyl; and
LG is 4-nitrophenoxy or pentafluorophenoxy.

6. The method of claim 5, wherein
each $R^a$ is PG where the PG groups are combined to form $-C(R^{19})_2-$,
$R^f$ is $C_1$-$C_8$ alkyl;
$R^{19}$ is $C_1$-$C_8$ alkyl.

7. The method of claim 5, wherein the compound of Formula (VIII) has the structure:

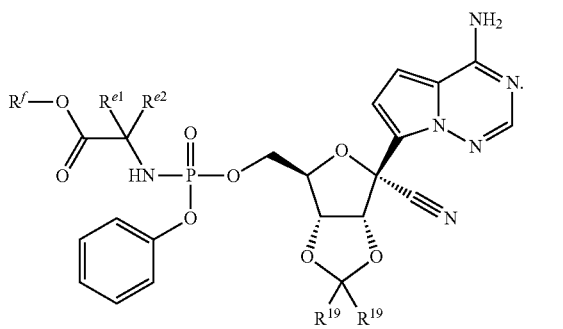

8. The method of claim 5, wherein the compound of Formula (VIII) has the structure:

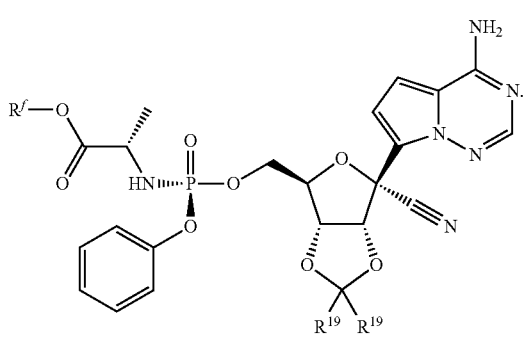

9. The method of claim 5, wherein the compound of Formula (VIII) has the structure:

10. The method of claim 5, wherein the method comprises:
forming the reaction mixture with $MgCl_2$, DIPEA, the compound of Formula (IX) having the structure:

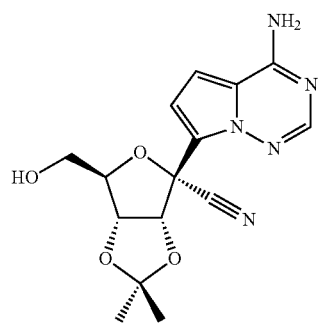

and the compound of Formula (X) having the structure:

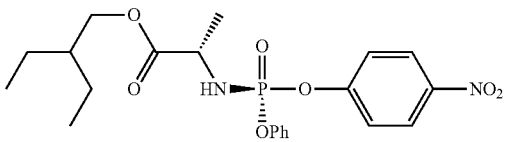 [SMILES: CCC(CC)COC(=O)[C@H](C)N[P@](=O)(Oc1ccccc1)Oc1ccc([N+](=O)[O-])cc1]

to form the compound of Formula (VIII) having the structure:

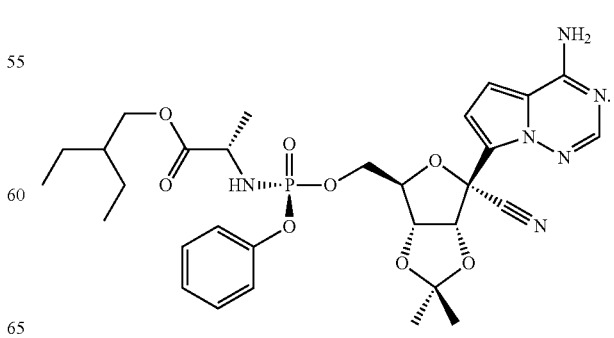

11. A method of preparing a compound of Formula (VIII):

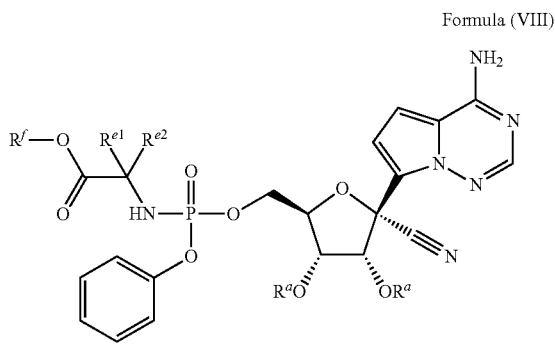

Formula (VIII)

the method comprising:
forming a reaction mixture with MgCl2, diisopropylethylamine, a compound of Formula (IX-a:)

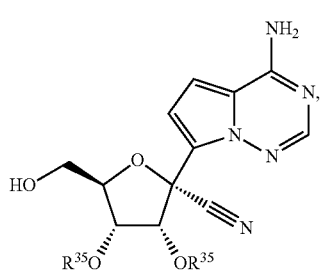

Formula (IX-a)

and a coumpound of Foruma (X):

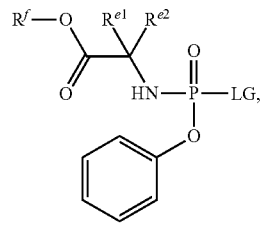

Formula (X)

to form the compound of Formula (VIII),
wherein
$R^a$ is a hydroxy protecting group;
each $R^{35}$ is independently a hydroxy protecting group, or both $R^{35}$ groups are combined to form $-C(R^{19})_2-$;
$R^{e1}$ and $R^{e2}$ are each independently H, $C_1$-$C_6$ alkyl or benzyl;
$R^f$ is H, $C_1$-$C_8$ alkyl, benzyl, C3-C6 cycloalkyl, or -CH2-C3-C6 cycloalkyl;
$R^{19}$ is H, $C_1$-$C_8$ alkyl, phenyl or substituted phenyl; and
LG is 4-nitrophenoxy or pentafluorophenoxy.

12. The method of claim 11 wherein
each $R^{35}$ are combined to form $-C(R^{19})_2-$,
$R^f$ is $C_1$-$C_8$ alkyl; and
$R^{19}$ is $C_1$-$C_8$ alkyl.

13. The method of claim 11 wherein the compound of Formula (VIII) has the structure:

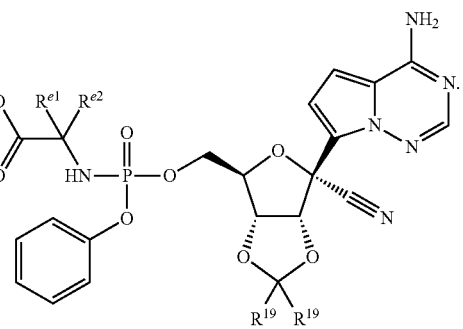

14. The method of claim 11 wherein the compound of Formula (VIII) has the structure:

15. The method of claim 11 wherein the compound of Formula (VIII) has the structure:

16. The method of claim 11 wherein the compound of Formula (VIII) has the structure:

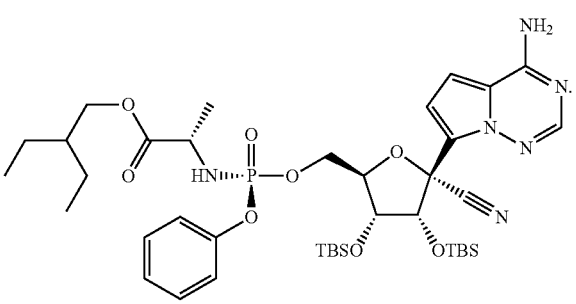 [SMILES: CCC(CC)COC(=O)[C@H](C)N[P@](=O)(OC[C@H]1O[C@@](C#N)(c2ccc3c(N)ncnn23)[C@H](O[Si](C)(C)C(C)(C)C)[C@@H]1O[Si](C)(C)C(C)(C)C)Oc1ccccc1]

17. The method of claim 11 wherein the method comprises:

forming the reaction mixture with MgCl$_2$, DIPEA, the compound of Formula (IX) having the structure:

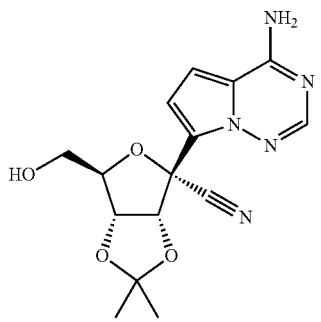 [SMILES: CC1(C)O[C@H]2[C@@H](O1)[C@](C#N)(c1ccc3c(N)ncnn13)O[C@@H]2CO]

and the compound of Formula (X) having the structure:

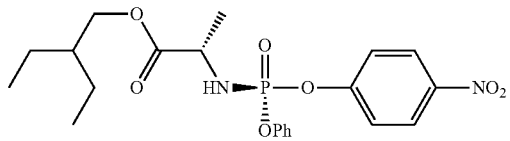 [SMILES: CCC(CC)COC(=O)[C@H](C)N[P@](=O)(Oc1ccccc1)Oc1ccc([N+](=O)[O-])cc1]

to form the compound of (VIII) having the structure:

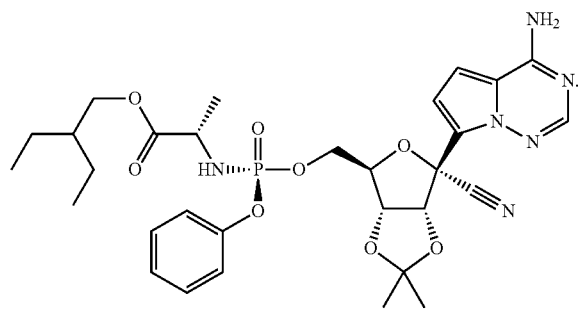 [SMILES: CCC(CC)COC(=O)[C@H](C)N[P@](=O)(OC[C@H]1O[C@@](C#N)(c2ccc3c(N)ncnn23)[C@@H]2OC(C)(C)O[C@@H]21)Oc1ccccc1]

18. The method of claim 11 wherein the method comprises:

forming the reaction mixture with MgCl$_2$, DIPEA, the compound of Formula (IX-a$^2$):

Formula (IX-a$^2$)

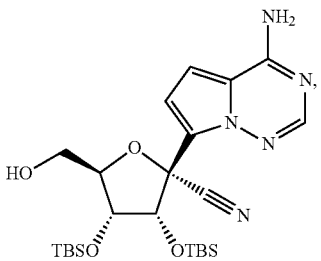

and the compound of Formula (X) having the structure:

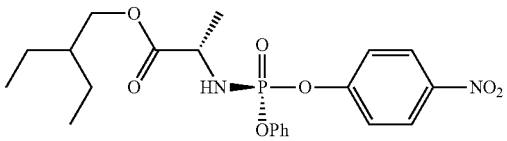 [SMILES: CCC(CC)COC(=O)[C@H](C)N[P@](=O)(Oc1ccccc1)Oc1ccc([N+](=O)[O-])cc1]

to form the compound of Formula (VIII) having the structure:

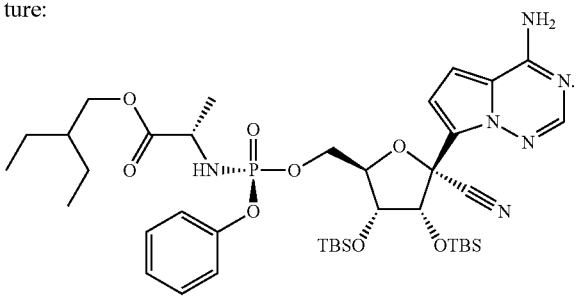

19. A compound of the formula

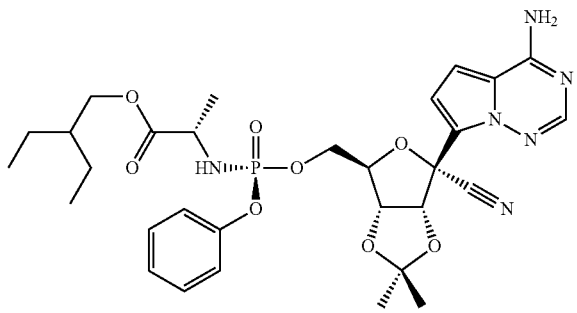

or a pharmaceutically acceptable salt thereof.

* * * * *

UNITED STATES PATENT AND TRADEMARK OFFICE
CERTIFICATE OF CORRECTION

PATENT NO. : 11,344,565 B2
APPLICATION NO. : 14/926063
DATED : May 31, 2022
INVENTOR(S) : Axt et al.

It is certified that error appears in the above-identified patent and that said Letters Patent is hereby corrected as shown below:

On the Title Page

Item (57), Column 2, Line 14, delete "chloride," and insert -- chloride; --.

In the Claims

Column 140, Line 66, Claim 1, delete "Bronsted" and insert -- Brönsted --.

Column 141, Line 19, Claim 1, delete "-C($R^{19}$)2" and insert -- -C($R^{19}$)$_2$ --.

Column 141, Line 20, Claim 1, delete "$R^{10°}$" and insert -- $R^{10}$ --.

Column 141, Line 21, Claim 1, delete "Ci-C8" and insert -- $C_1$-$C_8$ --.

Column 141, Line 22, Claim 2, delete "A" and insert -- The --.

Column 141, Line 30-43, Claim 3, delete "claim 1

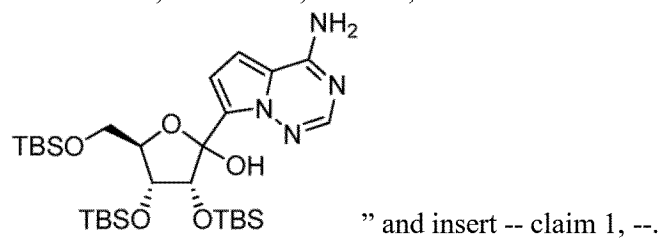

" and insert -- claim 1, --.

Signed and Sealed this
First Day of November, 2022

Katherine Kelly Vidal
*Director of the United States Patent and Trademark Office*

CERTIFICATE OF CORRECTION (continued)

Column 141, Line 47, Claim 3, after "structure:" insert -- 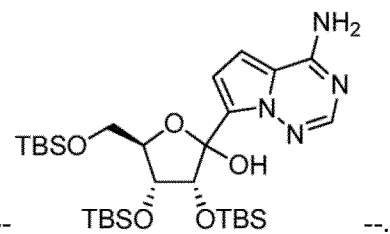 --.

Column 141, Line 65, Claim 4, delete "mixture comprising" and insert -- mixture with --.

Column 142, Line 26, Claim 5, delete "VIII:" and insert -- (VIII): --.

Column 142, Line 51, Claim 5, delete "IX:" and insert -- (IX): --.

Column 143, Line 15, Claim 5, delete "Formula" and insert -- Formula (VIII), --.

Column 143, Line 18, Claim 5, delete "-C(R19)$_2$-;" and insert -- -C(R$^{19}$)$_2$-; --.

Column 143, Line 19, Claim 5, delete "R$^{ei}$ and R$^{ei}$" and insert -- R$^{e1}$ and R$^{e2}$ --.

Column 143, Line 21, Claim 5, delete "C3-C6" and insert -- C$_3$-C$_6$ --.

Column 143, Line 21-22, Claim 5, delete "'CH2-C3-C6" and insert -- -CH$_2$-C$_3$-C$_6$ --.

Column 143, Line 27, Claim 6, delete "-C(R$^{19}$)$_2$-," and insert -- -C(R$^{19}$)$_2$-; --.

Column 143, Line 28, Claim 6, delete "alkyl;" and insert -- alkyl; and --.

Column 145, Line 19, Claim 11, delete "MgCl2," and insert -- MgCl$_2$, --.

Column 145, Line 20, Claim 11, delete "(IX-a:)" and insert -- (IX-a): --.

Column 145, Line 36, Claim 11, delete "coumpound of Foruma" and insert -- compound of Formula --.

Column 145, Line 52, Claim 11, delete "R$^a$" and insert -- each R$^a$ --.

Column 145, Line 55, Claim 11, delete "C$_i$-C$_6$" and insert -- C$_1$-C$_6$ --.

Column 145, Line 57, Claim 11, delete "C3-C6" and insert -- C$_3$-C$_6$ --.

Column 145, Lines 57-58, Claim 11, delete "-CH2-C3-C6" and insert -- -CH$_2$-C$_3$-C$_6$ --.

Column 145, Line 62, Claim 12, delete "-C(R$^{19}$)$_2$-," and insert -- -C(R$^{19}$)$_2$-; --.

Column 147, Line 31, Claim 17, delete "of" and insert -- of Formula --.